United States Patent
Kutok

(10) Patent No.: US 11,147,818 B2
(45) Date of Patent: Oct. 19, 2021

(54) COMBINATION THERAPIES

(71) Applicant: Infinity Pharmaceuticals, Inc., Cambridge, MA (US)

(72) Inventor: Jeffery L. Kutok, Natick, MA (US)

(73) Assignee: Infinity Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 16/312,896

(22) PCT Filed: Jun. 23, 2017

(86) PCT No.: PCT/US2017/038966
§ 371 (c)(1),
(2) Date: Dec. 21, 2018

(87) PCT Pub. No.: WO2017/223422
PCT Pub. Date: Dec. 28, 2017

(65) Prior Publication Data
US 2019/0216816 A1    Jul. 18, 2019

Related U.S. Application Data

(60) Provisional application No. 62/354,637, filed on Jun. 24, 2016.

(51) Int. Cl.
*A61K 39/00* (2006.01)
*A61K 31/52* (2006.01)
*A61P 35/00* (2006.01)
*A61K 31/497* (2006.01)
*A61K 39/395* (2006.01)
*C07K 16/28* (2006.01)

(52) U.S. Cl.
CPC ............ *A61K 31/52* (2013.01); *A61K 31/497* (2013.01); *A61K 39/39566* (2013.01); *A61P 35/00* (2018.01); *C07K 16/2803* (2013.01); *C07K 16/2818* (2013.01); *A61K 2039/505* (2013.01); *C07K 2317/21* (2013.01); *C07K 2317/24* (2013.01)

(58) Field of Classification Search
CPC ............ A61P 35/00; A61K 39/39566; A61K 2039/505; A61K 39/395; A61K 45/06; A61K 2300/00
See application file for complete search history.

(56) References Cited

U.S. PATENT DOCUMENTS

| | | | |
|---|---|---|---|
| 4,547,508 A | 10/1985 | Konz et al. | |
| 4,656,159 A | 4/1987 | McPherson et al. | |
| 4,704,381 A | 11/1987 | Schaumann et al. | |
| 4,795,627 A | 1/1989 | Fisher et al. | |
| 5,240,941 A | 8/1993 | Bruneau | |
| 5,294,612 A | 3/1994 | Bacon et al. | |
| 5,310,731 A | 5/1994 | Olsson et al. | |
| 5,364,862 A | 11/1994 | Spada et al. | |
| 5,409,930 A | 4/1995 | Spada et al. | |
| 5,420,419 A | 5/1995 | Wood | |
| 5,428,125 A | 6/1995 | Hefner, Jr. et al. | |
| 5,442,039 A | 8/1995 | Hefner, Jr. et al. | |
| 5,480,883 A | 1/1996 | Spada et al. | |
| 5,504,103 A | 4/1996 | Bonjouklian et al. | |
| 5,506,347 A | 4/1996 | Erion et al. | |
| 5,561,134 A | 10/1996 | Spada et al. | |
| 5,563,257 A | 10/1996 | Zilch et al. | |
| 5,593,997 A | 1/1997 | Dow et al. | |
| 5,646,128 A | 7/1997 | Firestein et al. | |
| 5,646,153 A | 7/1997 | Spada et al. | |
| 5,652,366 A | 7/1997 | Spada et al. | |
| 5,654,307 A | 8/1997 | Bridges et al. | |
| 5,656,643 A | 8/1997 | Spada et al. | |
| 5,665,721 A | 9/1997 | Bhagwat et al. | |
| 5,674,998 A | 10/1997 | Boyer et al. | |
| 5,686,455 A | 11/1997 | Adams et al. | |
| 5,710,158 A | 1/1998 | Spada et al. | |
| 5,714,493 A | 2/1998 | Spada et al. | |
| 5,721,237 A | 2/1998 | Spada et al. | |
| 5,736,554 A | 4/1998 | Spada et al. | |
| 5,747,235 A | 5/1998 | Farid et al. | |
| 5,756,711 A | 5/1998 | Zilch et al. | |
| 5,763,596 A | 6/1998 | Boyer et al. | |
| 5,763,597 A | 6/1998 | Ugarkar et al. | |

(Continued)

FOREIGN PATENT DOCUMENTS

| CA | 1338379 C | 6/1996 |
|---|---|---|
| CN | 101602768 A | 12/2009 |

(Continued)

OTHER PUBLICATIONS

Nelson et al., Ann. Intern Med. 2009; 151:727-737 (Year: 2009).*
Kataja et al., Ann Oncol 2009; 20(sup 4): iv10-14 (Year: 2009).*
Balmana et al. Ann Oncol 2009; 20(supp 4):iv19-20 (Year: 2009).*
WO 2016/024228 pp. 1-349 (Year: 2016).*
WO 2016/024228, pp. 351-680 (Year: 2016).*
Bea et al Blood, vol. 106 p. 3183 (2005). (Year: 2005).*
Robak et al Expert Opin. Emerging Drugs col. 20 p. 423 (2015). (Year: 2015).*

(Continued)

*Primary Examiner* — Sheela J. Huff
(74) *Attorney, Agent, or Firm* — Cooley LLP

(57) ABSTRACT

Provided herein are pharmaceutical compositions comprising a phosphatidylinositol 3-kinase inhibitor, or pharmaceutically acceptable form thereof, in combination with a second agent, or a pharmaceutically acceptable form thereof, wherein the second agent is chosen from one or more of 1) a checkpoint modulator, 2) an XPO1 inhibitor, 3) an anti-CD19 antibody, 4) a TLR agonist, 5) a STING agonist, or 6) a Flt3 ligand, or a combination thereof. Also provided herein are methods of treatment comprising administration of the compositions, and uses of the compositions, e.g., for treatment of cancer.

36 Claims, 1 Drawing Sheet

(56) References Cited

U.S. PATENT DOCUMENTS

| | | |
|---|---|---|
| 5,763,885 A | 6/1998 | Murphy et al. |
| 5,795,977 A | 8/1998 | Ugarkar et al. |
| 5,811,454 A | 9/1998 | Springer |
| 5,824,492 A | 10/1998 | Hiles et al. |
| 5,858,753 A | 1/1999 | Chantry et al. |
| 5,914,488 A | 6/1999 | Sone |
| RE36,256 E | 7/1999 | Spada et al. |
| 5,919,808 A | 7/1999 | Petrie et al. |
| 5,922,753 A | 7/1999 | Petrie et al. |
| 5,948,776 A | 9/1999 | Petrie et al. |
| 5,962,457 A | 10/1999 | Chenard et al. |
| 5,965,573 A | 10/1999 | Petrie et al. |
| 5,977,061 A | 11/1999 | Holy et al. |
| 5,981,533 A | 11/1999 | Traxler et al. |
| 5,985,589 A | 11/1999 | Chantry et al. |
| 5,990,109 A | 11/1999 | Chen et al. |
| 5,990,169 A | 11/1999 | Petrie et al. |
| 5,994,358 A | 11/1999 | Petrie et al. |
| 6,001,839 A | 12/1999 | Calderwood et al. |
| 6,057,305 A | 5/2000 | Holy et al. |
| 6,057,320 A | 5/2000 | Spada et al. |
| 6,057,371 A | 5/2000 | Glennon |
| 6,084,095 A | 7/2000 | Bridges et al. |
| 6,093,737 A | 7/2000 | Anthony et al. |
| 6,127,121 A | 10/2000 | Meyer, Jr. et al. |
| 6,153,631 A | 11/2000 | Petrie et al. |
| 6,191,170 B1 | 2/2001 | Medina |
| 6,242,453 B1 | 6/2001 | Cirillo et al. |
| 6,251,901 B1 | 6/2001 | Petrie et al. |
| 6,265,410 B1 | 7/2001 | Bridges et al. |
| 6,268,370 B1 | 7/2001 | Adams et al. |
| 6,312,894 B1 | 11/2001 | Hedgpeth et al. |
| 6,323,201 B1 | 11/2001 | Carson et al. |
| 6,342,514 B1 | 1/2002 | Petrie et al. |
| 6,350,741 B1 | 2/2002 | Golec et al. |
| 6,358,945 B1 | 3/2002 | Breitfelder et al. |
| 6,362,216 B1 | 3/2002 | Burgess et al. |
| RE37,650 E | 4/2002 | Spada et al. |
| 6,383,790 B1 | 5/2002 | Shokat |
| 6,384,039 B1 | 5/2002 | Fossa |
| 6,387,894 B1 | 5/2002 | Fossa |
| 6,390,821 B1 | 5/2002 | Shokat |
| 6,455,534 B2 | 9/2002 | Bridges et al. |
| 6,472,153 B1 | 10/2002 | Dempcy et al. |
| 6,472,562 B1 | 10/2002 | Klingler et al. |
| 6,482,623 B1 | 11/2002 | Vanhaesebroeck et al. |
| 6,485,906 B2 | 11/2002 | Meyer, Jr. et al. |
| 6,492,346 B1 | 12/2002 | Hedgpeth et al. |
| 6,506,769 B2 | 1/2003 | Snow et al. |
| 6,518,277 B1 | 2/2003 | Sadhu et al. |
| 6,521,417 B1 | 2/2003 | Shokat |
| 6,521,620 B1 | 2/2003 | Bridges et al. |
| 6,531,491 B1 | 3/2003 | Kania et al. |
| 6,534,524 B1 | 3/2003 | Kania et al. |
| 6,545,005 B1 | 4/2003 | Baxter et al. |
| 6,552,192 B1 | 4/2003 | Hanus et al. |
| 6,562,819 B2 | 5/2003 | Carson et al. |
| 6,583,161 B1 | 6/2003 | Medina |
| 6,613,798 B1 | 9/2003 | Porter et al. |
| 6,630,495 B1 | 10/2003 | Cooke et al. |
| 6,632,789 B1 | 10/2003 | June |
| 6,645,969 B1 | 11/2003 | Spada et al. |
| 6,645,989 B2 | 11/2003 | Adams et al. |
| 6,649,631 B1 | 11/2003 | Orme et al. |
| 6,653,296 B1 | 11/2003 | Holy et al. |
| 6,653,306 B1 | 11/2003 | Alexander et al. |
| 6,660,744 B1 | 12/2003 | Hirst et al. |
| 6,660,845 B1 | 12/2003 | Gall et al. |
| 6,664,269 B2 | 12/2003 | Martin et al. |
| 6,664,393 B2 | 12/2003 | Klingler et al. |
| 6,667,300 B2 | 12/2003 | Sadhu et al. |
| 6,667,398 B2 | 12/2003 | Dunn et al. |
| 6,690,583 B1 | 2/2004 | Bergstedt et al. |
| 6,713,484 B2 | 3/2004 | Bridges et al. |
| 6,720,344 B2 | 4/2004 | Kerwin et al. |
| 6,734,187 B1 | 5/2004 | Tanaka et al. |
| 6,770,639 B2 | 8/2004 | Snow et al. |
| 6,777,425 B2 | 8/2004 | Burli et al. |
| 6,777,439 B2 | 8/2004 | Durden |
| 6,790,844 B2 | 9/2004 | Ueno et al. |
| 6,800,620 B2 | 10/2004 | Sadhu et al. |
| 6,825,219 B2 | 11/2004 | Cywin et al. |
| 6,849,420 B2 | 2/2005 | Vanhasebroeck et al. |
| 6,849,637 B2 | 2/2005 | Andrianjara et al. |
| 6,849,713 B2 | 2/2005 | Zhang et al. |
| 6,852,727 B2 | 2/2005 | Goulet et al. |
| 6,858,756 B2 | 2/2005 | Rampf et al. |
| 6,906,103 B2 | 6/2005 | Zhang et al. |
| 6,916,949 B2 | 7/2005 | Springer et al. |
| 6,919,332 B2 | 7/2005 | Noe et al. |
| 6,921,763 B2 | 7/2005 | Hirst et al. |
| 6,949,535 B2 | 9/2005 | Sadhu et al. |
| 7,005,520 B2 | 2/2006 | Dunn et al. |
| 7,026,461 B1 | 4/2006 | Shokat |
| 7,041,676 B2 | 5/2006 | McDonald et al. |
| 7,049,116 B2 | 5/2006 | Shokat |
| 7,049,312 B1 | 5/2006 | Rafferty et al. |
| 7,064,218 B2 | 6/2006 | Dyatkina et al. |
| 7,071,355 B2 | 7/2006 | Leban et al. |
| 7,087,597 B1 | 8/2006 | Miwa et al. |
| 7,102,046 B2 | 9/2006 | Rampf et al. |
| 7,115,627 B2 | 10/2006 | Pinto et al. |
| 7,115,653 B2 | 10/2006 | Baxter et al. |
| 7,144,903 B2 | 12/2006 | Collins et al. |
| 7,157,487 B2 | 1/2007 | Nakayama et al. |
| 7,166,293 B2 | 1/2007 | Teng et al. |
| 7,208,493 B2 | 4/2007 | Wrasidlo et al. |
| 7,208,601 B2 | 4/2007 | Mjalli et al. |
| 7,217,794 B2 | 5/2007 | Abdel-Meguid et al. |
| 7,223,780 B2 | 5/2007 | Nazare et al. |
| 7,235,585 B2 | 6/2007 | Springer et al. |
| 7,244,741 B2 | 7/2007 | Simon et al. |
| 7,247,736 B2 | 7/2007 | Leban et al. |
| 7,262,204 B2 | 8/2007 | Collins et al. |
| 7,265,111 B2 | 9/2007 | Bigot et al. |
| 7,265,131 B2 | 9/2007 | Johnson et al. |
| 7,317,027 B2 | 1/2008 | Nazare et al. |
| 7,329,765 B2 | 2/2008 | Burli et al. |
| 7,332,497 B2 | 2/2008 | Hirst et al. |
| 7,348,427 B2 | 3/2008 | Burli et al. |
| 7,365,088 B2 | 4/2008 | Nazare et al. |
| 7,365,094 B2 | 4/2008 | Leban et al. |
| 7,384,967 B2 | 6/2008 | Polisetti et al. |
| 7,396,836 B2 | 7/2008 | Harada et al. |
| 7,414,036 B2 | 8/2008 | Sevillano et al. |
| 7,429,596 B2 | 9/2008 | Tanaka et al. |
| 7,439,254 B2 | 10/2008 | Bergnes |
| 7,449,477 B2 | 11/2008 | Barda et al. |
| 7,459,462 B2 | 12/2008 | Simon et al. |
| 7,459,472 B2 | 12/2008 | Mjalli et al. |
| 7,465,806 B2 | 12/2008 | Bauer et al. |
| 7,470,721 B2 | 12/2008 | Durden |
| 7,501,538 B2 | 3/2009 | Mjalli et al. |
| 7,514,445 B2 | 4/2009 | Freyne et al. |
| 7,534,797 B2 | 5/2009 | Arnold et al. |
| 7,541,373 B2 | 6/2009 | Polisetti et al. |
| 7,569,571 B2 | 8/2009 | Dong et al. |
| 7,572,913 B2 | 8/2009 | McKerracher et al. |
| 7,579,348 B2 | 8/2009 | Wang et al. |
| 7,585,868 B2 | 9/2009 | Knight et al. |
| 7,608,594 B2 | 10/2009 | Blagg et al. |
| 7,615,552 B2 | 11/2009 | Ono et al. |
| 7,622,451 B2 | 11/2009 | Blagg et al. |
| 7,642,272 B2 | 1/2010 | Shankar et al. |
| 7,678,803 B2 | 3/2010 | Huang et al. |
| 7,700,552 B2 | 4/2010 | Waehling et al. |
| 7,700,607 B2 | 4/2010 | Hu et al. |
| 7,705,018 B2 | 4/2010 | Chen et al. |
| 7,745,485 B2 | 6/2010 | Durden |
| 7,829,590 B2 | 11/2010 | Brenchley et al. |
| 7,919,046 B2 | 4/2011 | Delapierre et al. |
| 7,932,260 B2 | 4/2011 | Fowler et al. |
| 8,053,445 B2 | 11/2011 | Yamamori et al. |
| 8,053,603 B2 | 11/2011 | Shao et al. |

(56) References Cited

U.S. PATENT DOCUMENTS

| | | |
|---|---|---|
| 8,088,385 B2 | 1/2012 | Tapolsky et al. |
| 8,101,637 B2 | 1/2012 | Bessis et al. |
| 8,106,146 B2 | 1/2012 | Benz et al. |
| 8,124,625 B2 | 2/2012 | Yamamori et al. |
| 8,188,134 B2 | 5/2012 | Brenchley et al. |
| 8,193,182 B2 | 6/2012 | Ren et al. |
| 8,399,483 B2 | 3/2013 | Allen et al. |
| 8,557,823 B2 | 10/2013 | Tapolsky et al. |
| 8,785,456 B2 | 7/2014 | Ren et al. |
| 2001/0019829 A1 | 9/2001 | Nelson et al. |
| 2001/0027197 A1 | 10/2001 | Bridges et al. |
| 2002/0016460 A1 | 2/2002 | Snow et al. |
| 2002/0016976 A1 | 2/2002 | Shokat |
| 2002/0037856 A1 | 3/2002 | Zhang et al. |
| 2002/0102590 A1 | 8/2002 | Taing et al. |
| 2002/0107245 A1 | 8/2002 | Wagle et al. |
| 2002/0127625 A1 | 9/2002 | Oxelius |
| 2002/0146690 A1 | 10/2002 | Meyer et al. |
| 2002/0147160 A1 | 10/2002 | Bhat et al. |
| 2002/0156073 A1 | 10/2002 | Wagle et al. |
| 2002/0156081 A1 | 10/2002 | Hirst et al. |
| 2002/0161014 A1 | 10/2002 | Sadhu et al. |
| 2002/0173524 A1 | 11/2002 | Collins et al. |
| 2002/0193377 A1 | 12/2002 | Andrianjara et al. |
| 2003/0001141 A1 | 1/2003 | Sun et al. |
| 2003/0008896 A1 | 1/2003 | Martin et al. |
| 2003/0018022 A1 | 1/2003 | Collins et al. |
| 2003/0022344 A1 | 1/2003 | Williams et al. |
| 2003/0064997 A1 | 4/2003 | Adams et al. |
| 2003/0073218 A1 | 4/2003 | Shokat |
| 2003/0083268 A1 | 5/2003 | Burli et al. |
| 2003/0113765 A1 | 6/2003 | Dempcy et al. |
| 2003/0119479 A1 | 6/2003 | Arima et al. |
| 2003/0119791 A1 | 6/2003 | Kerwin et al. |
| 2003/0139427 A1 | 7/2003 | Castelhano et al. |
| 2003/0143602 A1 | 7/2003 | Meyer et al. |
| 2003/0166929 A1 | 9/2003 | Snow et al. |
| 2003/0180924 A1 | 9/2003 | DeSimone |
| 2003/0186987 A1 | 10/2003 | Bridges et al. |
| 2003/0187001 A1 | 10/2003 | Calderwood et al. |
| 2003/0195211 A1 | 10/2003 | Sadhu et al. |
| 2003/0199516 A1 | 10/2003 | Moser et al. |
| 2003/0208800 A1 | 11/2003 | Eby et al. |
| 2003/0212113 A1 | 11/2003 | Dyatkina et al. |
| 2003/0232849 A1 | 12/2003 | Noe et al. |
| 2003/0235822 A1 | 12/2003 | Lokhov et al. |
| 2004/0029875 A1 | 2/2004 | Fauchere et al. |
| 2004/0039035 A1 | 2/2004 | Collins et al. |
| 2004/0043959 A1 | 3/2004 | Bloom et al. |
| 2004/0043983 A1 | 3/2004 | Li |
| 2004/0067901 A1 | 4/2004 | Bhat et al. |
| 2004/0067915 A1 | 4/2004 | McMahon et al. |
| 2004/0072766 A1 | 4/2004 | June |
| 2004/0072788 A1 | 4/2004 | Bhat et al. |
| 2004/0072871 A1 | 4/2004 | Dublanchet et al. |
| 2004/0102423 A1 | 5/2004 | McLaughlan et al. |
| 2004/0102437 A1 | 5/2004 | Takami et al. |
| 2004/0110717 A1 | 6/2004 | Carroll et al. |
| 2004/0110945 A1 | 6/2004 | Nakayama et al. |
| 2004/0116689 A1 | 6/2004 | Gall et al. |
| 2004/0122235 A1 | 6/2004 | Polisetti et al. |
| 2004/0127434 A1 | 7/2004 | Bigot et al. |
| 2004/0146941 A1 | 7/2004 | Zhang et al. |
| 2004/0176458 A1 | 9/2004 | Leban et al. |
| 2004/0176601 A1 | 9/2004 | Goulet et al. |
| 2004/0192758 A1 | 9/2004 | Leban et al. |
| 2004/0235849 A1 | 11/2004 | Beyreuther et al. |
| 2004/0266780 A1 | 12/2004 | Sadhu et al. |
| 2005/0004149 A1 | 1/2005 | Harada et al. |
| 2005/0043239 A1 | 2/2005 | Douangpanya et al. |
| 2005/0049310 A1 | 3/2005 | Mjalli et al. |
| 2005/0054614 A1 | 3/2005 | Diacovo et al. |
| 2005/0059713 A1 | 3/2005 | Mjalli et al. |
| 2005/0085472 A1 | 4/2005 | Tanaka et al. |
| 2005/0101551 A1 | 5/2005 | Sevillano et al. |
| 2005/0124637 A1 | 6/2005 | Cheng et al. |
| 2005/0143317 A1 | 6/2005 | Abdel-Meguid et al. |
| 2005/0153997 A1 | 7/2005 | Simon et al. |
| 2005/0171148 A1 | 8/2005 | Mjalli et al. |
| 2005/0182045 A1 | 8/2005 | Nagase et al. |
| 2005/0187418 A1 | 8/2005 | Small et al. |
| 2005/0197340 A1 | 9/2005 | Arora et al. |
| 2005/0214310 A1 | 9/2005 | Toki et al. |
| 2005/0215579 A1 | 9/2005 | Simon et al. |
| 2005/0239809 A1 | 10/2005 | Watts et al. |
| 2005/0250770 A1 | 11/2005 | Ono et al. |
| 2005/0256066 A1 | 11/2005 | Abel et al. |
| 2005/0261317 A1 | 11/2005 | Sadhu et al. |
| 2005/0272751 A1 | 12/2005 | McKerracher et al. |
| 2005/0282814 A1 | 12/2005 | Wrasidlo et al. |
| 2006/0019967 A1 | 1/2006 | Wu et al. |
| 2006/0019988 A1 | 1/2006 | McDonald et al. |
| 2006/0069034 A1 | 3/2006 | Burli et al. |
| 2006/0079538 A1 | 4/2006 | Hallahan et al. |
| 2006/0106038 A1 | 5/2006 | Bouscary et al. |
| 2006/0116326 A1 | 6/2006 | Burli et al. |
| 2006/0135790 A1 | 6/2006 | Hyett et al. |
| 2006/0156485 A1 | 7/2006 | Lim |
| 2006/0183783 A1 | 8/2006 | Polisetti et al. |
| 2006/0199776 A1 | 9/2006 | Blagg et al. |
| 2006/0205694 A1 | 9/2006 | Alonso et al. |
| 2006/0235031 A1 | 10/2006 | Arnold et al. |
| 2006/0276470 A1 | 12/2006 | Jackson et al. |
| 2006/0287295 A1 | 12/2006 | Barlaam et al. |
| 2006/0293274 A1 | 12/2006 | Wu |
| 2007/0015773 A1 | 1/2007 | Bergeron et al. |
| 2007/0017915 A1 | 1/2007 | Weder et al. |
| 2007/0027193 A1 | 2/2007 | Leban et al. |
| 2007/0032640 A1 | 2/2007 | Varghese et al. |
| 2007/0054915 A1 | 3/2007 | Arora et al. |
| 2007/0072897 A1 | 3/2007 | Mahaney et al. |
| 2007/0099871 A1 | 5/2007 | Davis et al. |
| 2007/0142405 A1 | 6/2007 | Dong et al. |
| 2007/0179122 A1 | 8/2007 | Urmann et al. |
| 2007/0179151 A1 | 8/2007 | Chen et al. |
| 2007/0224672 A1 | 9/2007 | Leban et al. |
| 2007/0249598 A1 | 10/2007 | Wang et al. |
| 2007/0254318 A1 | 11/2007 | Sebti et al. |
| 2007/0270452 A1 | 11/2007 | Blagg et al. |
| 2008/0032960 A1 | 2/2008 | Knight et al. |
| 2008/0058521 A1 | 3/2008 | Krishnan et al. |
| 2008/0070935 A1 | 3/2008 | Huang et al. |
| 2008/0119454 A1 | 5/2008 | Polisetti et al. |
| 2008/0119455 A1 | 5/2008 | Polisetti et al. |
| 2008/0119461 A1 | 5/2008 | Sin et al. |
| 2008/0125432 A1 | 5/2008 | Blom et al. |
| 2008/0200461 A1 | 8/2008 | Anderson et al. |
| 2008/0200465 A1 | 8/2008 | Burli et al. |
| 2008/0249090 A1 | 10/2008 | Hu et al. |
| 2008/0261956 A1 | 10/2008 | Choi et al. |
| 2008/0287469 A1 | 11/2008 | Diacovo et al. |
| 2008/0292626 A1 | 11/2008 | Wang et al. |
| 2008/0293674 A1 | 11/2008 | Schwarz et al. |
| 2008/0306053 A1 | 12/2008 | Tachdjian et al. |
| 2008/0306093 A1 | 12/2008 | Servant et al. |
| 2008/0312180 A1 | 12/2008 | Liang et al. |
| 2008/0318942 A1 | 12/2008 | Simon et al. |
| 2009/0023729 A1 | 1/2009 | Nakamura et al. |
| 2009/0030023 A1 | 1/2009 | Harada et al. |
| 2009/0053192 A1 | 2/2009 | Millan et al. |
| 2009/0088452 A1 | 4/2009 | Coleman et al. |
| 2009/0099214 A1 | 4/2009 | Fairhurst et al. |
| 2009/0105233 A1 | 4/2009 | Chua et al. |
| 2009/0118283 A1 | 5/2009 | Defert et al. |
| 2009/0124638 A1 | 5/2009 | Shokat et al. |
| 2009/0124654 A1 | 5/2009 | Mjalli et al. |
| 2009/0137581 A1 | 5/2009 | Chen et al. |
| 2009/0163481 A1 | 6/2009 | Murphy et al. |
| 2009/0163709 A1 | 6/2009 | Blagg |
| 2009/0170879 A1 | 7/2009 | Szucova et al. |
| 2009/0181920 A1 | 7/2009 | Watkins et al. |
| 2009/0181988 A1 | 7/2009 | Tanaka et al. |
| 2009/0187014 A1 | 7/2009 | Blagg |
| 2009/0203689 A1 | 8/2009 | Dhalla et al. |

(56) References Cited

U.S. PATENT DOCUMENTS

| | | |
|---|---|---|
| 2009/0232768 A1 | 9/2009 | Birkus et al. |
| 2009/0247513 A1 | 10/2009 | Burli et al. |
| 2009/0253694 A1 | 10/2009 | Ono et al. |
| 2009/0264409 A1 | 10/2009 | Dong et al. |
| 2009/0264423 A2 | 10/2009 | Chua et al. |
| 2009/0270426 A1 | 10/2009 | Knight et al. |
| 2009/0270567 A1 | 10/2009 | Small et al. |
| 2009/0312319 A1 | 12/2009 | Ren et al. |
| 2009/0312406 A1 | 12/2009 | Hsieh et al. |
| 2009/0318411 A1 | 12/2009 | Castanedo et al. |
| 2009/0318503 A1 | 12/2009 | Crooks et al. |
| 2009/0325967 A1 | 12/2009 | Fairhurst et al. |
| 2010/0009963 A1 | 1/2010 | Knight et al. |
| 2010/0022531 A1 | 1/2010 | Kincaid et al. |
| 2010/0022585 A1 | 1/2010 | deLong et al. |
| 2010/0029658 A1 | 2/2010 | Gavish et al. |
| 2010/0029693 A1 | 2/2010 | Douangpanya et al. |
| 2010/0048540 A1 | 2/2010 | Boyle et al. |
| 2010/0048882 A1 | 2/2010 | Blagg et al. |
| 2010/0056494 A1 | 3/2010 | Winzeler et al. |
| 2010/0063047 A1 | 3/2010 | Borchardt et al. |
| 2010/0105630 A1 | 4/2010 | Blagg |
| 2010/0168153 A1 | 7/2010 | Stowasser et al. |
| 2010/0179167 A1 | 7/2010 | Xu et al. |
| 2010/0190749 A1 | 7/2010 | Ren et al. |
| 2010/0202963 A1 | 8/2010 | Gallatin et al. |
| 2010/0216791 A1 | 8/2010 | Aquila et al. |
| 2010/0278811 A1 | 11/2010 | Wrasidlo et al. |
| 2010/0280067 A1 | 11/2010 | Sarma et al. |
| 2010/0280255 A1 | 11/2010 | Moniz et al. |
| 2010/0298290 A1 | 11/2010 | Anand et al. |
| 2011/0009378 A1 | 1/2011 | Lange et al. |
| 2011/0046165 A1 | 2/2011 | Ren et al. |
| 2011/0112137 A1 | 5/2011 | Eissenstat et al. |
| 2011/0124641 A1 | 5/2011 | Ren et al. |
| 2011/0135655 A1 | 6/2011 | Katsikis et al. |
| 2011/0144134 A1 | 6/2011 | Shokat et al. |
| 2011/0160463 A1 | 6/2011 | Moniz et al. |
| 2011/0172228 A1 | 7/2011 | Ren et al. |
| 2011/0172335 A1 | 7/2011 | Deshpande |
| 2011/0190157 A1 | 8/2011 | Kipps et al. |
| 2011/0212975 A1 | 9/2011 | Kao et al. |
| 2011/0224223 A1 | 9/2011 | Shokat et al. |
| 2011/0251182 A1 | 10/2011 | Sun et al. |
| 2011/0269779 A1 | 11/2011 | Wilson et al. |
| 2011/0275803 A1 | 11/2011 | Remenar et al. |
| 2011/0281866 A1 | 11/2011 | Ren et al. |
| 2011/0301144 A1 | 12/2011 | Knight et al. |
| 2011/0306622 A1 | 12/2011 | Lannutti et al. |
| 2012/0004198 A1 | 1/2012 | Liao et al. |
| 2012/0046307 A1 | 2/2012 | Engel et al. |
| 2012/0059000 A1 | 3/2012 | Ren et al. |
| 2012/0065154 A1 | 3/2012 | Tanaka et al. |
| 2012/0094997 A1 | 4/2012 | England et al. |
| 2012/0122838 A1 | 5/2012 | Ren et al. |
| 2012/0149701 A1 | 6/2012 | Ren et al. |
| 2012/0149715 A1 | 6/2012 | Kao et al. |
| 2012/0157696 A1 | 6/2012 | Chopra et al. |
| 2012/0177749 A1 | 7/2012 | Tapolsky et al. |
| 2012/0183535 A1 | 7/2012 | Buggy et al. |
| 2012/0184568 A1 | 7/2012 | Ren et al. |
| 2012/0196905 A1 | 8/2012 | Cashman |
| 2012/0202784 A1 | 8/2012 | Aronov et al. |
| 2012/0220575 A1 | 8/2012 | Chang et al. |
| 2012/0225851 A1 | 9/2012 | Cardone et al. |
| 2012/0238549 A1 | 9/2012 | Cusack et al. |
| 2012/0238559 A1 | 9/2012 | Baldwin et al. |
| 2012/0245169 A1 | 9/2012 | Ren et al. |
| 2012/0258953 A1 | 10/2012 | Aay et al. |
| 2012/0293063 A1 | 11/2012 | Kang et al. |
| 2012/0322769 A1 | 12/2012 | Yang et al. |
| 2012/0329776 A1 | 12/2012 | Ren et al. |
| 2013/0029982 A1 | 1/2013 | Castro et al. |
| 2013/0029984 A1 | 1/2013 | Castro et al. |
| 2013/0039945 A1 | 2/2013 | Iadonato et al. |
| 2013/0045229 A1 | 2/2013 | Iadonato et al. |
| 2013/0053362 A1 | 2/2013 | Castro et al. |
| 2013/0064812 A1 | 3/2013 | Gallatin et al. |
| 2013/0102608 A1 | 4/2013 | Hoelzemann et al. |
| 2013/0109713 A1 | 5/2013 | Lavoie et al. |
| 2013/0158003 A1 | 6/2013 | Campbell et al. |
| 2013/0172388 A1 | 7/2013 | Xie et al. |
| 2013/0344061 A1 | 12/2013 | Palombella et al. |
| 2014/0024637 A1 | 1/2014 | Rice |
| 2014/0031547 A1 | 1/2014 | Sheridan et al. |
| 2014/0037622 A1 | 2/2014 | Boshoff et al. |
| 2014/0120060 A1 | 5/2014 | Palombella et al. |
| 2014/0120083 A1 | 5/2014 | Stern et al. |
| 2014/0371246 A1 | 12/2014 | Evarts et al. |
| 2014/0377258 A1 | 12/2014 | Stern et al. |
| 2015/0065431 A1 | 3/2015 | Xu et al. |
| 2015/0118222 A1* | 4/2015 | Levy ..................... A61P 43/00 424/130.1 |
| 2015/0184249 A1 | 7/2015 | Chang et al. |
| 2016/0113932 A1 | 4/2016 | Stern et al. |

FOREIGN PATENT DOCUMENTS

| | | |
|---|---|---|
| CN | 102206172 | 10/2011 |
| CN | 102731492 | 10/2012 |
| DE | 2139107 A1 | 2/1973 |
| EP | 773023 A1 | 5/1997 |
| EP | 1 262 176 A1 | 4/2002 |
| EP | 1020445 B1 | 8/2008 |
| GB | 812366 A | 4/1959 |
| GB | 937725 A | 9/1963 |
| JP | 61-109797 A | 5/1986 |
| JP | H04211063 | 8/1992 |
| JP | 05-256693 A | 10/1993 |
| JP | 08295667 A | 11/1996 |
| JP | 09143163 A | 6/1997 |
| JP | 10206995 A | 8/1998 |
| JP | 2000072773 A | 3/2000 |
| JP | 2002131859 A | 5/2002 |
| JP | 2003073357 A | 3/2003 |
| JP | 2004161716 A | 6/2004 |
| JP | 4834699 | 12/2011 |
| JP | 4846769 | 12/2011 |
| WO | WO 1983/001446 A1 | 4/1983 |
| WO | WO 1991/017161 A1 | 11/1991 |
| WO | WO 1992/014733 A1 | 9/1992 |
| WO | WO 1993/016091 A1 | 8/1993 |
| WO | WO 1993/016092 A1 | 8/1993 |
| WO | WO 1993/018035 A1 | 9/1993 |
| WO | WO 1993/019767 A1 | 10/1993 |
| WO | WO 1993/022443 A1 | 11/1993 |
| WO | WO 1994/013677 A1 | 6/1994 |
| WO | WO 1994/017803 A1 | 8/1994 |
| WO | WO 1994/029436 A1 | 12/1994 |
| WO | WO 1995/010628 A2 | 4/1995 |
| WO | WO 1995/012588 A1 | 5/1995 |
| WO | WO 1995/019774 | 7/1995 |
| WO | WO 1995/029673 A1 | 11/1995 |
| WO | WO 1995/032984 A1 | 12/1995 |
| WO | WO 1995/010628 A3 | 9/1996 |
| WO | WO 1996/040706 A1 | 12/1996 |
| WO | WO 1997/028133 A1 | 8/1997 |
| WO | WO 1997/028161 A1 | 8/1997 |
| WO | WO 1998/041525 A1 | 9/1998 |
| WO | WO 1998/052611 A1 | 11/1998 |
| WO | WO 1998/057952 A1 | 12/1998 |
| WO | WO 2000/017202 A1 | 3/2000 |
| WO | WO 2001/002369 A2 | 1/2001 |
| WO | WO 2001/016114 A2 | 3/2001 |
| WO | WO 2001/019829 A2 | 3/2001 |
| WO | WO 2001/021160 | 3/2001 |
| WO | WO 2001/025238 A2 | 4/2001 |
| WO | WO 2001/031063 A1 | 5/2001 |
| WO | WO 2001/038584 A2 | 5/2001 |
| WO | WO 2001/016114 A3 | 8/2001 |
| WO | WO 2001/055140 A1 | 8/2001 |
| WO | WO 2001/056988 A1 | 8/2001 |
| WO | WO 2001/060824 | 8/2001 |
| WO | WO 2001/019829 A3 | 9/2001 |

(56) References Cited

FOREIGN PATENT DOCUMENTS

| | | |
|---|---|---|
| WO | WO 2001/025238 A3 | 10/2001 |
| WO | WO 2001/038584 A3 | 10/2001 |
| WO | WO 2001/081346 A2 | 11/2001 |
| WO | WO 2002/006192 A1 | 1/2002 |
| WO | WO 2001/081346 A3 | 3/2002 |
| WO | WO 2001/002369 A3 | 4/2002 |
| WO | WO 2002/030944 A2 | 4/2002 |
| WO | WO 2002/057425 A2 | 7/2002 |
| WO | WO 2002/076986 A1 | 10/2002 |
| WO | WO 2002/080926 A1 | 10/2002 |
| WO | WO 2002/083143 A1 | 10/2002 |
| WO | WO 2002/028853 A1 | 11/2002 |
| WO | WO 2002/088025 A1 | 11/2002 |
| WO | WO 2002/090334 A1 | 11/2002 |
| WO | WO 2002/030944 A3 | 1/2003 |
| WO | WO 2003/000187 A2 | 1/2003 |
| WO | WO 2003/016275 A1 | 2/2003 |
| WO | WO 2003/020880 A2 | 3/2003 |
| WO | WO 2003/024969 A1 | 3/2003 |
| WO | WO 2003/028341 A2 | 4/2003 |
| WO | WO 2003/035075 A1 | 5/2003 |
| WO | WO 2003/059884 A1 | 7/2003 |
| WO | WO 2003/020880 A3 | 10/2003 |
| WO | WO 2003/082341 A1 | 10/2003 |
| WO | WO 2003/106426 A1 | 12/2003 |
| WO | WO 2004/006906 A2 | 1/2004 |
| WO | WO 2004/006906 A3 | 3/2004 |
| WO | WO 2004/018058 A2 | 3/2004 |
| WO | WO 2004/031177 A1 | 4/2004 |
| WO | WO 2004/039774 A2 | 5/2004 |
| WO | WO 2004/046128 | 6/2004 |
| WO | WO 2004/018058 A3 | 7/2004 |
| WO | WO 2004/039774 A3 | 7/2004 |
| WO | WO 2004/058717 A1 | 7/2004 |
| WO | WO 2003/000187 A3 | 8/2004 |
| WO | WO 2004/075917 A1 | 9/2004 |
| WO | WO 2004/087053 A2 | 10/2004 |
| WO | WO 2004/087679 | 10/2004 |
| WO | WO 2004/089877 | 10/2004 |
| WO | WO 2004/111014 A1 | 12/2004 |
| WO | WO 2005/002585 A1 | 1/2005 |
| WO | WO 2005/007085 A2 | 1/2005 |
| WO | WO 2005/012323 A2 | 2/2005 |
| WO | WO 2005/016348 A1 | 2/2005 |
| WO | WO 2005/016349 A1 | 2/2005 |
| WO | WO 2005/016528 A2 | 2/2005 |
| WO | WO 2005/021533 A1 | 3/2005 |
| WO | WO 2002/057425 A3 | 4/2005 |
| WO | WO 2005/012323 A3 | 5/2005 |
| WO | WO 2005/016528 A3 | 5/2005 |
| WO | WO 2005/044181 A2 | 5/2005 |
| WO | WO 2005/047289 A1 | 5/2005 |
| WO | WO 2005/061460 A1 | 7/2005 |
| WO | WO 2005/063258 A1 | 7/2005 |
| WO | WO 2005/067901 A2 | 7/2005 |
| WO | WO 2005/074603 A2 | 8/2005 |
| WO | WO 2005/007085 A3 | 9/2005 |
| WO | WO 2005/097800 A1 | 10/2005 |
| WO | WO 2005/105760 A1 | 11/2005 |
| WO | WO 2005/067901 A3 | 12/2005 |
| WO | WO 2005/112935 A1 | 12/2005 |
| WO | WO 2005/113556 A1 | 12/2005 |
| WO | WO 2005/117889 A1 | 12/2005 |
| WO | WO 2005/120511 A1 | 12/2005 |
| WO | WO 2006/015279 | 2/2006 |
| WO | WO 2005/044181 A3 | 3/2006 |
| WO | WO 2006/030032 A1 | 3/2006 |
| WO | WO 2006/038865 A1 | 4/2006 |
| WO | WO 2006/050501 A2 | 5/2006 |
| WO | WO 2006/050946 A1 | 5/2006 |
| WO | WO 2006/068760 A2 | 6/2006 |
| WO | WO 2004/087053 A3 | 8/2006 |
| WO | WO 2006/089106 A2 | 8/2006 |
| WO | WO 2006/108107 A1 | 10/2006 |
| WO | WO 2006/112666 A1 | 10/2006 |
| WO | WO 2005/074603 A3 | 11/2006 |
| WO | WO 2006/114064 A2 | 11/2006 |
| WO | WO 2006/114065 A2 | 11/2006 |
| WO | WO 2006/068760 A3 | 12/2006 |
| WO | WO 2006/089106 A3 | 12/2006 |
| WO | WO 2007/002293 A2 | 1/2007 |
| WO | WO 2007/006547 A1 | 1/2007 |
| WO | WO 2007/020046 A1 | 2/2007 |
| WO | WO 2007/002293 A3 | 3/2007 |
| WO | WO 2007/025090 A2 | 3/2007 |
| WO | WO 2007/029121 | 3/2007 |
| WO | WO 2006/050501 A3 | 5/2007 |
| WO | WO 2007/061737 A2 | 5/2007 |
| WO | WO 2006/114064 A3 | 6/2007 |
| WO | WO 2006/114065 A3 | 6/2007 |
| WO | WO 2007/025090 A3 | 6/2007 |
| WO | WO 2007/075554 A2 | 7/2007 |
| WO | WO 2007/079164 A2 | 7/2007 |
| WO | WO 2007/079164 A3 | 9/2007 |
| WO | WO 2007/103308 A2 | 9/2007 |
| WO | WO 2007/112005 A2 | 10/2007 |
| WO | WO 2007/114926 A2 | 10/2007 |
| WO | WO 2007/121453 A2 | 10/2007 |
| WO | WO 2007/121920 A2 | 11/2007 |
| WO | WO 2007/121924 A2 | 11/2007 |
| WO | WO 2007/124854 A1 | 11/2007 |
| WO | WO 2007/125310 A2 | 11/2007 |
| WO | WO 2007/125315 A2 | 11/2007 |
| WO | WO 2007/126841 A2 | 11/2007 |
| WO | WO 2007/134828 A1 | 11/2007 |
| WO | WO 2007/135380 A2 | 11/2007 |
| WO | WO 2007/135398 A1 | 11/2007 |
| WO | WO 2007/061737 A3 | 12/2007 |
| WO | WO 2007/125315 A3 | 12/2007 |
| WO | WO 2007/121920 A3 | 1/2008 |
| WO | WO 2008/001236 A2 | 1/2008 |
| WO | WO 2008/012326 A1 | 1/2008 |
| WO | WO 2007/103308 A3 | 2/2008 |
| WO | WO 2007/112005 A3 | 2/2008 |
| WO | WO 2007/125310 A3 | 3/2008 |
| WO | WO 2008/025755 A1 | 3/2008 |
| WO | WO 2008/047821 A1 | 4/2008 |
| WO | WO 2008/063625 A2 | 5/2008 |
| WO | WO 2008/064018 A1 | 5/2008 |
| WO | WO 2008/070507 A2 | 6/2008 |
| WO | WO 2007/121453 A3 | 7/2008 |
| WO | WO 2008/079028 A1 | 7/2008 |
| WO | WO 2008/082487 A2 | 7/2008 |
| WO | WO 2008/094737 A2 | 8/2008 |
| WO | WO 2007/121924 A3 | 9/2008 |
| WO | WO 2008/112715 A2 | 9/2008 |
| WO | WO 2007/114926 A3 | 10/2008 |
| WO | WO 2008/117050 | 10/2008 |
| WO | WO 2008/118454 A2 | 10/2008 |
| WO | WO 2008/118455 A1 | 10/2008 |
| WO | WO 2008/118468 A1 | 10/2008 |
| WO | WO 2008/125014 A1 | 10/2008 |
| WO | WO 2008/125207 A1 | 10/2008 |
| WO | WO 2008/127226 A2 | 10/2008 |
| WO | WO 2007/126841 A3 | 11/2008 |
| WO | WO 2008/112715 A3 | 11/2008 |
| WO | WO 2008/118454 A3 | 11/2008 |
| WO | WO 2008/136457 A1 | 11/2008 |
| WO | WO 2008/082487 A3 | 12/2008 |
| WO | WO 2008/127226 A3 | 12/2008 |
| WO | WO 2009/000412 A1 | 12/2008 |
| WO | WO 2009/004621 A1 | 1/2009 |
| WO | WO 2009/010925 A2 | 1/2009 |
| WO | WO 2009/019531 A2 | 2/2009 |
| WO | WO 2009/023718 A2 | 2/2009 |
| WO | WO 2008/094737 A3 | 3/2009 |
| WO | WO 2009/029617 A1 | 3/2009 |
| WO | WO 2009/023718 A3 | 4/2009 |
| WO | WO 2009/044707 A1 | 4/2009 |
| WO | WO 2009/050506 A2 | 4/2009 |
| WO | WO 2009/064802 A2 | 5/2009 |
| WO | WO 2009/010925 A3 | 7/2009 |
| WO | WO 2009/064802 A3 | 7/2009 |
| WO | WO 2009/088986 A1 | 7/2009 |

(56) References Cited

FOREIGN PATENT DOCUMENTS

| | | |
|---|---|---|
| WO | WO 2009/088990 A1 | 7/2009 |
| WO | WO 2009/100406 A2 | 8/2009 |
| WO | WO 2009/103022 | 8/2009 |
| WO | WO 2009/117157 A1 | 9/2009 |
| WO | WO 2009/118765 | 10/2009 |
| WO | WO 2009/050506 A3 | 11/2009 |
| WO | WO 2009/100406 A3 | 11/2009 |
| WO | WO 2010/006086 A2 | 1/2010 |
| WO | WO 2010/009207 A1 | 1/2010 |
| WO | WO 2010/019210 A2 | 2/2010 |
| WO | WO 2010/036380 A1 | 4/2010 |
| WO | WO 2010/039534 A2 | 4/2010 |
| WO | WO 2010/019210 A3 | 5/2010 |
| WO | WO 2010/053998 | 5/2010 |
| WO | WO 2010/057048 A1 | 5/2010 |
| WO | WO 2010/065923 A2 | 6/2010 |
| WO | WO 2010/070032 A1 | 6/2010 |
| WO | WO 2010/039534 A3 | 8/2010 |
| WO | WO 2010/092340 A1 | 8/2010 |
| WO | WO 2010/133836 A1 | 11/2010 |
| WO | WO 2011/008302 A1 | 1/2011 |
| WO | WO 2011/058108 A1 | 5/2011 |
| WO | WO 2011/058109 A1 | 5/2011 |
| WO | WO 2011/058110 A1 | 5/2011 |
| WO | WO 2011/075628 A1 | 6/2011 |
| WO | WO 2011/094890 | 8/2011 |
| WO | WO 2011/111880 | 9/2011 |
| WO | WO 2011/146882 A1 | 11/2011 |
| WO | WO 2012/009452 | 1/2012 |
| WO | WO 2012/032334 A1 | 3/2012 |
| WO | WO 2012/037204 | 3/2012 |
| WO | WO 2012/052540 | 4/2012 |
| WO | WO 2012/061696 A1 | 5/2012 |
| WO | WO 2012/064973 A2 | 5/2012 |
| WO | WO 2012/068096 | 5/2012 |
| WO | WO 2012/068106 | 5/2012 |
| WO | WO 2012/071519 | 5/2012 |
| WO | WO 2012/097000 A1 | 7/2012 |
| WO | WO 2012/121953 A1 | 9/2012 |
| WO | WO 2012/129562 | 9/2012 |
| WO | WO 2012/135750 | 10/2012 |
| WO | WO 2012/136549 | 10/2012 |
| WO | WO 2013/006532 | 1/2013 |
| WO | WO 2013/012915 A1 | 1/2013 |
| WO | WO 2013/013504 | 1/2013 |
| WO | WO 2013/013505 | 1/2013 |
| WO | WO 2013/025498 | 2/2013 |
| WO | WO 2013/044169 | 3/2013 |
| WO | WO 2013/059738 A2 | 4/2013 |
| WO | WO 2013/066483 | 5/2013 |
| WO | WO 2013/074583 | 5/2013 |
| WO | WO 2013/086131 | 6/2013 |
| WO | WO 2013/090725 | 6/2013 |
| WO | WO 2013/113838 | 8/2013 |
| WO | WO 2013/113841 | 8/2013 |
| WO | WO 2013/188763 | 12/2013 |
| WO | WO 2014/004470 | 1/2014 |
| WO | WO 2014/018567 A1 | 1/2014 |
| WO | WO 2014/046617 | 3/2014 |
| WO | WO 2014/071105 | 5/2014 |
| WO | WO 2014/071109 A1 | 5/2014 |
| WO | WO 2014/071125 A1 | 5/2014 |
| WO | WO 2014/072937 A1 | 5/2014 |
| WO | WO 2014/075393 | 5/2014 |
| WO | WO 2014/124458 | 8/2014 |
| WO | WO 2014/141165 | 9/2014 |
| WO | WO 2014/168975 | 10/2014 |
| WO | WO 2014/175267 | 10/2014 |
| WO | WO 2014/194254 A1 | 12/2014 |
| WO | WO 2014/203959 | 12/2014 |
| WO | WO 2015/002729 | 1/2015 |
| WO | WO 2015/010641 A1 | 1/2015 |
| WO | WO 2015/037005 | 3/2015 |
| WO | WO 2015/051252 | 4/2015 |
| WO | WO 2015/054099 | 4/2015 |
| WO | WO 2015/054355 | 4/2015 |
| WO | WO 2015/081127 | 6/2015 |
| WO | WO 2015/083008 | 6/2015 |
| WO | WO 2015/095807 | 6/2015 |
| WO | WO 2015/095819 | 6/2015 |
| WO | WO 2015/095825 | 6/2015 |
| WO | WO 2015/095829 | 6/2015 |
| WO | WO 2015/095831 | 6/2015 |
| WO | WO 2015/095834 | 6/2015 |
| WO | WO 2015/095838 | 6/2015 |
| WO | WO 2015/095840 | 6/2015 |
| WO | WO 2015/095842 | 6/2015 |
| WO | WO 2015/109286 | 7/2015 |
| WO | WO 2015/143382 | 9/2015 |
| WO | WO 2015/160975 | 10/2015 |
| WO | WO 2015/160986 | 10/2015 |
| WO | WO 2015/175966 | 11/2015 |
| WO | WO 2015/179772 | 11/2015 |
| WO | WO 2015/181053 | 12/2015 |
| WO | WO 2015/181055 | 12/2015 |
| WO | WO 2015/188119 | 12/2015 |
| WO | WO 2016024228 * | 2/2016 |
| WO | WO-2016054555 A2 * | 4/2016 ......... C07K 16/3069 |

OTHER PUBLICATIONS

Abdel-Mohsen, "Synthesis, Reactions and Antimicrobial Activity of 2-Amino-4-(8-quinolinol-5-yl)-1-(p-tolyl)-pyrrole-3-carbonitrile," *Bull. Korean Chem. Soc.* 26(5):719-728 (2005).

Abe et al., "T cell receptor-mediated recognition of self-ligand induces signaling in immature thymocytes before negative selection," *J. Exp. Med.* 176(2):459-468 (1992).

Abrahamian et al., "Immunological and Clinical Profile of Adult Patients with Selective Immunoglobulin Subclass deficiency: response to intravenous immunoglobulin therapy," *Clin. Exp. Immunol.* 159(3):344-350 (2010).

Abraham, T., "Thermally induced intramolecular cycloaddition reaction of N-phenyl-2-phenylethynlbenzamide potential cure reaction for thermosetting polymers," *J. Polym. Sci. Polym. Chem. Ed.* 20(7):1953-1957 (1982).

Ames et al., "Heterocyclic Syntheses from o-Halogeno-acids. Part II. Thienopyridinones and Thienopyranones from 3-Bromothiophen-2- and 4-Bromothiophen-3-carboxylic Acids," *J.C.S. Perkin I* 1390-1395 (1975).

Anderson et al., "Paradoxical inhibition of T-cell function in response to CTLA-4 blockade; heterogeneity within the human T-cell population," *Nat. Med.* 6(2):211-214 (2000).

Andrews et al., "Effects of the 11β-hydroxysteroid dehydrogenase inhibitor carbenoxolone on insulin sensitive in men with type 2 diabetes," *J. Clin. Endocrinol. Metab.* 88(1):285-291 (2003).

Arcaro et al., "Wortmannin is a potent phosphatidylinositol 3-kinase inhibitor: the role of phosphatidylinositol 3,4,5-triphosphate in neutrophil responses," *Biochem. J.*, 296(Pt 2):297-301 (1993).

Arnold et al., "Pyrrolo[2,3-d]pyrimidines containing an extended 5-substituent as potent and selective inhibitors of Ick I," *Bioorg. Med. Chem. Lett.* 10(19):2167-2170 (2000).

Augustine et al., "Interleukin 2- and polyomavirus middle T antigen-induced modification of phosphatidylinositol 3-kinase activity in activated T lymphocytes," *Mol. Cell. Biol.* 11(9):4431-4440 (1991).

Baggiolini et al., "Inhibition of the phagocytosis-induced respiratory burst by the fungal metabolite wortmannin and some analogues," *Exp. Cell. Res.* 169(2): 408-418 (1987).

Ballell et al. "New Thiopyrazolo[3,4-d] pyrimidine derivatives as anti-mycobacterial agents," *Bioorg. Med. Chem. Lett.* 17(6):1736-1740 (2007).

Banker et al., Modern Pharmaceutics, pp. 451, 596, 3$^{rd}$ ed, Marcel Dekker, New York (1996).

Bansal et al., "The Molecular Biology of Endometrial Cancers and the Implications for Pathogenesis, Classification, and Targeted Therapies," *Cancer Control* 16(1):8-13 (2009).

Barber et al., "PI3Kgamma inhibition blocks glomerulonephritis and extends lifespan in a mouse model of systemic lupus," *Nat. Med.* 11(9):933-935 (2005). (Epub Aug. 28, 2005).

(56) References Cited

OTHER PUBLICATIONS

Barf et al., "Arylsulfonamidothiazoles as a new class of potential antidiabetic drugs. Discovery of potent and selective inhibitors of the 11β-hydroxysteroid dehydrogenase Type 1," *J. Med. Chem.* 45(18):3813-3815 (2002).
Barnes et al., "Efficacy and Safety of Inhaled Corticosteroids in Asthma—Report of a Workshop Held in Eze, France Oct. 1992," *Am. Rev. Respir. Dis.* 148:S1-S26 (1993).
Bartholomeusz et al., "Targeting the PI3K Signaling Pathway in Cancer Therapy," *Expert Opin. Ther. Targets* 16(1):121-130 (2012).
Basotest®, Test Kit for the Quantitative Determination of the Degranulation of Basophilic Granulocytes in Heparinized Human Whole Blood, version Apr. 2002, pp. 1-10, [www.biocarta.com/TDS/10-0500.pdf], Retreived from the Internet Nov. 29, 2011.
Beeram et al., "Akt-induced endocrine therapy resistance is reversed by inhibition of mTOR signaling," *Ann Oncol.* 18(8):1323-1328 (2007).
Bell et al., "Glucokinase mutations insulin secretion, and diabetes mellitus", *Annu. Rev. Physiol.* 58:171-186 (1996).
Berndt et al., "The p110δ crystal structure uncovers mechanisms for selectivity and potency of novel PI3K inhibitors," *Nat. Chem. Biol.* 6(2):117-124 (2010).
Bhat et al., "Pyrazolopyrimidine nucleosides. 12. Synthesis and biological activity of certain pyrazolo[3,4-d]pyrimidine nucleosides related to adenosine," *J. Med. Chem.* 24(10):1165-1172 (1981).
Bhatt et al., "Dual inhibition of PI3K and mTOR inhibits autocrine and paracrine proliferative loops in PI3K/Akt/mTOR-addicted lymphomas," *Blood* 115(22):4455-4463 (2010).
Bi et al., "Proliferative defect and embryonic lethality in mice homozygous for a deletion in the p110α subunit of phosphoinositide 3-kinase," *J. Biol. Chem.* 274:10963-10968 (1999).
Billottet et al., "A selective inhibitor of the p110δ isoform of PI 3-kinase inhibits AML cell proliferation and survival and increases the cytotoxic effects of VP16," *Oncogene* 25:6648-6659 (2006).
Billottet et al., "Inhibition of Class 1 Phosphoinositide 3-Kinase Activity Impairs Proliferation and Triggers Apoptosis in Acute Promyelocytic Leukemia without Affecting Atra-Induced Differentiation," *Cancer Res.* 69(3):1027-1036 (2009).
Bishop et al., "Generation of monospecific nanomolar tyrosine kinase inhibitors via a chemical genetic approach," *J. Am. Chem. Soc.* 121(4):627-631 (1999).
Blunden et al., "Mycotoxins in food," *Med. Lab. Sci.* 48(4):271-282 (1991).
Bochner et al., "Immunological aspects of allergic asthma," *Annu. Rev. Immunol.* 12:295-335 (1994).
Bohren et al., "Expression, crystallization and preliminary crystallographic analysis of human carbonyl reductase," *J. Mol. Biol.* 224:659-664 (1994).
Bone et al., "Phosphoinositide 3-kinase signalling regulates early development and developmental haemopoiesis," *J. Cell. Sci.* 120(Pt 10):1752-1762 (2007).
Bowers et al., "A platelet biomarker for assessing phosphoinositide 3-kinase inhibition during cancer chemotherapy," *Mol. Cancer Ther.* 6(9):2600-2607 (2007).
Brzezianska et al., "A Minireview: The Role of MAPK/ERK and PI3K/Akt Pathways in Thyroid Follicular Cell-Derived Neoplasm," *Front. Biosci.* 16:422-439 (2011).
Buitenhuis et al., "The role of the PI3k-PKB signaling module in regulation of hematopoiesis," *Cell Cycle* 8(4):560-566 (2009).
Burger et al., "High-level expression of the T-cell chemokines CCL3 and CCL4 by chronic lymphocytic leukemia B cells in nurselike cell cocultures and after BCR stimulation," *Blood* 113(13):3050-3058 (2009).
Burger et al., "Phosphoinositide 3'-kinase delta: turning off BCR signaling in Chronic Lymphocytic Leukemia," *Oncotarget* 2(10):737-738 (2011).
Burger, "Inhibiting B-Cell Receptor Signaling Pathways in Chronic Lymphocytic Leukemia," *Curr. Mematol. Malig. Rep.* 7:26-33 (2012).

Byrd et al., "Translating PI3K-Delta Inhibitors to the Clinic in Chronic Lymphocytic Leukemia: The Story of CAL-101 (GS1101)," *ASCO Program Proceedings*, pp. 691-694 (2012).
Campora et al., "Binuclear complexes of nickel bridged by hydrocarbon ligands. Isocyanide insertion chemistry and amide formation by intramolecular coupling of acyl and imidoyl functionalities," *Organometallics* 11(1):11-13 (1992).
Campora et al., "Isocyanide insertion chemistry. Synthesis and structural characterization of bridging imidoyl complexes of nickel and amide formation by intramolecular coupling of acyl and imidoyl functionalities," *Organometallics* 12(10):4025-4031 (1993).
Camps et al., "Blockade of PI3Kγ suppresses joint inflammation and damage in mouse models of rheumatoid arthritis," *Nat. Med.* 11(9):936-943 (2005).
Chaisuparat et al., "Dual inhibition of PI3Kα and mTOR as an alternative treatment for Kaposi's Sarcoma," *Cancer Res.* 68:8361-8368 (2008).
Chang et al., "The Bruton tyrosine kinase inhibitor PCI-32765 ameliorates autoimmune arthritis by inhibition of multiple effector cells," *Arthritis Research & Therapy* 13:R115 (2011).
Chappelow et al., "Neovascular age-related macular degeneration: potential therapies," *Drugs* 68(8):1029-1036 (2008).
Chapuis et al., "Dual Inhibition of PI3K and mTORC1/2 Signaling by NVP-BEZ235 as a New Therapeutic Strategy for Acute Myeloid Leukemia," *Clin. Cancer Res.* 16(22):5424-5435 (2010).
Chawla et. al., "Challenges in Polymorphism of Pharmaceuticals," *Current Research & Information on Pharmaceutical Science* 5(1):9-12 (2004).
Chen et al., "Characterization of Structurally Distinct, Isoform-Selective Phosphoinositide 3'-Kinase Inhibitors in Combination with Radiation in the Treatment of Glioblastoma," *Mol. Cancer Ther.* 7(4):841-850 (2008).
Cheson et al., "Bendamustine: Rebirth of an Old Drug," *J. Clin. Oncol.* 27(9):1492-1501 (2009).
Chiarini et al., "Activity of the Novel Dual Phosphatidylinositol 3-Kinase/Mammalian Target of Rapamycin Inhibitor NVP-BEZ235 against T-Cell Acute Lymphoblastic Leukemia," *Cancer Res.* 70(20):8097-8107 (2010).
Chiarini et al., "Dual Inhibition of Class IA Phosphatidylinositol 3-Kinase and Mammalian Target of Rapamycin as a New Therapeutic Option for T-Cell Acute Lymphoblastic Leukemia," *Cancer Res.* 69(8): 3520-3528 (2009).
Cho et al., "A novel synthesis of benzo[c]phenanthridine skeleton and biological evaluation of isoquinoline derivatives," *Chem. Pharm. Bull.*(Tokyo) 47(6):900-902 (1999).
Clayton et al., "A crucial role for the p110delta subunit of phosphatidylinositol 3-kinase in B cell development and activation," *J. Exp. Med.* 196:753-763 (2002).
Closse et al., "2,3-dihydrobenzofuran-2-ones: a new class of highly potent antiinflammatory agents," *J. Med. Chem.* 24:1465-1471 (1981).
Courtney et al., "The PI3K Pathway as Drug Target in Human Cancer," *J. Clin. Oncol.* 28(6):1075-1083 (2010).
Cox et al., "Human colorectal cancer cells efficiently conjugate the cyclopentenone prostaglandin, prostaglandin $J_2$, to glutathione," *Biochem. Biophys. Acta.* 1584:37-45 (2002).
Cushing et al., "PI3Kδ and PI3Kγ as Targets for Autoimmune and Inflammatory Diseases," *J. Med. Chem.* 55:8559-8581 (2012).
Dai et al., "Distinct Roles of Phosphoinositide-3 Kinase and Phospholipase Cγ2 in B-Cell Receptor-Mediated Signal Transduction," *Mol. Cell. Biol.* 26(1):88-99 (2006).
Davids et al., "Decreased mitochondrial apoptotic priming underlies stroma-mediated treatment resistance in chronic lymphocytic leukemia," *Blood* 120(17):3501-3509 (2012).
Davies et al., "The Human T3 γ Chain is Phosphorylated at Serine 126 in Response to T Lymphocyte Activation," *J. Biol. Chem.* 262(23):10918-10921 (1987).
Davis et al., "The preparation of substituted 1(2H)-isoquinolinones from dilithiated 2-methyl-N-arylbenzamides, 2-methyl-N-(arylmethyl)-benzamides, or 2-methylbenzoic acid, 2, 2-dimethylhydrazide," *Synthetic Commun.* 27(17):2961-2969 (1997).
Davis et al., "Chronic active B-cell-receptor signaling in diffuse large B-cell lymphoma," *Nature* 463:88-92 (2010).

(56) References Cited

OTHER PUBLICATIONS

De Weers et al., "The Bruton's tyrosine kinase gene is expressed throughout B cell differentiation, from early precursor B cell stages preceding immunoglobulin gene rearrangement up to mature B cell stages," *Eur. J. Immunol.* 23:3109-3114 (1993).

Diederich et al., "In search for specific inhibitors of human 11β-hydroxysteroid-dehydrogenases (11βHSDs): chenodeoxycholic acid selectively inhibits 11β-HSD-I," *Eur. J. Endocrinol.* 142(2):200-207 (2000).

Dijksman et al., "271.1 : 2-dihydro-2-thianaphthalene derivatives. Part I. Preparation and reactions of 1 : 2-dihydro-1-keto-2-thianaphthalenes," *J. Chem. Soc.* 1213-1218 (1951).

Ding et al., "A combinatorial scaffold approach toward kinase-directed heterocycle libraries," *J. Am. Chem. Soc.* 124(8):1594-1596 (2002).

Ding et al., "A concise and traceless linker strategy toward combinatorial libraries of 2,6,9-substituted purines," *J. Org. Chem.* 66(24):8273-8276 (2001).

Ding et al., "Resin-capture and release strategy toward combinatorial libraries of 2,6,9-substituted purines," *J. Comb. Chem.* 4(2):183-186 (2002).

Donati, G., "Emerging therapies for neovascular age-related macular degeneration: state of the art," *Ophthalmologica* 221(6):366-377 (2007).

European Examination Report for EP Application No. 07873406.8 dated Sep. 14, 2011.

European Search Report for EP Application No. 05857011.0 dated Feb. 4, 2011.

European Search Report for EP Application No. 09700784.3 dated Oct. 28, 2011.

European Search Report and Search Opinion for EP Application No. 09700424.6 dated Oct. 26, 2011.

European Search Report for EP Application No. 07873406.8 dated Mar. 1, 2010.

European Search Report for EP Application No. 07754845.1 dated Sep. 20, 2011.

Examination Report for GB Application No. GB 0819947.3 dated Oct. 27, 2010.

Extended European Search Report for EP Application No. 09816603.6 dated Mar. 19, 2012.

Extended European Search Report from European Application No. 09700784.3 dated Oct. 28, 2011.

Fajans et al., "Maturity onset diabetes of the young (MODY)," *Diabet. Med.* 13(9 Suppl 6):S90-S95 (1996).

Feinstein et al., "Regulation of the action of hydrocotisone in airway epithelial cells by 11b-hydroxysteroid dehydrogenase," *Am. J. Respir. Cell. Mol. Biol.* 21(3):403-408 (1999).

Feldman et al., "Active-Site Inhibitors of mTOR Target Rapamycin-Resistant Outputs of mTORC1 and mTORC2," *PLoS Biol.* 7(2):371-383 (2009).

Fingl et al., "Chapter 1—General Principles," The Pharmacological Basis of Therapeutics, 5th edition, Goodman and Gilman editors, MacMillan Publishings Co., Inc., New York, pp. 1-46, (1975).

Flinn et al., "Preliminary Evidence of Clinical Activity in a Phase I Study of CAL-101, a Selective Inhibitor of the p110δ Isoform of Phosphatidylinositol 3-Kinase (P13K), in Patients with Select Hematologic Malignancies," *J. Clin. Oncol.* 27(15s) (Suppl: Abstr 3543) (2009).

Forrest et al., "Carbonyl Reductase," *Chem. Biol. Interact.* 129(1-2): 21-40 (2000).

Forrest et al., "Induction of a human carbonyl reductase gene located on chromosome 21," *Biochem. Biophys. Acta.* 1048(2-3):149-155 (1990).

Franzen, "The Suzuki, the Heck, and the Stille reaction—three versatile methods for the introduction of new C-C bonds on solid support," *Can. J. Chem.* 78:957-962 (2000).

Funder et al., "Mineralocorticoid action: target tissue specificity is enzyme, not receptor, mediated," *Science* 242:583-585 (1998).

Fung-Leung, W. P., "Phosphoinositide 3-kinase delta (PI3Kδ) in leukocyte signaling and function," *Cell Signal* 23:603-608 (2011).

Furukawa, T., "Molecular Targeting Therapy for Pancreatic Cancer: Current Knowledge and Perspectives from Bench to Bedside," *J. Gastroenterol.* 43(12):905-911 (2008).

Garber et al., "Diversity of gene expression in adenocarcinoma of the lung," *Proc. Natl. Acad. Sci. U.S.A.* 98(24):13784-13789 (2001).

Gillespie et al., "Antagonists of the human adenosine $A_{2A}$ receptor. Part 3: Design and synthesis of pyrazolo[3,4-d]pyrimidines, pyrrolo[2,3-d]pyrimidines and 6-arylpurines," *Bioorg. Med. Chem. Lett.* 18(9):2924-2929 (2008).

Gonzalez et al., "Protection against daunorubicin cytotoxicity by expression of a cloned human carbonyl reductase cDNA in K562 leukemia cells," *Cancer Res.* 55(20):4646-4650 (1995).

Graber et al., "The protein tyrosine kinase inhibitor herbimycin A, but not genistein, specifically inhibits signal transduction by the T cell antigen receptor," *Int. Immunol.* 4(1):1201-1210 (1992).

Graupera et al., "Angiogenesis selectively requires the p110α isoform of PI3K to control endothelial cell migration," *Nature* 453(7195):662-666 (2008).

Gunther et al., "Acute pathological effects on rats of orally administered wortmannin-containing preparations and purified wortmannin from Fusarium oxysporum," *Food Chem. Toxicol.* 27(3):173-179 (1989).

Gunther et al., "Immunosuppressive effects of dietary wortmannin on rats and mice," *Immunopharmacol. Immunotoxicol.* 11(4):559-570 (1989).

Haase et al., "Detection of viral nucleic acids by in situ hybridization," *Methods in Virology* 7:189-226 (1984).

Haluska et al., "The RTK/RAS/BRAF/P13K Pathways in Melanoma: Biology, Small Molecule Inhibitors, and Potential Applications," *Semin. Oncol.* 34(6):546-554 (2007).

Hanefeld et al., "One-pot synthesis of tetrasubstituted pyrazoles proof of regiochemistry," *J. Chem. Soc. Perkin 1* 1545-1552 (1996).

Harada et al., "Novel role of phosphatidylinositol 3-kinase in CD28-mediated costimulation," *J. Biol. Chem.* 276(12):9003-9008 (2001).

Harding et al., "CD28-mediated signalling co-stimulates murine T cells and prevents induction of anergy in T-cell clones," *Nature* 356(6370):607-609 (1992).

Hasselblom et al., "High immunohistochemical expression of p-AKT predicts inferior survival in patients with diffuse large B-cell lymphoma treated with immunochemotherapy," *Brit. J. Haematol.* 149:560-568 (2010).

Haylock-Jacobs et al., "PI3Kδ drives the pathogenesis of experimental autoimmune encephalomyelitis by inhibiting effector T cell apoptosis and promoting Th17 differentiation," *J. Autoimmun.* 36:278-287 (2011).

Hellwinkel et al., "Heterocyclensynthesen mit MF/Al2O3-basensystemen; 2-arylbenzofurane and 2,3-diarylisochinolin-1(2H)-one," *Synthesis* 1995( 9):1135-1141 (1995).

Herishanu et al., "The lymph node microenvironment promotes B-cell receptor signaling, NF-κb activation, and tumor proliferation in chronic lymphocytic leukemia," *Blood* 117(2):563-574 (2011).

Herman et al., "Phosphatidylinositol 3-kinase-δ inhibitor CAL-101 shows promising preclinical activity in chronic lymphocytic leukemia by antagonizing intrinsic and extrinsic cellular survival signals," *Blood* 116(12):2078-2088 (2010).

Herman et al., "The role of phosphatidylinositol 3-kinase-δ in the immunomodulatory effects of lenalidomide in chronic lymphocytic leukemia," *Blood* 117(16):4323-4327 (2011).

Herrera et al., "The dual PI3K/mTOR inhibitor BEZ235 is effective in lung cancer cell lines," *Anticancer Res.* 31:849-854 (2011).

Hickey et al., "BCR-ABL Regulates Phosphatidylinositol 3-Kinase-p110γ Transcription and Activation and Is Required for Proliferation and Drug Resistance," *J. Biol. Chem.* 281(5):2441-2450 (2006).

Hirsch et al., "CALming Down T Cell Acute Leukemia," *Cancer Cell* 21:449-450 (2012).

Hirsch et al., "Central Role for G Protein-Coupled Phosphoinositide 3-Kinase γ in Inflammation," *Science* 287:1049-1053 (2000).

Hoellenriegel and Burger, "Phosphoinositide 3'-kinase delta: turning off BCR signaling in Chronic Lymphocytic Leukemia," *Oncotarget* 2(10):737-738 (2011).

(56) References Cited

OTHER PUBLICATIONS

Hoellenriegel et al., "The phosphoinositide 3'-kinase delta inhibitor, CAL-101, inhibits B-cell receptor signaling and chemokine networks in chronic lymphocytic leukemia," *Blood* 118(13):3603-3612 (2011).
Hoellenriegel et al., "Phosphoinositide 3'-kinase (PI3K) Delta Inhibition with CAL-101 Blocks B-cell Receptor (BCR) Signaling and the Prosurvival Actions of Nurse-Like Cells (NLC) in Chronic Lymphocytic Leukemia (CLL)," (ASH Annual Meeting 2010).
Honigberg et al., "The Bruton tyrosine kinase inhibitor PCI-32765 blocks B-Cell activation and is efficacious in models of autoimmune disease and B-cell malignancy," *PNAS* 107(29):13075-13080 (2010).
Ikeda et al., "PI3K/p110δ is a novel therapeutic target in multiple myeloma," *Blood* 116(9):1460-1468 (2010).
International Preliminary Report on Patentability and Written Opinion for PCT/US2005/042524 dated May 22, 2007.
International Preliminary Report on Patentability and Written Opinion for PCT/US2007/008355 dated Nov. 4, 2008.
International Preliminary Report on Patentability and Written Opinion for PCT/US2007/008395 dated Oct. 8, 2008.
International Preliminary Report on Patentability and Written Opinion for PCT/US2009/049969 dated Jan. 11, 2011.
International Preliminary Report on Patentability and Written Opinion for PCT/US2009/060985 dated Apr. 19, 2011.
International Preliminary Report on Patentability for PCT/US2009/000038 dated Jul. 6, 2010.
International Preliminary Report on Patentability for PCT/US2009/005380 dated Apr. 7, 2011.
International Preliminary Report on Patentability for PCT/US2010/002020 dated Jan. 26, 2012.
International Preliminary Report on Patentability for PCT/US2009/000042 dated Jul. 6, 2010.
International Search Report & Written Opinion for PCT/US2011/060212 dated Jun. 1, 2012.
International Search Report & Written Opinion issued after Submission of Request for Additional Search for PCT/US2011/060212 dated Jul. 6, 2012.
International Search Report and Written Opinion for PCT/US2009/005380 dated Nov. 20, 2009.
International Search Report and Written Opinion for PCT/US2009/049969 dated Mar. 15, 2010.
International Search Report and Written Opinion for PCT/US2010/033939, dated Nov. 5, 2010.
International Search Report and Written Opinion for PCT/US2012/047190 dated Oct. 2, 2012.
International Search Report and Written Opinion for PCT/US2012/020831 dated May 2, 2012.
International Search Report for PCT/US2011/037412 dated Aug. 22, 2011.
International Search Report for PCT/US1995/005213 dated Aug. 21, 1995.
International Search Report for PCT/US2007/008395 (4 pages) dated Aug. 27, 2008.
International Search Report for PCT/US2009/000038 dated Mar. 11, 2009.
International Search Report for PCT/US2009/000042 dated Mar. 23, 2009.
International Search Report for PCT/US2005/042524 (7 pages) dated Oct. 2, 2006.
International Search Report for PCT/US2007/008355 dated Sep. 25, 2008.
International Search Report for PCT/US2009/060985 dated Jun. 28, 2010.
International Search Report for PCT/US2010/002020 dated Nov. 2, 2010.
Ishiyama et al., "A stoichiometric aromatic C—H borylation catalyzed by iridium(I)/2,2'-bipyridine complexes at room temperature," *Angew. Chem. Int. Ed. Engl.* 41(16):3056-3058 (2002).
Ishiyama et al., "Mild iridium-catalyzed borylation of arenes. High turnover numbers, room temperature reactions, and isolation of a potential intermediate," *J. Am. Chem. Soc.* 124(3):390-391 (2002).
Jackson et al., "PI 3-kinase p110β: a new target for antithrombotic therapy," *Nat. Med.* 11:507-514 (2005).
Jimeno et al., "Phase I Trial of PX-866, a Novel Phosphoinositide-3-Kinase (PI-3K) Inhibitor," *J. Clin. Oncol.* 27:15s (Suppl; Abstract 3542) (2009).
Johnson et al., "Accessory cell-derived signals required for T cell activation," *Immunol. Res.* 48-64 (1993).
Jou et al., "Essential, nonredundant role for the phosphoinositide 3-kinase p110delta in signaling by the B-cell receptor complex," *Mol. Cell. Biol.* 22:8580-8591 (2002).
June et al., "Evidence for the involvement of three distinct signals in the induction of IL-2 gene expression in human T lymphocytes," *J. Immunol.* 143(1):153-161 (1989).
June et al., "Inhibition of tyrosine phosphorylation prevents T-cell receptor mediated signal transduction," *Proc. Natl. Acad. Sci. U.S.A.* 87:7722-7726 (1990).
June et al., "Role of CD28 receptor in T-cell activation," *Immunol. Today* 11(6):211-216 (1990).
June, C.H., "Signaling transduction in T cells," *Curr. Opin. Immunol.* 3(3):287-293 (1991).
Kajita et al., "Nickel-catalyzed decarbonylative addition of phthalimides to alkynes," *J. Am. Chem. Soc.* 130(19):6058-6059 (2008).
Kallberg et al., "Short-chain dehydrogenase/reductase (SDR) relationships: a large family with eight clusters common to human, animal, and plant genomes," *Protein Sci.* 11(3):636-641 (2002).
Kallberg et al., "Short-Chain Dehydrogenases/Reductases (SDRs)—Coenzyme-Based Functional Assignments in Completed Genomes," *Eur. J. Biochem.* 269(18):4409-4417 (2002).
Kang et al., "Oncogenic transformation induced by the p110β, -γ, and -δ isoforms of class I phosphoinositide 3-kinase," *PNAS* 103(5):1289-1294 (2006).
Karpeiskii et al., "Pyridoxal-5'-Derivatives of Nucleobases," *Bioorganicheskaya Khimiya* 11(8): 1097-1104 (1985).
Khwaja, A., "PI3K as a Target for Therapy in Haematological Malignancies," *Curr. Top. Microbiol. Immunol.* 347:169-188 (2010).
Kim et al., "Activation and Function of the mTORC1 Pathway in Mast Cells," *J. Immunol.* 180(7):4586-4595 (2008).
Knight et al., "A Pharmacological Map of the PI3-K Family Defines a Role for p110α in Insulin Signaling," *Cell* 125(4):733-747 (2006).
Kong, D. and Yamori, T., "Advances in Development of Phosphatidylinositol 3-Kinase Inhibitors," *Curr. Med. Chem.* 16:2839-2854 (2009).
Kost et al., "Recyclization of 3-Alkyl- and 1,3-Dialkylisoquinolinium Salts to Naphthylamines," *Chemistry of Heterocyclic Compounds* 16(9): 965-970 (1981).
Kraybill et al., "Inhibitor scaffolds as new allele specific kinase substrates," *J. Am. Chem. Soc.* 124(41):12118-12128 (2002).
Kreutzberger et al. "5-Substituierte 4-Aminopyrimidine durch Aminomethinylierung von Acetonitrilen," *Liebigs Ann. Chem.* 537-544 (1977).
Kulkarni et al., "PI3Kbeta plays a critical role in neutrophil activation by immune complexes," *Sci. Signal* 2011, vol. 4, ra23.
Kumar et al., "Keten Dithioacetals. Part 11. Reaction of 3-Cyano-4-Methylthio-2(1H)-pyridones with Hydrazine and Guanidine: Synthesis of Novel Substituted and Fused Pyrazolo[4,3-c]pyridone and Pyrido[4,3-d]pyrimidine derivatives," *J. Chem. Soc. Perkin 1* 8:857-862 (1978).
Kundu et al., "Palladium-catalysed heteroannualation with terminal alkynes; a highly regio- and stereoselective synthesis of (Z)-3-aryl(alykl)idene isoindolin-1-ones," *Tetrahedron* 56(27):4777-4792 (2000).
Kurtova et al., "Diverse marrow stromal cells protect CLL cells from spontaneous and drug-induced apoptosis: development of a reliable and reproducible system to assess stromal cell adhesion-mediated drug resistance," *Blood* 114(20): 4441-4450 (2009).
Kwok et al., "The anti-inflammatory natural product parthenolide from the medicinal herb Feverfew directly binds to and inhibits IκB kinase," *Chem. Biol.* 8(8):759-766 (2001).

(56) References Cited

OTHER PUBLICATIONS

Lannutti et al., "CAL-101 a p110δ selective phosphatidylinositol-3-kinase inhibitor for the treatment of B-cell malignancies, inhibits PI3K signaling and cellular viability," *Blood* 117(2):591-594 (2011).
Larabi et al., "Crystal Structure and Mechanism of Activation of TANK-Binding Kinase 1," *Cell Reports* 3:734-746 (2013).
Ledbetter et al.,"CD28 ligation in T-cell activation: evidence for two signal transduction pathways," *Blood* 75(7):1531-1539 (1990).
Ledbetter et al., "Crosslinking of surface antigens causes mobilization of intracellular ionized calcium in T lymphocytes," *Proc. Natl. Acad. Sci. U. S. A.* 84(5):1384-1388 (1987).
Lee et al., "All roads lead to mTOR: integrating inflammation and tumor angiogenesis," *Cell Cycle* 6(24):3011-3014 (2007).
Lee et al., "The CD28 signal transduction pathway in T cell activation", Advances in Cell Regulation of Cell Growth, vol. 2, pp. 141-160, New York: Raven Press, Ltd. (1991).
Ley et al., "The T cell receptor/CD3 complex and CD2 stimulate the tyrosine phosphorylation of indistinguishable patterns of polypeptides in the human T leukemic cell line Jurkat," *Eur. J. Immunol.* 21(9):2203-2209 (1991).
Li et al., "Roles of PLC-beta2 and -beta3 and PI3Kgamma in chemoattractant-mediated signal transduction," *Science* 287(5455):1046-1049 (2000).
Liu et al., "Costimulation of T-cell growth," *Curr. Opin. Immunol.* 4(3):265-270 (1992).
Lu et al., "CD28-induced T cell activation. Evidence for a protein-tyrosine kinase signal transduction pathway," *J. Immunol.* 149(1):24-29 (1992).
Majumder et al., "mTOR inhibition reverses Akt-dependent prostate intraepithelial neoplasia through regulation of apoptotic and HIF-1-dependent pathways," *Nat. Med.* 10(6):594-601 (2004).
Markman et al., "Status of PI3K inhibition and biomarker development in cancer therapeutics," *Ann. Oncol.* 21(4):683-691 (2010).
Martelli et al., "The emerging role of the phosphatidylinositol 3-kinase/Akt/mammalian target of rapamycin signaling network in normal myelopoiesis and leukemogenesis," *Biochim. Biophys. Acta.* 803:991-1002 (2010).
Martinez et al., "The Molecular Signature of Mantle Cell Lymphoma Reveals Multiple Signals Favoring Cell Survival," *Cancer Res.* 63:8226-8232 (2003).
Martin-Sanchez et al., "PI3K Inhibition as a Potential Therapeutic Strategy in Peripheral T-Cell Lymphomas," *Blood (ASH Annual Meeting Abstracts)* 118: Abstract 3493 (2011).
Mattes et al., "DNA sequence selectivity of guanine-N7 alkylation by nitrogen mustards," *Nucleic Acids Res.* 14(7):2971-2987 (1986).
Maxwell et al., "Attenuation of phosphoinositide 3-kinase δ signaling restrains autoimmune disease," *J. Autoimmun.* 38:381-391 (2012).
Mayer et al., "Small molecule inhibitor of mitotic spindle bipolarity identified in a phenotype-based screen," *Science* 286(5441):971-974 (1999).
Mazzoletti and Broggini, "PI3K/AKT/mTOR inhibitors in ovarian cancer," Curr. Med. Chem. 17(36):4433-4447 (2010).
Meadows, S.A., et al., "CAL-101, a Potent Selective Inhibitor of the p110δ Isoform of Phosphatidylinositol 3-Kinase, Attenuates Pathway Signaling, Induces Apoptosis, and Overcomes Signals From the Microenvironment in Cellular Models of Hodgkin Lymphoma," Blood (ASH Annual Meeting Abstracts), 116:Abstract 3926 (2010).
Mellinghoff et al., "TORward AKTually useful mouse models," *Nat. Med.* 10(6):579-580 (2004).
Merida et al., "IL-2 binding activates a tyrosine-phosphorylated phosphatidylinositol-3-kinase," *J. Immunol.* 147(7): 2202-2207 (1991).
Miyaura et al., "Palladium-catalyzed cross-coupling reactions of organoboron compounds," *Chem. Rev.* 95(7):2457-2483 (1995).
Modi et al., "Isoquinolones; part IV-synthesis of methyl, 3-formyl & other 3-substituted N-arylisoquinolones." *Indian J Chem.* 18B:304-306 (1979).
Moon et al., "A novel microtubule destabilizing entity from orthogonal synthesis of triazine library and zebrafish embryo screening," *J. Am. Chem. Soc.* 124(39):11608-11609 (2002).

Mosmann et al., "The expanding universe of T-cell subsets: Th1, Th2 and more," *Immunology Today* 17(3):138-146 (1996).
Nakanishi et al., "Cloning and sequence analysis of a cDNA encoding tetrameric carbonyl reductase of pig lung," *Biochem. Biophys. Res. Commun.* (3):1311-1316 (1993).
Nemazanyi et al., "3-Amino-4-aryl-1(2H)-isoquinolones," *Chemistry of Heterocyclic Compounds* 27(3):307-308 (1991).
Newman et al., "Solid state analysis of the active pharmaceutical ingredient in drug products," *Drug Discov. Today* 8(19):898-905 (2003).
Nisitani et al., "Posttranscriptional regulation of Bruton's tyrosine kinase expression in antigen receptor-stimulated splenic B cells," *PNAS* 97(6):2737-2742 (2000).
Niswender et al., "Protein engineering of protein kinase a catalytic subunits results in the acquisition of novel inhibitor sensitivity," *J. Biol. Chem.* 277(32):28916-28922 (2002).
Nobel et al., "Purification of full-length recombinant human and rat type 1 11β-hydroxysteroid dehydrogenases with retained oxidoreductase activities," *Protein Expr. Purif.* 26(3):349-356 (2002).
Norman, "Selective PI3K-delta Inhibitors, a Review of the Patent Literature," Expert Opinion on Therapeutic Patents, 21(11): 1773-1790 (2011).
Nunes et al., "Signalling through CD28 T-cell activation pathway involves an inositol phospholipid-specific phospholipase C activity," *Biochem. J.* 293(Pt 3):835-842 (1993).
Oda et al., "PIK3CA cooperates with other phosphatidylinositol 3'-kinase pathway mutations to effect oncogenic transformation," *Cancer Res.* 68(19):8127-8136 (2008).
Office Action dated Dec. 13, 2012 for U.S. Appl. No. 13/112,611.
Okada et al., "Essential role of phosphatidylinositol 3-kinase in insulin-induced glucose transport and antilipolysis in rat adipocytes. Studies with a selective inhibitor wortmannin," *J. Biol. Chem.* 269(5):3568-3573 (1994).
Okada et al., "Blockage of chemotactic peptide-induced stimulation of neutrophils by wortmannin as a result of selective inhibition of phosphatidylinositol 3-kinase," *J. Biol. Chem.* 269(5):3563-3567 (1994).
Oppermann et al., "Forms and functions of human SDR enzymes," *Chem. Biol. Interact.* 130-132(1-3):699-705 (2001).
O'Shea et al., "Activation of human peripheral blood T lymphocytes by pharmacological induction of protein-tyrosine phosphorylation," *Proc. Natl. Acad. Sci. U. S. A.* 89(21):10306-10310 (1992).
Ozaki et al., "Studies on 4(1H)-quinazolinones. IV. Convenient synthesis of 12-methyl-6H-isoquino [2,1-a] quinazolin-6-one and 6-methyl-13H-quinazolino [3,4-a] quinazolin-13-one," *Chem. Pharm. Bull.* 32(6):2160-2164 (1984).
Ozol et al., "Autoxidative transformations of 2-substituted 3-alkyl-4-hydroxy-1-oxo-1, 2-dihydroisoquinolines," *Chemistry of Heterocyclic Compounds* 14(6):644-648 (1978).
Patel et al., "Immunopathological aspects of age-related macular degeneration," *Semin. Immunopathol.* 30(2):97-110 (2008).
Pérez-Blas et al., "Impaired T cell signal transduction through CD28 in a patient with idiopathic thrombocytopenia," *Clin. Exp. Immunol.* 85(3):424-428 (1991).
Persson, "Glucocorticoids for asthma—early contributions," *Pulm. Pharmacol.* 2(3):163-166 (1989).
Petrie et al., "Novel biotinylated adenylate analogue derived from pyrazolo[3,4-d]pyrimidine for labeling DNA probes," *Bioconjug. Chem.* 2(6):441-446 (1991).
Pighi et al., "Phospho-proteomic analysis of mantle cell lymphoma cells suggests a pro-survival role of B-cell receptor signaling," *Cell Oncol. (Dordr)* 34(2):141-153 (2011).
Polak et al., "The PI3K/PKB signaling module as key regulator of hematopoiesis: implications for therapeutic strategies in leukemia," *Blood* 119(4):911-923 (2012).
Porta and Figlin, "Phosphatidylinositol-3-kinase/Akt signaling pathway and kidney cancer, and the therapeutic potential of phosphatidylinositol-3-kinase/Akt inhibitors," *J. Urol.* 182(6):2569-2577 (2009).
Prasad et al., "Phosphatidylinositol (PI) 3-kinase and PI 4-kinase binding to the CD4-p56$^{lck}$ complex: the p56$^{lck}$ SH3 domain binds to PI 3-kinase but not PI 4-kinase," *Mol. Cell. Biol.* 13(12): 7708-7717 (1993).

(56) References Cited

OTHER PUBLICATIONS

Prasad et al., "Src-homology 3 domain of protein kinase p59$^{fyn}$ mediates binding to phosphatidylinositol 3-kinase in T cells," *Proc. Natl. Acad. Sci. U. S. A.* 90(15): 7366-7370 (1993).

Prasad et al., "T-cell antigen CD28 interacts with the lipid kinase phosphatidylinositol 3-kinase by a cytoplasmic Tyr(P)-Met-Xaa-Met motif," *Proc. Natl. Acad. Sci. U. S. A.* 91(7): 2834-2838 (1994).

Pudlo et al., "Synthesis, antiproliferative, and antiviral activity of certain 4-substituted and 4,5 disubstituted 7-[1,3-dihydroxy-2-propoxy)methyl]pyrrolo[2,3-d]pyrimidines," *J. Med. Chem.* 33(7):1984-1992 (1990).

Puri and Gold, "Selective inhibitors of phosphoinositide 3-kinase delta: modulators of B-cell function with potential for treating autoimmune inflammatory disease and B-cell malignancies," *Front. Immunol.* 3:256 (2012).

Quiroga et al., "B-cell antigen receptor signaling enhances chronic lymphocytic leukemia cell migration and survival: specific targeting with a novel spleen tyrosine kinase inhibitor, R406," *Blood* 114(5):1029-1037 (2009).

Reif et al., "Divergent regulation of phosphatidylinositol 3-kinase P85α and P85β isoforms upon T cell activation," *J. Biol. Chem.* 268(15):10780-10788 (1993).

Report of the Expert Committee on the Diagnosis and Classification of Diabetes Mellitus, *Diabetes Care* 2( Suppl. 1):S5-S19 (1992).

Rizzatti et al., "Gene expression profiling of mantle cell lymphoma cells reveals aberrant expression of genes from the PI3K-AKT, WNT and TGFβ signaling pathways," *Brit. J. Haematol.* 130:516-526 (2005).

Robertson, "Eicosanoids and human disease", Harrison's Principles of Internal Medicine, Isselbacher K.J. et al. (eds.), vol. 1, pp. 431-435, McGraw-Hill, New York City (1994).

Roller et al., "Blockade of Phosphatidylinositol 3-Kinase (PI3K)δ or PI3Kγ Reduces IL-17 and Ameliorates Imiquimod-Induced Psoriasislike Dermatitis," *J. Immunol.* 189:4612-4620 (2012).

Romero et al., "Cloning and expression of the bovine 11b-hydroxysteroid dehydrogenase type-2," *J. Steroid Biochem. Mol. Biol.* 72(5):231-237 (2000).

Rommel et al., "PI3Kδ and PI3Kγ: partners in crime in inflammation in rheumatoid arthritis and beyond?" *Nat. Rev. Immunol.* 7:191-201 (2007).

Rott et al., "Recent developments in the use of biologics in psoriasis and autoimmune disorders. The role of autoantibodies," *BMJ* 330(7493):716-720 (2005).

Rudelius et al., "Constitutive activation of Akt contributes to the pathogenesis and survival of mantle cell lymphoma," *Blood* 108(5):1668-1676 (2006).

Saif and Chu, "Biology of colorectal cancer," *Cancer J.* 16(3):196-201 (2010).

Salmena et al., "Tenets of PTEN Tumor Suppression," *Cell* 133(3):403-414 (2008).

Sarker et al., "Targeting the PI3K/AKT pathway for the treatment of prostate cancer," *Clin. Cancer Res.* 15(15):4799-4805 (2009).

Sasaki et al., "Function of PI3Kγ in Thymocyte Development, T Cell Activation, and Neutrophil Migration," *Science* 287:1040-1046 (2000).

Schwartz et al., "Quercetin inhibition of the induction and function of cytotoxic T lymphocytes," *Immunopharmacology* 4(2):125-138 (1982).

Schwartz, "A cell culture model for T lymphocyte clonal anergy," *Science* 248(4961):1349-1356 (1990).

Shapiro et al., "Phase I Dose-Escalation Study of XL147, a PI3K Inhibitor Administered Orally to Patients with Solid Tumors," *J. Clin. Oncol.* 27:146x (Suppl Abstr 3500) (2009).

Shibasaki et al., "Different properties of monomer and heterodimer forms of phosphatidylinositol 3-kinases," *Biochem. J.* 289 ( Pt 1):227-231 (1993).

Sinclair et al., "Phosphatidylinositol-3 Kinase Delta (PI3Kδ) Inhibitor AMG 319 Is a Potent, Selective and Orally Bioavailable Small Molecule Inhibitor That Suppresses PI3K-Mediated Signaling and Viability in Neoplastic B Cells," *Blood* (*ASH Annual Meeting Abstracts*) 118:Abstract 4964 (2011).

Singer et al., "Optimization of in situ hybridization using isotopic and non-isotopic detection methods," *Biotechniques* 4(3):230-250 (1986).

Smith et al., "Expression of Bruton's Agammaglobulinemia Tyrosine Kinase Gene, BTK, Is Selectively Down-Regulated in T Lymphocytes and Plasma Cells," *J. Immunol.* 152:557-565 (1994).

Soldan et al., "Induction of daunorubicin carbonyl reducing enzymes by daunorubicin in sensitive and resistant pancreas carcinoma cells," *Biochem. Pharmacol.* 51(2):117-123 (1996).

Soond et al., "PI3K p110δ regulates T-cell cytokine production during primary and secondary immune responses in mice and humans," *Blood* 115(11):2203-2213 (2010).

Srinivasan et al., "PI3 Kinase Signals BCR-Dependent Mature B Cell Survival," *Cell* 139:573-586 (2009).

Stanoeva et al., "Homophthalic anhydrides and their application to the synthesis of heterocyclic compounds (review)," *Chemistry of Heterocyclic Compounds* 20(12):1305-1315 (1984).

Subramaniam et al., "Targeting Nonclassical Oncogenes for Therapy in T-ALL," *Cancer Cell* 21:459-472 (2012).

Sujobert et al., "Essential role for the p110δ isoform in phosphoinositide 3-kinase activation and cell proliferation in acute myeloid leukemia," *Blood* 106(3):1063-1066 (2005).

Supplementary European Examination Report EP Application No. 07754845.1 dated Sep. 20, 2011.

Supplementary European Search Report for EP Application No. 07754845 (4 pages) dated Feb. 24, 2010.

Supplementary European Search Report for EP Application No. 10800175.1 dated Nov. 7, 2012.

Sykes et al., "Treatment of severe autoimmune disease by stem-cell transplantation," *Nature* 35(7042):620-627 (2005).

Takeuchi et al., "Synergistic Augmentation of Rapamycin-Induced Autophagy in Malignant Glioma Cells by Phosphatidylinositol 3-Kinase/Protein Kinase B Inhibitors," *Cancer Res.* 65(8):3336-3346 (2005).

Tanaka et al., "An unbiased cell morphology-based screen for new, biologically active small molecules," *PLoS Biol.* 3(5):0764-0776 (2005).

Thompson et al., "Identification of distinct populations of PI-3 kinase activity following T-cell activation," *Oncogene* 7(4):719-725 (1992).

Torbett et al., "A chemical screen in diverse breast cancer cell lines reveals genetic enhancers and suppressors of sensitivity to PI3K isoform-selective inhibition," *Biochem. J.* 415(1):97-110 (2008).

Truitt et al., "Stimulation of CD28 triggers an association between CD28 and phosphatidylinositol 3-kinase in Jurkat T cells," *J. Exp. Med.* 179(3):1071-1076 (1994).

Tyukavkina et al., Bioorganicheskaya Khimiya, Moskva, DROFA, pp. 83-85 (2004).

Uddin et al., "Role of phosphatidylinositol 3'-kinase/AKT pathway in diffuse large B-cell lymphoma survival," *Blood* 108(13):4178-4186 (2006).

Ugarkar et al., "Adenosine kinase inhibitors. 2. Synthesis, enzyme inhibition, and antiseizure activity of diatyltubercidin analogues," *J. Med. Chem.* 43(15):2894-2905 (2000).

Vandenberghe et al., "Antibody and B7/BB1-mediated ligation of the CD28 receptor induces tyrosine phosphorylation in human T cells," *J. Exp. Med.* 175(4):951-960 (1992).

Vanhaesebroeck et al., "PI3K: from the bench to the clinic and back," *Curr. Top. Microbiol. Immunol.* 347:1-19 (2010).

Vara et al., "PI3K/Akt Signalling Pathway and Cancer," *Cancer Treat. Rev.* 30(2):193-204 (2004).

Vasilevsky et al., "Study of the Heterocyclization of vic-Substituted Hydrazides of Acetylenylpyrazolecarboxylic Acids into N-Amino Pyrazolopyridinones," *Journal of Heterocyclic Chemistry* 39(6): 1229-1233 (2002).

Vasilevsky et al., "Unexpected results in the heterocyclization of 5-acetylenylpyrazole-4-carboxylic acid hydrazides under the influence of CuCl: formation of a diazepinone and dehydrodimerization into the corresponding bis(pyrazolo [4,3-d] [1,2] diazepinone)," *Tetrahedron Lett.* 46(26):4457-4459 (2005).

(56) References Cited

OTHER PUBLICATIONS

Vippagunta et al., "Crystalline Solids," *Adv. Drug Deliv. Rev.* 48(1):3-26 (2001).
Vitali et al., "Immunotherapy in rheumatoid arthritis: a review," *Int. J. Artif. Organs* 16 Suppl. 5:196-200 (1993).
Vlahos et al., "A specific inhibitor of phosphatidylinositol 3-kinase, 2-(4-morpholinyl)-8-phenyl-4H-1-benzopyran-4-one (LY294002)," *J. Biol. Chem.* 269(7):5241-5248 (1994).
Vogt et al., "Phosphatidylinositol 3-kinase the oncoprotein," *Curr. Top. Microbiol. Immunol.* 347:79-104 (2010).
Vogt et al., "Phosphoinositide 3-kinase from viral oncoprotein to drug target," *Virology* 344(1):131-138 (2006).
Wagner et al., "A First-in-Human Phase I Study to Evaluate the Pan-PI3K Inhibitor GDC-0941 Administered QD or BID in Patients with Advanced Solid Tumors," *J. Clin. Oncol.* 27:146s (Suppl, Abstr 3501) (2009).
Wahlstrom et al., "Aberrant MAPK and PI3K Signaling Contribute to Chemotherapy Resistance in T Cell Acute Lymphobalstic Leukemia by Altering the Balance of Apoptosis Mediators," *Blood (ASH Annual Meeting Abstracts)* 118: Abstract 3490 (2011).
Ward et al., "Inhibition of CD28-mediated T cell costimulation by the phosphoinositide 3-kinase inhibitor wortmannin," *Eur. J. Immunol.* 25(2):526-532 (1995).
Ward et al., "Ligation of CD28 receptor by B7 induces formation of D-3 phosphoinositides in T lymphocytes independently of T cell receptor/CD3 activation," *Eur. J. Immunol.* 23(10):2572-2577 (1993).
Ward et al., "Regulation of D-3 phosphoinositides during T cell activation via the T cell antigen receptor/CD3 complex and CD2 antigens," *Eur. J. Immunol.* 22(1):45-49 (1992).
Ward et al., "Regulation of phosphoinositide kinases in T cells. Evidence that phosphatidylinositol 3-kinase is not a substrate for T cell antigen receptor-regulated tyrosine kinases," *J. Biol. Chem.* 267(33):23862-23869 (1992).
Ward et al., "Therapeutic potential of phosphoinositide 3-kinase inhibitors," *Chem. Biol.* 10(3):207-213 (2003).
White et al., "11β-Hydroxysteroid Dehyrdogenase and the Syndrome of Apparent Mineralocorticoid Excess," *Endocr. Rev.* 18(1):135-156 (1997).
Widler et al., "7-alkyl- and 7-Cycloalkyl-5-aryl-pyrrolo[2,3-d]pyrimidines—potent inhibitors of the tyrosine kinase c-Src," Bioorg. Med. Chem. Lett. 11(6):849-852 (2001).
Wiesinger et al., "Antiinflammatory activity of the new mould metabolite 11-desacetoxy-wortmannin and of some of its derivatives," *Experientia* 30(2):135-136 (1974).
Wolff, Burger's Medicinal Chemistry, $5^{th}$ ed, Part 1, pp. 975-977, John Wiley & Sons (1995).
Woscholski et al., "A comparison of demethoxyviridin and wortmannin as inhibitors of phosphatidylinositol 3-kinase," *FEBS Lett.* 342(2):109-114 (1994).
Wu et al., "Decreased immunological responses by wortmannin-containing rice culture of Fusarium oxysporum and by purified wortmannin in avian species," *Immunopharmacol. Immunotoxicol.* 14(4):913-923 (1992).
Wu et al., "Wortmannin (a mycotoxin) inhibited immune responses in chickens," *Poultry Sci.* Vo. 71, Suppl 1, pp. 13 (1992).
Yaguchi et al., "Antitumor activity of ZSTK474, a new phosphatidylinositol 3-kinase inhibitor," *J. Natl. Cancer Inst.* 98(8):545-556 (2006).
Yang et al., "A novel activation pathway for mature thymocytes. Costimulation of CD2 (T,p50) and CD28 (T,p44) induces autocrine interleukin 2/interleukin 2 receptor-mediated cell proliferation," *J. Exp. Med.* 168(4):1457-1468 (1988).
Yano et al., "Inhibition of histamine secretion by wortmannin through the blockade of phosphatidylinositol 3-kinase in RBL-2H3 cells," *J. Biol. Chem.* 268(34):25846-25856 (1993).
Yoshida et al., "Quercetin arrests human leukemic T-cells in late G1 phase of the cell cycle," *Cancer Res.* 52(23):6676-6681 (1992).
Zhao and Vogt, "Class I PI3K in oncogenic cellular transformation," *Oncogene* 27(40:5486-5496 (2008).

U.S. Appl. No. 13/552,460, filed Jul. 18, 2012, U.S. Pat. No. 8,969,363, Heterocyclic Compounds and Uses Thereof.
U.S. Appl. No. 13/552,473, filed Jul. 18, 2012, U.S. Pat. No. 9,056,877, Heterocyclic Compounds and Uses Thereof.
U.S. Appl. No. 13/552,516, filed Jul. 18, 2012, U.S. Pat. No. 8,785,470, Heterocyclic Compounds and Uses Thereof.
U.S. Appl. No. 13/841,265, filed Mar. 15, 2013, U.S. Pat. No. 8,940,742, Heterocyclic Compounds and Uses Thereof.
U.S. Appl. No. 13/839,912, filed Mar. 15, 2013, 2014-0120060, Treatment of Rheumatoid Arthritis and Asthma Using PI3 Kinase Inhibitors.
U.S. Appl. No. 14/209,842, filed Mar. 13, 2014, U.S. Pat. No. 9,481,667, Salts and Solid Forms of Isoquinolinones and Composition Comprising and Methods of Using the Same.
U.S. Appl. No. 13/840,822, filed Mar. 15, 2013, 2014-0120083, Treatment of Cancers Using PI3 Kinase Isoform Modulators.
U.S. Appl. No. 12/811,695, filed Nov. 11, 2010, U.S. Pat. No. 8,703,777, Substituted Bicyclic Compounds and Methods of Use Thereof.
U.S. Appl. No. 12/503,776, filed Jul. 15, 2009, U.S. Pat. No. 8,193,182, Substituted Isoquinolin-1(2H)-Ones, and Methods of Use Thereof.
U.S. Appl. No. 13/403,394, filed Feb. 23, 2012, U.S. Pat. No. 8,785,456, Certain Chemical Entities, Compositions and Methods.
U.S. Appl. No. 13/350,444, filed Jan. 13, 2012, U.S. Pat. No. 8,569,323, Substituted Isoquinolin-1(2H)-One Compounds, Compositions, and Methods Thereof.
U.S. Appl. No. 13/121,157, filed Aug. 2, 2011, U.S. Pat. No. 8,703,778, Heterocyclic Kinase Inhibitors.
U.S. Appl. No. 13/289,540, filed Nov. 4, 2011, U.S. Pat. No. 8,785,454, Heterocyclic Compounds and Uses Thereof.
U.S. Appl. No. 13/293,828, filed Nov. 10, 2011, U.S. Pat. No. 8,901,133, Heterocyclic Compounds and Uses Thereof.
U.S. Appl. No. 13/112,611, filed May 20, 2011, U.S. Pat. No. 8,604,032, Chemical Compounds, Compositions and Methods for Kinase Modulation.
U.S. Appl. No. 13/347,423, filed Jan. 10, 2012, U.S. Pat. No. 8,809,349, Processes for Preparing Isoquinolinones and Solid Forms of Isoquinolinones.
U.S. Appl. No. 13/837,195, filed Mar. 15, 2013, U.S. Pat. No. 8,828,998, Treatment of Lupus, Fibrotic Conditions, and Inflammatory Myopathies and Other Disorders Using PI3 Kinase Inhibitors.
U.S. Appl. No. 14/222,488, filed Mar. 21, 2014, 2014-0206684, Certain Chemical Entities, Compositions and Methods.
U.S. Appl. No. 14/085,660, filed Nov. 20, 2013, U.S. Pat. No. 9,181,221, Chemical Compounds, Compositions and Methods for Kinase Modulation.
U.S. Appl. No. 14/099,831, filed Dec. 6, 2013, U.S. Pat. No. 9,115,141, Heterocyclic Compounds and Uses Thereof.
U.S. Appl. No. 14/776,604, filed Sep. 14, 2015, 2016-0024051, Salts and Solid Forms of Isoquinolinones and Composition Comprising and Methods of Using the Same.
U.S. Appl. No. 13/971,793, filed Aug. 20, 2013, U.S. Pat. No. 9,206,182, Certain Chemical Entities, Compositions and Methods.
U.S. Appl. No. 15/026,947, filed Apr. 1, 2016, U.S. Pat. No. 9,751,888, Heterocyclic Compounds and Uses Thereof.
U.S. Appl. No. 14/506,429, filed Oct. 3, 2014, U.S. Pat. No. 9,359,365, Heterocyclic Compounds and Uses Thereof.
U.S. Appl. No. 14/222,500, filed Mar. 21, 2014, U.S. Pat. No. 9,296,742, Heterocyclic Kinase Inhibitors.
U.S. Appl. No. 14/292,475, filed May 30, 2014, 2014-0377258, Treatment of Cancers Using PI3 Kinase Isoform Modulators.
U.S. Appl. No. 15/030,701, filed Apr. 20, 2016, 2016-0244452, Heterocyclic Compounds and Uses Thereof.
U.S. Appl. No. 14/297,526, filed Jun. 5, 2014, U.S. Pat. No. 9,546,180, Heterocyclic Compounds and Uses Thereof.
U.S. Appl. No. 14/296,953, filed Jun. 5, 2014, U.S. Pat. No. 9,216,982, Certain Chemical Entities, Compositions and Methods.
U.S. Appl. No. 14/302,340, filed Jun. 11, 2014, U.S. Pat. No. 9,315,505, Heterocyclic Compounds and Uses Thereof.

(56) References Cited

OTHER PUBLICATIONS

U.S. Appl. No. 14/327,499, filed Jul. 9, 2014, U.S. Pat. No. 9,290,497, Processes for Preparing Isoquinolinones and Solid Forms of Isoquinolinones.
U.S. Appl. No. 14/439,965, filed Apr. 30, 2015, 2015-0283142, Treatment of Cancers Using PI3 Kinase Isoform Modulators.
U.S. Appl. No. 14/448,998, filed Jul. 31, 2014, U.S. Pat. No. 9,527,847, Treatment of Lupus, Fibrotic Conditions, and Inflammatory Myopathies and Other Disorders Using PI3 Kinase Inhibitors.
U.S. Appl. No. 14/512,262, filed Oct. 10, 2014, U.S. Pat. No. 9,388,183, Heterocyclic Compounds and Uses Thereof.
U.S. Appl. No. 14/573,961, filed Dec. 17, 2014, U.S. Pat. No. 9,255,108, Heterocyclic Compounds and Uses Thereof.
U.S. Appl. No. 15/059,962, filed Mar. 3, 2016, U.S. Pat. No. 9,822,131, Certain Chemical Entities, Compositions and Methods.
U.S. Appl. No. 14/661,656, filed Mar. 18, 2015, U.S. Pat. No. 9,775,844, Heterocyclic Compounds and Uses Thereof.
U.S. Appl. No. 14/592,628, filed Jan. 8, 2015, U.S. Pat. No. 9,718,815, Heterocyclic Compounds and Uses Thereof.
U.S. Appl. No. 14/687,714, filed Apr. 15, 2015, 2015-0320754, Combination Therapies.
U.S. Appl. No. 14/687,768, filed Apr. 15, 2015, 2015-0320755, Combination Therapies.
U.S. Appl. No. 14/695,699, filed Apr. 24, 2015, U.S. Pat. No. 9,828,377, Heterocyclic Compounds and Uses Thereof.
U.S. Appl. No. 14/710,336, filed May 12, 2015, U.S. Pat. No. 9,605,003, Heterocyclic Compounds and Uses Thereof.
U.S. Appl. No. 15/051,529, filed Feb. 23, 2016, RE46,621, Processes for Preparing Isoquinolinones and Solid Forms of Isoquinolinones.
U.S. Appl. No. 14/874,328, filed Oct. 2, 2015, U.S. Pat. No. 9,708,348, Heterocyclic Compounds and Uses Thereof.
U.S. Appl. No. 15/264,417, filed Sep. 13, 2016, U.S. Pat. No. 10,160,761, Solid Forms of Isoquinolinones, and Process of Making, Composition Comprising, and Methods of Using the Same.
U.S. Appl. No. 14/869,637, filed Sep. 29, 2015, U.S. Pat. No. 9,738,644, Chemical Compounds, Compositions and Methods for Kinase Modulation.
U.S. Appl. No. 14/876,589, filed Oct. 6, 2015, 2016-0022692, Treatment of Rheumatoid Arthritis and Asthma Using PI3 Kinase Inhibitors.
U.S. Appl. No. 14/884,612, filed Oct. 15, 2015, U.S. Pat. No. 9,522,146, Certain Chemical Entities, Compositions and Methods.
U.S. Appl. No. 14/894,854, filed Nov. 30, 2015, 2016-0113932, Treatment of Cancers Using PI3 Kinase Isoform Modulators.
U.S. Appl. No. 14/938,647, filed Nov. 11, 2015, U.S. Pat. No. 9,655,892, Certain Chemical Entities, Compositions and Methods.
U.S. Appl. No. 14/971,954, filed Dec. 16, 2015, 2016-0207940, Heterocyclic Compounds and Uses Thereof.
U.S. Appl. No. 15/016,117, filed Feb. 4, 2016, U.S. Pat. No. 9,840,505, Processes for Preparing Isoquinolinones and Solid Forms of Isoquinolinones.
U.S. Appl. No. 16/085,536, filed Sep. 14, 2018, Unpublished, Isotopologues of Isoquinolinone and Quinazolinone Compounds and Uses Thereof as PI3K Kinase Inhibitors.
U.S. Appl. No. 15/050,029, filed Feb. 22, 2016, U.S. Pat. No. 9,790,228, Heterocyclic Kinase Inhibitors.
U.S. Appl. No. 16/308,377, filed Dec. 7, 2018, 2019-0135833, Heterocyclic Compounds and Uses Thereof.
U.S. Appl. No. 15/179,570, filed Jun. 10, 2016, Unpublished, Heterocyclic Compounds and Uses Thereof.
U.S. Appl. No. 15/333,803, filed Oct. 25, 2016, 2017-0137407, Heterocyclic Compounds and Uses Thereof.
U.S. Appl. No. 15/347,489, filed Nov. 9, 2016, 2017-0281614, Certain Chemical Entities, Compositions and Methods.
U.S. Appl. No. 15/599,378, filed May 18, 2017, 2018-0098983, Certain Chemical Entities, Compositions and Methods.
U.S. Appl. No. 15/621,815, filed Jun. 13, 2017, U.S. Pat. No. 10,253,047, Heterocyclic Compounds and Uses Thereof.
U.S. Appl. No. 15/621,764, filed Jun. 13, 2017, Unpublished, Chemical Compounds, Compositions and Methods for Kinase Modulation.
U.S. Appl. No. 15/672,964, filed Aug. 9, 2017, 2018-0055852, Heterocyclic Compounds and Uses Thereof.
U.S. Appl. No. 15/675,185, filed Aug. 11, 2017, Unpublished, Heterocyclic Compounds and Uses Thereof.
U.S. Appl. No. 15/794,816, filed Oct. 26, 2017, U.S. Pat. No. 10,329,299, Heterocyclic Compounds and Uses Thereof.
U.S. Appl. No. 15/799,612, filed Oct. 31, 2017, 2018-0273535, Processes for Preparing Isoquinolinones and Solid Forms of Isoquinolinones.
U.S. Appl. No. 15/789,868, filed Oct. 20, 2017, 2018-0258103, Certain Chemical Entities, Compositions and Methods.
U.S. Appl. No. 16/172,539, filed Oct. 26, 2018, Unpublished, Certain Chemical Entities, Compositions and Methods.
U.S. Appl. No. 16/197,195, filed Nov. 20, 2018, 2019-0185477, Solid Forms of Isoquinolinones, and Process of Making, Composition Comprising, and Methods of Using the Same.
U.S. Appl. No. 16/290,545, filed Mar. 1, 2019, Unpublished, Heterocyclic Compounds and Uses Thereof.
U.S. Appl. No. 16/417,420, filed May 20, 2019, Unpublished, Heterocyclic Compounds and Uses Thereof.
Ameriks et al., "Small Molecule Inhibitors of Phosphoinositide 3-Kinase (PI3K) δ and γ", Curr. Top Med Chem, 2009, vol. 9, pp. 738-753.
Barnes et al., "Glucocortiod resistance in inflammatory diseases," *The Lancet*, 373:1905-1917 (2009).
Bojarczuk et al., "B-cell receptor pathway inhibitors affect CD20 levels and impair antitumor activity of anti-CD20 monoclonal antibodies," Leukemia (2014), 1-5.
Bouska et al. ,"Genome-wide copy-number analyses reveal genomic abnormalities involved in transformation of follicular lymphoma", Blood, Mar. 13, 2014, vol. 123, N. 11, pp. 1681-1690.
Boyle et al., "Efficacy of the potent PI3K-δ,γ inhibitor IPI-145 in rat adjuvant arthritis," *Arthritis & Rheumatism*, 64:S879 (2012).
Brown et al. "Phase I Trial of SAR245408 (S08), a Pan-Phosphatidylinositol 3 Kinase (PI3K) Inhibitor, in Patients with Chronic Lymphocytic Leukemia (CLL) and Lymphoma", Blood (ASH Annual Meeting Abstracts) 2011 118: Abstract 2683, Downloaded from the Internet.
Brown et al., "Idelalisib, an inhibitor of phosphatidylinositol 3-kinase p110d, for relapsed/refractory chronic lymphocytic leukemia", BLOOD, May 29, 2014, vol. 123, No. 22, pp. 3390-3397.
Caira, M., "Crystalline Polymorphism of Organic Compounds," Topics in Current Chemistry, Springer, Berlin, DE, v. 198 (Jan. 1, 1998), p. 163-208.
Castor et al., "Pl$_3$Kγ controls leukocyte recruitment, tissue injury, and lethality in a model of graft-versus-host disease in mice," *J. Leukoc. Biol.*, 89:955-964 (2011).
Cheson et al., "Novel Targeted Agents and the Need to Refine Clinical End Points in Chronic Lymphocytic Leukemia", Journal of Clinical Oncology, vol. 30, No. 23 (Aug. 10, 2012), pp. 2820-2822.
Cheung et al., "Genome-wide profiling of follicular lymphoma by array comparative genomic hybridization reveals prognostically significant DNAcopy number imbalances", Blood, Jan. 1, 2009, , vol. 113, No. 1, pp. 137-148.
Cheung et al., "High Resolution Analysis of Follicular Lymphoma Genomes Reveals Somatic Recurrent Sites of Copy-Neutral Loss of Heterozygosity and Copy Number Alterations that Target Single Genes", Genes, Chromosomes & Cancer 49; 669-681 (2010), DOI 10.1002/gcc.
Chiron et al., "Cell-Cycle Reprogramming for PI3K Inhibition Overrides a Relapse-Specific C481S BTK Mutation Revealed by Longitudinal Functional Genomics in Mantle Cell Lymphoma", Cancer Discovery, (Sep. 2014), vol. 4, pp. 1022-1035, Published OnlineFirst Jul. 31, 2014; DOI: 10.1158/2159-8290.CD-14-0098.
ClinicalTrials.gov, "Dose Escalation Study of CAL-101 in Select Relapsed or Refractory Hematologic Malignancies" [online] (2008) [Retrieved on Jul. 23, 2014] Retrieved from <http://clinicaltrials.gov/ct2/show/NCT00710528>.

(56) References Cited

OTHER PUBLICATIONS

ClinicalTrials.gov, NCT01476657 Study, "A Phase 1 Study of IPI-145 in Patients with Advanced Hematologic Malignancies", Nov. 17, 2011.
Conte et al., "Inhibition of PI3K Prevent the Proliferation and Differentiation of Human Lung Fibroblasts into Myofibroblasts: The Role of Class I P110 Isoforms," PLOS ONE (2011), 6(10):e24663, pp. 1-10.
D'Amore et al., "Clonal Evolution in t(14;18)-Positive Follicular Lymphoma, Evidence for Multiple Common Pathways, and Frequent Parallel Clonal Evolution", Clin Cancer Res 2008;14(22) Nov. 15, 2008, pp. 7180-7187.
D'Cruz et al. "Novel Bruton's tyrosine kinase inhibitors currently in development," OncoTargets and Therapy, Mar. 5, 2013, vol. 6, pp. 161-176.
De Frias et al., "Akt inhibitors induce apoptosis in chronic lynphocytic leukemia cells", Haematologica (2009), vol. 94, pp. 1698-1707.
De Vos et al., "A Phase 1 Study of the Selective Phosphatidylinositol 3-Kinase-Delta (PI3K delta) Inhibitor, Cal-101 (GS1101), in Combination with Rituximab and/or Bendamustine in Patients with Previously Treated, Indolent Non-Hodgkin Lymphoma (iNHL)", BLOOD, ASH, US, vol. 118, No. 21, Dec. 13, 2011, p. 1160, XP008152289, ISSN: 0006-4971.
Flinn et al., "Clinical Safety and Activity in a Phase 1 Trial of IPI-145, a Potent Inhibitor of Phosphoinositide-3-Kinase-δ, γ, in Patients with advanced Hematologic Malignancies," Blood, vol. 120, No. 21, Nov. 16, 2012, p. 3663, XP008166549, & 54th ASH Annual Meeting (Dec. 10, 2012).
Fruman et al., "PI3Kδ Inhibitors in Cancer: Rationale and Serendipity Merge in the Clinic," Cancer Discovery, 1:562-572 (2011).
Furman et al., "CAL-101, an Isoform-Selective Inhibitor of Phosphatidylinositol 3-Kinase P110 delta, Demonstrates Clinical Activity and Pharmacodynamic Effects in patients with Relapsed or Refractory Chronic Lymphocytic Leukemia," BLOOD; 52nd Annual Meeeting of ASH, Orlando, FL, USA, vol. 116, No. 21, Nov. 1, 2010, p. 31, XP008168032, ISSN: 0006-4971.
Ghigo et al., "PI3K Inhibition in Inflammation. Toward tailored therapies for specific diseases," BioEssays 32 (2010), pp. 185-196.
Hall et al., "The dual PI3K/mTOR inhibitor NVP-BEZ235 enhances dexamethasone induced apoptosis in models of T-cell ALL with PTEN dysfunction and hyperactivated PI3K/Akt pathway.", Cancer Research: Apr. 15, 2013; vol. 73, Issue 8, Supplement 1, doi: 10.1158/1538-7445.AM2013-2757.
Harris et al., "PI3K isoforms as drug targets in inflammatory diseases: Lessons from pharmacological and genetic strategies", Curr. Opin. In Inv. Drugs, 2009, vol. 10(11), pp. 1151-1162.
Henderson et al., "Delineation of a Minimal Region of Deletion at 6q16.3 in Follicular Lymphoma and Construction of a Bacterial Artificial Chromosome Contig Spanning a 6-Megabase Region of 6q16-q21", Genes, Chromosomes & Cancer 40:60-65 (2004).
Herman et al., "Molecular Pathways: Targeting the Phosphoinositide 3-Kinase (PI3-Kinase) p110 delta in Chronic Lymphocytic Leukemia", Clin. Cancer Res. (Aug. 2012), vol. 18, pp. 4013-4018.
Higgs et al., "Patients with systemic lupus erythematosus, myositis, rheumatoid arthritis and scleroderma share activation of a common type I interferon pathway", Ann Rheum Dis, 2011, vol. 70 pp. 2029-2036.
Hoe et al., "Drugging the p53 pathway: understanding the rout to clinical efficacy", Nature Reviews Drug Discovery, Mar. 2014, vol. 13, pp. 217-236.
Infinity Pharmaceuticals, Inc.—Press Release dated Jul. 18, 2012, "Infinity Regains Worldwide Rights to PI3K, FAAH and Early Discovery Programs," Retrieved from the Internet: URL:http://phx.corporate-.net/phoenix.zhtml?c=121941&p=irol-newsArticle_print&ID=1715695&hightlight= [retrieved on Jan. 10, 2014].
Kassern, Noreen, "Top Ten Bone Diseases," LiveStrong.com, Apr. 29, 2011. <http://www.livestrong.com/article/119479-top-ten-bone-diseases/>.
Kridel et al., "Pathogenesis of follicular lymphoma", J. of Clinical Investigation, vol. 122, No. 10, Oct. 2012, pp. 3424-3431.

Kukulski et al., "The P2 receptor antagonist PPADS abrogates LPS-induced neutrophil migration in the murine air pouch via inhibition of MIP-2 and KC production," Mol. Immun., 47(4):833-839 (2010).
Macias-Perez and Flinn, "B-Cell Receptor Pathobiology and Tarteting in NHL," Curr. Oncol. Rep., 14:411-418 (2012).
Mansour et al., "Discovery of a Secreted Tumor Suppressor Provides a Promising Therapeutic Strategy for Follicular Lymphoma", Cancer Cell 20, Nov. 15, 2011, pp. 559-561.
MedicineNet.com, Cancer Definition, http://www.medterms.com, 2004.
Medline Plus, Autoimmune Diseases, NIH, 2014. <http://www.nlm.nih.gov/medlineplus/autoimmunediseases.html>.
NCBI, Nutritional and Metabolic Diseases, NCBI Bookshelf, 1998. <http://www.ncbi.nlm.nih.gov/books/NBK22259/>.
NCBI, The Nervous System, NCBI Bookshelf, 1998. <http://www.ncbi.nlm.nih.gov/books/NBK22197/>.
Okosun et al., "Integrated genomic analysis identifies recurrent mutations and evolution patterns driving the initiation and progression of follicular lymphoma", Nature Genetics (2014) vol. 46, No. 2, pp. 176-181.
Okosun et al., Supplementary Information "Integrated genomic analysis identifies recurrent mutations and evolution patterns driving the initiation and progression of follicular lymphoma", Nature Genetics (2014), doi:10.1038/ng.2856.
Oricchio et al., "The Eph-Receptor A7 Is a Soluble Tumor Suppressor for Follicular Lymphoma", Cell 147, 554-564, Oct. 28, 2011.
Pharmacyclics Inc. Form 8-K Filing. May 16, 2013. Article retrieved from the Internet: <http://www.sec.gov/Archives/edgar/data/949699/000092189513001115/0000921895-13-001115-index.htm> on Dec. 11, 2014.
Porter et al, "The Potent Phosphoinositide-3-Kinase-(δ,γ) Inhibitor IPI-145 is Active in Preclinical Models of Arthritis and Well Tolerated in Healthy Adult Subjects," *Arthritis & Rheumatism*, 64:S147 (2012).
Ross et al., "ComprehensiveAnalysis of Copy Number and Allele Status Identifies Multiple Chromosome Defects Underlying Follicular Lymphoma Pathogenesis", Clin Cancer Res 2007; 13(16), pp. 4777-4785, Aug. 15, 2007.
Schwaenen et al., "Microarray-Based Genomic Profiling Reveals Novel Genomic Aberrations in Follicular Lymphoma Which Associate with Patient Survival and Gene Expression Status", Genes, Chromosomes & Cancer 48:39-54 (2009) DOI 10.1002/gcc.
Sharman et al., "A Phase 1 Study of the Selective Phosphatidylinositol 3-Kinase-Delta (PI3K delta) Inhibitor, CAL-101 (GS-1101), in Combination with Rituximab and/or Bendamustine in Patients with Relapsed or Refractory Chronic Lymphocytic Leukemia (CLL)", BLOOD; 53rd ASH Annual Meeting, San Diego, CA, vol. 118, No. 21, Nov. 18, 2011, p. 779-780, XP008152290, ISSN: 006-4971 Retrieved from the Internet.
Song et al., "The antagonistic effect of PI3K-gamma inhibitor AS605240 on cardiac hypertrophy and cardiac fibrosis induced by isoproterenol in rats," Sichuan Da Xue Xue Bao Yi Xue Ban 42(4):471-474 (2011) (abstract only).
Suralkar et al., "In-Vivo Animal Models for Evaluationof Anti-Inflammatory Activity," Pharmainfo.net/reviews, vol. 6, Issue 2, Mar. 17, 2008; downloaded Nov. 4, 2014.
Treon et al., "A Prospective Multicenter Study of the Bruton's Tyrosine Kinase Inhibitor Ibrutinib in Patients with Relapsed or Refractory Waldenstrom's Macroglobulinemia," ASH Annual Meeting, Oral Presentation 251, Dec. 9, 2013.
Venable et al., "Phosphoinositide 3-kinase gamma (PI3Kgamma) inhibitors for the treatment of inflammation and autoimmune disease", Recent Pat Inflamm Allergy Drug Discov (2010) 4: 1-15.
Viardot et al., "Clinicopathologic Correlations of Genomic Gains and Losses in Follicular Lymphoma", Journal of Clinical Oncology, vol. 20, No. 23 (Dec. 1, 2002): pp. 4523-4530.
Vora et al., "CDK 4/6 Inhibitors Sensitize PIK3CA Mutant Breast Cancer to PI3K Inhibitors", Cancer Cell (Jul. 2014), vol. 26, pp. 136-149.
WebMD, Lung Disease Overview. (2014). <http://www.webmd.com/lung/lung-diseases-overview>.

(56) References Cited

OTHER PUBLICATIONS

Wei et al., "A phosphoinositide 3-kinase-γ inhibitor, AS605240 prevents bleomycin-induced pulmonary fibrosis in rats," Biochem. Biophy. Res. Comm. 397:311-317 (2010).
Wen et al., "Current clinical development of PI3K pathway inhibitors in glioblastoma", Neuro-Oncology (2012) vol. 14, pp. 819-829.
Winkler et al., "PI3K-d and PI3K-g Inhibition by IPI-145 Abrogates Immune Responses and Suppresses Activity in Autoimmune and Inflammatory Disease Models," Chemistry & Biology (2013),://dx.doi.org/10.1016/j.chembiol.2013.09.017.
Wong et al., "Targeting the PI3K signaling pathway in Cancer," Current Opinion in Genetics & Development, vol. 20, (2010), pp. 87-90.
Woyach et al., "Resistance Mechanisms for the Bruton's Tyrosine Kinase Inhibitor Ibrutinib," N Engl J Med 2014; 370; p. 2286-2294.
Zhao et al, "TNF-α promotes LPA1- and LPA3-mediated recruitment of leukocytes in vivo through CXCR2 ligand chemokines," J. Lipid Res., 52(7):1307-1318 (2011).
American Cancer Society. Non-Hodgkin's Lymphoma. Last Revised Mar. 11, 2015, Retrieved online: <http://www.cancer.org/cancer/nonhodgkinlymphoma/detailedguide/non-hodgkin-lymphoma-types-of-non-hodgkin-lymphoma>.
Ashizawa, Kazuhide, Science of polymorphism and crystallization in pharmaceutical products:, Maruzen Planet Co., Sep. 20, 2002, pp. 3-16.
Buet et al., "Cotargeting signaling pathways driving survival and cell cycle circumvents resistance to Kit inhibitors in leukemia", Blood, 119(18):4228-4241 (2012).
Calin et al., "A MicroRNA Signature Associated with Prognosis and Progression in Chronic Lymphocytic Leukemia", N Engl J Med, 353:1793-801 (2005).
Campbell, et al., "The Potent PI3K-δ,γ Inhibitor, IPI-145, Exhibits Differential Activity in Diffuse Large B-cell Lymphoma (DLBCL) Cell Lines", Dec. 7, 2013, 55th ASH Annual Meeting and Exposition, New Orleans, LA, Poster 1832.
Cao et al., "The BCL2 antagonist ABT-199 triggers apoptosis, and augments ibrutinib and idelalisib mediated cytotoxicity in CXCR4Wildtype and CXCR4WHIM mutated Watdenstmm macroglabulinaemia cells", British Journal of Haematology, 170(12):134-138 (2015).
Chang et al., "PI3-Kinase Inhibitors in Chronic Lymphocytic Leukemia", Current Hematologic Malignancy Reports, 9(1):33-43 (2014).
Chang et al., "Novel Synthesis and Reactions of 5, 7-Dialkyl-4,6-dioxo-4,5,6,7-tetrahydro-isothiazolo[3,4,-d]pyrimidine-3-carbonitriles and 6-Methyl-4-oxo-4H-1-aza-5-oxa-2-thiaindene-3-carbonitrile", Org. Lett. 5(4):507-510 (2003).
Chiron et al., "791 Induction of Early G1-Arrest by CDK4/CDK6 Inhibition Sensitizes Mantle Cell Lymphoma Cells to Selective PI3Kδ Inhibition by GS-1101 Through Enhancing the Magnitude and Duration of p-AKT Inhibition", American Society of Hematology, Dec. 10, 2013, retrieved from the internet: https://ash.confex.com/ash/2012/webprogram/Paper52021.html.
Choudhary et al., "MCL-1 and BCL-xL-dependent resistance to the BGL-2 inhibitor ABT-199 can be overcome by preventing PI3KJ AKT/mT4R activation in lymphoid malignancies", Cell Death & Disease 2015, 6: e1593 (2015).
Cui et al., "MicroRNA-155 influences B-cell receptor signaling and associates with aggressive disease in chronic lymphocytic leukemia", Blood, 124(4):546-554 (2014).
Engelman, J. "Targeting PI3K signalling in cancer: opportunities, challenges and limitations", Nature Reviews: Cancer, 9:550-562 (2009).
Flinn et al., "A Phase 1 Evaluation of Duvelisib (IPI-145), a PI3K-delta,gamma Inhibitor, in Patients with Relapsed/Refractory iNHL", American Society of Hematology Meeting, Dec. 6, 2014.
Flinn et al., "Preliminary Safety and Efficacy of IPI-145, a Potent Inhibitor of Phosphoinositide-3-Kinase-δ,γ, in Patients With Chronic Lymphocytic Leukemia", Blood, 122(21):677 (2013).

Fulci et al., "Quantitative technologies establish a novel microRNA profile of chronic lymphocytic leukemia", Blood, 109(11):4944-4951 (2007).
Goodman, A., "Encouraging Early Results With Novel Agents in CLL", The ASCO Post, Mar. 1, 2014, Reterieved from the internet: URL: http://www.ascopost.com/issues/march-1,-2014/encouraging-early-results-with-novel-agents-in-cll. aspx.
Graham et al., "The TAM family: phosphatidylserinesensing receptor tyrosine kinases gone awry in cancer", Nature Rev Cancer, 14:769-785 (2014).
Harb et al., "Combined Pharmacologic Inhibition of Bcl-Xl/Bcl-2 and mTORC1/2 Survival Signals Trigger Apoptosis in BCR-ABL1+ πin Vitro Models of Blast Crisis Chronic Myelogenous Leukemia (CML-BC), and Primary CD34+/CD38– Stem and CD34+ progenitor Cells From CML-BC Patients", Blood, 53rd Ash Annual Meeting and Exposition, San Diego, CA, Dec. 10-13, 2011, Retrieved from: https://ash.confex.com/ash/2011Jwebprogram/Paper44381.html.
Horwitz et al., "Duvelisib (IPI-145), a Phosphoinositide-3-Kinase-Delta,Gamma Inhibitor, Shows Activity in Patients with Relapsed/Refractory T-Cell Lymphoma", American Society of Hematology Meeting, Dec. 6, 2014.
Infinity Pharmaceuticals, Inc., "Infinity Reports Preclinical Data at ASH Annual Meeting in Diffuse Large B-Cell Lymphoma and T-Cell Acute Lymphoblastic Leukemia Suggesting Broad Potential of IPI-145 in Blood Cancers", http://businesswire.com, Dec. 7, 2013, Downloaded from: http://www.businesswire.com/news/home/20131207005015/en/Infinity-Reports-Preclinical-Data-Ash-Annual-Meeting.
Kavanagh, et al., "Patient. Mylodysplastic syndromes. 2012," [online], Retrieved on Apr. 24, 2015, <http://www.patient.co.uk/doctor/myelodysplastic-syndromes-pro>.
Kiefer, "Lymphoma Prevention," Healthline. 2011, <http://www.healthline.com/health/lymphoma/prevention>.
Letai et al., "Antiapoptotic BCL-2 is required for maintenance of a model leukemia", Cancer. Cell, 6(3):241-249 (2004).
Linhua et al., "Efficacy and Mechanisms of Apoptosis Induction by Simultaneous Inhibition of PI3K with GDC-0941 and Blockade of Bc1-2 (ABT-737) or FLT3 (Sorafenib) in AML Cells in the Hypoxic Bone Marrow Microenvironment", Blood, 116:777 (2010).
Liu et al., "Improved synthesis of α-BOC-aminoketones from α-BOC-amino-Weinreb amides using a pre-deprotonation protocol", Tetrahedron Letters, 43(46):8223-8226 (2002).
Martin-Sanchez et al., "Simultaneous inhibition of pan-phosphatidylinositol-3-kinases and MEK as a potential therapeutic strategy in peripheral T-cell lymphomas", Haematologica, 98(1):57-64 (2013).
Milella et al., 566 POSTER Anti-leukemic activity of the novel MEK inhibitor PD0325901, European Journal of Cancer Supplement, 4(12):172 (2006).
Morrison, C., "First P13k inhibitor launches info crowded hematology markets", Nature Biotechnology, 32(10):963-964 (2014).
Mraz and Kipps, "MicroRNAs and B cell receptor signaling in chronic lymphocytic leukemia", Leukemia & Lymphoma, 54(8):1836-1839 (2013).
Mraz et al., "MicroRNAs in chronic lymphocytic leukemia pathogenesis and disease subtypes", Leukemia & Lymphoma, 50(3):506-509 (2009).
Mraz et al., "miR-150 influences B-cell receptor signaling in chronic lymphocytic leukemia by regulating expression of GAB1 and FOXP1", Blood 124(1):84-95 (2014).
Muranen et al., "Inhibition of P13K/mTOR Leads to Adaptive Resistance in Matrix-Attached Cancer Cells", Cancer Cell, 21(2):227-239 (2011).
Muranen et al., "Promising Rationally Derived Combination Therapy with PI3K and CDK4/6 Inhibitors", Cancer Cell, 26(1):7-9 (2014).
Musilova and Mraz, "MicroRNAs in B-cell lymphomas: how a complex biology gets more complex", Leukemia 1-14 (2015).
Nakai, Yoshinobu, et. al., ed., New galenical pharmacy, Nanzando Co., Ltd., Apr. 25, 1984, pp. 102-103, 232-233.
National Cancer Institute, "AIDS-Related Lymphoma Treatment," 2015. <http://www.cancer.gov/cancertopics/pdq/treatment/AIDS-related-lymphoma/Patient/page1>.

(56) References Cited

OTHER PUBLICATIONS

Nishigaki, Sadao, Dispensing pharmacy (Principle and application), Nanzando Co., Ltd, Sep. 20, 1977, pp. 142-145.
O'Connor, "Adult T-Cell Leukemia/Lymphoma (HTLV-1)", Lymphoma Research Foundation, 2008, 1-4.
Okano, Teisuke, New general remarks of practical pharmacy, 3rd ed., Nankodo Co., Ltd, Apr. 10, 1987, p. 111.
Okkenhaug, K., "Two Birds with One Stone: Dual p110δ and p110γ Inhibition", Chemistry and Biology, 20(11):1309-1310 (2013).
Oltersdorf et al., "An inhibitor of Bcl-2 family proteins induces regression of solid tumours", Nature, 435:677-681 (2005).
Patel et al., "Early Clinical Activity and Pharmacodynamic Effects of Duvelisib, a PI3K-delta,gamma Inhibitor, in Patients with Treatment-Naïve CLL", ASCO Annua Meeting, May 29-Jun. 2, 2015, Chicago, IL (poster).
Qian et al., "Synergy between phosphatidylinositol 3-kinase/Akt pathway and Bcl-xL in the control of apoptosis in adenocarcinoma cells of the lung", Molecular Cancer Therapeutics, 8(1):101-109 (2009).
Rahmani et al., "Dual Inhibition of Bcl-2 and Bcl-xL, Strikingly Enhances PI3K Inhibition-Induced Apoptosis in Human Myeloid Leukemia Cells through a GSK3- and Bim-Dependent Mechanism", Cancer Research, 73(4):1340-1351 (2013).
Roberts et al., "Substantial Susceptibility of Chronic Lymphocytic Leukemia to BCL2 Inhibition: Results of a Phase I Study of Navitoclax in Patients With Relapsed or Refractory Disease", Journal of Clinical Oncology, 30(5):488-496 (2012).
Schwamb et al., "B-cell receptor triggers drug sensitivity of primary CLL cells by controlling glucosylation of ceramides", Blood, 120(19):3978-3985 (2012).
Seda and Mraz, "B-cell receptor signalling and its crosstalk with other pathways in normal and malignant cells", European Journal of Haematology 94(3):193-205 (2015).
Seymour et al., "Bcl-2 Inhibitor ABT-199 (GDC-0199) Monotherapy Shows Anti-Tumor Activity Including Complete Remissions in High-Risk Relapsed/Refractory (R/R) Chronic Lymphocytic Leukemia (CLL) and Small Lymphocytic Lymphoma (SLL)", Blood, 122(21):872 (2013).
Simioni et al., "Cytotoxic activity of the novel Akt inhibitor, MK-2206, in T-cell acute lymphoblastic leukemia", Leukemia, 26(11):2336-2342 (2012).
Stone, Richard. "Mast Cell Leukemia and Other Mast Cell Neoplasms." In: Kufe DW, Pollock RE, Weichselbaum RR, et al., editors. Holland-Frei Cancer Medicine. 6th Edition. Hamilton (ON): BC Decker, 2003. URL: <http://www.ncbi.nlm.nih.gov/books/NBK13427/>.
Sylvester Comprehensive Cancer Center, "Definition: Leukemia, Lymphoma and Myeloma," 2015. URL: <http://sylvester.org/cancer/leukemia-lymphoma-and-myeloma/education/definition>.
The Chemical Society of Japan ed., Jikken kagaku kouza (zoku), 2. Bunri to seisei (Experimental chemical lecture, second series, 2. Separation and purification), Maruzen Co., Ltd., Jan. 25, 1967, pp. 159-178, 186-187.
Tong et al., "Perifosine induces protective autophagy and upregulation of ATG5 in human chronic myelogenous leukemia cells in vitro", Acta Pharmacologica Sinica, 33(4):542-550 (2012).
Vachhani et al., "Ratianal combination of dual PI3K/mTOR blockade and Bcl-2/-xl inhibition in AML", Physiological Genomics, 46(13):448-456 (2014).
Veliz et al., "Treatment of relapsed or refractory chronic lymphocytic leukemia", Cancer Control, 19:37-53 (2012).
WebMD, "Chronic Myeloproliferative Disorders Treatment (PDQ®): Treatment-Patient Information [NCI]—General Information About Chronic Myeloproliferative Disorders," 2014. <http://webmd.com/cancer/tc/chronic-myeloproliferative-disorders-treatment-patient-information-nci-pdq-general-information>.
WebMD, "HIV & AIDS Heath Center HTLV Type I and Type II," 2014. <http://www.webmd.com/hiv-aids/htlv-type-i-and-type-ii>.
WebMD, Leukemia-Prevention. Cancer Health Center. 2012. <http://www.webmd.com/cancer/tc/leukemia-prevention>.

Wullschleger et al., "Quantitative MRI Establishes the Efficacy of PI3K Inhibitor (GDC-0941) Multi-Treatments in PTEN-deficient Mice Lymphoma", Anticancer Research, 32(2):415-420 (2012).
Wymann et al., "Phosphoinositide 3-kinase γ: a key modulator in inflammation and allergy," Biochem Soc. Transactions, 31(part 1):275-280 (2003).
Yu et al., "Development of a Practical Synthesis of DPP IV Inhibitor LY2497282", Organic Process Research & Development, 12(2):218-225 (2008).
Zhu et al., "PI3K inhibition potentiates Bcl-2-dependent apoptosis in renal carcinoma cells", Journal of Cellular and Molecular Medicine, 17(3):377-385 (2013).
Equivalent Surface Area Dosage Conversion Factors (https://ncifrederick.cancer.gov/lasp/acuc/frederick/Media/Documents/ACUC42.pdf, Aug. 2007).
CAL-101, PubChem CID 11625818, created date Oct. 26, 2006.
Mashkovskiy, Lekarstvennye sredstva, vol. 1, 2001, p. 11.
Akinleye et al., "Phosphatidylinositol 3-kinase (PI3K) inhibitors as cancer therapeutics", Journal of Hematology & Oncology, Nov. 2013, vol. 6:88, pp. 1-18.
Brittain, H.G., et al. "Polymorphism in pharmaceutical solids" edited by H. G. Brittain, Marcel Dekker, D.J.W., Grant (chapter 1), p. 1-10 and J. K. Guillory (chapter 5); p. 183-226 (1999).
Byrn, S. et al. "Pharmaceutical Solids: A Strategic Approach to Regulatory Considerations"; S. Byrn et al.; Pharmaceutical research, vol. 12, No. 7, p. 945-954 (1995).
Chabner et al., "Chemotherapy and the war on cancer", Nature Reviews Cancer, 2005, Nature Publishing Group, vol. 5, pp. 65-72.
D'Cruz et al., "Protein kinase inhibitors against malignant lymphoma", Expert Opinion on Pharmacotherapy, Mar. 2013, Taylor and Francis Group, vol. 14(6), pp. 707-721.
Kakkola et al., "Anticancer compound ABT-263 accelerates apoptosis in virus-infected cells and imbalances cytokine production and lowers survival rates of infected mice", Cell Death & Disease (2013) 4, e742.
Leaf, "Why We're Losing the War on Cancer—and How to Win it", Fortune, Mar. 9, 2004, Time Inc., pp. 1-28.
Vaillant et al., "Targeting BCL-2 with the BH3 Mimetic ABT-199 in Estrogen Receptor-Positive Breast Cancer", Cancer Cell 24, pp. 120-129, Jul. 8, 2013.
Vanhaesebroek et al., "Molecules in medicine mini-review: isoforms of PI3K in biology and disease," J. Mol. Med., 94(1):5-11 (2016). e-published Dec. 10, 2015.
Stedman's Medical Dictionary Stedman's online. Autoimmune disease; <http://stedmansonline.com/content.aspx?id=mlrA210000248l&termtype=> (accessed Mar. 11, 2017).
Hirayama, Noriaki, Yuki Kagoubutsu Kessyo Sakusei Handbook—Genri to Nouhau (Handbook of organic compound crystal production—principle and know-how-), Maruzen Co., Ltd., Jul. 25, 2008, pp. 57-74.
Akira Ogata, Chemical experiment manual, Nankodo Co.,Ltd., Jun. 20, 1977, 36th edit., pp. 515-535.
Shadan-hojin Japan Chemistry Association, Kagaku Binran Ouyou Kagaku hen, 6th edit., Maruzen Co., Ltd., Jan. 30, 2003, pp. 178.
White et al., "Abstract 376: Combination of duvelisib with either ibrutinib or dexamethasone prevents mTOR-dependent feedback in aggressive B-cell lymphoma cell lines", Cancer Research, vol. 76, No. Suppl. 14, Apr. 2016, Proceedings of the 107th Annual Meeting of the American Association for Cancer Research; Apr. 16-20, 2016; New Orleans, LA, Retrieved from the Internet: URL:http://cancerres.aacrjournals.org/content/76/14_Supplement/376 [retrieved on Sep. 13, 2017].
Bedognetti et al., "Checkpoint Inhibitors and Their Application in Breast Cancer (including supplementary information)", Breast Care, vol. 11, No. 2, Apr. 26, 2016, pp. 108-115.
De Henau et al., "Abstract 554: Checkpoint blockade therapy is improved by altering the immune suppressive microenvironment with IPI-549, a potent and selective inhibitor of PI3K-gamma, in preclinical models", Cancer Research, Apr. 2016, 107th Annual Meeting of the American Association for Cancer Research; Apr. 16-20, 2016; New Orleans, LA, Retrieved from the Internet: URL:http://cancerres.aacrjournals.org/content/76/14_Supplement/554 [retrieved on Sep. 13, 2017].

(56) References Cited

OTHER PUBLICATIONS

Mittendorf et al., "PD-L1 expression in triple-negative breast cancer", Cancer Immunol. Res. 2014, 2:361-370.
Attiyeh et al., "Pharmacodynamic and genomic markers associated with response to the XPO1/CRM1 inhibitor selinexor (KPT-330): a report from the pediatric preclinical testing program," Journal: Pediatric Blood & Cancer 63(2):276-286 (2016).
Corrales et al., "Direct Activation of STING in the Tumor Microenvironment Leads to Potent and Systemic Tumor Regression and Immunity," Cell Rep. 11(7):1018-1030 (2015).
Naddafi et al., "Anti-CD19 Monoclonal Antibodies: a New Approach to Lymphoma Therapy," Int. J Mol Cell Med. 4(3):143-151 (2015).
Sato et al. "FLT3 Ligand Impedes the Efficacy of FLT3 Inhibitors in Vitro and in Vivo," Blood 117(12):3286-3293 (2011).
Shcheblyakov et al. "Toll-Like Receptors (TLRs): The Role in Tumor Progression," Acta Naturae, vol. 2, No. 3(6), pp. 21-29 (2010).

\* cited by examiner

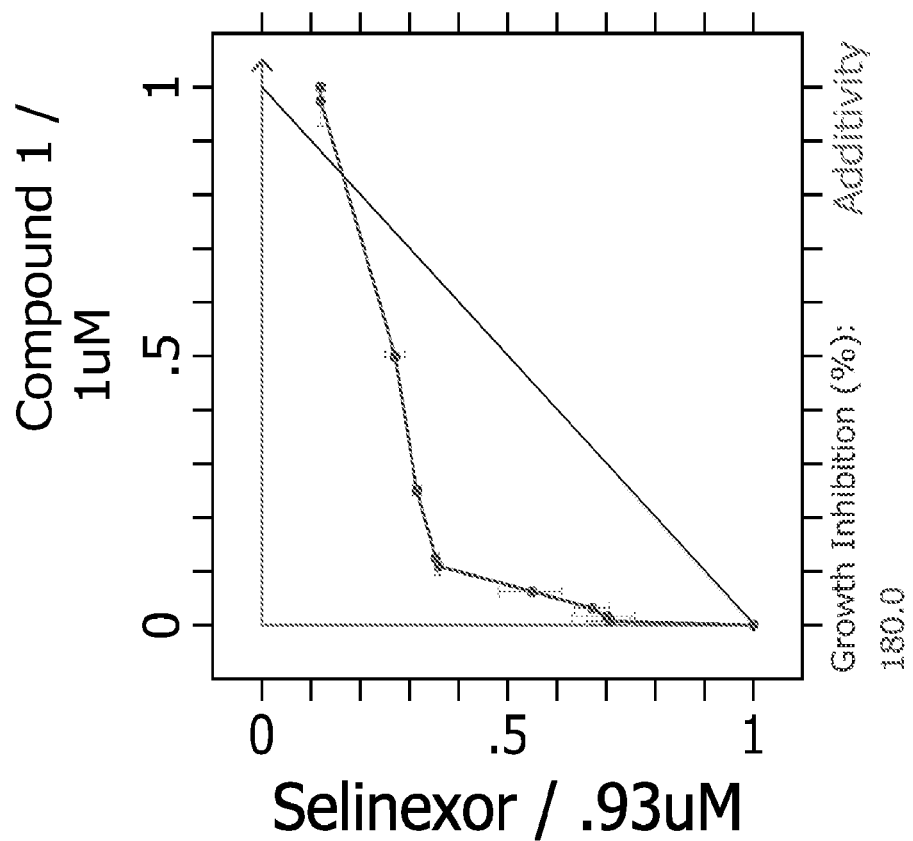

COMBINATION THERAPIES

This application is a national phase entry pursuant to 35 U.S.C. § 371 of International Application No. PCT/US2017/038966, filed Jun. 23, 2017, which claims priority to U.S. Provisional Application No. 62/354,637, filed Jun. 24, 2016, the entirety of each of which is incorporated herein by reference.

BACKGROUND

The phosphoinositide 3-kinases (PI3Ks) signaling pathway is one of the most highly mutated systems in human cancers. PI3Ks are members of a unique and conserved family of intracellular lipid kinases that phosphorylate the 3'—OH group on phosphatidylinositols or phosphoinositides. The PI3K family comprises 15 kinases with distinct substrate specificities, expression patterns, and modes of regulation. The class I PI3Ks (p110α, p110β, p110δ, and p110γ) are typically activated by tyrosine kinases or G-protein coupled receptors to generate phosphatidylinositol (3,4,5)-trisphosphate (PIP3), which engages downstream effectors such as those in the AKT/PDK1 pathway, mTOR, the Tec family kinases, and the Rho family GTPases. The class II and III PI3Ks play a key role in intracellular trafficking through the synthesis of phosphatidylinositol 3-bisphosphate (PI(3)P) and phosphatidylinositol (3,4)-bisphosphate (PI(3,4)P2). The PI3Ks are protein kinases that control cell growth (mTORC1) or monitor genomic integrity (ATM, ATR, DNA-PK, and hSmg-1).

There are four mammalian isoforms of class I PI3Ks: PI3K-α, β, δ (class Ia PI3Ks) and PI3K-γ (a class Ib PI3K). These enzymes catalyze the production of PIP3, leading to activation of downstream effector pathways important for cellular survival, differentiation, and function. PI3K-α and PI3K-β are widely expressed and are important mediators of signaling from cell surface receptors. PI3K-α is the isoform most often found mutated in cancers and has a role in insulin signaling and glucose homeostasis (Knight et al. Cell (2006) 125(4):733-47; Vanhaesebroeck et al. Current Topic Microbiol. Immunol. (2010) 347:1-19). PI3K-β is activated in cancers where phosphatase and tensin homolog (PTEN) is deleted. Both isoforms are targets of small molecule therapeutics in development for cancer.

PI3K-δ and -γ are preferentially expressed in leukocytes and are important in leukocyte function. These isoforms also contribute to the development and maintenance of hematologic malignancies (Vanhaesebroeck et al. Current Topic Microbiol. Immunol. (2010) 347:1-19; Clayton et al. J Exp Med. (2002) 196(6):753-63; Fung-Leung Cell Signal. (2011) 23(4):603-8; Okkenhaug et al. Science (2002) 297 (5583): 1031-34). PI3K-δ is activated by cellular receptors (e.g., receptor tyrosine kinases) through interaction with the Sarc homology 2 (SH2) domains of the PI3K regulatory subunit (p85), or through direct interaction with RAS.

SUMMARY

Provided herein are, at least in part, compositions and methods comprising a PI3K inhibitor in combination with a selected second therapeutic agent. In one embodiment, it has been discovered that combinations of a PI3K inhibitor with a second therapeutic agent chosen from one or more of: 1) a checkpoint modulator, 2) an XPO1 inhibitor, 3) an anti-CD19 antibody, 4) a TLR agonist, 5) a STING agonist, or 6) a Flt3 ligand, or a combination thereof, have a synergistic effect in treating a cancer (e.g., in reducing cancer cell growth or viability, or both). The combinations of PI3K inhibitors and selected second therapeutic agents can allow the PI3K inhibitor, the second therapeutic agent, or both, to be administered at a lower dosage than would be required to achieve the same therapeutic effect compared to a monotherapy dose. In some embodiments, the combination can allow the PI3K inhibitor, the second therapeutic agent, or both, to be administered at a lower frequency than if the PI3K inhibitor or the second therapeutic agent were administered as a monotherapy. Such combinations can provide advantageous effects, e.g., in reducing, preventing, delaying, and/or decreasing in the occurrence of one or more of: a side effect, toxicity, or resistance that would otherwise be associated with administration of a higher dose of the agents.

Accordingly, in one aspect, provided herein is a composition (e.g., one or more pharmaceutical compositions or dosage forms), comprising a PI3K inhibitor (e.g., one or more PI3K inhibitors), or a pharmaceutically acceptable form thereof, in combination with a second agent (e.g., one or more second therapeutic agents), or a pharmaceutically acceptable form thereof. In certain embodiments, the second therapeutic agent is chosen from one or more of: 1) a checkpoint modulator, 2) an XPO1 inhibitor, 3) an anti-CD19 antibody, 4) a TLR agonist, 5) a STING agonist, or 6) a Flt3 ligand, or a combination thereof. The PI3K inhibitor and the second agent can be present in a single composition or as two or more different compositions. The PI3K inhibitor and the second agent can be administered via the same administration route or via different administration routes.

In some embodiments, the composition (e.g., one or more compositions or dosage forms) comprising the combination of PI3K inhibitor and the second agent is synergistic, e.g., has a synergistic effect in treating a cancer (e.g., in reducing cancer cell growth or viability, or both). In certain embodiments, the amount or dosage of the PI3K inhibitor, the second agent, or both, present in the composition(s) does not exceed the level at which each agent is used individually, e.g., as a monotherapy. In certain embodiments, the amount or dosage of the PI3K inhibitor, the second agent, or both, present in the composition(s) is lower (e.g., at least 20%, at least 30%, at least 40%, or at least 50%) than the amount or dosage of each agent used individually, e.g., as a monotherapy. In other embodiments, the amount or dosage of the PI3K inhibitor, the second agent, or both, present in the composition(s) that results in a desired effect (e.g., treatment of cancer, achieve inhibition (e.g., 50% inhibition), achieve growth inhibition (e.g., 50% growth inhibition), or achieve a therapeutic effect) is lower (e.g., at least 20%, at least 30%, at least 40%, or at least 50% lower) than the amount or dosage of each agent used individually, e.g., as a monotherapy. In certain embodiments, the frequency of administration of the PI3K inhibitor that achieves a therapeutic effect is lower (e.g., at least 20%, 30%, 40%, or 50% lower), when the PI3K inhibitor is administered in combination with the second agent than when the PI3K inhibitor is administered alone. In some embodiments, the frequency of administration of the second agent that achieves a therapeutic effect is lower (e.g., at least 20%, 30%, 40%, or 50% lower), when the second agent is administered in combination with PI3K inhibitor than when the second agent is administered alone.

In another aspect, provided herein is a method of treating, managing, or preventing a cancer in a subject. The method comprises administering to the subject a PI3K inhibitor (e.g., one or more PI3K inhibitors), or a pharmaceutically acceptable form thereof, in combination with a second agent (e.g., one or more second therapeutic agents), or pharmaceutically acceptable form thereof. In certain embodiments, the second agent is chosen from one or more of: 1) a checkpoint modulator, 2) an XPO1 inhibitor, 3) an anti-CD19 antibody, 4) a TLR agonist, 5) a STING agonist, or 6) a Flt3 ligand, or a combination thereof. In another aspect, provided herein is a composition for use in the treatment of a cancer. The composition for use in the treatment of cancer comprises a PI3K inhibitor (e.g., one or more PI3K inhibitors), or a pharmaceutically acceptable form thereof, in combination with a second agent (e.g., one or more second therapeutic agents), or pharmaceutically acceptable form thereof. The PI3K inhibitor and the second therapeutic agent can be present in a single dose form, or as two or more dose forms.

The combination of the PI3K inhibitor and the second agent can be administered together in a single composition or administered separately in two or more different compositions, e.g., pharmaceutical compositions or dosage forms as described herein. The administration of the PI3K inhibitor and the second agent can be in any order. For example, the PI3K inhibitor can be administered concurrently with, prior to, or subsequent to, the second agent. In one embodiment, the second agent is administered to a subject at least 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, 12 weeks, or 16 weeks before the PI3K inhibitor (e.g., Compound 1), or a pharmaceutically acceptable form thereof, is administered. In another embodiment, the second agent is administered concurrently with the PI3K inhibitor (e.g., Compound 1), or a pharmaceutically acceptable form thereof, e.g., in a single dosage form or separate dosage forms. In yet another embodiment, the second agent is administered to the subject at least 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, 12 weeks, or 16 weeks after the PI3K inhibitor (e.g., Compound 1), or a pharmaceutically acceptable form thereof, is administered. In some embodiments, the PI3K inhibitor and the second agent are administered with a timing that results in both agents being present at therapeutic levels at the same time in the patient. In some embodiments, the PI3K inhibitor and the second agent are administered sequentially. In some embodiments, administration of the PI3K inhibitor and the second agent overlaps in part with each other. In some embodiments, initiation of administration of the PI3K inhibitor and the second agent occurs at the same time. In some embodiments, the PI3K inhibitor is administered before initiating treatment with the second agent. In some embodiments, the second agent is administered before initiating treatment with the PI3K inhibitor. In some embodiments, the administration of the PI3K inhibitor continues after cessation of the administration of the second agent. In some embodiments, the administration of the second agent continues after cessation of the administration of the PI3K inhibitor.

In some embodiments, the combination of the PI3K inhibitor and the second agent is additive, e.g., the effect of the combination is similar to their individual effects added together. In certain embodiments, the combination of the PI3K inhibitor and the second agent is synergistic, e.g., has a synergistic effect in treating the cancer (e.g., in reducing cancer cell growth or viability, or both). In some embodiments, the amount or dosage of the PI3K inhibitor, the second agent, or both, used in combination does not exceed the level at which each agent is used individually, e.g., as a monotherapy. In certain embodiments, the amount or dosage of the PI3K inhibitor, the second agent, or both, used in combination is lower (e.g., at least 20%, at least 30%, at least 40%, or at least 50% lower) than the amount or dosage of each agent used individually, e.g., as a monotherapy. In other embodiments, the amount or dosage of the PI3K inhibitor, the second agent, or both, used in combination that results in treatment of cancer is lower (e.g., at least 20%, at least 30%, at least 40%, or at least 50% lower) than the amount or dosage of each agent used individually, e.g., as a monotherapy. In certain embodiments, the frequency of administration of the PI3K inhibitor, the second agent, or both, used in combination that results in treatment of cancer is lower (e.g., at least 20%, 30%, 40%, or 50% lower), than the frequency of administration of each agent used individually, e.g., as a monotherapy.

The combination of PI3K inhibitor and the second agent can be administered during periods of active disorder, or during a period of remission or less active disease. The combination can be administered before a third treatment (e.g., a third therapeutic agent or a procedure (e.g., radiation or surgery)), concurrently with the third treatment, after the third treatment, or during remission of the disorder.

In another aspect, provided herein is a method of inhibiting the growth, the viability, or both, of a cancer cell, comprising contacting the cancer cell with a PI3K inhibitor (e.g., one or more PI3K inhibitors), or a pharmaceutically acceptable form thereof, in combination with a second agent (e.g., one or more second therapeutic agents), or pharmaceutically acceptable form thereof. In certain embodiments, the second agent is chosen from one or more of: 1) a checkpoint modulator, 2) an XPO1 inhibitor, 3) an anti-CD19 antibody, 4) a TLR agonist, 5) a STING agonist, or 6) a Flt3 ligand, or a combination thereof. The methods described herein can be used in vitro or in vivo, e.g., in an animal subject or as part of a therapeutic protocol.

The contacting of the cell with the PI3K inhibitor and the second agent can be in any order. In certain embodiments, the cell is contacted with the PI3K inhibitor concurrently, prior to, or subsequent to, the second agent. In certain embodiments, the combination of the PI3K inhibitor and the second agent is synergistic, e.g., has a synergistic effect in reducing cancer cell growth or viability, or both. In some embodiments, the amount or dosage of the PI3K inhibitor, the second agent, or both, used in combination does not exceed the level at which each agent is used individually, e.g., as a monotherapy. In certain embodiments, the amount or dosage of the PI3K inhibitor, the second agent, or both, used in combination is lower (e.g., at least 20%, at least 30%, at least 40%, or at least 50% lower) than the amount or dosage of each agent used individually, e.g., as a monotherapy.

In another aspect, provided herein is a synergistic combination of a PI3K inhibitor, or a pharmaceutically acceptable form thereof, and a second therapeutic agent, or a pharmaceutically acceptable form thereof, wherein the second agent is selected from one or more of 1) a checkpoint modulator, 2) an XPO1 inhibitor, 3) an anti-CD19 antibody, 4) a TLR agonist, 5) a STING agonist, or 6) a Flt3 ligand, or a combination thereof, for use in treating cancer. In another aspect, provided herein is a synergistic combination of a PI3K inhibitor, or a pharmaceutically acceptable form thereof, and a second therapeutic agent, or a pharmaceutically acceptable form thereof, wherein the second agent is selected from one or more of 1) a checkpoint modulator, 2) an XPO1 inhibitor, 3) an anti-CD19 antibody, 4) a TLR agonist, 5) a STING agonist, or 6) a Flt3 ligand, or a combination thereof, for use in a medicament. In another aspect, provided herein is a use of a synergistic combination of a PI3K inhibitor, or a pharmaceutically acceptable form thereof, and a second therapeutic agent, or a pharmaceutically acceptable form thereof, wherein the second agent is selected from one or more of 1) a checkpoint modulator, 2) an XPO1 inhibitor, 3) an anti-CD19 antibody, 4) a TLR agonist, 5) a STING agonist, or 6) a Flt3 ligand, or a combination thereof, for treating cancer. In another aspect, provided herein is a use of a synergistic combination of a PI3K inhibitor, or a pharmaceutically acceptable form thereof, and a second therapeutic agent, or a pharmaceutically acceptable form thereof, wherein the second agent is selected from one or more of 1) a checkpoint modulator, 2) an XPO1 inhibitor, 3) an anti-CD19 antibody, 4) a TLR agonist, 5) a STING agonist, or 6) a Flt3 ligand, or a combination thereof for the manufacture of a medicament for treating cancer.

Additional features or embodiments of the compositions or methods described herein include one or more of the following:

In certain embodiments, the combination of the PI3K inhibitor and the second agent used in the compositions and methods described herein is synergistic, e.g., as indicated by a combination index value that is less than 1 for the combination of the PI3K inhibitor and the second agent. In certain embodiments, the combination is synergistic as indicated by a combination index value that is less than 0.7 for the combination of the PI3K inhibitor and the second agent. In certain embodiments, the combination is synergistic as indicated by a combination index value that is less than 0.5 for the combination of the PI3K inhibitor and the second agent. In certain embodiments, the combination is synergistic as indicated by a combination index value that is less than 0.7, 0.6, 0.5, 0.4, 0.3, 0.2, or 0.1 for the combination of the PI3K inhibitor and the second agent. In some embodiments, the combination of the PI3K inhibitor and the second agent used in the compositions and methods described herein is additive, e.g., as indicated by a combination index value that is equal to about 1 for the combination of the PI3K inhibitor and the second agent. In certain embodiments, the combination index value is assessed at 50% inhibition, e.g., as described herein in the Examples. In certain embodiments, the combination index value is assessed at 50% growth inhibition, e.g., as described herein in the Examples. In certain embodiments, the combination index value is assessed at 10%, 20%, 30%, 40%, 50%, 60%, 60%, 70%, 80%, or 90% inhibition or growth inhibition. In certain embodiments, the combination index value is calculated as described herein in the Examples.

In other embodiments, the combination of the PI3K inhibitor and the second agent used in the compositions and methods described herein is synergistic, e.g., as indicated by a synergy score value of greater than 1, 2, or 3. In certain embodiments, the combination is synergistic as indicated by a synergy score value of greater than 1. In certain embodiments, the combination is synergistic as indicated by a synergy score value of greater than 2. In certain embodiments, the combination is synergistic as indicated by a synergy score value of greater than 3. In some embodiments, the combination of the PI3K inhibitor and the second agent used in the compositions and methods described herein is additive, e.g., as indicated by a synergy score value of zero. In certain embodiments, the synergy score is calculated as described herein in the Examples.

In some embodiments, the anti-cancer effect provided by the combination of the PI3K inhibitor and the second agent used in the compositions and methods described herein is greater than the anti-cancer effect provided by an agent (e.g., the PI3K inhibitor or the second agent) used individually, e.g., as a monotherapy. In certain embodiments, the anti-cancer effect provided by the combination of the PI3K inhibitor and the second agent is at least 2 fold greater, at least 3 fold greater, at least 5 fold greater, or at least 10 fold greater than the anti-cancer effect provided by an agent used individually, e.g., as a monotherapy (e.g., by a monotherapy with the same dose of the PI3K inhibitor, or by a monotherapy with the same dose of the second agent).

In some embodiments, the anti-cancer effect provided by the combination of the PI3K inhibitor and the second agent used in the compositions and methods described herein is greater than the anti-cancer effect provided by a monotherapy with the same dose of the PI3K inhibitor. In certain embodiments, the anti-cancer effect provided by the combination is at least 2 fold greater, at least 3 fold greater, at least 5 fold greater, or at least 10 fold greater than the anti-cancer effect provided by the monotherapy with the same dose of the PI3K inhibitor.

In some embodiments, the anti-cancer effect of the combination of the PI3K inhibitor and the second agent used in the compositions and methods described herein is greater than the anti-cancer effect provided by a monotherapy with the same dose of the second agent. In certain embodiments, the anti-cancer effect of the combination of the PI3K inhibitor and the second agent is at least 2 fold greater, at least 3 fold greater, at least 5 fold greater, or at least 10 fold greater than the anti-cancer effect provided by the monotherapy with the same dose of the second agent.

In some embodiments, one or more side effects of the PI3K inhibitor, the second agent, or both, is reduced compared with the side effects of each agent when used individually, e.g., as a monotherapy (e.g., a monotherapy comprising the PI3K inhibitor without the second agent at a dose that achieves the same therapeutic effect; or a monotherapy comprising the second agent without the PI3K inhibitor). For example, a reduction, prevention, delay, or decrease in the occurrence or the likelihood of occurrence of one or more side effects, toxicity, or resistance, that would otherwise be associated with administration of at least one of the agents, e.g., the PI3K inhibitor.

In some embodiments, one or more side effects of the compositions or methods described herein is reduced compared with the side effects of a monotherapy comprising either the second agent (or pharmaceutically acceptable form thereof) or the PI3K inhibitor (or pharmaceutically acceptable form thereof) at a dose that achieves the same therapeutic effect.

In some embodiments, said one or more side effects includes a liver enzyme level, e.g., a liver enzyme level indicative of toxicity.

In some embodiments, the combination of the PI3K inhibitor and the second agent used in the compositions and methods described herein results in a reduction in resistance (e.g., a decrease in a measure of resistance or a decreased likelihood of developing resistance), or a delay in the development of resistance, to at least one of the agents, e.g., resistance (e.g., acquired resistance) to the PI3K inhibitor.

In some embodiments, the combination of the PI3K inhibitor and the second agent used in the compositions and methods described herein results in a reduction in minimal residual disease (MRD). In certain embodiments, the combination of a PI3K inhibitor (e.g. a PI3K inhibitor described herein) and a second agent (e.g., a second agent described herein) is effective to reduce the MRD in the subject, e.g., below a level previously measured in the subject (e.g., the level measured before the combination was administered). In certain embodiments, the combination of a PI3K inhibitor and a second agent is effective to reduce the MRD in the subject below the level observed during or after treatment with a monotherapy, e.g., a monotherapy comprising either the PI3K inhibitor or the second agent. In certain embodiments, the MRD is decreased below the level observed during treatment with a monotherapy comprising the PI3K inhibitor. In certain embodiments, the MRD is decreased below the level observed during treatment with a monotherapy comprising the second agent. In certain embodiments, the combination is effective to reduce the level of MRD below a preselected cutoff value (e.g., 1 malignant cell in 100 normal cells, 1 malignant cell in 1000 normal cells, or 1 malignant cell in 10,000 normal cells). In certain embodiments, the preselected cutoff value is 1 malignant cell in 1000 or 10,000 normal cells. In some embodiments, a subject exhibits MRD negativity (or is MRD-negative) if the MRD is below a preselected cutoff value (e.g., a preselected cutoff value as described herein). In some embodiments, the level of MRD is not detectable by standard laboratory methodologies.

In another aspect, provided herein is a method of decreasing the level of MRD in a subject having a cancer. The method comprises:

(a) administering to the subject a PI3K inhibitor (e.g., Compound 1), or a pharmaceutically acceptable form thereof, in combination with a second agent (e.g., a second agent chosen from one or more of a checkpoint modulator, an XPO1 inhibitor, an anti-CD19 antibody, a TLR agonist, a STING agonist, or a Flt3 ligand, or a combination thereof, as described herein) (also referred to as "a first treatment");

(b) monitoring the level of MRD in the subject, e.g., by one or more methods described herein or known in the art (e.g., flow cytometry, sequencing, or PCR); and (c) if the subject has a level of MRD below a preselected cutoff value ((e.g., 1 malignant cell in 100 normal cells, 1 malignant cell in 1000 normal cells, or 1 malignant cell in 10,000 normal cells), e.g., for a time period after therapy (e.g., at least 1, 2, 3, 6, 9, 12 months)), alter the combination treatment (e.g., reduce the dose or frequency (e.g., by about 20%, 30%, 40%, or 50%) of the PI3K inhibitor, the second agent, or both, or cease the first treatment).

In some embodiments, the method further comprises monitoring the subject after altering the combination treatment (e.g., after reducing the dose or frequency (e.g., by about 20%, 30%, 40%, or 50%) of the PI3K inhibitor, the second agent, or both, or ceasing the first treatment), (e.g., for a period of at least 6 months, 9 months or 12 months), and if the level of MRD increases, e.g., increases above a preselected cutoff value (e.g., a preselected cutoff value as described herein (e.g., 1 malignant cell in 100 normal cells, 1 malignant cell in 1000 normal cells, or 1 malignant cell in 10,000 normal cells)), a second treatment is administered. In one embodiment, the second treatment is a PI3K inhibitor monotherapy. In another embodiment, the second treatment comprises a PI3K inhibitor in combination with a second agent (e.g., a second agent as described herein, e.g., one or more of a checkpoint modulator, an XPO1 inhibitor, an anti-CD19 antibody, a TLR agonist, a STING agonist, or a Flt3 ligand, or a combination thereof, as described herein). In one embodiment, the second treatment includes the same second agent as the first treatment. In another embodiment, the second treatment includes a different second agent as the first treatment. In yet another embodiment, the second treatment comprises a PI3K inhibitor in combination with a third agent (e.g., an anti-CD20 antibody or a BTK inhibitor such as ibrutinib). In yet another embodiment, the second treatment comprises a PI3K inhibitor, a second agent (e.g., a second agent as described herein, e.g., one or more of a checkpoint modulator, an XPO1 inhibitor, an anti-CD19 antibody, a TLR agonist, a STING agonist, or a Flt3 ligand, or a combination thereof, as described herein) and a third agent (e.g., an anti-CD20 antibody or a BTK inhibitor such as ibrutinib).

In another aspect, provided herein is a method of decreasing the level of MRD detected in a subject having a cancer. The method comprises:

(a) administering to the subject a PI3K inhibitor (e.g., Compound 1), or a pharmaceutically acceptable form thereof, in combination with a second agent (e.g., a second agent chosen from one or more of a checkpoint modulator, an XPO1 inhibitor, an anti-CD19 antibody, a TLR agonist, a STING agonist, or a Flt3 ligand, or a combination thereof, as described herein) (also referred to as "a first treatment");

(b) monitoring the level of MRD in the subject, e.g., by one or more methods described herein or known in the art (e.g., flow cytometry, sequencing, or PCR); and (c) stop administering the first treatment (e.g., the combination) if the level of MRD in the subject decreases below a preselected cutoff value (e.g., 1 malignant cell in 100 normal cells, 1 malignant cell in 1000 normal cells, or 1 malignant cell in 10,000 normal cells).

In some embodiments, the method further comprises (d) monitoring the level of MRD in the subject, e.g., by one or more of the methods described herein or known in the art (e.g., flow cytometry, sequencing, or PCR) and (e) administering a second treatment (e.g., a monotherapy comprising a PI3K inhibitor, or administering a further combination comprising the PI3K inhibitor, or a pharmaceutically acceptable form thereof), if the level of MRD increases, e.g., increase above a preselected cutoff value (e.g., 1 malignant cell in 100 normal cells, 1 malignant cell in 1000 normal cells, or 1 malignant cell in 10,000 normal cells). In one embodiment, steps (b), (c), (d) and (e) are repeated one or more times. In one embodiment the second treatment is a PI3K inhibitor monotherapy. In another embodiment, the second treatment comprises a PI3K inhibitor in combination with a second agent (e.g., a second agent as described herein, e.g., one or more of a checkpoint modulator, an XPO1 inhibitor, an anti-CD19 antibody, a TLR agonist, a STING agonist, or a Flt3 ligand, or a combination thereof, as described herein). In one embodiment, the second treatment includes the same second agent as the first treatment. In another embodiment, the second treatment includes a different second agent as the first treatment. In yet another embodiment, the second treatment comprises a PI3K inhibitor in combination with a third agent (e.g., an anti-CD20 antibody or a BTK inhibitor such as ibrutinib). In yet another embodiment, the second treatment comprises a PI3K inhibitor, a second agent (e.g., a second agent as described herein, e.g., one or more of a checkpoint modulator, an XPO1 inhibitor, an anti-CD19 antibody, a TLR agonist, a STING agonist, or a Flt3 ligand, or a combination thereof, as described herein) and a third agent (e.g., an anti-CD20 antibody or a BTK inhibitor such as ibrutinib).

The aforesaid compositions and methods can be used in combination with a monotherapy (e.g., a monotherapeutic administration or dose of the PI3K inhibitor, the second agent or a third agent). In one embodiment, the subject is administered a monotherapy with a PI3K inhibitor, which can be followed with a combination composition or method described herein. For example, if the subject is developing, or is identified as developing, a decreased responsiveness to a first monotherapy, (e.g., with a PI3K inhibitor, a second agent, or third agent), any of the combination compositions or methods described herein can be administered. In certain embodiments, the combination compositions or methods described herein improve responsiveness (e.g., as indicated by a decrease in the level of MRD, e.g., a decrease below the level of MRD observed during treatment with the first monotherapy). Alternatively, administration of any of the combination compositions or methods described herein can be followed by administration of a monotherapy, e.g., with a PI3K inhibitor, the second agent, or third agent.

In other embodiments, the composition and methods described herein can include further agents or therapies, including but not limited to, chemotherapeutics, radiation, or surgery.

In some embodiments, the PI3K inhibitor is chosen from one or more of Compound 1, AMG-319, GSK 2126458, GSK 1059615, GDC-0032, GDC-0980, GDC-0941, XL147, XL499, XL765, BKM 120, GS1101, CAL 263, SF1126, PX-866, BEZ235, CAL-120, BYL719, RP6503, RP6530, TGR1202, INK1117, PX-886, BAY 80-6946, IC87114, Palomid 529, ZSTK474, PWT33597, TG100-115, GNE-477, CUDC-907, AEZS-136, BGT-226, PF-05212384, LY3023414, PI-103, LY294002, INCB-040093, CAL-130 and wortmannin.

In one embodiment, the PI3K inhibitor is Compound 1, or a pharmaceutically acceptable form thereof. Compound 1 has the chemical name of (S)-3-(1-((9H-purin-6-yl)amino)ethyl)-8-chloro-2-phenylisoquinolin-1(2H)-one, and is of the following structure:

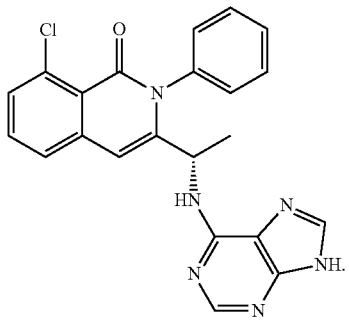 [SMILES: C[C@H](Nc1ncnc2[nH]cnc12)c1cc2cccc(Cl)c2c(=O)n1-c1ccccc1]

In one embodiment, the PI3K inhibitor is Idelalisib (GS1101, CAL-101), or a pharmaceutically acceptable form thereof. Idelalisib (GS1101, CAL-101) has the chemical name of (S)-2-(1-(9H-purin-6-ylamino)propyl)-5-fluoro-3-phenylquinazolin-4(3H)-one, and is of the following structure:

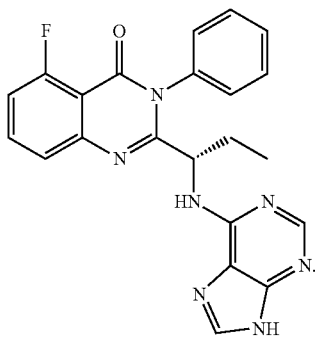 [SMILES: CC[C@H](Nc1ncnc2[nH]cnc12)c1nc2cccc(F)c2c(=O)n1-c1ccccc1]

In certain embodiments of the compositions and methods described herein, the PI3K inhibitor is a PI3K delta inhibitor. In one embodiment, the PI3K inhibitor is a dual inhibitor of PI3K delta/gamma.

The combinations described herein can further comprise a third therapeutic agent which is a chemotherapeutic agent. The chemotherapeutic agent can be, for example, bendamustine, chlorambucil, cyclophosphamide, doxorubicin, vincristine, fludarabine, or any combination thereof such as CHOP (cyclophosphamide, doxorubicin, vincristine, prednisone) or FC (fludarabine, cyclophosphamide).

In some embodiments, the pharmaceutical composition further comprises a pharmaceutically acceptable excipient (e.g., one or more pharmaceutically acceptable excipients).

In some embodiments of the compositions and methods described herein, the combination of the PI3K inhibitor and the second agent is therapeutically effective (e.g., synergistically effective), in treating a cancer in the subject, e.g., for treatment of a cancer described herein.

In one embodiment, the cancer is of hematopoietic origin. In one embodiment, the cancer is lymphoma or leukemia. In one embodiment, the cancer is B-cell lymphoma, mantle cell lymphoma, non-Hodgkin's lymphoma (e.g., non-Hodgkin's B-cell lymphoma), T-cell lymphoma, cutaneous lymphoma, anaplastic large cell lymphoma, multiple myeloma, myeloma, or plasmacytoma. In one embodiment, the cancer is a multiple myeloma. In one embodiment, the cancer is a chronic lymphocytic leukemia (CLL).

In other embodiments, the cancer is a non-Hodgkin's lymphoma. In certain embodiments, the cancer is a B cell non-Hodgkin's lymphoma. In certain embodiments, the non-Hodgkin's lymphoma is a diffuse large B-cell lymphoma. In certain embodiments, the non-Hodgkin's lymphoma is a diffuse large B-cell lymphoma activated B-cell like or a diffuse large B-cell lymphoma germinal center B-cell-like. In certain embodiments, the cancer is an indolent non-Hodgkin's lymphoma, e.g., a follicular lymphoma. In certain embodiments, the cancer is a mantle cell lymphoma. In certain embodiments, the cancer is a T-cell non-Hodgkin's lymphoma.

In some embodiments, the cancer is a T cell lymphoma, e.g., a peripheral T cell lymphoma (PTCL) or a cutaneous T cell lymphoma (CTCL).

In one embodiment, the subject is a mammal, e.g., a human. In one embodiment, the subject is at risk or suffers from a cancer, e.g., a cancer described herein.

In one embodiment, the method delays resistance of the cancer, e.g., to a therapeutic agent, e.g., to the PI3K inhibitor such as Compound 1, or to the second agent. In one embodiment, the method reduces the risk that the cancer becomes resistant, e.g., to a therapeutic agent, e.g., to the PI3K inhibitor such as Compound 1, or to the second agent. In one embodiment, the cancer does not become resistant (e.g., to the PI3K inhibitor) for at least 1, 2, 3, 4, 5, 6, 7, 8, 9, 10, 11, 12, 18, 24, 30, or 36 months. In one embodiment, the method prolongs remission (e.g., complete remission or partial remission) in the subject. In one embodiment, the subject experiences remission (e.g., complete remission or partial remission) for at least 1, 2, 3, 4, 5, 6, 7, 8, 9, 10, 11, 12, 18, 24, 30, or 36 months. In one embodiment, the method increases the likelihood that the subject experiences complete remission. In one embodiment, the subject experiences complete remission. In one embodiment, the method results in a reduction in the level of minimal residual disease (MRD). In one embodiment, the subject has substantially no detectable MRD. In certain embodiments, the subject displays one or more of these characteristics (e.g., remission)

after treatment with the PI3K inhibitor and the second agent for a therapeutically effective period of time, e.g., at least 1, 2, 3, or 4 weeks, or 1, 2, 4, 6, 9, or 12 months.

In one embodiment, the subject shows decreased responsiveness to a PI3K inhibitor (e.g., is resistant or refractive to treatment with a PI3K inhibitor, e.g., Compound 1). In one embodiment, the subject is identified as having a decreased susceptibility (e.g., resistance or acquired resistance) to a monotherapy treatment with a PI3K inhibitor (e.g., Compound 1 or Idelalisib), or a pharmaceutically acceptable form thereof. In one embodiment, the subject is identified as having a decreased susceptibility (e.g., resistance or acquired resistance) to a monotherapy treatment of a PI3K inhibitor (e.g., Compound 1), or a pharmaceutically acceptable form thereof. In one embodiment, the subject is identified as having an increased susceptibility to a combination therapy treatment provided herein.

In some embodiments of the compositions and methods described herein, the PI3K inhibitor and the second therapeutic agent are the only therapeutically active ingredients for treating a cancer.

Additional combinations of three or more agents are encompassed by the methods and compositions described herein.

In certain embodiments, provided herein is a composition (e.g., a pharmaceutical composition) comprising a PI3K inhibitor, e.g., one or more PI3K inhibitors (e.g., Compound 1 or Idelalisib, or both), or a pharmaceutically acceptable form thereof, in combination with a checkpoint modulator (e.g., one or more checkpoint modulators), or a pharmaceutically acceptable form thereof. The PI3K inhibitor and the checkpoint modulator can be present in a single composition or as two or more different compositions. In some embodiments, the composition (e.g., one or more compositions comprising the combination of PI3K inhibitor and the checkpoint modulator) is synergistic, e.g., has a synergistic effect in treating a cancer (e.g., in reducing cancer cell growth or viability, or both, e.g., as described herein). In certain embodiments, the amount or dosage of the PI3K inhibitor, the checkpoint modulator, or both, present in the composition(s) is lower (e.g., at least 20%, at least 30%, at least 40%, or at least 50% lower) than the amount or dosage of each agent used individually, e.g., as a monotherapy.

In certain embodiments, provided herein is a method of treating, managing, or preventing a cancer in a subject comprising administering to the subject a PI3K inhibitor, e.g., one or more PI3K inhibitors (e.g., Compound 1 or Idelalisib, or both) or a pharmaceutically acceptable form thereof, in combination with a checkpoint modulator (e.g., one or more checkpoint modulators), or a pharmaceutically acceptable form thereof. In certain embodiments, the combination of the PI3K inhibitor and the checkpoint modulator is synergistic, e.g., has a synergistic effect in treating the cancer (e.g., in reducing cancer cell growth or viability, or both). In some embodiments, the amount or dosage of the PI3K inhibitor, the checkpoint modulator, or both, used in combination does not exceed the level at which each agent is used individually, e.g., as a monotherapy. In certain embodiments, the amount or dosage of the PI3K inhibitor, the checkpoint modulator, or both, used in combination is lower (e.g., at least 20%, at least 30%, at least 40%, or at least 50% lower) than the amount or dosage of each agent used individually, e.g., as a monotherapy. In other embodiments, the amount or dosage of the PI3K inhibitor, the checkpoint modulator, or both, used in combination that results in treatment of cancer is lower (e.g., at least 20%, at least 30%, at least 40%, or at least 50% lower) than the amount or dosage of each agent used individually, e.g., as a monotherapy.

In one embodiment of the compositions and methods provided herein, the checkpoint modulator is an anti-PD-1 antibody, an anti-PD-L1 antibody, an anti-PD-L2 antibody, or an anti-CTLA-4 antibody, or a combination thereof. In one embodiment, the anti-PD-1 antibody is Nivolumab, Pembrolizumab, Pidilizumab, AMP-514, or AMP-224, or a combination thereof. In one embodiment, the anti-PD-L1 antibody is MDX-1105, YW243.55.S70, MDPL3280A, MSB0010718C, or durvalumab, or a combination thereof. In one embodiment, the an anti-CTLA-4 antibody is Tremelimumab or Ipilimumab, or a combination thereof.

In certain embodiments, provided herein is a composition (e.g., one or more pharmaceutical compositions or dosage forms), comprising a PI3K inhibitor, e.g., one or more PI3K inhibitors (e.g., Compound 1 or Idelalisib, or both) or a pharmaceutically acceptable form thereof, in combination with an XPO1 inhibitor (e.g., one or more XPO1 inhibitors), or a pharmaceutically acceptable form thereof. The PI3K inhibitor and the XPO1 inhibitor can be present in a single composition or as two or more different compositions. In some embodiments, the composition (e.g., one or more compositions comprising the combination of PI3K inhibitor and the XPO1 inhibitor) is synergistic, e.g., has a synergistic effect in treating a cancer (e.g., in reducing cancer cell growth or viability, or both, e.g., as described herein). In certain embodiments, the amount or dosage of the PI3K inhibitor, the XPO1 inhibitor, or both, present in the composition(s) is lower (e.g., at least 20%, at least 30%, at least 40%, or at least 50% lower) than the amount or dosage of each agent used individually, e.g., as a monotherapy.

In certain embodiments, provided herein is a method of treating, managing, or preventing a cancer in a subject comprising administering to the subject a PI3K inhibitor, e.g., one or more PI3K inhibitors (e.g., Compound 1 or Idelalisib, or both) or a pharmaceutically acceptable form thereof, in combination with an XPO1 inhibitor (e.g., one or more XPO1 inhibitors), or a pharmaceutically acceptable form thereof. In certain embodiments, the combination of the PI3K inhibitor and the XPO1 inhibitor is synergistic, e.g., has a synergistic effect in treating the cancer (e.g., in reducing cancer cell growth or viability, or both). In some embodiments, the amount or dosage of the PI3K inhibitor, the XPO1 inhibitor, or both, used in combination does not exceed the level at which each agent is used individually, e.g., as a monotherapy. In certain embodiments, the amount or dosage of the PI3K inhibitor, the XPO1 inhibitor, or both, used in combination is lower (e.g., at least 20%, at least 30%, at least 40%, or at least 50% lower) than the amount or dosage of each agent used individually, e.g., as a monotherapy. In other embodiments, the amount or dosage of the PI3K inhibitor, the XPO1 inhibitor, or both, used in combination that results in treatment of cancer is lower (e.g., at least 20%, at least 30%, at least 40%, or at least 50% lower) than the amount or dosage of each agent used individually, e.g., as a monotherapy.

In one embodiment of the methods and compositions described herein, the XPO1 inhibitor is selinexor, KPT-251, KPT-276, or SL-801, or a combination thereof. In one embodiment, the XPO1 inhibitor is selinexor.

In certain embodiments, provided herein is a composition (e.g., a pharmaceutical composition) comprising a PI3K inhibitor (e.g., Compound 1 or Idelalisib), or a pharmaceutically acceptable form thereof, in combination with an anti-CD19 antibody (e.g., one or more anti-CD19 antibodies), or a pharmaceutically acceptable form thereof. The PI3K inhibitor and the anti-CD19 antibody can be present in a single composition or as two or more different compositions. In some embodiments, the composition (e.g., one or more compositions comprising the combination of PI3K inhibitor and the anti-CD19 antibody) is synergistic, e.g., has a synergistic effect in treating a cancer (e.g., in reducing cancer cell growth or viability, or both, e.g., as described herein). In certain embodiments, the amount or dosage of the PI3K inhibitor, the anti-CD19 antibody, or both, present in the composition(s) is lower (e.g., at least 20%, at least 30%, at least 40%, or at least 50% lower) than the amount or dosage of each agent used individually, e.g., as a monotherapy.

In certain embodiments, provided herein is a method of treating, managing, or preventing a cancer in a subject comprising administering to the subject a PI3K inhibitor, e.g., one or more PI3K inhibitors (e.g., Compound 1 or Idelalisib, or both) or a pharmaceutically acceptable form thereof, in combination with an anti-CD19 antibody (e.g., one or more anti-CD19 antibodies), or a pharmaceutically acceptable form thereof. In certain embodiments, the combination of the PI3K inhibitor and the anti-CD19 antibody is synergistic, e.g., has a synergistic effect in treating the cancer (e.g., in reducing cancer cell growth or viability, or both). In some embodiments, the amount or dosage of the PI3K inhibitor, the anti-CD19 antibody, or both, used in combination does not exceed the level at which each agent is used individually, e.g., as a monotherapy. In certain embodiments, the amount or dosage of the PI3K inhibitor, the anti-CD19 antibody, or both, used in combination is lower (e.g., at least 20%, at least 30%, at least 40%, or at least 50% lower) than the amount or dosage of each agent used individually, e.g., as a monotherapy. In other embodiments, the amount or dosage of the PI3K inhibitor, the anti-CD19 antibody, or both, used in combination that results in treatment of cancer is lower (e.g., at least 20%, at least 30%, at least 40%, or at least 50% lower) than the amount or dosage of each agent used individually, e.g., as a monotherapy.

In one embodiment of the methods and compositions described herein, the anti-CD19 antibody is blinatumomab.

In certain embodiments, provided herein is a composition, e.g., one or more pharmaceutical composition, comprising a PI3K inhibitor, e.g., one or more PI3K inhibitors (e.g., Compound 1 or Idelalisib), or a pharmaceutically acceptable form thereof, in combination with a TLR agonist (e.g., one or more TLR agonists), or a pharmaceutically acceptable form thereof. The PI3K inhibitor and the TLR agonist can be present in a single composition or as two or more different compositions. In some embodiments, the composition (e.g., one or more compositions comprising the combination of PI3K inhibitor and the TLR agonist) is synergistic, e.g., has a synergistic effect in treating a cancer (e.g., in reducing cancer cell growth or viability, or both, e.g., as described herein). In certain embodiments, the amount or dosage of the PI3K inhibitor, the TLR agonist, or both, present in the composition(s) is lower (e.g., at least 20%, at least 30%, at least 40%, or at least 50% lower) than the amount or dosage of each agent used individually, e.g., as a monotherapy.

In certain embodiments, provided herein is a method of treating, managing, or preventing a cancer in a subject. The method includes administering to the subject a PI3K inhibitor, e.g., one or more PI3K inhibitors (e.g., Compound 1 or Idelalisib, or both) or a pharmaceutically acceptable form thereof, in combination with a TLR agonist (e.g., one or more TLR agonists), or a pharmaceutically acceptable form thereof. In certain embodiments, the combination of the PI3K inhibitor and the TLR agonist is synergistic, e.g., has a synergistic effect in treating the cancer (e.g., in reducing cancer cell growth or viability, or both). In some embodiments, the amount or dosage of the PI3K inhibitor, the TLR agonist, or both, used in combination does not exceed the level at which each agent is used individually, e.g., as a monotherapy. In certain embodiments, the amount or dosage of the PI3K inhibitor, the TLR agonist, or both, used in combination is lower (e.g., at least 20%, at least 30%, at least 40%, or at least 50% lower) than the amount or dosage of each agent used individually, e.g., as a monotherapy. In other embodiments, the amount or dosage of the PI3K inhibitor, the TLR agonist, or both, used in combination that results in treatment of cancer is lower (e.g., at least 20%, at least 30%, at least 40%, or at least 50% lower) than the amount or dosage of each agent used individually, e.g., as a monotherapy.

In certain embodiments, provided herein is a composition, e.g., one or more pharmaceutical composition, comprising a PI3K inhibitor, e.g., one or more PI3K inhibitors (e.g., Compound 1 or Idelalisib), or a pharmaceutically acceptable form thereof, in combination with a STING agonist (e.g., one or more STING agonists), or a pharmaceutically acceptable form thereof. The PI3K inhibitor and the STING agonist can be present in a single composition or as two or more different compositions. In some embodiments, the composition (e.g., one or more compositions comprising the combination of PI3K inhibitor and the STING agonist) is synergistic, e.g., has a synergistic effect in treating a cancer (e.g., in reducing cancer cell growth or viability, or both, e.g., as described herein). In certain embodiments, the amount or dosage of the PI3K inhibitor, the STING agonist, or both, present in the composition(s) is lower (e.g., at least 20%, at least 30%, at least 40%, or at least 50% lower) than the amount or dosage of each agent used individually, e.g., as a monotherapy.

In certain embodiments, provided herein is a method of treating, managing, or preventing a cancer in a subject. The method includes administering to the subject a PI3K inhibitor, e.g., one or more PI3K inhibitors (e.g., Compound 1 or Idelalisib, or both) or a pharmaceutically acceptable form thereof, in combination with a STING agonist (e.g., one or more STING agonists), or a pharmaceutically acceptable form thereof. In certain embodiments, the combination of the PI3K inhibitor and the STING agonist is synergistic, e.g., has a synergistic effect in treating the cancer (e.g., in reducing cancer cell growth or viability, or both). In some embodiments, the amount or dosage of the PI3K inhibitor, the STING agonist, or both, used in combination does not exceed the level at which each agent is used individually, e.g., as a monotherapy. In certain embodiments, the amount or dosage of the PI3K inhibitor, the STING agonist, or both, used in combination is lower (e.g., at least 20%, at least 30%, at least 40%, or at least 50% lower) than the amount or dosage of each agent used individually, e.g., as a monotherapy. In other embodiments, the amount or dosage of the PI3K inhibitor, the STING agonist, or both, used in combination that results in treatment of cancer is lower (e.g., at least 20%, at least 30%, at least 40%, or at least 50% lower) than the amount or dosage of each agent used individually, e.g., as a monotherapy.

In certain embodiments, provided herein is a composition, e.g., one or more pharmaceutical composition, comprising a PI3K inhibitor, e.g., one or more PI3K inhibitors (e.g., Compound 1 or Idelalisib), or a pharmaceutically acceptable form thereof, in combination with a Flt3 ligand (e.g., one or more Flt3 ligands), or a pharmaceutically acceptable form thereof. The PI3K inhibitor and the Flt3 ligand can be present in a single composition or as two or more different compositions. In some embodiments, the composition (e.g., one or more compositions comprising the combination of PI3K inhibitor and the Flt3 ligand) is synergistic, e.g., has a synergistic effect in treating a cancer (e.g., in reducing cancer cell growth or viability, or both, e.g., as described herein). In certain embodiments, the amount or dosage of the PI3K inhibitor, the Flt3 ligand, or both, present in the composition(s) is lower (e.g., at least 20%, at least 30%, at least 40%, or at least 50% lower) than the amount or dosage of each agent used individually, e.g., as a monotherapy.

In certain embodiments, provided herein is a method of treating, managing, or preventing a cancer in a subject. The method includes administering to the subject a PI3K inhibitor, e.g., one or more PI3K inhibitors (e.g., Compound 1 or Idelalisib, or both) or a pharmaceutically acceptable form thereof, in combination with a Flt3 ligand (e.g., one or more Flt3 ligands), or a pharmaceutically acceptable form thereof. In certain embodiments, the combination of the PI3K inhibitor and the Flt3 ligand is synergistic, e.g., has a synergistic effect in treating the cancer (e.g., in reducing cancer cell growth or viability, or both). In some embodiments, the amount or dosage of the PI3K inhibitor, the Flt3 ligand, or both, used in combination does not exceed the level at which each agent is used individually, e.g., as a monotherapy. In certain embodiments, the amount or dosage of the PI3K inhibitor, the Flt3 ligand, or both, used in combination is lower (e.g., at least 20%, at least 30%, at least 40%, or at least 50% lower) than the amount or dosage of each agent used individually, e.g., as a monotherapy. In other embodiments, the amount or dosage of the PI3K inhibitor, the Flt3 ligand, or both, used in combination that results in treatment of cancer is lower (e.g., at least 20%, at least 30%, at least 40%, or at least 50% lower) than the amount or dosage of each agent used individually, e.g., as a monotherapy.

Embodiments relating to dosages of the agents included in the compositions and methods described herein follow. In one embodiment, the PI3K inhibitor, e.g., Compound 1, is administered at a dosage of from about 0.01 mg to about 75 mg daily, and the second therapeutic agent is administered at a dosage of from about 0.01 to about 1100 mg daily.

In certain embodiments, the amount or dosage of the PI3K inhibitor, the second agent, or both, that is used in the method or composition is lower (e.g., at least 20%, at least 30%, at least 40%, at least 50%, at least 60%, at least 70%, or at least 80% lower) than the amount or dosage of each agent used individually, e.g., as a monotherapy. In other embodiments, the amount or dosage of the PI3K inhibitor, the second agent, or both, present in the composition(s) that results in a desired effect (e.g., treatment of cancer) is lower (e.g., at least 20%, at least 30%, at least 40%, at least 50%, at least 60%, at least 70%, or at least 80% lower) than the amount or dosage of each agent used individually, e.g., as a monotherapy.

In one embodiment, the molar ratio of the PI3K inhibitor, or the pharmaceutically acceptable form thereof, to the second therapeutic agent, or the pharmaceutically acceptable form thereof, is in the range of from about 10000:1 to about 1:10000.

In one embodiment, the composition comprises the PI3K inhibitor, or a pharmaceutically acceptable form thereof, at an amount of in the range of from about 0.01 mg to about 75 mg and the second therapeutic agent, or a pharmaceutically acceptable form thereof, at an amount of in the range of from about 0.01 mg to about 1100 mg.

In certain embodiments, the PI3K inhibitor is Compound 1 at a dosage of 25 mg (e.g., 25 mg BID). In certain embodiments, Compound 1 is effective as a monotherapy at a dosage of 25 mg (e.g., 25 mg BID). In certain embodiments, the combination of Compound 1 and the second agent is effective, e.g., in treating a cancer and/or in reducing cancer cell growth or viability, with Compound 1 at a dosage lower than 25 mg (e.g., 25 mg BID). In other embodiments, the dosage of Compound 1 included in the combination is 5 mg to 20 mg (e.g., 5 mg to 20 mg BID). In other embodiments, the dosage of Compound 1 included in the combination is 10 mg to 25 mg (e.g., 10 mg to 25 mg BID), 15 mg to 25 mg (e.g., 15 mg to 25 mg BID), 5 mg to 50 mg (e.g., 5 mg to 50 mg BID), 5 mg to 25 mg (e.g., 5 mg to 25 mg BID), 5 mg to 10 mg (e.g., 5 mg to 10 mg BID), 10 mg to 15 mg (e.g., 10 mg to 15 mg BID), 15 mg to 20 mg (e.g., 15 mg to 20 mg BID), 20 mg to 25 mg (e.g., 20 mg to 25 mg BID), 25 mg to 30 mg (e.g., 25 mg to 30 mg BID), 30 mg to 35 mg (e.g., 30 mg to 35 mg BID), 35 mg to 40 mg (e.g., 35 mg to 40 mg BID), 40 mg to 45 mg (e.g., 40 mg to 45 mg BID), or 45 mg to 50 mg (e.g., 45 mg to 50 mg BID). In certain embodiments, the dosage of Compound 1 is 22.5 mg (e.g., 22.5 mg BID), 20 mg (e.g., 20 mg BID), 17.5 mg (e.g., 17.5 mg BID), 15 mg (e.g., 15 mg BID), 12.5 mg (e.g., 12.5 mg BID), 10 mg (e.g., 10 mg BID), 7.5 mg (e.g., 7.5 mg BID), or 5 mg (e.g., 5 mg BID).

In some embodiments, the PI3K inhibitor, e.g., Compound 1, is administered at a dose frequency of twice per day (BID), once per day, once per two days, once per three days, once per four days, once per five days, once per six days, or once per week. In certain embodiments, the combination of the PI3K inhibitor (e.g., Compound 1) and the second agent is effective, e.g., in treating a cancer and/or in reducing cancer cell growth or viability, with the PI3K inhibitor (e.g., Compound 1) administered at a dose frequency of twice per day (BID), once per day, once per two days, once per three days, once per four days, once per five days, once per six days, or once per week.

In some embodiments, the PI3K inhibitor is Idelalisib at a dosage of 150 mg (e.g., 150 mg BID). In certain embodiments, Idelalisib is effective as a monotherapy at a dosage of 150 mg (e.g., 150 mg BID). In certain embodiments, the combination of Idelalisib and the second agent is effective, e.g., in treating a cancer and/or in reducing cancer cell growth or viability, with Idelalisib at a dosage lower than 150 mg (e.g., 150 mg BID). In some embodiments, the dosage of Idelalisib included in the combination is 30 mg to 135 mg (e.g., 30 mg to 135 mg BID). In certain embodiments, the dosage of Idelalisib is 135 mg (e.g., 135 mg BID), 120 mg (e.g., 120 mg BID), 105 mg (e.g., 105 mg BID), 90 mg (e.g., 90 mg BID), 75 mg (e.g., 75 mg BID), 60 mg (e.g., 60 mg BID), 45 mg (e.g., 45 mg BID), or 30 mg (e.g., 30 mg BID).

In some embodiments, the PI3K inhibitor is Idelalisib and is administered at a dose frequency of twice per day, once per day, once per two days, once per three days, once per four days, once per five days, once per six days, or once per week. In certain embodiments, the combination of Idelalisib and the second agent is effective, e.g., in treating a cancer and/or in reducing cancer cell growth or viability, with Idelalisib administered at a dose frequency of twice per day (BID), once per day, once per two days, once per three days, once per four days, once per five days, once per six days, or once per week.

In one embodiment, the second agent is administered to a subject at least 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, 12 weeks, or 16 weeks before the PI3K inhibitor (e.g., Compound 1), or a pharmaceutically acceptable form thereof, is administered. In another embodiment, the second agent is administered concurrently with the PI3K inhibitor (e.g., Compound 1), or a pharmaceutically acceptable form thereof, e.g., in a single dosage form or separate dosage forms. In yet another embodiment, the second agent is administered to the subject at least 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, 12 weeks, or 16 weeks after the PI3K inhibitor (e.g., Compound 1), or a pharmaceutically acceptable form thereof, is administered.

In one embodiment, provided herein is a method of reducing the likelihood for a subject to develop resistance to a treatment with a PI3K inhibitor, comprising:

(a) administering to the subject a therapeutically effective amount of a monotherapy comprising the PI3K inhibitor, or a pharmaceutically acceptable form thereof, for a first period of time;

(b) after the first period of time, administering to the subject a therapeutically effective amount of a combination therapy comprising the PI3K inhibitor in combination with a second agent or a pharmaceutically acceptable form thereof, wherein the second agent is chosen from one or more of 1) a checkpoint modulator, 2) an XPO1 inhibitor, 3) an anti-CD19 antibody, 4) a TLR agonist, 5) a STING agonist, or 6) a Flt3 ligand, for a second period of time; and (c) optionally repeating steps (a) and (b) one or more times.

In one embodiment, provided herein is a method of reducing the likelihood for a subject to develop resistance to a treatment with a PI3K inhibitor, comprising:

(a) administering to the subject a therapeutically effective amount of a monotherapy comprising the second agent, or a pharmaceutically acceptable form thereof, wherein the second agent is chosen from one or more of 1) a checkpoint modulator, 2) an XPO1 inhibitor, 3) an anti-CD19 antibody, 4) a TLR agonist, 5) a STING agonist, or 6) a Flt3 ligand, for a first period of time;

(b) after the first period of time, administering to the subject a therapeutically effective amount of a combination therapy comprising the PI3K inhibitor in combination with the second agent or a pharmaceutically acceptable form thereof; and (c) optionally repeating steps (a) and (b) one or more times.

In certain embodiments, the subject is identified as developing resistance (e.g., acquired resistance) to the monotherapy.

In certain aspects, the disclosure provides a method of delaying or decreasing resistance of a subject having a cancer, comprising administering to the subject a synergistic amount of a PI3K inhibitor, or a pharmaceutically acceptable form thereof, and a second therapeutic agent selected from 1) a checkpoint modulator, 2) an XPO1 inhibitor, 3) an anti-CD19 antibody, 4) a TLR agonist, 5) a STING agonist, or 6) a Flt3 ligand, or a pharmaceutically acceptable form thereof. In a related aspect, provided herein is a composition for use in delaying or decreasing resistance of a subject having a cancer, said composition comprising a synergistic amount of a PI3K inhibitor, or a pharmaceutically acceptable form thereof, and a second therapeutic agent selected from 1) a checkpoint modulator, 2) an XPO1 inhibitor, 3) an anti-CD19 antibody, 4) a TLR agonist, 5) a STING agonist, or 6) a Flt3 ligand, or a pharmaceutically acceptable form thereof. In an embodiment, the resistance is resistance to the PI3K inhibitor. In an embodiment, the method comprises administering the PI3K inhibitor before the second therapeutic agent.

In some aspects, provided herein is a method of reducing the risk that a cancer becomes resistant to the PI3K inhibitor, comprising administering to a subject having a cancer a synergistic amount of a PI3K inhibitor, or a pharmaceutically acceptable form thereof, and a second therapeutic agent selected from one or more of 1) a checkpoint modulator, 2) an XPO1 inhibitor, 3) an anti-CD19 antibody, 4) a TLR agonist, 5) a STING agonist, or 6) a Flt3 ligand, or a pharmaceutically acceptable form thereof.

In some aspects, provided herein is a method of prolonging remission in a subject having a cancer, comprising administering to the subject a synergistic amount of a PI3K inhibitor, or a pharmaceutically acceptable form thereof, and a second therapeutic agent selected from 1) a checkpoint modulator, 2) an XPO1 inhibitor, 3) an anti-CD19 antibody, 4) a TLR agonist, 5) a STING agonist, or 6) a Flt3 ligand, or a pharmaceutically acceptable form thereof.

In some aspects, provided herein is a method of increasing the likelihood that a subject having a cancer experiences complete remission, comprising administering to the subject a synergistic amount of a PI3K inhibitor, or a pharmaceutically acceptable form thereof, and a second therapeutic agent selected from one or more of 1) a checkpoint modulator, 2) an XPO1 inhibitor, 3) an anti-CD19 antibody, 4) a TLR agonist, 5) a STING agonist, or 6) a Flt3 ligand, or a pharmaceutically acceptable form thereof.

In some aspects, provided herein is a method of reducing the level of minimal residual disease (MRD) in a subject having a cancer, comprising administering to the subject a synergistic amount of a PI3K inhibitor, or a pharmaceutically acceptable form thereof, and a second therapeutic agent selected from one or more of 1) a checkpoint modulator, 2) an XPO1 inhibitor, 3) an anti-CD19 antibody, 4) a TLR agonist, 5) a STING agonist, or 6) a Flt3 ligand, or a pharmaceutically acceptable form thereof. In another aspect, provided herein is a composition for use in reducing the level of minimal residual disease (MRD), said composition comprising a synergistic amount of a PI3K inhibitor, or a pharmaceutically acceptable form thereof, and a second therapeutic agent selected from one or more of 1) a checkpoint modulator, 2) an XPO1 inhibitor, 3) an anti-CD19 antibody, 4) a TLR agonist, 5) a STING agonist, or 6) a Flt3 ligand, or a pharmaceutically acceptable form thereof.

The disclosure includes all combinations of any one or more of the foregoing aspects and/or embodiments, as well as combinations with any one or more of the embodiments set forth in the detailed description and examples.

INCORPORATION BY REFERENCE

All publications, patents, and patent applications mentioned in this specification are herein incorporated by reference in their entirety and to the same extent as if each individual publication, patent, or patent application is specifically and individually indicated to be incorporated by reference.

BRIEF DESCRIPTION OF THE DRAWINGS

FIG. 1 shows an isobologram depicting the synergistic effect of the combination of Compound 1 and selinexor in H9 cell line.

DETAILED DESCRIPTION

1. Definitions

Unless defined otherwise, all technical and scientific terms used herein have the same meaning as is commonly understood by one of skill in the art to which this specification pertains.

As used in the specification and claims, the singular form "a", "an" and "the" includes plural references unless the context clearly dictates otherwise.

As used herein, and unless otherwise indicated, the term "about" or "approximately" means an acceptable error for a particular value as determined by one of ordinary skill in the art, which depends in part on how the value is measured or determined. In certain embodiments, the term "about" or "approximately" means within 1, 2, 3, or 4 standard deviations. In certain embodiments, the term "about" or "approximately" means within 50%, 20%, 15%, 10%, 9%, 8%, 7%, 6%, 5%, 4%, 3%, 2%, 1%, 0.5%, or 0.05% of a given value or range.

The term "agonist" as used herein refers to a compound or agent having the ability to initiate or enhance a biological function of a target protein or polypeptide, such as increasing the activity or expression of the target protein or polypeptide. Accordingly, the term "agonist" is defined in the context of the biological role of the target protein or polypeptide. While some agonists herein specifically interact with (e.g., bind to) the target, compounds and/or agents that initiate or enhance a biological activity of the target protein or polypeptide by interacting with other members of the signal transduction pathway of which the target polypeptide is a member are also specifically included within this definition.

The terms "antagonist" and "inhibitor" are used interchangeably, and they refer to a compound or agent having the ability to reduce or inhibit a biological function of a target protein or polypeptide, such as by reducing or inhibiting the activity or expression of the target protein or polypeptide. Accordingly, the terms "antagonist" and "inhibitor" are defined in the context of the biological role of the target protein or polypeptide. An inhibitor need not completely abrogate the biological function of a target protein or polypeptide, and in some embodiments reduces the activity by at least 50%, 60%, 70%, 80%, 90%, 95%, or 99%. While some antagonists herein specifically interact with (e.g., bind to) the target, compounds that inhibit a biological activity of the target protein or polypeptide by interacting with other members of the signal transduction pathway of which the target protein or polypeptide are also specifically included within this definition. Non-limiting examples of biological activity inhibited by an antagonist include those associated with the development, growth, or spread of a tumor, or an undesired immune response as manifested in autoimmune disease.

The term "effective amount" or "therapeutically effective amount" refers to that amount of a compound or pharmaceutical composition described herein that is sufficient to effect the intended application including, but not limited to, disease treatment, as illustrated below. The therapeutically effective amount can vary depending upon the intended application (in vitro or in vivo), or the subject and disease condition being treated, e.g., the weight and age of the subject, the severity of the disease condition, the manner of administration and the like, which can readily be determined by one of ordinary skill in the art. The term also applies to a dose that will induce a particular response in target cells, e.g., reduction of platelet adhesion and/or cell migration. The specific dose will vary depending on, for example, the particular compounds chosen, the dosing regimen to be followed, whether it is administered in combination with other agents, timing of administration, the tissue to which it is administered, and the physical delivery system in which it is carried.

As used herein, a daily dosage can be achieved by a single administration of the targeted dosage amount or multiple administrations of smaller dosage amount(s). For example, a 150 mg daily dosage can be achieved by a single administration of 150 mg of the therapeutic agent per day, two administrations of 75 mg of the therapeutic agent per day, or three administrations of 50 mg of the therapeutic agent per day, or the like.

As used herein, the terms "treatment" and "treating" are used herein to refer to an approach for obtaining beneficial or desired results including, but not limited to, therapeutic benefit. A therapeutic benefit includes, but is not limited to, eradication, inhibition, reduction, or amelioration of the underlying disorder being treated. Also, a therapeutic benefit is achieved with the eradication, inhibition, reduction, or amelioration of one or more of the physiological symptoms associated with the underlying disorder such that an improvement is observed in the patient, notwithstanding that the patient can still be afflicted with the underlying disorder.

As used herein, the terms "prevention" and "preventing" are used herein to refer to an approach for obtaining beneficial or desired results including, but not limited, to prophylactic benefit. For prophylactic benefit, the pharmaceutical compositions may be administered to a patient at risk of developing a particular disease, or to a patient reporting one or more of the physiological symptoms of a disease, even though a diagnosis of this disease may not have been made.

A "therapeutic effect," as that term is used herein, encompasses a therapeutic benefit and/or a prophylactic benefit as described above. A prophylactic effect includes delaying or eliminating the appearance of a disease or condition, delaying or eliminating the onset of symptoms of a disease or condition, slowing, halting, or reversing the progression of a disease or condition, or any combination thereof.

The phrase "a method of treating" or its equivalent, when applied to, for example, cancer refers to a procedure or course of action that is designed to reduce or eliminate the number of cancer cells in an animal, or to alleviate the symptoms of a cancer. "A method of treating" cancer or another proliferative disorder does not necessarily mean that the cancer cells or other disorder will, in fact, be eliminated, that the number of cells or disorder will, in fact, be reduced, or that the symptoms of a cancer or other disorder will, in fact, be alleviated. Often, a method of treating cancer will be performed even with a low likelihood of success, but which, given the medical history and estimated survival expectancy of an animal, is nevertheless deemed an overall beneficial course of action.

The term "therapeutically effective agent" or "therapeutic agent" means a composition that will elicit the biological or medical response of a tissue, system, animal or human that is being sought by the researcher, veterinarian, medical doctor or other clinician.

As used herein, the "aggressiveness" of a tumor or cancer refers to the rate at which the tumor is growing. Thus, a tumor is more aggressive than another tumor or cancer if it is proliferating at a higher rate. Other determinants can be used to measure the level of aggressiveness of a tumor or cancer, for example, based on the appearance of tumor or cancer cells under a microscope to determine the extent to which tumors are differentiated. A well-differentiated tumor tends to be more aggressive than a poorly-differentiated tumor or cancer.

The term "selective inhibition" or "selectively inhibit" as applied to a biologically active agent refers to the agent's ability to selectively reduce the target signaling activity as compared to off-target signaling activity, via direct or indirect interaction with the target. For example, a compound that selectively inhibits one isoform of PI3K over another isoform of PI3K has an activity of at least greater than about 1× against a first isoform relative to the compound's activity against the second isoform (e.g., at least about 2×, 3×, 5×, 10×, 20×, 50×, 100×, 200×, 500×, or 1000×). In certain embodiments, these terms refer to (1) a compound described herein that selectively inhibits the gamma isoform over the alpha, beta, or delta isoform; or (2) a compound described herein that selectively inhibits the delta isoform over the alpha, beta, or gamma isoform. By way of non-limiting example, the ratio of selectivity can be greater than a factor of about 1, greater than a factor of about 2, greater than a factor of about 3, greater than a factor of about 5, greater than a factor of about 10, greater than a factor of about 50, greater than a factor of about 100, greater than a factor of about 200, greater than a factor of about 400, greater than a factor of about 600, greater than a factor of about 800, greater than a factor of about 1000, greater than a factor of about 1500, greater than a factor of about 2000, greater than a factor of about 5000, greater than a factor of about 10,000, or greater than a factor of about 20,000, where selectivity can be measured by $IC_{50}$. In certain embodiments, the $IC_{50}$ can be measured by in vitro or in vivo assays.

"Subject" or "patient" to which administration is contemplated includes, but is not limited to, humans (e.g., a male or female of any age group, e.g., a pediatric subject (e.g., infant, child, adolescent) or adult subject (e.g., young adult, middle-aged adult or senior adult)) and/or other primates (e.g., cynomolgus monkeys, rhesus monkeys); mammals, including commercially relevant mammals such as cattle, pigs, horses, sheep, goats, cats, and/or dogs; and/or birds, including commercially relevant birds such as chickens, ducks, geese, quail, and/or turkeys.

The term "in vivo" refers to an event that takes place in a subject's body.

The term "in vitro" refers to an event that takes places outside of a subject's body. For example, an in vitro assay encompasses any assay conducted outside of a subject. In vitro assays encompass cell-based assays in which cells, alive or dead, are employed. In vitro assays also encompass a cell-free assay in which no intact cells are employed.

Combination therapy, or "in combination with" refer to the use of more than one compound or agent to treat a particular disorder or condition. For example, Compound 1 may be administered in combination with at least one additional therapeutic agent. By "in combination with," it is not intended to imply that the other therapy and Compound 1 must be administered at the same time and/or formulated for delivery together, although these methods of delivery are within the scope of this disclosure. Compound 1 can be administered concurrently with, prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, 12 weeks, or 16 weeks before), or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, 12 weeks, or 16 weeks after), one or more other additional agents. In general, each therapeutic agent will be administered at a dose and/or on a time schedule determined for that particular agent. The other therapeutic agent can be administered with Compound 1 herein in a single composition or separately in a different composition. Higher combinations, e.g., triple therapy, are also contemplated herein.

The terms "co-administration of" and "co-administering" and their grammatical equivalents, as used herein, encompass administration of two or more agents to subject so that both agents and/or their metabolites are present in the subject at the same or substantially the same time. In one embodiment, co-administration of a PI3K inhibitor with an additional anti-cancer agent (both components referred to hereinafter as the "two active agents") refer to any administration of the two active agents, either separately or together, where the two active agents are administered as part of an appropriate dose regimen designed to obtain the benefit of the combination therapy. Thus, the two active agents can be administered either as part of the same pharmaceutical composition or in separate pharmaceutical compositions. The additional agent can be administered prior to, at the same time as, or subsequent to administration of the PI3K inhibitor, or in some combination thereof. Where the PI3K inhibitor is administered to the patient at repeated intervals, e.g., during a standard course of treatment, the additional agent can be administered prior to, at the same time as, or subsequent to, each administration of the PI3K inhibitor, or some combination thereof, or at different intervals in relation to the PI3K inhibitor treatment, or in a single dose prior to, at any time during, or subsequent to the course of treatment with the PI3K inhibitor. In certain embodiments, a first agent can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), essentially concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapeutic agent.

As used herein, a "monotherapy" refers to the use of an agent individually (also referred to herein as alone) (e.g., as a single compound or agent), e.g., without a second active ingredient to treat the same indication, e.g., cancer. For example, in this context, the term monotherapy includes the use of either the PI3K inhibitor or the second agent individually to treat the cancer.

The term "synergy" or "synergistic" encompasses a more than additive effect of a combination of two or more agents compared to their individual effects. In certain embodiments, synergy or synergistic effect refers to an advantageous effect of using two or more agents in combination, e.g., in a pharmaceutical composition, or in a method of treatment. In certain embodiments, one or more advantageous effects is achieved by using a PI3K inhibitor in combination with a second therapeutic agent (e.g., one or more second therapeutic agents) as described herein.

In some embodiments, the synergistic effect is that a lower dosage of one or both of the agents is needed to achieve an effect. For example, the combination can provide a selected effect, e.g., a therapeutic effect, when at least one of the agents is administered at a lower dosage than the dose of that agent that would be required to achieve the same therapeutic effect when the agent is administered as a monotherapy. In certain embodiments, the combination of a PI3K inhibitor (e.g., Compound 1) and a second agent (as described herein) allows the PI3K inhibitor to be administered at a lower dosage than would be required to achieve the same therapeutic effect if the PI3K inhibitor were administered as a monotherapy.

In some embodiments, the synergistic effect is a reduction, prevention, delay, or decrease in the occurrence or the likelihood of occurrence of one or more side effects, toxicity, resistance, that would otherwise be associated with administration of at least one of the agents.

In some embodiments, the synergistic effect is a reduction in resistance (e.g., a decrease in a measure of resistance or a decreased likelihood of developing resistance), or a delay in the development of resistance, to at least one of the agents.

In some embodiments, the synergistic effect is a reduction in minimal residual disease (MRD). In certain embodiments, the combination of a PI3K inhibitor (e.g. a PI3K inhibitor described herein) and a second agent (e.g., a second agent described herein) is effective to reduce the MRD in the subject, e.g., below a level previously measured in the subject (e.g., the level measured before the combination was administered). In certain embodiments, the combination of a PI3K inhibitor and a second agent is effective to reduce the MRD in the subject below the level observed during or after treatment with a monotherapy, e.g., a monotherapy comprising either the PI3K inhibitor or the second agent. In certain embodiments, the MRD is decreased below the level observed during treatment with a monotherapy comprising the PI3K inhibitor. In certain embodiments, the MRD is decreased below the level observed during treatment with a monotherapy comprising the second agent. In certain embodiments, the combination is effective to reduce the level of MRD below a preselected cutoff value (e.g., 1 malignant cell in 100 normal cells, 1 malignant cell in 1000 normal cells, or 1 malignant cell in 10,000 normal cells, or 1 malignant cell in 100,000 normal cells). In certain embodiments, the preselected cutoff value is 1 malignant cell in 1000 normal cells. In certain embodiments, the preselected cutoff value is 1 malignant cell in 100,000 normal cells.

In some embodiments, a synergistic effect refers to the combination of a PI3K inhibitor (e.g., Compound 1, or a pharmaceutically acceptable form thereof), and a second therapeutic agent (e.g., one or more additional therapeutic agent(s), or a pharmaceutically acceptable form thereof, as described herein), results in a therapeutic effect greater than the additive effect of the PI3K inhibitor and the second agent.

In some embodiments, a synergistic effect means that combination index value is less than a selected value, e.g., for a given effect, e.g., at a selected percentage (e.g., 50%) inhibition or growth inhibition, e.g., as described herein in the Examples. In certain embodiments, the selected value is 1. In certain embodiments, the selected value is 0.7. In certain embodiments, the selected value is 0.5.

In some embodiments, a synergistic effect means that the synergy score is 1 or more. In certain embodiments, the synergy score is greater than 1. In certain embodiments, the synergy score is greater than 2. In certain embodiments, the synergy score is greater than 3.

Combination index (CI) is a measure of potency shifting. The combination index is known in the art and is described, e.g., in Chou et al., Adv Enzyme Regul 1984; 22: 27-55 and in U.S. Patent Publication No. 2013/0295102, the contents of which are incorporated herein by reference. A CI value of greater than 1 indicates antagonistic effect; a CI value of 1.0 is indicative of an additive effect; and a CI value of less than 1 is indicative of a synergistic effect resulting from the combination. The CI value can be determined at various percentages of inhibition or growth inhibition.

The CI provides an estimate of the fraction of the original (monotherapy) doses of each of two drugs would be needed in combination relative to the single agent doses required to achieve a chosen effect level. For example, when the combination index has a value of 0.1, only about one tenth of the total fractional amounts of the individual agents (expressed as a fraction of the amount of that agent when administered as a monotherapy to achieve a chosen effect) are needed for the combination to reach the same chosen effect level. For example, if a dose of 100 mg/kg of drug A individually or a dose of 200 mg/kg of drug B individually is needed to achieve the chosen effect, and the combination index is 0.1, then approximately 5 mg/kg of drug A and 10 mg/kg of drug B would achieve the chosen effect (one twentieth of the original doses of each of the single agents adds up to a total of one tenth). The doses of the single agents need not be reduced by the same fractional value so long as the sum of their fractional values adds up to the combination index; thus, in this example, a dose of approximately 8 mg/kg of drug A and 4 mg/kg of drug B would also achieve the chosen effect (this is 0.08 times the original dose of drug A and 0.02 times the original dose of drug B; the sum of the fractional amounts (0.08+0.02) is equal to the combination index of 0.1.)

According to one embodiment, synergy score is a measure of the combination effects in excess of Loewe additivity. In one example, synergy score is a scalar measure to characterize the strength of synergistic interaction. The Synergy score can be calculated as:

$$\text{Synergy Score} = \log f_X \log f_Y \Sigma \max(0, I_{data})(I_{data} - I_{Loewe})$$

In this example, the fractional inhibition for each component agent and combination point in the matrix is calculated relative to the median of all vehicle-treated control wells. The example Synergy Score equation integrates the experimentally-observed activity volume at each point in the matrix in excess of a model surface numerically derived from the activity of the component agents using the Loewe model for additivity. Additional terms in the Synergy Score equation (above) are used to normalize for various dilution factors used for individual agents and to allow for comparison of synergy scores across an entire experiment. The inclusion of positive inhibition gating or an $I_{data}$ multiplier removes noise near the zero effect level, and biases results for synergistic interactions at that occur at high activity levels. According to other embodiments, a synergy score can be calculated based on a curve fitting approach where the curvature of the synergy score is extrapolated by introducing a median value and origin value (e.g., a dose zero value).

The synergy score measure can be used for the self-cross analysis. Synergy scores of self-crosses are expected to be additive by definition and, therefore, maintain a synergy score of zero. However, while some self-cross synergy scores are near zero, many are greater suggesting that experimental noise or non-optimal curve fitting of the single agent dose responses are contributing to the slight perturbations in the score. This strategy is cell line-centric, focusing on self-cross behavior in each cell line versus a global review of cell line panel activity. Combinations where the synergy score is greater than the mean self-cross plus two standard deviations or three standard deviations can be considered candidate synergies at 95% and 99% confidence levels, respectively. Additivity should maintain a synergy score of zero, and synergy score of two or three standard deviations indicate synergism at statistically significant levels of 95% and 99%.

Loewe Volume (Loewe Vol) is used to assess the overall magnitude of the combination interaction in excess of the Loewe additivity model. Loewe Volume is particularly useful when distinguishing synergistic increases in a phenotypic activity (positive Loewe Volume) versus synergistic antagonisms (negative Loewe Volume). When antagonisms are observed, the Loewe Volume should be assessed to examine if there is any correlation between antagonism and a particular drug target-activity or cellular genotype. This model defines additivity as a non-synergistic combination interaction where the combination dose matrix surface should be indistinguishable from either drug crossed with itself. The calculation for Loewe additivity is:

$I_{Loewe}$ that satisfies $(X/X_1)+(Y/Y_1)=1$ where $X_I$ and $Y_I$ are the single agent effective concentrations for the observed combination effect I. For example, if 50% inhibition is achieved separately by 1 µM of drug A or 1 µM of drug B, a combination of 0.5 µM of A and 0.5 µM of B should also inhibit by 50%.

The term "anti-cancer effect" refers to the effect a therapeutic agent has on cancer, e.g., a decrease in growth, viability, or both of a cancer cell. The $IC_{50}$ of cancer cells can be used as a measure the anti-cancer effect.

$IC_{50}$ refers to a measure of the effectiveness of a therapeutic agent in inhibiting cancer cells by 50%.

The term "tumor" refers to any neoplastic cell growth and proliferation, whether malignant or benign, and any precancerous and cancerous cells and tissues. As used herein, the term "neoplastic" refers to any form of dysregulated or unregulated cell growth, whether malignant or benign, resulting in abnormal tissue growth. Thus, "neoplastic cells" include malignant and benign cells having dysregulated or unregulated cell growth.

The term "cancer" includes, but is not limited to, solid tumors and blood born tumors. The term "cancer" refers to disease of skin tissues, organs, blood, and vessels, including, but not limited to, cancers of the bladder, bone or blood, brain, breast, cervix, chest, colon, endometrium, esophagus, eye, head, kidney, liver, lymph nodes, lung, mouth, neck, ovaries, pancreas, prostate, rectum, stomach, testis, throat, and uterus.

Hematopoietic origin refers to involving cells generated during hematopoiesis, a process by which cellular elements of blood, such as lymphocytes, leukocytes, platelets, erythrocytes and natural killer cells are generated. Cancers of hematopoietic origin includes lymphoma and leukemia.

Resistant or refractive refers to when a cancer that has a reduced responsiveness to a treatment, e.g., up to the point where the cancer does not respond to treatment. The cancer can be resistant at the beginning of treatment, or it may become resistant during treatment. The cancer subject may have one or more mutations that cause it to become resistant to the treatment, or the subject may have developed such mutations during treatment. The term "refractory" can refer to a cancer for which treatment (e.g. chemotherapy drugs, biological agents, and/or radiation therapy) has proven to be ineffective. A refractory cancer tumor may shrink, but not to the point where the treatment is determined to be effective. Typically however, the tumor stays the same size as it was before treatment (stable disease), or it grows (progressive disease).

"Responsiveness," to "respond" to treatment, and other forms of this term, as used herein, refer to the reaction of a subject to treatment with a therapeutic, e.g., a PI3K inhibitor, alone or in combination, e.g., monotherapy or combination therapy. In one embodiment, a response to a PI3K inhibitor is determined. Responsiveness to a therapy, e.g., treatment with a PI3K inhibitor alone or in combination, can be evaluated by using any of the alterations/biomarkers disclosed herein and/or comparing a subject's response to the therapy using one or more clinical criteria, such as IWCLL 2008 (for CLL) described in, e.g., Hallek, M. et al. (2008) *Blood* 111 (12): 5446-5456; RECIST criteria for solid tumors (Response Evaluation Criteria In Solid Tumors), and the like. Additional classifications of responsiveness are provided in Brown, J. R. (2014) *Blood,* 123(22):3390-3397 and Chesson, B. D. et al. *Journal of Clinical Oncology,* 30(23):2820-2822.

These criteria provide a set of published rules that define when cancer patients improve ("respond"), stay the same ("stable") or worsen ("progression") during treatments.

In one embodiment, a subject having CLL can be determined to be in complete remission (CR) or partial remission (PR). For example, according to IWCLL 2008, a subject is considered to be in CR if at least all of the following criteria as assessed after completion of therapy are met: (i) Peripheral blood lymphocytes (evaluated by blood and different count) below $4 \times 10^9$/L (4000 µL); (ii) no hepatomegaly or splenomegaly by physical examination; (iii) absence of constitutional symptoms; and (iv) blood counts (e.g., neutrophils, platelets, hemoglobin) above the values set forth in Hallek, M. et al. supra at page 5451). Partial remission (PR) for CLL is defined according to IWCLL 2008 as including one of: (i) a decrease in number of blood lymphocytes by 50% or more from the value before therapy; (ii) a reduction in lymphadenopathy, as detected by CT scan or palpation; or (iii) a reduction in pretreatment enlargement of spleen or liver by 50% or more, as detected by CT scan or palpation; and blood counts (e.g., neutrophils, platelets, hemoglobin) according to the values set forth in Hallek, M. et al. supra at page 5451).

In other embodiments, a subject having CLL is determined to have progressive disease (PD) or stable disease (SD). For example, according to IWCLL 2008, a subject is considered to be in PD during therapy or after therapy if at least one of the following criteria is met: (i) progression on lymphadenopathy; (ii) an increase in pretreatment enlargement of spleen or liver by 50% or more, or de novo appearance of hepatomegaly or splenomegaly; (iii) an increase in the number of blood lymphocytes by 50% or more with at least 5000 B lymphocytes per microliter; (iv) transformation to a more aggressive histology (e.g., Richter syndrome); or (v) occurrence of cytopenia (neutropenia, anemia or thrombocytopenia) attributable to CLL, as described in Hallek, M. et al. supra at page 5452. Stable disease (SD) for CLL is defined according to IWCLL 2008 as a patient who has not achieved CR or a PR, and who has not exhibited progressive disease, see Hallek, M. et al. supra at page 5452.

In one embodiment, a subject with CLL responds to treatment with an PI3K inhibitor if at least one of the criteria for disease progression according to IWCLL is retarded or reduced, e.g., by about 10%, 20%, 30%, 40%, 50%, 60%, 70%, 80%, 90% or more. In another example, a subject responds to treatment with a PI3K inhibitor, if the subject experiences a life expectancy extension, e.g., extended by about 5%, 10%, 20%, 30%, 40%, 50% or more beyond the life expectancy predicted if no treatment is administered. In another example, a subject responds to treatment with a PI3K inhibitor, if the subject has one or more of: an increased progression-free survival, overall survival or increased time to progression (TTP), e.g., as described in Hallek, M. et al. supra at page 5452.

In another embodiment in solid tumors, a subject responds to treatment with a PI3K inhibitor if growth of a tumor in the subject is retarded about 10%, 20%, 30%, 40%, 50%, 60%, 70%, 80%, 90% or more. In another example, a subject responds to treatment with a PI3K inhibitor, if a tumor in the subject shrinks by about 5%, 10%, 20%, 30%, 40%, 50% or more as determined by any appropriate measure, e.g., by mass or volume. In another example, a subject responds to treatment with a PI3K inhibitor, if the subject experiences a life expectancy extended by about 5%, 10%, 20%, 30%, 40%, 50% or more beyond the life expectancy predicted if no treatment is administered. In another example, a subject responds to treatment with a PI3K inhibitor, if the subject has an increased disease-free survival, overall survival or increased time to progression. Several methods can be used to determine if a patient responds to a treatment including the RECIST criteria, as set forth above.

"Acquire" or "acquiring" as the terms are used herein, refer to obtaining possession of, determining, or evaluating, a value or information (e.g., one or more of: the presence, absence, amount or level) of an alteration or biomarker, by "directly acquiring" or "indirectly acquiring" the same. "Directly acquiring" means performing a process (e.g., performing a test) to obtain the value or information of the alteration or biomarker. "Indirectly acquiring" refers to receiving the value or information of the alteration or biomarker from another party or source (e.g., a diagnostic provider, a third party clinician or health professional).

Chemical Definitions

As used herein, a "pharmaceutically acceptable form" of a disclosed compound includes, but is not limited to, pharmaceutically acceptable salts, hydrates, solvates, isomers, prodrugs, and isotopically labeled derivatives of disclosed compounds. In one embodiment, a "pharmaceutically acceptable form" includes, but is not limited to, pharmaceutically acceptable salts, isomers, prodrugs and isotopically labeled derivatives of disclosed compounds.

In certain embodiments, the pharmaceutically acceptable form is a pharmaceutically acceptable salt. As used herein, the term "pharmaceutically acceptable salt" refers to those salts which are, within the scope of sound medical judgment, suitable for use in contact with the tissues of subjects without undue toxicity, irritation, allergic response and the like, and are commensurate with a reasonable benefit/risk ratio. Pharmaceutically acceptable salts are well known in the art. For example, Berge et al. describes pharmaceutically acceptable salts in detail in J Pharmaceutical Sciences (1977) 66:1-19. Pharmaceutically acceptable salts of the compounds provided herein include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, besylate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. In some embodiments, organic acids from which salts may be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like.

Pharmaceutically acceptable salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, iron, zinc, copper, manganese, aluminum, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate. Organic bases from which salts may be derived include, for example, primary, secondary, and tertiary amines, substituted amines including naturally occurring substituted amines, cyclic amines, basic ion exchange resins, and the like, such as isopropylamine, trimethylamine, diethylamine, triethylamine, tripropylamine, and ethanolamine. In some embodiments, the pharmaceutically acceptable base addition salt is chosen from ammonium, potassium, sodium, calcium, and magnesium salts.

In certain embodiments, the pharmaceutically acceptable form is a solvate (e.g., a hydrate). As used herein, the term "solvate" refers to compounds that further include a stoichiometric or non-stoichiometric amount of solvent bound by non-covalent intermolecular forces. The solvate may be of a disclosed compound or a pharmaceutically acceptable salt thereof. Where the solvent is water, the solvate is a "hydrate". Pharmaceutically acceptable solvates and hydrates are complexes that, for example, can include 1 to about 100, or 1 to about 10, or one to about 2, about 3 or about 4, solvent or water molecules. It will be understood that the term "compound" as used herein encompasses the compound and solvates of the compound, as well as mixtures thereof.

In certain embodiments, the pharmaceutically acceptable form is a prodrug. As used herein, the term "prodrug" refers to compounds that are transformed in vivo to yield a disclosed compound or a pharmaceutically acceptable form of the compound. A prodrug may be inactive when administered to a subject, but is converted in vivo to an active compound, for example, by hydrolysis (e.g., hydrolysis in blood). In certain cases, a prodrug has improved physical and/or delivery properties over the parent compound. Prodrugs are typically designed to enhance pharmaceutically and/or pharmacokinetically based properties associated with the parent compound. The prodrug compound often offers advantages of solubility, tissue compatibility or delayed release in a mammalian organism (see, e.g., Bundgard, H., *Design of Prodrugs* (1985), pp. 7-9, 21-24 (Elsevier, Amsterdam). A discussion of prodrugs is provided in Higuchi, T., et al., "Pro-drugs as Novel Delivery Systems," *A.C.S. Symposium Series*, Vol. 14, Chp 1, pp 1-12 and in *Bioreversible Carriers in Drug Design*, ed. Edward B. Roche, American Pharmaceutical Association and Pergamon Press, 1987, both of which are incorporated in full by reference herein. Exemplary advantages of a prodrug can include, but are not limited to, its physical properties, such as enhanced water solubility for parenteral administration at physiological pH compared to the parent compound, or it enhances absorption from the digestive tract, or it can enhance drug stability for long-term storage.

The term "prodrug" is also meant to include any covalently bonded carriers, which release the active compound in vivo when such prodrug is administered to a subject. Prodrugs of an active compound, as described herein, may be prepared by modifying functional groups present in the active compound in such a way that the modifications are cleaved, either in routine manipulation or in vivo, to the parent active compound. Prodrugs include compounds wherein a hydroxy, amino or mercapto group is bonded to any group that, when the prodrug of the active compound is administered to a subject, cleaves to form a free hydroxy, free amino or free mercapto group, respectively. Examples of prodrugs include, but are not limited to, acetate, formate and benzoate derivatives of an alcohol or acetamide, formamide and benzamide derivatives of an amine functional group in the active compound and the like. Other examples of prodrugs include compounds that comprise —NO, —$NO_2$, —ONO, or —$ONO_2$ moieties. Prodrugs can typically be prepared using well-known methods, such as those described in *Burger's Medicinal Chemistry and Drug Discovery*, 172-178, 949-982 (Manfred E. Wolff ed., 5th ed., 1995), and *Design of Prodrugs* (H. Bundgaard ed., Elsevier, New York, 1985).

For example, if a disclosed compound or a pharmaceutically acceptable form of the compound contains a carboxylic acid functional group, a prodrug can comprise a pharmaceutically acceptable ester formed by the replacement of the hydrogen atom of the acid group with a group such as ($C_1$-$C_8$)alkyl, ($C_2$-$C_{12}$)alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N—(alkoxycarbonyl)aminomethyl having from 3 to 9 carbon atoms, 1-(N—(alkoxycarbonyl)amino)ethyl having from 4 to 10 carbon atoms, 3-phthalidyl, 4-crotonolactonyl, gamma-butyrolacton-4-yl, di—N,N—($C_1$-$C_2$)alkylamino($C_2$-$C_3$)alkyl (such as (3-dimethylaminoethyl), carbamoyl-($C_1$-$C_2$)alkyl, N,N—di($C_1$-$C_2$)alkylcarbamoyl-($C_1$-$C_2$)alkyl and piperidino-, pyrrolidino- or morpholino($C_2$-$C_3$)alkyl.

Similarly, if a disclosed compound or a pharmaceutically acceptable form of the compound contains an alcohol functional group, a prodrug may be formed by the replacement of the hydrogen atom of the alcohol group with a group such as ($C_1$-$C_6$)alkanoyloxymethyl, 1-(($C_1$-$C_6$)alkanoyloxy)ethyl, 1-methyl-1-(($C_1$-$C_6$)alkanoyloxy)ethyl ($C_1$-$C_6$)alkoxycarbonyloxymethyl, N—($C_1$-$C_6$)alkoxycarbonylaminomethyl, succinoyl, ($C_1$-$C_6$)alkanoyl, α-amino($C_1$-$C_4$)alkanoyl, arylacyl and α-aminoacyl, or α-aminoacyl-α-aminoacyl, where each α-aminoacyl group is independently selected from naturally occurring L-amino acids, P(O)(OH)$_2$, —P(O)(O($C_1$-$C_6$)alkyl)$_2$, and glycosyl (the radical resulting from the removal of a hydroxyl group of the hemiacetal form of a carbohydrate).

If a disclosed compound or a pharmaceutically acceptable form of the compound incorporates an amine functional group, a prodrug may be formed by the replacement of a hydrogen atom in the amine group with a group such as R-carbonyl, RO-carbonyl, NRR'-carbonyl where R and R' are each independently ($C_1$-$C_{10}$)alkyl, ($C_3$-$C_7$)cycloalkyl, benzyl, a natural α-aminoacyl or natural α-aminoacyl-natural α-aminoacyl, —C(OH)C(O)OY$^1$ wherein Y$^1$ is H, ($C_1$-$C_6$)alkyl or benzyl, —C(OY$^2$)Y$^3$ wherein Y$^2$ is ($C_1$-$C_4$) alkyl and Y$^3$ is ($C_1$-$C_6$)alkyl, carboxy($C_1$-$C_6$)alkyl, amino($C_1$-$C_4$) alkyl or mono—N— or di—N,N—($C_1$-$C_6$)alkylaminoalkyl, —C(Y$^4$)Y$^5$ wherein Y$^4$ is H or methyl and Y$^5$ is mono—N— or di—N,N—($C_1$-$C_6$)alkylamino, morpholino, piperidin-1-yl or pyrrolidin-1-yl.

In certain embodiments, the pharmaceutically acceptable form is an isomer. "Isomers" are different compounds that have the same molecular formula. "Stereoisomers" are isomers that differ only in the way the atoms are arranged in space. As used herein, the term "isomer" includes any and all geometric isomers and stereoisomers. For example, "isomers" include geometric double bond cis- and trans-isomers, also termed E- and Z-isomers; R- and S-enantiomers; diastereomers, (d)-isomers and (l)-isomers, racemic mixtures thereof; and other mixtures thereof, as falling within the scope of this disclosure.

"Enantiomers" are a pair of stereoisomers that are non-superimposable mirror images of each other. A 1:1 mixture of a pair of enantiomers is a "racemic" mixture. The term "(±)" is used to designate a racemic mixture where appropriate. "Diastereoisomers" are stereoisomers that have at least two asymmetric atoms, but which are not mirror-images of each other. The absolute stereochemistry is specified according to the Cahn-Ingold-Prelog R-S system. When a compound is a pure enantiomer the stereochemistry at each chiral carbon may be specified by either R or S. Resolved compounds whose absolute configuration is unknown may be designated (+) or (−) depending on the direction (dextro- or levorotatory) which they rotate plane polarized light at the wavelength of the sodium D line. Certain of the compounds described herein contain one or more asymmetric centers and can thus give rise to enantiomers, diastereomers, and other stereoisomeric forms that may be defined, in terms of absolute stereochemistry, as (R)- or (S)—. The present chemical entities, pharmaceutical compositions and methods are meant to include all such possible isomers, including racemic mixtures, optically pure forms and intermediate mixtures. Optically active (R)- and (S)-isomers may be prepared using chiral synthons or chiral reagents, or resolved using conventional techniques. When the compounds described herein contain olefinic double bonds or other centers of geometric asymmetry, and unless specified otherwise, it is intended that the compounds include both E and Z geometric isomers.

"Enantiomeric purity" as used herein refers to the relative amounts, expressed as a percentage, of the presence of a specific enantiomer relative to the other enantiomer. For example, if a compound, which can potentially have an (R)- or an (S)-isomeric configuration, is present as a racemic mixture, the enantiomeric purity is about 50% with respect to either the (R)- or (S)-isomer. If that compound has one isomeric form predominant over the other, for example, 80% (S)- and 20% (R)-, the enantiomeric purity of the compound with respect to the (S)-isomeric form is 80%. The enantiomeric purity of a compound may be determined in a number of ways known in the art, including but not limited to chromatography using a chiral support, polarimetric measurement of the rotation of polarized light, nuclear magnetic resonance spectroscopy using chiral shift reagents which include but are not limited to lanthanide containing chiral complexes or the Pirkle alcohol, or derivatization of a compounds using a chiral compound such as Mosher's acid followed by chromatography or nuclear magnetic resonance spectroscopy.

In certain embodiments, the pharmaceutically acceptable form is a tautomer. As used herein, the term "tautomer" is a type of isomer that includes two or more interconvertable compounds resulting from at least one formal migration of a hydrogen atom and at least one change in valency (e.g., a single bond to a double bond, a triple bond to a double bond, or a triple bond to a single bond, or vice versa). "Tautomerization" includes prototropic or proton-shift tautomerization, which is considered a subset of acid-base chemistry. "Prototropic tautomerization" or "proton-shift tautomerization" involves the migration of a proton accompanied by changes in bond order. The exact ratio of the tautomers depends on several factors, including temperature, solvent, and pH. Where tautomerization is possible (e.g., in solution), a chemical equilibrium of tautomers may be reached. Tautomerizations (i.e., the reaction providing a tautomeric pair) may be catalyzed by acid or base, or can occur without the action or presence of an external agent. Exemplary tautomerizations include, but are not limited to, keto-enol; amide-imide; lactam-lactim; enamine-imine; and enamine-(a different) enamine tautomerizations. A specific example of keto-enol tautomerization is the interconversion of pentane-2,4-dione and 4-hydroxypent-3-en-2-one tautomers. Another example of tautomerization is phenol-keto tautomerization. A specific example of phenol-keto tautomerization is the interconversion of pyridin-4-ol and pyridin-4(1H)-one tautomers.

Unless otherwise stated, structures depicted herein are also meant to include compounds which differ only in the presence of one or more isotopically enriched atoms. For example, compounds having the present structures except for the replacement or enrichment of a hydrogen by deuterium or tritium at one or more atoms in the molecule, or the replacement or enrichment of a carbon by $^{13}C$ or $^{14}C$ at one or more atoms in the molecule, are within the scope of this disclosure. In one embodiment, provided herein are isotopically labeled compounds having one or more hydrogen atoms replaced by or enriched by deuterium. In one embodiment, provided herein are isotopically labeled compounds having one or more hydrogen atoms replaced by or enriched by tritium. In one embodiment, provided herein are isotopically labeled compounds having one or more carbon atoms replaced or enriched by $^{13}C$. In one embodiment, provided herein are isotopically labeled compounds having one or more carbon atoms replaced or enriched by $^{14}C$.

The disclosure also embraces isotopically labeled compounds which are identical to those recited herein, except that one or more atoms are replaced by an atom having an atomic mass or mass number different from the atomic mass or mass number usually found in nature. Examples of isotopes that may be incorporated into disclosed compounds include isotopes of hydrogen, carbon, nitrogen, oxygen, phosphorus, sulfur, fluorine, and chlorine, such as, e.g., $^{2}H$, $^{3}H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. Certain isotopically-labeled disclosed compounds (e.g., those labeled with $^{3}H$ and/or $^{14}C$) are useful in compound and/or substrate tissue distribution assays. Tritiated (i.e., $^{3}H$) and carbon-14 (i.e., $^{14}C$) isotopes can allow for ease of preparation and detectability. Further, substitution with heavier isotopes such as deuterium (i.e., $^{2}H$) can afford certain therapeutic advantages resulting from greater metabolic stability (e.g., increased in vivo half-life or reduced dosage requirements). Isotopically labeled disclosed compounds can generally be prepared by substituting an isotopically labeled reagent for a non-isotopically labeled reagent. In some embodiments, provided herein are compounds that can also contain unnatural proportions of atomic isotopes at one or more of atoms that constitute such compounds. All isotopic variations of the compounds as disclosed herein, whether radioactive or not, are encompassed within the scope of the present disclosure.

As used herein, and unless otherwise specified, "polymorph" may be used herein to describe a crystalline material, e.g., a crystalline form. In certain embodiments, "polymorph" as used herein are also meant to include all crystalline and amorphous forms of a compound or a salt thereof, including, for example, crystalline forms, polymorphs, pseudopolymorphs, solvates, hydrates, co-crystals, unsolvated polymorphs (including anhydrates), conformational polymorphs, tautomeric forms, disordered crystalline forms, and amorphous forms, as well as mixtures thereof, unless a particular crystalline or amorphous form is referred to. Compounds of the present disclosure include crystalline and amorphous forms of those compounds, including, for example, crystalline forms, polymorphs, pseudopolymorphs, solvates, hydrates, co-crystals, unsolvated polymorphs (including anhydrates), conformational polymorphs, tautomeric forms, disordered crystalline forms, and amorphous forms of the compounds or a salt thereof, as well as mixtures thereof.

"Pharmaceutically acceptable carrier" or "pharmaceutically acceptable excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions as disclosed herein is contemplated. Supplementary active ingredients can also be incorporated into the pharmaceutical compositions.

It should be noted that if there is a discrepancy between a depicted structure and a name given that structure, the depicted structure is to be accorded more weight. In addition, if the stereochemistry of a structure or a portion of a structure is not indicated with, for example, bold or dashed lines, the structure or portion of the structure is to be interpreted as encompassing all stereoisomers of the structure.

2. Compositions and Methods

In the methods and compositions described herein, the PI3K inhibitor can be any PI3K inhibitor as described herein below, including pharmacologically acceptable salts or polymorphs thereof.

As used herein, a "phosphoinositide 3-kinase (PI3K) inhibitor" or "PI3K inhibitor" refers to an inhibitor of any PI3K. PI3Ks are members of a unique and conserved family of intracellular lipid kinases that phosphorylate the 3'—OH group on phosphatidylinositols or phosphoinositides. The PI3K family includes kinases with distinct substrate specificities, expression patterns, and modes of regulation (see, e.g., Katso et al., 2001, *Annu. Rev. Cell Dev. Biol.* 17, 615-675; Foster, F. M. et al., 2003, *J Cell Sci* 116, 3037-3040). The class I PI3Ks (e.g., p110 α, p110 β, p110 γ, and p110 δ) are typically activated by tyrosine kinases or G-protein coupled receptors to generate PIP3, which engages downstream mediators such as those in the Akt/PDK1 pathway, mTOR, the Tec family kinases, and the Rho family GTPases. The class II PI3Ks (e.g., PI3K-C2α, PI3K-C2β, PI3K-C2γ) and III PI3Ks (e.g., Vps34) play a key role in intracellular trafficking through the synthesis of PI(3)P and PI(3,4)P2. Specific exemplary PI3K inhibitors are disclosed herein.

The class I PI3Ks comprise a p110 catalytic subunit and a regulatory adapter subunit. See, e.g., Cantrell, D. A. (2001) *Journal of Cell Science* 114: 1439-1445. Four isoforms of the p110 subunit (including PI3K-α (alpha), PI3K-β (beta), PI3K-γ (gamma), and PI3K-δ (delta) isoforms) have been implicated in various biological functions. Class I PI3Kα is involved, for example, in insulin signaling, and has been found to be mutated in solid tumors. Class I PI3K-β is involved, for example, in platelet activation and insulin signaling. Class I PI3K-γ plays a role in mast cell activation, innate immune function, and immune cell trafficking (chemokines). Class I PI3K-δ is involved, for example, in B-cell and T-cell activation and function and in Fc receptor signaling in mast cells. In some embodiments provided herein, the PI3K inhibitor is a class I PI3K inhibitor. In some such embodiments, the PI3K inhibitor inhibits a PI3K-α (alpha), PI3K-β (beta), PI3K-γ (gamma), or PI3K-δ (delta) isoform, or a combination thereof.

Downstream mediators of the PI3K signal transduction pathway include Akt and mammalian target of rapamycin (mTOR). Manning et al., Cell 129, 1261-1274 Jun. 29, 2007. Akt possesses a plckstrin homology (PH) domain that binds PIP3, leading to Akt kinase activation. Akt phosphorylates many substrates and is a central downstream effector of PI3K for diverse cellular responses. One important function of Akt is to augment the activity of mTOR, through phosphorylation of TSC2 and other mechanisms. mTOR is a serine-threonine kinase related to the lipid kinases of the PI3K family. Laplante et al., Cell 149, 274-293 Apr. 13, 2012 mTOR has been implicated in a wide range of biological processes including cell growth, cell proliferation, cell motility and survival. Disregulation of the mTOR pathway has been reported in various types of cancer. mTOR is a multifunctional kinase that integrates growth factor and nutrient signals to regulate protein translation, nutrient uptake, autophagy, and mitochondrial function.

In certain embodiments, provided herein are pharmaceutical compositions comprising a PI3K inhibitor, or a pharmaceutically acceptable form thereof, in combination with a second agent or a pharmaceutically acceptable form thereof, wherein the second agent is selected from one or more of 1) a checkpoint modulator, 2) an XPO1 inhibitor, 3) an anti-CD19 antibody, 4) a TLR agonist, 5) a STING agonist, or 6) a Flt3 ligand. In certain embodiments, the combination is therapeutically effective. In certain embodiments, the combination is synergistic, e.g., has one or more synergistic effects, e.g., synergistic therapeutic effects.

Also provided herein are methods of treating, managing, or preventing a cancer in a subject comprising administering to the subject a PI3K inhibitor, or a pharmaceutically acceptable form thereof, in combination with a second agent (e.g., one or more second agents), or a pharmaceutically acceptable form thereof, wherein the second agent is selected from one or more of 1) a checkpoint modulator, 2) an XPO1 inhibitor, 3) an anti-CD19 antibody, 4) a TLR agonist, 5) a STING agonist, or 6) a Flt3 ligand. In certain embodiments, the combination is therapeutically effective. In certain embodiments, the combination is synergistic, e.g., has one or more synergistic effects, e.g., synergistic therapeutic effects.

In certain embodiments, the compositions and methods provided herein are utilized where a monotherapy of one of the therapeutic agents is becoming less effective due to drug resistance or where the relatively high dosage of monotherapy lead to undesirable side effects.

2.1 PI3K Inhibitors

PI3K inhibitors that can be used in the compositions and methods provided herein include, but are not limited to, those described in, e.g., WO 09/088990, WO 09/088086, WO 2011/008302, WO 2010/036380, WO 2010/006086, WO 09/114870, WO 05/113556, WO2014072937, WO2014071125, US 2009/0312310, and US 2011/0046165, the entirety of each incorporated herein by reference. Additional PI3K inhibitors that can be used in the compositions and methods provided herein include, but are not limited to, AMG-319, GSK 2126458 (2,4-Difluoro—N—{2-(methyloxy)-5-[4-(4-pyridazinyl)-6-quinolinyl]-3-pyridinyl}benzenesulfonamide), GSK 1059615 (5Z-[[4-(4-pyridinyl)-6-quinolinyl]methylene]-2,4-thiazolidinedione), GDC-0032 (4-[5,6-dihydro-2-[3-methyl-1-(1-methylethyl)-1H-1,2,4-triazol-5-yl]imidazo[1,2-d][1,4]benzoxazepin-9-yl]-α,α-dimethyl-1H-Pyrazole-1-acetamide), GDC-0980 ((S)-1-(4-((2-(2-aminopyrimidin-5-yl)-7-methyl-4-morpholinothieno[3,2-d]pyrimidin-6-yl)methyl)piperazin-1-yl)-2-hydroxypropan-1-one), GDC-0941 (2-(1H-indazol-4-yl)-6-((4-(methylsulfonyl)piperazin-1-yl)methyl)-4-morpholinothieno[3,2-d]pyrimidine), XL147 (N—(3-(benzo[c][1,2,5]thiadiazol-5-ylamino)quinoxalin-2-yl)-4-methylbenzenesulfonamide), XL499, XL765 (SAR245409, N—[4-[[[3-[(3,5-dimethoxyphenyl)amino]-2-quinoxalinyl]amino]sulfonyl]phenyl]-3-methoxy-4-methyl-benzamide), PF-4691502 (2-amino-6-(6-methoxypyridin-3-yl)-4-methyl-8-[(1R,4R)-4-(2-hydroxyethoxy)cyclohexyl]-7H, 8H-pyrido[2,3-d]pyrimidin-7-one), BKM 120 (buparlisib, 5-(2,6-dimorpholinopyrimidin-4-yl)-4-(trifluoromethyl) pyridin-2-amine), Idelalisib (CAL-101, GS1101, (S)-2-(1-(9H-purin-6-ylamino)propyl)-5-fluoro-3-phenylquinazolin-4(3H)-one), CAL 263, SF1126 (3-[[2-[[5-[[amino (azaniumyl)methylidene]amino]-2-[[4-oxo-4-[4-(4-oxo-8-phenylchromen-2-yl)morpholin-4-ium-4-yl]oxybutanoyl] amino]pentanoyl]amino]acetyl]amino]-4-(1-carboxylatopropylamino)-4-oxobutanoate), PX-866 (sonolisib, [(3aR,6E,9S,9aR,10R,11aS)-6-[[bis(prop-2-enyl)amino]methylidene]-5-hydroxy-9-(methoxymethyl)-9a, 11a-dimethyl-1,4,7-trioxo-2,3,3a,9,10,11-hexahydroindeno[4,5-h]isochromen-10-yl]acetate), BEZ235 (2-methyl-2-(4-(3-methyl-2-oxo-8-(quinolin-3-yl)-2,3-dihydroimidazo [4,5-c]quinolin-1-yl)phenyl)propanenitrile), GS9820 (CAL-120, (S)-2-(1-((9H-purin-6-yl)amino)ethyl)-6-fluoro-3-phenylquinazolin-4(3H)-one), BYL719 ((2S)-1,2-Pyrrolidinedicarboxamide, N1-[4-methyl-5-[2-(2,2,2-trifluoro-1,1-dimethylethyl)-4-pyridinyl]-2-thiazolyl]), RP6503, RP6530, TGR1202 (((S)-2-(l-(4-amino-3-(3-fluoro-4-isopropoxyphenyl)-1H-pyrazolo[3,4-d]pyrimidin-1-yl)ethyl)-6-fluoro-3-(3-fluorophenyl)-4H-chromen-4-one)), INK1117 (MLN—1117), PX-866, BAY 80-6946 (2-amino—N—(7-methoxy-8-(3-morpholinopropoxy)-2,3-dihydroimidazo[1,2-c]quinazolin-5-yl)pyrimidine-5-carboxamide), IC87114 (2-((6-amino-9H-purin-9-yl)methyl)-5-methyl-3-o-tolylquinazolin-4(3H)-one), Palomid 529 (3-(4-methoxybenzyloxy)-8-(1-hydroxyethyl)-2-methoxy-6H- benzo[c]chromen-6-one), ZSTK474 (2-(difluoromethyl)-1-(4,6-dimorpholino-1,3,5-triazin-2-yl)-1H-benzo[d]imidazole), PWT33597, TG100-115 (6,7-Bis(3-hydroxyphenyl)pteridine-2,4-diamine), GNE-477 (5-[7-methyl-4-(morpholin-4-yl)-6-[(4-methylsulfonylpiperazin-1-yl)methyl]thieno[3,2-d]pyrimidin-2-yl]pyrimidin-2-amine), CUDC-907 (N—hydroxy-2-(((2-(6-methoxypyridin-3-yl)-4-morpholinothieno[3,2-d]pyrimidin-6-yl)methyl)(methyl)amino)pyrimidine-5-carboxamide), AEZS-136, BGT-226 (8-(6-methoxypyridin-3-yl)-3-methyl-1-(4-(piperazin-1l-yl)-3-(trifluoromethyl)phenyl)-1H-imidazo[4,5-c]quinolin-2(3H)-one maleic acid), PF-05212384 (1-(4-(4-(dimethylamino)piperidine-1-carbonyl)phenyl)-3-(4-(4,6-dimorpholino-1,3,5-triazin-2-yl)phenyl)urea), LY3023414, PI-103 (3-[4-(4-morpholinyl)pyrido[3',2':4,5]furo[3,2-d]pyrimidin-2-yl]-phenol), INCB040093, CAL-130 ((S)-2-(1-((2-amino-9H-purin-6-yl)amino)ethyl)-5-methyl-3-(o-tolyl)quinazolin-4(3H)-one), LY294002 (2-Morpholin-4-yl-8-phenylchromen-4-one) and wortmannin.

In one embodiment, the PI3K inhibitor is Idelalisib (GS1101), CAL-130, BKM 120, GDC-0941, PX-866, GDC-0032, BAY 80-6946, BEZ235, BYL719, BGT-226, PF-4691502, GDC-0980, GSK 2126458, PF-05212384, XL765, or XL147.

In one embodiment, the PI3K inhibitor is Idelalisib (also known as GS1101 or CAL-101) and has the chemical name (S)-2-(1-(9H-purin-6-ylamino)propyl)-5-fluoro-3-phenylquinazolin-4(3H)-one and the following structure:

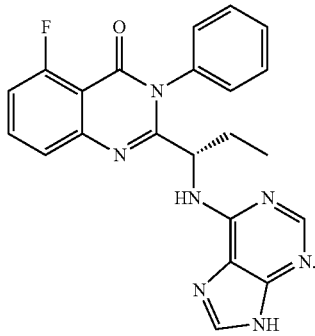 [SMILES: CC[C@H](Nc1ncnc2[nH]cnc12)c1nc2cccc(F)c2c(=O)n1-c1ccccc1]

In certain embodiments, a PI3K inhibitor is a compound that inhibits one or more PI3K isoforms, e.g., alpha, beta, delta, or gamma isoform. In one embodiment, a PI3K inhibitor is a compound that inhibits one or more PI3K isoforms with an $IC_{50}$ of less than about 1000 nM, less than about 900 nM, less than about 800 nM, less than about 700 nM, less than about 600 nM, less than about 500 nM, less than about 400 nM, less than about 300 nM, less than about 200 nM, less than about 100 nM, less than about 75 nM, less than about 50 nM, less than about 25 nM, less than about 20 nM, less than about 15 nM, less than about 10 nM, less than about 10 nM, less than about 5 nM, or less than about 1 nM.

In one embodiment, the PI3K inhibitor is a compound that inhibits alpha, beta, delta and gamma isoforms of PI3K. In another embodiment, the PI3K inhibitor is a compound that inhibits beta, delta, and gamma isoforms of PI3K. In another embodiment, the PI3K inhibitor is a compound that inhibits the delta and gamma isoforms of PI3K.

In certain embodiments, the PI3K inhibitor is a PI3K isoform selective inhibitor. In one embodiment, the PI3K inhibitor is a PI3K alpha selective inhibitor. In another embodiment, the PI3K inhibitor is a PI3K beta selective inhibitor.

In certain embodiments, the PI3K inhibitor is a PI3K delta selective inhibitor. In one embodiment, the PI3K delta selective inhibitor selectively inhibits PI3K delta isoform over PI3K gamma isoform. In one embodiment, the PI3K delta selective inhibitor has a gamma/delta selectivity ratio of greater than 1, greater than about 5, greater than about 10, greater than about 50, greater than about 100, greater than about 200, greater than about 400, greater than about 600, greater than about 800, greater than about 1000, greater than about 1500, greater than about 2000, greater than about 5000, greater than about 10,000, or greater than about 20,000. In one embodiment, the PI3K delta selective inhibitor has a gamma/delta selectivity ratio in the range of from greater than 1 to about 5, from about 5 to about 10, from about 10 to about 50, from about 50 to about 850, or greater than about 850. In one embodiment, the gamma/delta selectivity ratio is determined by dividing the inhibitor's $IC_{50}$ against PI3K gamma isoform by the inhibitor's $IC_{50}$ against PI3K delta isoform.

In certain embodiments, the PI3K inhibitor is a PI3K delta selective inhibitor. In one embodiment, the PI3K delta selective inhibitor selectively inhibits PI3K delta isoform over PI3K alpha isoform. In one embodiment, the PI3K delta selective inhibitor has an alpha/delta selectivity ratio of greater than 1, greater than about 5, greater than about 10, greater than about 50, greater than about 100, greater than about 200, greater than about 400, greater than about 600, greater than about 800, greater than about 1000, greater than about 1500, greater than about 2000, greater than about 5000, greater than about 10,000, or greater than about 20,000. In one embodiment, the PI3K delta selective inhibitor has an alpha/delta selectivity ratio in the range of from greater than 1 to about 5, from about 5 to about 10, from about 10 to about 50, from about 50 to about 850, or greater than about 850. In one embodiment, the alpha/delta selectivity ratio is determined by dividing the inhibitor's $IC_{50}$ against PI3K alpha isoform by the inhibitor's $IC_{50}$ against PI3K delta isoform.

In certain embodiments, the PI3K inhibitor is a PI3K delta selective inhibitor. In one embodiment, the PI3K delta selective inhibitor selectively inhibits PI3K delta isoform over PI3K beta isoform. In one embodiment, the PI3K delta selective inhibitor has a beta/delta selectivity ratio of greater than 1, greater than about 5, greater than about 10, greater than about 50, greater than about 100, greater than about 200, greater than about 400, greater than about 600, greater than about 800, greater than about 1000, greater than about 1500, greater than about 2000, greater than about 5000, greater than about 10,000, or greater than about 20,000. In one embodiment, the PI3K delta selective inhibitor has a beta/delta selectivity ratio in the range of from greater than 1 to about 5, from about 5 to about 10, from about 10 to about 50, from about 50 to about 850, or greater than about 850. In one embodiment, the beta/delta selectivity ratio is determined by dividing the inhibitor's $IC_{50}$ against PI3K beta isoform by the inhibitor's $IC_{50}$ against PI3K delta isoform.

In certain embodiments, the PI3K inhibitor is selective for both gamma and delta. In one embodiment, the PI3K gamma and delta selective inhibitor selectively inhibits PI3K gamma and delta isoforms over PI3K beta isoform. In one embodiment, the PI3K gamma and delta selective inhibitor has a beta/delta selectivity ratio of greater than 1, greater than about 5, greater than about 10, greater than about 50, greater than about 100, greater than about 200, greater than about 400, greater than about 600, greater than about 800, greater than about 1000, greater than about 1500, greater than about 2000, greater than about 5000, greater than about 10,000, or greater than about 20,000 and a beta/gamma selectivity ratio of greater than 1, greater than about 5, greater than about 10, greater than about 50, greater than about 100, greater than about 200, greater than about 400, greater than about 600, greater than about 800, greater than about 1000, greater than about 1500, greater than about 2000, greater than about 5000, greater than about 10,000, or greater than about 20,000. In one embodiment, the PI3K delta selective inhibitor has a beta/delta selectivity ratio in the range of from greater than 1 to about 5, from about 5 to about 10, from about 10 to about 50, from about 50 to about 850, or greater than about 850 and a beta/gamma selectivity ratio in the range of from greater than 1 to about 5, from about 5 to about 10, from about 10 to about 50, from about 50 to about 850, or greater than about 850. In one embodiment, the beta/delta selectivity ratio is determined by dividing the inhibitor's IC50 against PI3K beta isoform by the inhibitor's IC50 against PI3K delta isoform and the beta/gamma selectivity ratio is determined by dividing the inhibitor's IC50 against PI3K beta isoform by the inhibitor's IC50 against PI3K gamma isoform.

PI3K delta inhibitors that can be used in the compositions and methods provided herein include, but are not limited to, GSK-2269557 (2-(6-(1H-indol-4-yl)-1H-indazol-4-yl)-5-((4-isopropylpiperazin-1-yl)methyl)oxazole), GS-9820, GS-1101 (5-fluoro-3-phenyl-2-([S)]-1-[9H-purin-6-ylamino]-propyl)-3H-quinazolin-4-one), AMG319, or TGR-1202 (((S)-2-(1-(4-amino-3-(3-fluoro-4-isopropoxyphenyl)-1H-pyrazolo[3,4-d]pyrimidin-1-yl)ethyl)-6-fluoro-3-(3-fluorophenyl)-4H-chromen-4-one)), or a mixture thereof. In one embodiment, the PI3K delta inhibitor is Idelalisib.

In one embodiment, the PI3K inhibitor is a PI3K inhibitor as described in WO 2005/113556, the entirety of which is incorporated herein by reference. In one embodiment, the PI3K inhibitor is Compound Nos. 113 or 107 as described in WO2005/113556.

In one embodiment, the PI3K inhibitor is a PI3K inhibitor as described in WO2014/006572, the entirety of which is incorporated herein by reference. In one embodiment, the PI3K inhibitor is Compound Nos. A1, A2, B, B1, or B2 as described in WO2014/006572.

In certain embodiments, the PI3K inhibitor is a PI3K delta/gamma dual inhibitor. In one embodiment, the PI3K delta/gamma dual inhibitor has an $IC_{50}$ value against PI3K alpha that is at least 5×, 10×, 20×, 50×, 100×, 200×, 500×, or 1000× higher than its $IC_{50}$ values against delta and gamma.

In certain embodiments, the PI3K inhibitor is Compound 1 of the structure:

Compound 1

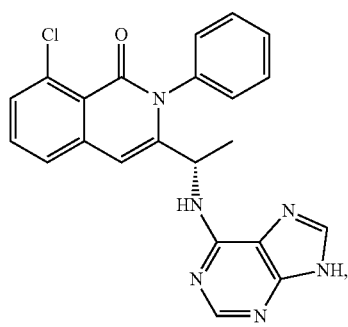

or a pharmaceutically acceptable form thereof.

Compound 1 has a chemical name of (S)-3-(1-((9H-purin-6-yl)amino)ethyl)-8-chloro-2-phenylisoquinolin-1(2H)-one. An exemplary method for synthesizing Compound 1 has been previously described in U.S. Pat. No. 8,193,182, which is incorporated by reference in its entirety. Without being limited by a particular theory, Compound 1 is a PI3K delta/gamma dual inhibitor and can be used to treat cancers. See U.S. Pat. No. 8,193,182.

Compound 1 provided herein contains one chiral center, and can exist as a mixture of enantiomers, e.g., a racemic mixture. This application encompasses the use of stereomerically pure forms of such a compound, as well as the use of mixtures of those forms. For example, mixtures comprising equal or unequal amounts of the enantiomers of Compound 1 provided herein may be used in methods and compositions disclosed herein. These isomers may be asymmetrically synthesized or resolved using standard techniques such as chiral columns or chiral resolving agents. See, e.g., Jacques, J., et al., *Enantiomers, Racemates and Resolutions* (Wiley-Interscience, New York, 1981); Wilen, S. H., et al., *Tetrahedron* 33:2725 (1977); Eliel, E. L., *Stereochemistry of Carbon Compounds* (McGraw-Hill, N Y, 1962); and Wilen, S. H., *Tables of Resolving Agents and Optical Resolutions p.* 268 (E. L. Eliel, Ed., Univ. of Notre Dame Press, Notre Dame, Ind., 1972).

In one embodiment, the PI3K inhibitor provided herein is a mixture of Compound 1 and its (R)-enantiomer. In one embodiment, the PI3K inhibitor provided herein is a racemic mixture of Compound 1 and its (R)-enantiomer. In other embodiments, the compound mixture has an (S)-enantiomeric purity of greater than about 55%, about 60%, about 65%, about 70%, about 75%, about 80%, about 85%, about 90%, about 95%, about 96%, about 97%, about 98%, about 99%, about 99.5%, or more. In other embodiments, the compound mixture has an (S)-enantiomeric purity of greater than about 55% to about 99.5%, greater than about 60% to about 99.5%, greater than about 65% to about 99.5%, greater than about 70% to about 99.5%, greater than about 75% to about 99.5%, greater than about 80% to about 99.5%, greater than about 85% to about 99.5%, greater than about 90% to about 99.5%, greater than about 95% to about 99.5%, greater than about 96% to about 99.5%, greater than about 97% to about 99.5%, greater than about 98% to greater than about 99.5%, greater than about 99% to about 99.5%, or more.

In other embodiments, the compound mixture has an (R)-enantiomeric purity of greater than about 55%, about 60%, about 65%, about 70%, about 75%, about 80%, about 85%, about 90%, about 95%, about 96%, about 97%, about 98%, about 99%, about 99.5%, or more. In other embodiments, the compound mixture has an (R)-enantiomeric purity of greater than about 55% to about 99.5%, greater than about 60% to about 99.5%, greater than about 65% to about 99.5%, greater than about 70% to about 99.5%, greater than about 75% to about 99.5%, greater than about 80% to about 99.5%, greater than about 85% to about 99.5%, greater than about 90% to about 99.5%, greater than about 95% to about 99.5%, greater than about 96% to about 99.5%, greater than about 97% to about 99.5%, greater than about 98% to greater than about 99.5%, greater than about 99% to about 99.5%, or more.

As used herein, Compound 1 also refers to any crystal form or polymorph of (S)-3-(1-((9H-purin-6-yl)amino) ethyl)-8-chloro-2-phenylisoquinolin-1(2H)-one. In some embodiments, a polymorph of Compound 1, or a pharmaceutically form thereof, disclosed herein is used. Exemplary polymorphs are disclosed in U.S. Patent Publication No. 2012/0184568, which is hereby incorporated by reference in its entirety. In one embodiment, the compound is Form A of Compound 1. In one embodiment, the compound is Form B of Compound 1. In one embodiment, the compound is Form C of Compound 1. In one embodiment, the compound is Form D of Compound 1. In one embodiment, the compound is Form E of Compound 1. In one embodiment, the compound is Form F of Compound 1. In one embodiment, the compound is Form G of Compound 1. In one embodiment, the compound is Form H of Compound 1. In one embodiment, the compound is Form I of Compound 1. In one embodiment, the compound is Form J of Compound 1. In one embodiment, the compound is a mixture of solid forms (e.g., polymorphs and/or amorphous forms) of Compound 1 disclosed herein.

In one embodiment, the composition comprises the PI3K delta selective inhibitor (e.g. Idelalisib), or a pharmaceutically acceptable form thereof, at an amount sufficient to deliver a blood plasma concentration profile with an AUC (area under curve) of from about 1 ng/mL*h to about 1 mg/mL*h, from about 10 ng/mL*h to about 100 µg/mL*h, from about 100 ng/mL*h to about 10 µg/mL*h, from about 1 µg/mL*h to about 10 µg/mL*h. In one embodiment the composition comprises the PI3K delta selective inhibitor (e.g. GS1101), or a pharmaceutically acceptable form thereof, at an amount sufficient to deliver a blood plasma concentration profile with an AUC (area under curve) of from about 0.1 µg/mL*h to about 10 µg/mL*h, from about 0.2 µg/mL*h to about 9 µg/mL*h, from about 0.3 µg/mL*h to about 8 µg/mL*h, from about 0.4 µg/mL*h to about 7 µg/mL*h, from about 0.5 µg/mL*h to about 6 µg/mL*h, from about 0.6 µg/mL*h to about 5 µg/mL*h, from about 0.7 µg/mL*h to about 4 µg/mL*h, from about 0.8 µg/mL*h to about 3 µg/mL*h, from about 0.9 µg/mL*h to about 2 µg/mL*h, or from about 0.9 µg/mL*h to about 1 µg/mL*h. In one embodiment the composition comprises the PI3K delta selective inhibitor which is Idelalisib, or a pharmaceutically acceptable form thereof, at an amount sufficient to deliver a blood plasma concentration profile with an AUC (area under curve) of from about 1 µg/mL*h to about 10 µg/mL*h, from about 5 µg/mL*h to about 9 µg/mL*h, or from about 6 µg/mL*h to about 8 µg/mL*h.

In one embodiment, the PI3K delta inhibitor (e.g., Idelalisib) is administered at an amount to reach an area under the plasma concentration-time curve at steady-state (AUCss) at about 5000 ng/mL*hr to about 10000 ng/mL*hr, about 5000 ng/mL*hr to about 9000 ng/mL*hr, about 6000 ng/mL*hr to about 9000 ng/mL*hr, about 6000 ng/mL*hr to about 8000 ng/mL*hr, about 6500 ng/mL*hr to about 7500 ng/mL*hr, or about 7000 ng/mL*hr.

In one embodiment, the PI3K delta inhibitor (e.g., Idelalisib) is administered at an amount to reach an area under the plasma concentration-time curve at steady-state (AUCss) at less than about 10000 ng/mL*hr, less than about 9500 ng/mL*hr, less than about 9000 ng/mL*hr, less than about 8500 ng/mL*hr, less than about 8000 ng/mL*hr, less than about 7000 ng/mL*hr, less than about 6000 ng/mL*hr, less than about 5000 ng/mL*hr, less than about 4000 ng/mL*hr, less than about 3000 ng/mL*hr, less than about 2000 ng/mL*hr, less than about 1000 ng/mL*hr, less than about 500 ng/mL*hr, less than about 100 ng/mL*hr, less than about 10 ng/mL*hr, or less than about 1 ng/mL*hr.

In one embodiment, the PI3K delta inhibitor (e.g., Idelalisib) is administered at an amount to reach maximum plasma concentration at steady state (Cmaxss) at about 1000 ng/mL to about 5000 ng/mL, about 1000 ng/mL to about 4000 ng/mL, about 1000 ng/mL to about 3000 ng/mL, about 1000 ng/mL to about 2500 ng/mL, about 1400 ng/mL to about 2300 ng/mL, about 2000 ng/mL to about 2300 ng/mL, or about 2200 ng/mL.

In one embodiment, the PI3K delta inhibitor (e.g., Idelalisib) is administered at an amount to reach maximum plasma concentration at steady state (Cmaxss) at less than about 5000 ng/mL, less than about 4000 ng/mL, less than about 3000 ng/mL, less than about 2000 ng/mL, less than about 1500 ng/mL, less than about 1000 ng/mL, less than about 500 ng/mL, less than about 100 ng/mL, less than about 50 ng/mL, less than about 25 ng/mL, less than about 10 ng/mL, or less than about 1 ng/mL.

In one embodiment, the composition comprises the PI3K delta inhibitor (e.g., Idelalisib), or a pharmaceutically acceptable form thereof, at an amount in the range of from about 0.1 mg to about 500 mg, from about 1 mg to about 500 mg, from about 10 mg to about 500 mg, from about 50 mg to about 500 mg, from about 100 mg to about 400 mg, from about 200 mg to about 400 mg, from about 250 mg to about 350 mg, or about 300 mg. In one embodiment, the composition comprises the PI3K delta inhibitor (e.g., Idelalisib), or a pharmaceutically acceptable form thereof, at an amount in the range of from about 0.1 mg to about 75 mg, from about 1 mg to about 75 mg, from about 5 mg to about 75 mg, from about 5 mg to about 60 mg, from about 5 mg to about 50 mg, from about 5 mg to about 30 mg, from about 5 mg to about 25 mg, from about 10 mg to about 25 mg, or from about 10 mg to about 20 mg.

In one embodiment, the composition comprises the PI3K delta inhibitor (e.g., Idelalisib), or a pharmaceutically acceptable form thereof, at an amount of less than about 500 mg, less than about 400 mg, less than about 350 mg, less than about 300 mg, less than about 250 mg, less than about 200 mg, less than about 150 mg, less than about 100 mg, less than about 75 mg, less than about 50 mg, less than about 30 mg, less than about 25 mg, less than about 20 mg, less than about 19 mg, less than about 18 mg, less than about 17 mg, less than about 16 mg, less than about 16 mg, less than about 15 mg, less than about 14 mg, less than about 13 mg, less than about 12 mg, less than about 11 mg, or less than about 10 mg.

In one embodiment, the PI3K delta inhibitor (e.g., Idelalisib), or a pharmaceutically acceptable form thereof, is administered at a dosage of in the range of from about 0.1 mg to about 500 mg, from about 1 mg to about 500 mg, from about 10 mg to about 500 mg, from about 50 mg to about 500 mg, from about 100 mg to about 400 mg, from about 200 mg to about 400 mg, from about 250 mg to about 350 mg, or about 300 mg. In one embodiment, the composition comprises the PI3K delta inhibitor (e.g., Idelalisib), or a pharmaceutically acceptable form thereof, at an amount in the range of from about 0.1 mg to about 75 mg, from about 1 mg to about 75 mg, from about 5 mg to about 75 mg, from about 5 mg to about 60 mg, from about 5 mg to about 50 mg, from about 5 mg to about 30 mg, from about 5 mg to about 25 mg, from about 10 mg to about 25 mg, or from about 10 mg to about 20 mg daily.

In one embodiment, the PI3K delta inhibitor (e.g., Idelalisib), or a pharmaceutically acceptable form thereof, is administered at a dosage of less than about 500 mg, less than about 400 mg, less than about 350 mg, less than about 300 mg, less than about 250 mg, less than about 200 mg, less than about 150 mg, less than about 100 mg, less than about 75 mg, less than about 50 mg, less than about 30 mg, less than about 25 mg, less than about 20 mg, less than about 19 mg, less than about 18 mg, less than about 17 mg, less than about 16 mg, less than about 16 mg, less than about 15 mg, less than about 14 mg, less than about 13 mg, less than about 12 mg, less than about 11 mg, or less than about 10 mg daily.

In one embodiment, the composition comprises the PI3K delta/gamma inhibitor (e.g., Compound 1), or a pharmaceutically acceptable form thereof, at an amount sufficient to deliver a blood plasma concentration profile with an AUC (area under curve) of from about 1 ng/mL*h to about 1 mg/mL*h, from about 10 ng/mL*h to about 100 µg/mL*h, from about 100 ng/mL*h to about 10 µg/mL*h, from about 1 µg/mL*h to about 10 µg/mL*h. In one embodiment the composition comprises the PI3K delta/gamma inhibitor (e.g., Compound 1), or a pharmaceutically acceptable form thereof, at an amount sufficient to deliver a blood plasma concentration profile with an AUC (area under curve) of from about 0.1 µg/mL*h to about 10 µg/mL*h, from about 0.2 µg/mL*h to about 9 µg/mL*h, from about 0.3 µg/mL*h to about 8 µg/mL*h, from about 0.4 µg/mL*h to about 7 µg/mL*h, from about 0.5 µg/mL*h to about 6 µg/mL*h, from about 0.6 µg/mL*h to about 5 µg/mL*h, from about 0.7 µg/mL*h to about 4 µg/mL*h, from about 0.8 µg/mL*h to about 3 µg/mL*h, from about 0.9 µg/mL*h to about 2 µg/mL*h, or from about 0.9 µg/mL*h to about 1 µg/mL*h. In one embodiment the composition comprises the PI3K delta/gamma inhibitor which is Compound 1, or a pharmaceutically acceptable form thereof, at an amount sufficient to deliver a blood plasma concentration profile with an AUC (area under curve) of from about 1 µg/mL*h to about 10 µg/mL*h, from about 5 µg/mL*h to about 9 µg/mL*h, or from about 6 µg/mL*h to about 8 µg/mL*h.

In one embodiment, the PI3K delta/gamma dual inhibitor (e.g., Compound 1) is administered at an amount to reach an area under the plasma concentration-time curve at steady-state (AUCss) at about 5000 ng/mL*hr to about 10000 ng/mL*hr, about 5000 ng/mL*hr to about 9000 ng/mL*hr, about 6000 ng/mL*hr to about 9000 ng/mL*hr, about 7000 ng/mL*hr to about 9000 ng/mL*hr, about 8000 ng/mL*hr to about 9000 ng/mL*hr, or about 8787 ng/mL*hr.

In one embodiment, the PI3K delta/gamma dual inhibitor (e.g., Compound 1) is administered at an amount to reach an area under the plasma concentration-time curve at steady-state (AUCss) at less than about 10000 ng/mL*hr, less than about 9500 ng/mL*hr, less than about 9000 ng/mL*hr, less than about 8500 ng/mL*hr, less than about 8000 ng/mL*hr, less than about 7000 ng/mL*hr, less than about 6000 ng/mL*hr, less than about 5000 ng/mL*hr, less than about 4000 ng/mL*hr, less than about 3000 ng/mL*hr, less than about 2000 ng/mL*hr, less than about 1000 ng/mL*hr, less than about 500 ng/mL*hr, less than about 100 ng/mL*hr, less than about 10 ng/mL*hr, or less than about 1 ng/mL*hr.

In one embodiment, the PI3K delta/gamma dual inhibitor (e.g., Compound 1) is administered at an amount to reach maximum plasma concentration at steady state (Cmaxss) at about 1000 ng/mL to about 5000 ng/mL, about 1000 ng/mL to about 4000 ng/mL, about 1000 ng/mL to about 3000 ng/mL, about 1000 ng/mL to about 2500 ng/mL, about 1400 ng/mL to about 2000 ng/mL, about 1400 ng/mL to about 1500 ng/mL, or about 1487 ng/mL.

In one embodiment, the PI3K delta/gamma dual inhibitor (e.g., Compound 1) is administered at an amount to reach maximum plasma concentration at steady state (Cmaxss) at less than about 5000 ng/mL, less than about 4000 ng/mL, less than about 3000 ng/mL, less than about 2000 ng/mL, less than about 1500 ng/mL, less than about 1000 ng/mL, less than about 500 ng/mL, less than about 100 ng/mL, less than about 50 ng/mL, less than about 25 ng/mL, less than about 10 ng/mL, or less than about 1 ng/mL.

In one embodiment, the composition comprises the PI3K delta/gamma dual inhibitor (e.g., Compound 1), or a pharmaceutically acceptable form thereof, at an amount in the range of from about 0.1 mg to about 75 mg, from about 1 mg to about 75 mg, from about 5 mg to about 75 mg, from about 5 mg to about 60 mg, from about 5 mg to about 50 mg, from about 5 mg to about 30 mg, from about 5 mg to about 25 mg, from about 10 mg to about 25 mg, or from about 10 mg to about 20 mg.

In one embodiment, the composition comprises the PI3K delta/gamma dual inhibitor (e.g., Compound 1), or a pharmaceutically acceptable form thereof, at an amount of less than about 25 mg, less than about 20 mg, less than about 19 mg, less than about 18 mg, less than about 17 mg, less than about 16 mg, less than about 16 mg, less than about 15 mg, less than about 14 mg, less than about 13 mg, less than about 12 mg, less than about 11 mg, or less than about 10 mg.

In one embodiment, the PI3K delta/gamma dual inhibitor (e.g., Compound 1), or a pharmaceutically acceptable form thereof, is administered at a dosage of in the range of from about 0.1 mg to about 75 mg, from about 1 mg to about 75 mg, from about 5 mg to about 75 mg, from about 5 mg to about 60 mg, from about 5 mg to about 50 mg, from about 5 mg to about 30 mg, from about 5 mg to about 25 mg, from about 10 mg to about 25 mg, or from about 10 mg to about 20 mg daily.

In one embodiment, the PI3K delta/gamma dual inhibitor (e.g., Compound 1), or a pharmaceutically acceptable form thereof, is administered at a dosage of less than about 25 mg, less than about 20 mg, less than about 19 mg, less than about 18 mg, less than about 17 mg, less than about 16 mg, less than about 16 mg, less than about 15 mg, less than about 14 mg, less than about 13 mg, less than about 12 mg, less than about 11 mg, or less than about 10 mg daily.

In one embodiment, the composition comprises Compound 1, or a pharmaceutically acceptable form thereof, at an amount sufficient to deliver a blood plasma concentration profile with an AUC (area under curve) of from about 1 ng/mL*h to about 1 mg/mL*h, from about 10 ng/mL*h to about 100 µg/mL*h, from about 100 ng/mL*h to about 10 µg/mL*h, from about 1 µg/mL*h to about 10 µg/mL*h. In one embodiment the composition comprises Compound 1, or a pharmaceutically acceptable form thereof, at an amount sufficient to deliver a blood plasma concentration profile with an AUC (area under curve) of from about 0.1 µg/mL*h to about 10 µg/mL*h, from about 0.2 µg/mL*h to about 9 µg/mL*h, from about 0.3 µg/mL*h to about 8 µg/mL*h, from about 0.4 µg/mL*h to about 7 µg/mL*h, from about 0.5 µg/mL*h to about 6 µg/mL*h, from about 0.6 µg/mL*h to about 5 µg/mL*h, from about 0.7 µg/mL*h to about 4 µg/mL*h, from about 0.8 µg/mL*h to about 3 µg/mL*h, from about 0.9 µg/mL*h to about 2 µg/mL*h, or from about 0.9 µg/mL*h to about 1 µg/mL*h. In one embodiment the composition comprises Compound 1, or a pharmaceutically acceptable form thereof, at an amount sufficient to deliver a blood plasma concentration profile with an AUC (area under curve) of from about 1 µg/mL*h to about 10 µg/mL*h, from about 5 µg/mL*h to about 9 µg/mL*h, or from about 6 µg/mL*h to about 8 µg/mL*h.

In one embodiment Compound 1 is administered at an amount to reach an area under the plasma concentration-time curve at steady-state (AUCss) at about 5000 ng/mL*hr to about 10000 ng/mL*hr, about 5000 ng/mL*hr to about 9000 ng/mL*hr, about 6000 ng/mL*hr to about 9000 ng/mL*hr, about 7000 ng/mL*hr to about 9000 ng/mL*hr, about 8000 ng/mL*hr to about 9000 ng/mL*hr, or about 8787 ng/mL*hr.

In one embodiment, Compound 1 is administered at an amount to reach an area under the plasma concentration-time curve at steady-state (AUCss) at less than about 10000 ng/mL*hr, less than about 9500 ng/mL*hr, less than about 9000 ng/mL*hr, less than about 8500 ng/mL*hr, less than about 8000 ng/mL*hr, less than about 7000 ng/mL*hr, less than about 6000 ng/mL*hr, less than about 5000 ng/mL*hr, less than about 4000 ng/mL*hr, less than about 3000 ng/mL*hr, less than about 2000 ng/mL*hr, less than about 1000 ng/mL*hr, less than about 500 ng/mL*hr, less than about 100 ng/mL*hr, less than about 10 ng/mL*hr, or less than about 1 ng/mL*hr.

In one embodiment, Compound 1 is administered at an amount to reach maximum plasma concentration at steady state (Cmaxss) at about 1000 ng/mL to about 5000 ng/mL, about 1000 ng/mL to about 4000 ng/mL, about 1000 ng/mL to about 3000 ng/mL, about 1000 ng/mL to about 2500 ng/mL, about 1400 ng/mL to about 2000 ng/mL, about 1400 ng/mL to about 1500 ng/mL, or about 1487 ng/mL.

In one embodiment, Compound 1 is administered at an amount to reach maximum plasma concentration at steady state (Cmaxss) at less than about 5000 ng/mL, less than about 4000 ng/mL, less than about 3000 ng/mL, less than about 2000 ng/mL, less than about 1500 ng/mL, less than about 1000 ng/mL, less than about 500 ng/mL, less than about 100 ng/mL, less than about 50 ng/mL, less than about 25 ng/mL, less than about 10 ng/mL, or less than about 1 ng/mL.

In one embodiment, the composition comprises Compound 1, or a pharmaceutically acceptable form thereof, at an amount in the range of from about 0.1 mg to about 75 mg, from about 1 mg to about 75 mg, from about 5 mg to about 75 mg, from about 5 mg to about 60 mg, from about 5 mg to about 50 mg, from about 5 mg to about 30 mg, from about 5 mg to about 25 mg, from about 10 mg to about 25 mg, or from about 10 mg to about 20 mg.

In one embodiment, the composition comprises Compound 1, or a pharmaceutically acceptable form thereof, at an amount of less than about 25 mg, less than about 20 mg, less than about 19 mg, less than about 18 mg, less than about 17 mg, less than about 16 mg, less than about 16 mg, less than about 15 mg, less than about 14 mg, less than about 13 mg, less than about 12 mg, less than about 11 mg, or less than about 10 mg. In one embodiment, the composition comprises Compound 1, or a pharmaceutically acceptable form thereof, at an amount of about 50 mg, about 37.5 mg, about 25 mg, about 20 mg, about 15 mg, about 10 mg, about 5 mg, or about 1 mg.

In one embodiment, Compound 1, or a pharmaceutically acceptable form thereof, is administered at a dosage of in the range of from about 0.1 mg to about 75 mg, from about 1 mg to about 75 mg, from about 5 mg to about 75 mg, from about 5 mg to about 60 mg, from about 5 mg to about 50 mg, from about 5 mg to about 30 mg, from about 5 mg to about 25 mg, from about 10 mg to about 25 mg, or from about 10 mg to about 20 mg daily.

In one embodiment, Compound 1, or a pharmaceutically acceptable form thereof, is administered at a dosage of less than about 25 mg, less than about 20 mg, less than about 19 mg, less than about 18 mg, less than about 17 mg, less than about 16 mg, less than about 16 mg, less than about 15 mg, less than about 14 mg, less than about 13 mg, less than about 12 mg, less than about 11 mg, or less than about 10 mg daily. In one embodiment, Compound 1, or a pharmaceutically acceptable form thereof, is administered at a dosage of about 50 mg, about 37.5 mg, about 25 mg, about 20 mg, about 15 mg, about 10 mg, about 5 mg, or about 1 mg daily.

Any of the compounds disclosed herein can be in the form of pharmaceutically acceptable salts, hydrates, solvates, chelates, non-covalent complexes, isomers, prodrugs, isotopically labeled derivatives, or mixtures thereof.

2.2 Combinations of PI3K Inhibitors and Checkpoint Modulators

In certain embodiments, provided herein are methods of treating, managing, or preventing a cancer in a subject comprising administering to the subject a therapeutically effective amount of a PI3K inhibitor, or a pharmaceutically acceptable form thereof, in combination with a checkpoint modulator, or a pharmaceutically acceptable form thereof.

In certain embodiments, provided herein are pharmaceutical compositions comprising a therapeutically effective amount of a PI3K inhibitor, or a pharmaceutically acceptable form thereof, and a checkpoint modulator, or a pharmaceutically acceptable form thereof.

As used herein, the term "immune checkpoint modulator" or "checkpoint modulator" refers to molecules that totally or partially interfere with or modulate one or more checkpoint molecules. In one embodiment, the checkpoint modulator is a "checkpoint inhibitor", which refers to a molecule that inhibits, decreases or interferes with the activity of an inhibitory checkpoint molecule. Without being bound by a particular theory, an inhibitory checkpoint molecule down-regulates immune responses (e.g., T-cell activation) by delivery of a negative signal to T-cells following their engagement by ligands or counter-receptors. In another embodiment, the checkpoint modulator is an activator of a costimulatory molecule.

In certain embodiments, checkpoint inhibitors for use with the methods and compositions provided herein can inhibit the activity of an inhibitory checkpoint molecule directly, or decrease the expression of an inhibitory checkpoint molecule, or interfere with the interaction of an inhibitory checkpoint molecule and a binding partner (e.g., a ligand). The checkpoint modulators for use with the methods and compositions provided herein include, but are not limited to, a protein, a polypeptide, a peptide, an antisense oligonucleotide, an antibody, an antibody fragment, or an RNA molecule (e.g., an inhibitory RNA molecule that targets the expression of an inhibitory checkpoint molecule).

In certain embodiments, the inhibitory checkpoint molecule is selected from the group consisting of Cytotoxic T-lymphocyte antigen-4 (CTLA-4), CD80, CD86, Programmed cell death 1 (PD-1), Programmed cell death ligand 1 (PD-L1), Programmed cell death ligand 2 (PD-L2), Lymphocyte activation gene-3 (LAG-3; also known as CD223), Galectin-3, B and T lymphocyte attenuator (BTLA), T-cell membrane protein 3 (TIM3), Galectin-9 (GAL9), B7-H1, B7-H3, B7-H4, T-Cell immunoreceptor with Ig and ITIM domains (TIGIT/Vstm3/WUCAM/VSIG9), V-domain Ig suppressor of T-Cell activation (VISTA), Glucocorticoid-induced tumor necrosis factor receptor-related (GITR) protein, Herpes Virus Entry Mediator (HVEM), OX40, CD27, CD28, CD137. CGEN—15001T, CGEN—15022, CGEN—15027, CGEN—15049, CGEN—15052, and CGEN—15092.

In one embodiment, the immune checkpoint modulator is an inhibitor of an inhibitory checkpoint molecule, for instance, an inhibitor of PD-1, PD-L1, PD-L2, CTLA-4, TIM3, LAG3, VISTA, BTLA, TIGIT, LAIR1, CD160, 2B4 and/or TGFR beta. For instance, the inhibitor of an inhibitory checkpoint molecule may inhibit PD-1, PD-L1, LAG-3, TIM-3 or CTLA-4, or any combination thereof.

Inhibition of an inhibitory molecule can be performed at the DNA, RNA or protein level. For example, an inhibitory nucleic acid (e.g., a dsRNA, siRNA or shRNA), can be used to inhibit expression of an inhibitory molecule. In other embodiments, the inhibitor of an inhibitory signal is, a polypeptide, e.g., a soluble ligand (e.g., PD-1-Ig or CTLA-4 Ig), or an antibody or antigen-binding fragment thereof, that binds to the inhibitory molecule; e.g., an antibody or fragment thereof (also referred to herein as "an antibody molecule") that binds to PD-1, PD-L1, PD-L2, CTLA4, TIM3, LAG3, VISTA, BTLA, TIGIT, LAIR1, CD160, 2B4 and/or TGFR beta, or a combination thereof.

The antibody molecule may be, e.g., a full antibody or fragment thereof (e.g., a Fab, F(ab')$_2$, Fv, or a single chain Fv fragment (scFv)). The antibody molecule may be, e.g., in the form of a bispecific antibody molecule. In one embodiment, the bispecific antibody molecule has a first binding specificity to PD-1 or PD-L1 and a second binding specificity, e.g., a second binding specificity to TIM-3, LAG-3, or PD-L2.

In certain embodiments, the immune checkpoint modulator is an inhibitor of PD-1, e.g., human PD-1. In another embodiment, the immune checkpoint modulator is an inhibitor of PD-L1, e.g., human PD-L1. In one embodiment, the inhibitor of PD-1 or PD-L1 is an antibody molecule to PD-1 or PD-L1. The PD-1 or PD-L1 inhibitor can be administered alone, or in combination with other immune checkpoint modulators, e.g., in combination with an inhibitor of LAG-3, TIM-3 or CTLA-4. In some embodiments, the inhibitor of PD-1 or PD-L1, e.g., the anti-PD-1 or anti-PD-L1 antibody molecule, is administered in combination with a LAG-3 inhibitor, e.g., an anti-LAG-3 antibody molecule. In another embodiment, the inhibitor of PD-1 or PD-L1, e.g., the anti-PD-1 or PD-L1 antibody molecule, is administered in combination with a TIM-3 inhibitor, e.g., an anti-TIM-3 antibody molecule. In yet other embodiments, the inhibitor of PD-1 or PD-L1, e.g., the anti-PD-1 antibody molecule, is administered in combination with a LAG-3 inhibitor, e.g., an anti-LAG-3 antibody molecule, and a TIM-3 inhibitor, e.g., an anti-TIM-3 antibody molecule. In yet another embodiment, provided herein are other combinations of immune checkpoint modulators with a PD-1 inhibitor (e.g., one or more of PD-L2, CTLA-4, TIM3, LAG3, VISTA, BTLA, TIGIT, LAIR1, CD160, 2B4 and/or TGFR). In one embodiment, the PI3K inhibitor molecules disclosed herein are used in the aforesaid combinations of inhibitors of checkpoint molecule.

In one embodiment, the checkpoint modulator is a PD-1/PD-L1 inhibitor. Examples of PD-1/PD-L1 inhibitors include, but are not limited to, those described in U.S. Pat. Nos. 7,488,802, 7,943,743, 8,008,449, 8,168,757, 8,217,149, 8,609,089, US 2010/028,330, US 2012/0114649, WO 2003/042,402, WO 2008/156,712, WO 2010/089,411, WO 2010/036,959, WO 2011/066,342, WO 2011/159,877, WO 2011/082,400, and WO 2011/161,699, all of which are incorporated herein in their entireties.

In one embodiment, the checkpoint modulator is a PD-1 inhibitor. In one embodiment, the checkpoint modulator is an anti-PD-1 antibody.

In some embodiments, the anti-PD-1 antibody is Nivolumab. Alternative names for Nivolumab include MDX-1106, MDX-1106-04, ONO-4538, or BMS-936558, and has a CAS Registry Number: 946414-94-4. Nivolumab is a fully human IgG4 monoclonal antibody which specifically blocks PD-1. Nivolumab (clone 5C4) and other human monoclonal antibodies that specifically bind to PD-1 are disclosed in U.S. Pat. No. 8,008,449 and WO 2006/121,168.

In other embodiments, the anti-PD-1 antibody is Pembrolizumab. Pembrolizumab (Trade name KEYTRUDA formerly Lambrolizumab, also known as Merck 3745, MK-3475 or SCH-900475) is a humanized IgG4 monoclonal antibody that binds to PD-1. Pembrolizumab is disclosed, e.g., in Hamid, O. et al. (2013) *New England Journal of Medicine* 369 (2): 134-44, WO 2009/114335, and U.S. Pat. No. 8,354,509.

In some embodiments, the anti-PD-1 antibody is Pidilizumab. Pidilizumab (CT-011; Cure Tech) is a humanized IgG1k monoclonal antibody that binds to PD-1. Pidilizumab and other humanized anti-PD-1 monoclonal antibodies are disclosed in WO 2009/101611. Other anti-PD1 antibodies are disclosed in U.S. Pat. No. 8,609,089, US 2010/028330, and/or US 2012/0114649.

In some embodiments, the anti-PD-1 antibody is AMP-514 (Amplimmune).

In some embodiments, the anti-PD-1 antibody is AMP-224, a fusion protein.

In some embodiments, the PD-1 inhibitor is an immunoadhesin (e.g., an immunoadhesin comprising an extracellular or PD-1 binding portion of PD-L1 or PD-L2 fused to a constant region (e.g., an Fc region of an immunoglobulin sequence)).

In one embodiment, the checkpoint modulator is a PD-L1 inhibitor. In one embodiment, the checkpoint modulator is an anti-PD-L1 antibody.

In one embodiment, the anti-PD-L1 antibody is MDX-1105. MDX-1105, also known as BMS-936559, is an anti-PD-L1 antibody, as described in WO 2007/005874.

In one embodiment, the anti-PD-L1 antibody is YW243.55.S70. The YW243.55.S70 antibody is an anti-PD-L1 antibody, as described in WO 2010/077634. Heavy and light chain variable region sequences of YW243.55.S70 are also described in WO 2010/077634.

In one embodiment, the anti-PD-L1 antibody is MDPL3280A (Genentech/Roche). MDPL3280A is a human Fc optimized IgG1 monoclonal antibody that binds to PD-L1. MDPL3280A and other human monoclonal antibodies to PD-L1 are described in U.S. Pat. No. 7,943,743 and US 2012/0039906.

In one embodiment, the anti-PD-L1 antibody is MSB0010718C. MSB0010718C (also referred to as A09-246-2; Merck Serono) is a monoclonal antibody that binds to PD-L1. Other humanized anti-PD-L1 antibodies are disclosed in WO 2013/079174.

In one embodiment, the anti-PD-L1 antibody is durvalumab (also known as MEDI-4736).

In one embodiment, the checkpoint modulator is a PD-L2 inhibitor. In one embodiment, the checkpoint modulator is an anti-PD-L2 antibody. In one embodiment, the anti-PD-L2 antibody is rHIgM12B7A.

In one embodiment, the checkpoint modulator is a lymphocyte activation gene-3 (LAG-3) inhibitor. In one embodiment, the checkpoint modulator is an anti-LAG-3 antibody. In one embodiment, the anti-LAG-3 antibody is BMS-986016. BMS-986016 (Bristol-Myers Squibb) is a monoclonal antibody that binds to LAG-3. BMS-986016 and other humanized anti-LAG-3 antibodies are described in US 2011/0150892, WO 2010/019570, and WO 2014/008218. In another embodiment, the anti-LAG-3 antibody is IMP321, a soluble Ig fusion protein (Brignone et al., *J. Immunol.*, 2007, 179, 4202-4211).

In one embodiment, the checkpoint modulator is a soluble ligand (e.g., a CTLA-4-Ig), or an antibody or antibody fragment that binds to CTLA-4. In one embodiment, the checkpoint modulator is a CTLA-4 inhibitor. In one embodiment, the checkpoint modulator is an anti-CTLA-4 antibody.

Examples of anti-CTLA-4 antibodies include, but are not limited to, those described in U.S. Pat. Nos. 5,811,097, 5,811,097, 5,855,887, 6,051,227, 6,207,157, 6,682,736, 6,984,720, and 7,605,238, all of which are incorporated herein in their entireties.

In one embodiment, the anti-CTLA-4 antibody is Tremelimumab (IgG2 monoclonal antibody available from Pfizer, formerly known as ticilimumab, CP-675,206).

In one embodiment, the anti-CTLA-4 antibody is Ipilimumab (also known as MDX-010, Yervoy, CAS No. 477202-00-9). Ipilimumab is a fully human monoclonal IgG antibody that binds to CTLA-4.

In one embodiment, the checkpoint modulator is a B7 inhibitor. In one embodiment, the B7 inhibitor is a B7-H3 inhibitor or a B7-H4 inhibitor. In one embodiment, the B7-H3 inhibitor is MGA271, an anti-B7-H3 antibody (Loo et al., *Clin. Cancer Res.*, 2012, 3834).

In one embodiment, the checkpoint modulator is a TIM3 inhibitor (Fourcade et al., *J. Exp. Med.*, 2010, 207, 2175-86; Sakuishi et al., *J. Exp. Med.*, 2010, 207, 2187-94).

In one embodiment, the checkpoint modulator is an IDO (indoleamine 2,3-dioxygenase) and/or TDO (tryptophan 2,3-dioxygenase) inhibitor. In one embodiment, the checkpoint modulator is an IDO inhibitor. In one embodiment, the IDO inhibitor is indoximod, NLG919, INCB024360, F001287, norharmane, rosmarinic acid, or alpha-methyltryptophan. In one embodiment, the IDO inhibitor is INCB024360. In another embodiment, the IDO inhibitor is indoximod. Although IDO inhibitors act within the TME, they do not specifically target MDSCs. The overexpression of IDO by dendritic cells creates an immunosuppressive tumor microenvironment.

In one embodiment, the checkpoint modulator is an activator of a costimulatory molecule. In one embodiment, the checkpoint modulator is chosen from an agonist (e.g., an agonistic antibody or antigen-binding fragment thereof, or a soluble fusion) of OX40, CD2, CD27, CDS, ICAM-1, LFA-1 (CD11a/CD18), ICOS (CD278), 4-1BB (CD137), GITR, CD30, CD40, BAFFR, HVEM, CD7, LIGHT, NKG2C, SLAMF7, NKp80, CD160, B7-H3 or CD83 ligand.

In one embodiment, the checkpoint modulator is an agonist of OX40. In one embodiment, the checkpoint modulator is an anti-OX40 antibody. In one embodiment, the anti-OX40 antibody is MEDI6469.

In one embodiment, the checkpoint modulator is an agonist associated with a positive signal that includes a costimulatory domain of CD28, CD27, ICOS and GITR.

In one embodiment, the checkpoint modulator is an agonist of GITR. In one embodiment, the checkpoint modulator is an anti-GITR antibody. Exemplary GITR agonists include, e.g., GITR fusion proteins and anti-GITR antibodies (e.g., bivalent anti-GITR antibodies), such as, a GITR fusion protein described in U.S. Pat. No. 6,111,090, EP 090505 B1, U.S. Pat. No. 8,586,023, WO 2010/003118 and WO 2011/090754, or an anti-GITR antibody described, e.g., in U.S. Pat. No. 7,025,962, EP 1947183 B1, U.S. Pat. Nos. 7,812,135, 8,388,967, 8,591,886, EP 1866339, WO 2011/028683, WO 2013/039954, WO 2005/007190, WO 2007/133822, WO 2005/055808, WO 99/40196, WO 2001/03720, WO 99/20758, WO 2006/083289, WO 2005/115451, U.S. Pat. No. 7,618,632, and WO 2011/051726. In one embodiment, the anti-GITR antibody is TRX518.

In one embodiment, the checkpoint modulator is a CD137 agonist. In one embodiment, the checkpoint modulator is an anti-CD137 antibody. In one embodiment, the anti-CD137 antibody is urelumab. In another embodiment, the anti-CD137 antibody is PF-05082566.

In one embodiment, the checkpoint modulator is a CD40 agonist. In one embodiment, the checkpoint modulator is an anti-CD40 antibody. In one embodiment, the anti-CD40 antibody is CF-870,893.

In some embodiments, the checkpoint modulator is a costimulatory ligand. In some embodiments, the costimulatory ligand is OX40L, 41BBL, CD153, ICOSL, CD40L, or GMCSF.

In some embodiments, the checkpoint modulator is a MCSF/CSF-1R inhibitor. An anti-CSF-1R can deplete TAMs, resulting in tumor growth inhibition. Cancer Cell 25, 1-14, Jun. 16, 2014. In some embodiments, the CSF-1R inhibitor is BLZ945, GW2850, R05509554, or PLX3397. In some embodiments, the CSF-1R inhibitor is BLZ945 or GW2850. In some embodiments, the CSF-1R inhibitor is PLX3397.

In some embodiments, the checkpoint modulator is a CXCR4/CXCL12 inhibitor. In some embodiments, the CXCR4/CXCL12 inhibitor is AMD3100, AMD11070, AMD12118, AMD11814, or AMD13073. In some embodiments, the CXCR4/CXCL12 inhibitor is AMD3100.

In some embodiments, the checkpoint modulator is a CCL2 and/or CCR2 antagonist. In some embodiments, the antagonist of CCL2 and/or CCR2 is an anti-CCL2 or CCR2 antibody. CCL2 is a chemokine and CCR2 is a chemokine receptor. CCL2 and CCR2, according to non-limiting theory, play a role in MDSC migration.

In one embodiment, provided herein is a method of treating, managing, or preventing a cancer in a subject comprising administering to the subject a therapeutically effective amount of a PI3K inhibitor, or a pharmaceutically acceptable form thereof, in combination with a checkpoint modulator, or a pharmaceutically acceptable form thereof, wherein the PI3K inhibitor is a PI3K delta inhibitor.

In one embodiment, provided herein is a pharmaceutical composition comprising a therapeutically effective amount of a PI3K inhibitor, or a pharmaceutically acceptable form thereof, and a checkpoint modulator, or a pharmaceutically acceptable form thereof, wherein the PI3K inhibitor is a PI3K delta inhibitor.

In one embodiment of the compositions and methods provided herein, the PI3K inhibitor is a PI3K delta inhibitor, and the checkpoint modulator is an anti-PD-1 antibody, an anti-PD-L1 antibody, an anti-PD-L2 antibody, or an anti-CTLA-4 antibody, or a combination thereof. In one embodiment, the anti-PD-1 antibody is Nivolumab, Pembrolizumab, Pidilizumab, AMP-514, or AMP-224, or a combination thereof. In one embodiment, the anti-PD-L1 antibody is MDX-1105, YW243.55.S70, MDPL3280A, MSB0010718C, or durvalumab, or a combination thereof. In one embodiment, the an anti-CTLA-4 antibody is Tremelimumab or Ipilimumab, or a combination thereof.

In one embodiment, the PI3K inhibitor is a PI3K delta inhibitor, and the checkpoint modulator is Nivolumab.

In one embodiment, the PI3K inhibitor is a PI3K delta inhibitor, and the checkpoint modulator is Pembrolizumab.

In one embodiment, the PI3K inhibitor is a PI3K delta inhibitor, and the checkpoint modulator is Pidilizumab.

In one embodiment, the PI3K inhibitor is a PI3K delta inhibitor, and the checkpoint modulator is MDX-1105.

In one embodiment, the PI3K inhibitor is a PI3K delta inhibitor, and the checkpoint modulator is MDPL3280A.

In one embodiment, the PI3K inhibitor is a PI3K delta inhibitor, and the checkpoint modulator is durvalumab.

In one embodiment, the PI3K inhibitor is a PI3K delta inhibitor, and the checkpoint modulator is Tremelimumab.

In one embodiment, the PI3K inhibitor is a PI3K delta inhibitor, and the checkpoint modulator is Ipilimumab.

In one embodiment of the methods described herein, the PI3K delta inhibitor (e.g., Idelalisib), or a pharmaceutically acceptable form thereof, is administered at a dosage of in the range of from about 0.01 mg to about 75 mg daily and the checkpoint modulator, or a pharmaceutically acceptable form thereof, is administered at a dosage of in the range of from about 0.01 mg to about 1100 mg daily.

In one embodiment of the compositions and methods described herein, the molar ratio of the PI3K delta inhibitor (e.g., Idelalisib), or a pharmaceutically acceptable form thereof, to the checkpoint modulator, or a pharmaceutically acceptable form thereof, is in the range of from about 500:1 to about 1:500, from about 400:1 to about 1:400, from about 300:1 to about 1:300, from about 200:1 to about 1:200, from about 100:1 to about 1:100, from about 75:1 to about 1:75, from about 50:1 to about 1:50, from about 40:1 to about 1:40, from about 30:1 to about 1:30, from about 20:1 to about 1:20, from about 10:1 to about 1:10, from about 5:1 to about 1:5.

In one embodiment, the PI3K delta inhibitor (e.g., Idelalisib) is administered at an amount that is decreased by about 1.5 fold to about 50 fold, about 1.5 fold to about 25 fold, about 1.5 fold to about 20 fold, about 1.5 fold to about 15 fold, about 1.5 fold to about 10 fold, about 2 fold to about 10 fold, about 2 fold to about 8 fold, about 4 fold to about 6 fold, or about 5 fold of the amount when administered individually; and the checkpoint modulator is administered at an amount that is decreased by about 1.1 fold to about 50 fold, about 1.1 fold to about 40 fold, about 1.1 fold to about 30 fold, about 1.1 fold to about 25 fold, about 1.1 fold to about 20 fold, about 1.1 fold to about 15 fold, about 1.1 fold to about 10 fold of the amount when administered individually.

In one embodiment, provided herein is a method of treating, managing, or preventing a cancer in a subject comprising administering to the subject a therapeutically effective amount of a PI3K inhibitor, or a pharmaceutically acceptable form thereof, in combination with a checkpoint modulator, or a pharmaceutically acceptable form thereof, wherein the PI3K inhibitor is Idelalisib.

In one embodiment, provided herein is a pharmaceutical composition comprising a therapeutically effective amount of a PI3K inhibitor, or a pharmaceutically acceptable form thereof, and a checkpoint modulator, or a pharmaceutically acceptable form thereof, wherein the PI3K inhibitor is Idelalisib.

In one embodiment of the compositions and methods provided herein, the PI3K inhibitor is Idelalisib, and the checkpoint modulator is an anti-PD-1 antibody, an anti-PD-L1 antibody, an anti-PD-L2 antibody, or an anti-CTLA-4 antibody, or a combination thereof. In one embodiment, the anti-PD-1 antibody is Nivolumab, Pembrolizumab, Pidilizumab, AMP-514, or AMP-224, or a combination thereof. In one embodiment, the anti-PD-L1 antibody is MDX-1105, YW243.55.S70, MDPL3280A, MSB0010718C, or durvalumab, or a combination thereof. In one embodiment, the an anti-CTLA-4 antibody is Tremelimumab or Ipilimumab, or a combination thereof.

In one embodiment, the PI3K inhibitor is Idelalisib, and the checkpoint modulator is Nivolumab.

In one embodiment, the PI3K inhibitor is Idelalisib, and the checkpoint modulator is Pembrolizumab.

In one embodiment, the PI3K inhibitor is Idelalisib, and the checkpoint modulator is Pidilizumab.

In one embodiment, the PI3K inhibitor is Idelalisib, and the checkpoint modulator is MDX-1105.

In one embodiment, the PI3K inhibitor is Idelalisib, and the checkpoint modulator is MDPL3280A.

In one embodiment, the PI3K inhibitor is Idelalisib, and the checkpoint modulator is durvalumab.

In one embodiment, the PI3K inhibitor is Idelalisib, and the checkpoint modulator is Tremelimumab.

In one embodiment, the PI3K inhibitor is Idelalisib, and the checkpoint modulator is Ipilimumab.

In one embodiment of the methods described herein, Idelalisib, or a pharmaceutically acceptable form thereof, is administered at a dosage of in the range of from about 0.01 mg to about 75 mg daily and the checkpoint modulator, or a pharmaceutically acceptable form thereof, is administered at a dosage of in the range of from about 0.01 mg to about 1100 mg daily.

In one embodiment of the compositions and methods described herein, the molar ratio of Idelalisib, or a pharmaceutically acceptable form thereof, to the checkpoint modulator, or a pharmaceutically acceptable form thereof, is in the range of from about 500:1 to about 1:500, from about 400:1 to about 1:400, from about 300:1 to about 1:300, from about 200:1 to about 1:200, from about 100:1 to about 1:100, from about 75:1 to about 1:75, from about 50:1 to about 1:50, from about 40:1 to about 1:40, from about 30:1 to about 1:30, from about 20:1 to about 1:20, from about 10:1 to about 1:10, from about 5:1 to about 1:5.

In one embodiment, Idelalisib is administered at an amount that is decreased by about 1.5 fold to about 50 fold, about 1.5 fold to about 25 fold, about 1.5 fold to about 20 fold, about 1.5 fold to about 15 fold, about 1.5 fold to about 10 fold, about 2 fold to about 10 fold, about 2 fold to about 8 fold, about 4 fold to about 6 fold, or about 5 fold of the amount when administered individually; and the checkpoint modulator is administered at an amount that is decreased by about 1.1 fold to about 50 fold, about 1.1 fold to about 40 fold, about 1.1 fold to about 30 fold, about 1.1 fold to about 25 fold, about 1.1 fold to about 20 fold, about 1.1 fold to about 15 fold, about 1.1 fold to about 10 fold of the amount when administered individually.

In one embodiment, provided herein is a method of treating, managing, or preventing a cancer in a subject comprising administering to the subject a therapeutically effective amount of a PI3K inhibitor, or a pharmaceutically acceptable form thereof, in combination with a checkpoint modulator, or a pharmaceutically acceptable form thereof, wherein the PI3K inhibitor is a PI3K delta/gamma dual inhibitor.

In one embodiment, provided herein is a pharmaceutical composition comprising a therapeutically effective amount of a PI3K inhibitor, or a pharmaceutically acceptable form thereof, and a checkpoint modulator, or a pharmaceutically acceptable form thereof, wherein the PI3K inhibitor is a PI3K delta/gamma dual inhibitor.

In one embodiment of the compositions and methods provided herein, the PI3K inhibitor is a PI3K delta/gamma dual inhibitor, and the checkpoint modulator is an anti-PD-1 antibody, an anti-PD-L1 antibody, an anti-PD-L2 antibody, or an anti-CTLA-4 antibody, or a combination thereof. In one embodiment, the anti-PD-1 antibody is Nivolumab, Pembrolizumab, Pidilizumab, AMP-514, or AMP-224, or a combination thereof. In one embodiment, the anti-PD-L1 antibody is MDX-1105, YW243.55.S70, MDPL3280A, MSB0010718C, or durvalumab, or a combination thereof. In one embodiment, the an anti-CTLA-4 antibody is Tremelimumab or Ipilimumab, or a combination thereof.

In one embodiment, the PI3K inhibitor is a PI3K delta/gamma dual inhibitor, and the checkpoint modulator is Nivolumab.

In one embodiment, the PI3K inhibitor is a PI3K delta/gamma dual inhibitor, and the checkpoint modulator is Pembrolizumab.

In one embodiment, the PI3K inhibitor is a PI3K delta/gamma dual inhibitor, and the checkpoint modulator is Pidilizumab.

In one embodiment, the PI3K inhibitor is a PI3K delta/gamma dual inhibitor, and the checkpoint modulator is MDX-1105.

In one embodiment, the PI3K inhibitor is a PI3K delta/gamma dual inhibitor, and the checkpoint modulator is MDPL3280A.

In one embodiment, the PI3K inhibitor is a PI3K delta/gamma dual inhibitor, and the checkpoint modulator is durvalumab.

In one embodiment, the PI3K inhibitor is a PI3K delta/gamma dual inhibitor, and the checkpoint modulator is Tremelimumab.

In one embodiment, the PI3K inhibitor is a PI3K delta/gamma dual inhibitor, and the checkpoint modulator is Ipilimumab.

In one embodiment of the methods described herein, the PI3K delta/gamma dual inhibitor (e.g., Compound 1), or a pharmaceutically acceptable form thereof, is administered at a dosage of in the range of from about 0.01 mg to about 75 mg daily and the checkpoint modulator, or a pharmaceutically acceptable form thereof, is administered at a dosage of in the range of from about 0.01 mg to about 1100 mg daily.

In one embodiment of the compositions and methods described herein, the molar ratio of the PI3K delta/gamma dual inhibitor (e.g., Compound 1), or a pharmaceutically acceptable form thereof, to the checkpoint modulator, or a pharmaceutically acceptable form thereof, is in the range of from about 500:1 to about 1:500, from about 400:1 to about 1:400, from about 300:1 to about 1:300, from about 200:1 to about 1:200, from about 100:1 to about 1:100, from about 75:1 to about 1:75, from about 50:1 to about 1:50, from about 40:1 to about 1:40, from about 30:1 to about 1:30, from about 20:1 to about 1:20, from about 10:1 to about 1:10, from about 5:1 to about 1:5.

In one embodiment, the PI3K delta/gamma dual inhibitor (e.g., Compound 1) is administered at an amount that is decreased by about 1.5 fold to about 50 fold, about 1.5 fold to about 25 fold, about 1.5 fold to about 20 fold, about 1.5 fold to about 15 fold, about 1.5 fold to about 10 fold, about 2 fold to about 10 fold, about 2 fold to about 8 fold, about 4 fold to about 6 fold, or about 5 fold of the amount when administered individually; and the checkpoint modulator is administered at an amount that is decreased by about 1.1 fold to about 50 fold, about 1.1 fold to about 40 fold, about 1.1 fold to about 30 fold, about 1.1 fold to about 25 fold, about 1.1 fold to about 20 fold, about 1.1 fold to about 15 fold, about 1.1 fold to about 10 fold of the amount when administered individually.

In one embodiment, provided herein is a method of treating, managing, or preventing a cancer in a subject comprising administering to the subject a therapeutically effective amount of a PI3K inhibitor, or a pharmaceutically acceptable form thereof, in combination with a checkpoint modulator, or a pharmaceutically acceptable form thereof, wherein the PI3K inhibitor is Compound 1:

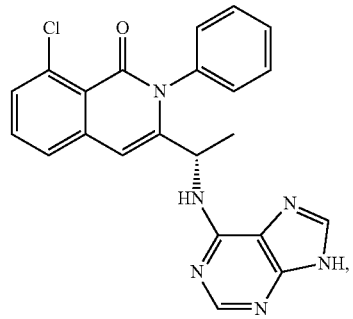

Compound 1 or a pharmaceutically acceptable form thereof.

In one embodiment, provided herein is a pharmaceutical composition comprising a therapeutically effective amount of a PI3K inhibitor, or a pharmaceutically acceptable form thereof, and a checkpoint modulator, or a pharmaceutically acceptable form thereof, wherein the PI3K inhibitor is Compound 1:

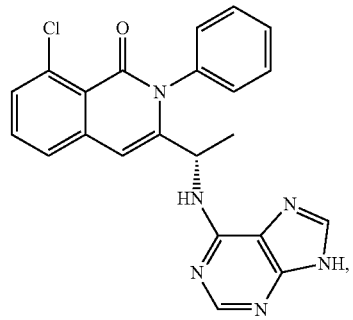

Compound 1 or a pharmaceutically acceptable form thereof.

In one embodiment of the compositions and methods provided herein, the PI3K inhibitor is Compound 1, and the checkpoint modulator is an anti-PD-1 antibody, an anti-PD-L1 antibody, an anti-PD-L2 antibody, or an anti-CTLA-4 antibody, or a combination thereof. In one embodiment, the anti-PD-1 antibody is Nivolumab, Pembrolizumab, Pidilizumab, AMP-514, or AMP-224, or a combination thereof. In one embodiment, the anti-PD-L1 antibody is MDX-1105, YW243.55.S70, MDPL3280A, MSB0010718C, or durvalumab, or a combination thereof. In one embodiment, the an anti-CTLA-4 antibody is Tremelimumab or Ipilimumab, or a combination thereof.

In one embodiment, the PI3K inhibitor is Compound 1, and the checkpoint modulator is Nivolumab.

In one embodiment, the PI3K inhibitor is Compound 1, and the checkpoint modulator is Pembrolizumab.

In one embodiment, the PI3K inhibitor is Compound 1, and the checkpoint modulator is Pidilizumab.

In one embodiment, the PI3K inhibitor is Compound 1, and the checkpoint modulator is MDX-1105.

In one embodiment, the PI3K inhibitor is Compound 1, and the checkpoint modulator is MDPL3280A.

In one embodiment, the PI3K inhibitor is Compound 1, and the checkpoint modulator is durvalumab.

In one embodiment, the PI3K inhibitor is Compound 1, and the checkpoint modulator is Tremelimumab.

In one embodiment, the PI3K inhibitor is Compound 1, and the checkpoint modulator is Ipilimumab.

In one embodiment of the methods described herein, Compound 1, or a pharmaceutically acceptable form thereof, is administered at a dosage of in the range of from about 0.01 mg to about 75 mg daily and the checkpoint modulator, or a pharmaceutically acceptable form thereof, is administered at a dosage of in the range of from about 0.01 mg to about 1100 mg daily.

In one embodiment of the compositions and methods described herein, the molar ratio of Compound 1, or a pharmaceutically acceptable form thereof, to the checkpoint modulator, or a pharmaceutically acceptable form thereof, is in the range of from about 500:1 to about 1:500, from about 400:1 to about 1:400, from about 300:1 to about 1:300, from about 200:1 to about 1:200, from about 100:1 to about 1:100, from about 75:1 to about 1:75, from about 50:1 to about 1:50, from about 40:1 to about 1:40, from about 30:1 to about 1:30, from about 20:1 to about 1:20, from about 10:1 to about 1:10, from about 5:1 to about 1:5.

In one embodiment, Compound 1 is administered at an amount that is decreased by about 1.5 fold to about 50 fold, about 1.5 fold to about 25 fold, about 1.5 fold to about 20 fold, about 1.5 fold to about 15 fold, about 1.5 fold to about 10 fold, about 2 fold to about 10 fold, about 2 fold to about 8 fold, about 4 fold to about 6 fold, or about 5 fold of the amount when administered individually; and the checkpoint modulator is administered at an amount that is decreased by about 1.1 fold to about 50 fold, about 1.1 fold to about 40 fold, about 1.1 fold to about 30 fold, about 1.1 fold to about 25 fold, about 1.1 fold to about 20 fold, about 1.1 fold to about 15 fold, about 1.1 fold to about 10 fold of the amount when administered individually.

In one embodiment, the PI3K inhibitor is Compound 1, the checkpoint modulator is nivolumab, and the cancer is T-cell lymphoma. In one embodiment, the T-cell lymphoma is peripheral T cell lymphomas (PTCL). In another embodiment, the T-cell lymphoma is cutaneous T-cell lymphoma (CTCL).

In one embodiment, the PI3K inhibitor is Compound 1, the checkpoint modulator is nivolumab, and the cancer is DLBCL.

In one embodiment, the PI3K inhibitor is Compound 1, the checkpoint modulator is nivolumab, and the cancer is follicular lymphoma.

In one embodiment, the PI3K inhibitor is Compound 1, the checkpoint modulator is pembrolizumab, and the cancer is T-cell lymphoma. In one embodiment, the T-cell lymphoma is peripheral T cell lymphomas (PTCL). In another embodiment, the T-cell lymphoma is cutaneous T-cell lymphoma (CTCL).

In one embodiment, the PI3K inhibitor is Compound 1, the checkpoint modulator is pembrolizumab, and the cancer is DLBCL.

In one embodiment, the PI3K inhibitor is Compound 1, the checkpoint modulator is pembrolizumab, and the cancer is follicular lymphoma.

In one embodiment of the methods provided herein, the checkpoint modulator is nivolumab, and it is administered intravenously. In one embodiment, nivolumab is administered at a dose of from about 0.1 mg/kg to about 5 mg/kg, from about 0.1 mg/kg to about 3 mg/kg, from about 0.1 mg/kg to about 2 mg/kg, from about 0.1 mg/kg to about 1 mg/kg, or from about 0.1 mg/kg to about 0.5 mg/kg every 2 weeks. In one embodiment, nivolumab is administered at a dose of about 3 mg/kg, about 2.5 mg/kg, about 2 mg/kg, about 1.5 mg/kg, about 1 mg/kg, or about 0.5 mg/kg every 2 weeks. In one embodiment, the frequency of the administration of nivolumab is reduced to once every 3 weeks or once every 4 weeks. In one embodiment, a dose of nivolumab is administered intravenously over about 60 minutes. In one embodiment, a dose of nivolumab is administered intravenously over about 30 minutes.

In one embodiment of the methods provided herein, the checkpoint modulator is pembrolizumab, and it is administered intravenously. In one embodiment, pembrolizumab is administered at a dose of from about 0.1 mg/kg to about 5 mg/kg, from about 0.1 mg/kg to about 3 mg/kg, from about 0.1 mg/kg to about 2 mg/kg, from about 0.1 mg/kg to about 1 mg/kg, or from about 0.1 mg/kg to about 0.5 mg/kg every 3 weeks. In one embodiment, pembrolizumab is administered at a dose of about 3 mg/kg, about 2.5 mg/kg, about 2 mg/kg, about 1.5 mg/kg, about 1 mg/kg, or about 0.5 mg/kg every 3 weeks. In one embodiment, the frequency of the administration of pembrolizumab is reduced to once every 4 weeks, once every 5 weeks, or once every 6 weeks. In one embodiment, a dose of pembrolizumab is administered intravenously over about 30 minutes. In one embodiment, a dose of pembrolizumab is administered intravenously over about 15 minutes.

In one embodiment, the checkpoint modulator, or a pharmaceutically acceptable form thereof, is administered to the subject at least 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, 12 weeks, or 16 weeks before the PI3K inhibitor (e.g., Compound 1), or a pharmaceutically acceptable form thereof, is administered. In another embodiment, the checkpoint modulator, or a pharmaceutically acceptable form thereof, is administered concurrently with the PI3K inhibitor (e.g., Compound 1), or a pharmaceutically acceptable form thereof, in a single dosage form or separate dosage forms. In yet another embodiment, the checkpoint modulator, or a pharmaceutically acceptable form thereof, is administered to the subject at least 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, 12 weeks, or 16 weeks after the PI3K inhibitor (e.g., Compound 1), or a pharmaceutically acceptable form thereof, is administered.

In certain embodiments, the PI3K inhibitor (e.g., Compound 1), or a pharmaceutically acceptable form thereof, and the checkpoint modulator are administered via a same route, e.g., both are administered orally. In other embodiments, the PI3K inhibitor (e.g., Compound 1), or a pharmaceutically acceptable form thereof, and the checkpoint modulator are administered via different routes, e.g., one is administered orally and the other is administered intravenously. In one embodiment, Compound 1 is administered orally and the checkpoint modulator is administered intravenously.

In certain embodiments, the PI3K inhibitor (e.g., Compound 1), or a pharmaceutically acceptable form thereof, and the checkpoint modulator, or a pharmaceutically acceptable form thereof, are the only therapeutically active ingredients of the compositions and methods provided herein. In other embodiments, the compositions provided herein comprise and the methods provided herein use at least one more therapeutically active ingredient. In one embodiment, the compositions provided herein comprise and the methods provided herein use a PI3K delta inhibitor (e.g., Idelalisib), a PI3K delta/gamma dual inhibitor, and a checkpoint modulator.

2.3 Combinations of PI3K Inhibitors and XPO1 Inhibitors

In certain embodiments, provided herein are methods of treating, managing, or preventing a cancer in a subject comprising administering to the subject a therapeutically effective amount of a PI3K inhibitor, or a pharmaceutically acceptable form thereof, in combination with an XPO1 inhibitor, or a pharmaceutically acceptable form thereof.

In certain embodiments, provided herein are pharmaceutical compositions comprising a therapeutically effective amount of a PI3K inhibitor, or a pharmaceutically acceptable form thereof, and an XPO1 inhibitor, or a pharmaceutically acceptable form thereof.

Exportin 1 (XPO1), also known as chromosomal maintenance 1 (CRM1), is an eukaryotic protein that mediates the nuclear export of proteins, rRNA, snRNA, and some mRNA. In certain embodiments, the XPO1 inhibitors for use in the methods and compositions provided herein include, but are not limited to, selinexor, KPT-251, KPT-276, and SL-801.

In one embodiment, the XPO1 inhibitor is selinexor. Selinexor, also known as KPT-330, has a chemical name of (Z)-3-(3-(3,5-bis(trifluoromethyl)phenyl)-1H-1,2,4-triazol-1-yl)—N'-(pyrazin-2-yl)acrylohydrazide, and is of the structure:

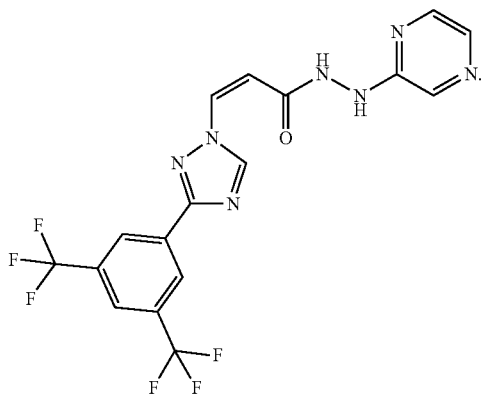 [SMILES: O=C(/C=C\n1cnc(-c2cc(C(F)(F)F)cc(C(F)(F)F)c2)n1)NNc1cnccn1]

In one embodiment, the XPO1 inhibitor is SL-801.

In one embodiment, provided herein is a method of treating, managing, or preventing a cancer in a subject comprising administering to the subject a therapeutically effective amount of a PI3K inhibitor, or a pharmaceutically acceptable form thereof, in combination with a XPO1 inhibitor, or a pharmaceutically acceptable form thereof, wherein the PI3K inhibitor is a PI3K delta inhibitor.

In one embodiment, provided herein is a pharmaceutical composition comprising a therapeutically effective amount of a PI3K inhibitor, or a pharmaceutically acceptable form thereof, and a XPO1 inhibitor, or a pharmaceutically acceptable form thereof, wherein the PI3K inhibitor is a PI3K delta inhibitor.

In one embodiment of the compositions and methods provided herein, the PI3K inhibitor is a PI3K delta inhibitor, and the XPO1 inhibitor is selinexor, KPT-251, KPT-276, or SL-801, or a combination thereof.

In one embodiment, the PI3K inhibitor is a PI3K delta inhibitor, and the XPO1 inhibitor is selinexor.

In one embodiment of the methods described herein, the PI3K delta inhibitor (e.g., Idelalisib), or a pharmaceutically acceptable form thereof, is administered at a dosage of in the range of from about 0.01 mg to about 75 mg daily and the XPO1 inhibitor (e.g., selinexor), or a pharmaceutically acceptable form thereof, is administered at a dosage of in the range of from about 0.01 mg to about 1100 mg daily.

In one embodiment of the compositions and methods described herein, the molar ratio of the PI3K delta inhibitor (e.g., Idelalisib), or a pharmaceutically acceptable form thereof, to the XPO1 inhibitor (e.g., selinexor), or a pharmaceutically acceptable form thereof, is in the range of from about 500:1 to about 1:500, from about 400:1 to about 1:400, from about 300:1 to about 1:300, from about 200:1 to about 1:200, from about 100:1 to about 1:100, from about 75:1 to about 1:75, from about 50:1 to about 1:50, from about 40:1 to about 1:40, from about 30:1 to about 1:30, from about 20:1 to about 1:20, from about 10:1 to about 1:10, from about 5:1 to about 1:5.

In one embodiment, the PI3K delta inhibitor (e.g., Idelalisib) is administered at an amount that is decreased by about 1.5 fold to about 50 fold, about 1.5 fold to about 25 fold, about 1.5 fold to about 20 fold, about 1.5 fold to about 15 fold, about 1.5 fold to about 10 fold, about 2 fold to about 10 fold, about 2 fold to about 8 fold, about 4 fold to about 6 fold, or about 5 fold of the amount when administered individually; and the XPO1 inhibitor (e.g., selinexor) is administered at an amount that is decreased by about 1.1 fold to about 50 fold, about 1.1 fold to about 40 fold, about 1.1 fold to about 30 fold, about 1.1 fold to about 25 fold, about 1.1 fold to about 20 fold, about 1.1 fold to about 15 fold, about 1.1 fold to about 10 fold of the amount when administered individually.

In one embodiment, provided herein is a method of treating, managing, or preventing a cancer in a subject comprising administering to the subject a therapeutically effective amount of a PI3K inhibitor, or a pharmaceutically acceptable form thereof, in combination with a XPO1 inhibitor, or a pharmaceutically acceptable form thereof, wherein the PI3K inhibitor is Idelalisib.

In one embodiment, provided herein is a pharmaceutical composition comprising a therapeutically effective amount of a PI3K inhibitor, or a pharmaceutically acceptable form thereof, and a XPO1 inhibitor, or a pharmaceutically acceptable form thereof, wherein the PI3K inhibitor is Idelalisib.

In one embodiment of the compositions and methods provided herein, the PI3K inhibitor is Idelalisib, and the XPO1 inhibitor is selinexor, KPT-251, KPT-276, or SL-801, or a combination thereof.

In one embodiment, the PI3K inhibitor is Idelalisib, and the XPO1 inhibitor is selinexor.

In one embodiment of the methods described herein, Idelalisib, or a pharmaceutically acceptable form thereof, is administered at a dosage of in the range of from about 0.01 mg to about 75 mg daily and the XPO1 inhibitor (e.g., selinexor), or a pharmaceutically acceptable form thereof, is administered at a dosage of in the range of from about 0.01 mg to about 1100 mg daily.

In one embodiment of the compositions and methods described herein, Idelalisib, or a pharmaceutically acceptable form thereof, to the XPO1 inhibitor (e.g., selinexor), or a pharmaceutically acceptable form thereof, is in the range of from about 500:1 to about 1:500, from about 400:1 to about 1:400, from about 300:1 to about 1:300, from about 200:1 to about 1:200, from about 100:1 to about 1:100, from about 75:1 to about 1:75, from about 50:1 to about 1:50, from about 40:1 to about 1:40, from about 30:1 to about 1:30, from about 20:1 to about 1:20, from about 10:1 to about 1:10, from about 5:1 to about 1:5.

In one embodiment, Idelalisib is administered at an amount that is decreased by about 1.5 fold to about 50 fold, about 1.5 fold to about 25 fold, about 1.5 fold to about 20 fold, about 1.5 fold to about 15 fold, about 1.5 fold to about 10 fold, about 2 fold to about 10 fold, about 2 fold to about 8 fold, about 4 fold to about 6 fold, or about 5 fold of the amount when administered individually; and the XPO1 inhibitor (e.g., selinexor) is administered at an amount that is decreased by about 1.1 fold to about 50 fold, about 1.1 fold to about 40 fold, about 1.1 fold to about 30 fold, about 1.1 fold to about 25 fold, about 1.1 fold to about 20 fold, about 1.1 fold to about 15 fold, about 1.1 fold to about 10 fold of the amount when administered individually.

In one embodiment, provided herein is a method of treating, managing, or preventing a cancer in a subject comprising administering to the subject a therapeutically effective amount of a PI3K inhibitor, or a pharmaceutically acceptable form thereof, in combination with a XPO1 inhibitor, or a pharmaceutically acceptable form thereof, wherein the PI3K inhibitor is a PI3K delta/gamma dual inhibitor.

In one embodiment, provided herein is a pharmaceutical composition comprising a therapeutically effective amount of a PI3K inhibitor, or a pharmaceutically acceptable form thereof, and a XPO1 inhibitor, or a pharmaceutically acceptable form thereof, wherein the PI3K inhibitor is a PI3K delta/gamma dual inhibitor.

In one embodiment of the compositions and methods provided herein, the PI3K inhibitor is a PI3K delta/gamma dual inhibitor, and the XPO1 inhibitor is selinexor, KPT-251, KPT-276, or SL-801, or a combination thereof.

In one embodiment, the PI3K inhibitor is a PI3K delta/gamma dual inhibitor, and the XPO1 inhibitor is selinexor.

In one embodiment of the methods described herein, the PI3K delta/gamma dual inhibitor (e.g., Compound 1), or a pharmaceutically acceptable form thereof, is administered at a dosage of in the range of from about 0.01 mg to about 75 mg daily and the XPO1 inhibitor (e.g., selinexor), or a pharmaceutically acceptable form thereof, is administered at a dosage of in the range of from about 0.01 mg to about 1100 mg daily.

In one embodiment of the compositions and methods described herein, the molar ratio of the PI3K delta/gamma dual inhibitor (e.g., Compound 1), or a pharmaceutically acceptable form thereof, to the XPO1 inhibitor (e.g., selinexor), or a pharmaceutically acceptable form thereof, is in the range of from about 500:1 to about 1:500, from about 400:1 to about 1:400, from about 300:1 to about 1:300, from about 200:1 to about 1:200, from about 100:1 to about 1:100, from about 75:1 to about 1:75, from about 50:1 to about 1:50, from about 40:1 to about 1:40, from about 30:1 to about 1:30, from about 20:1 to about 1:20, from about 10:1 to about 1:10, from about 5:1 to about 1:5.

In one embodiment, the PI3K delta/gamma dual inhibitor (e.g., Compound 1) is administered at an amount that is decreased by about 1.5 fold to about 50 fold, about 1.5 fold to about 25 fold, about 1.5 fold to about 20 fold, about 1.5 fold to about 15 fold, about 1.5 fold to about 10 fold, about 2 fold to about 10 fold, about 2 fold to about 8 fold, about 4 fold to about 6 fold, or about 5 fold of the amount when administered individually; and the XPO1 inhibitor (e.g., selinexor) is administered at an amount that is decreased by about 1.1 fold to about 50 fold, about 1.1 fold to about 40 fold, about 1.1 fold to about 30 fold, about 1.1 fold to about 25 fold, about 1.1 fold to about 20 fold, about 1.1 fold to about 15 fold, about 1.1 fold to about 10 fold of the amount when administered individually.

In one embodiment, provided herein is a method of treating, managing, or preventing a cancer in a subject comprising administering to the subject a therapeutically effective amount of a PI3K inhibitor, or a pharmaceutically acceptable form thereof, in combination with a XPO1 inhibitor, or a pharmaceutically acceptable form thereof, wherein the PI3K inhibitor is Compound 1:

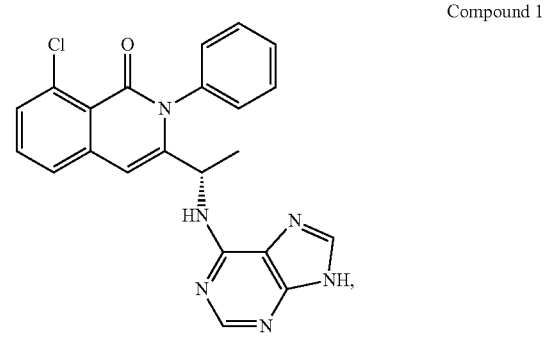 [SMILES: C[C@H](Nc1ncnc2[nH]cnc12)c1cc2cccc(Cl)c2c(=O)n1-c1ccccc1]

Compound 1 or a pharmaceutically acceptable form thereof.

In one embodiment, provided herein is a pharmaceutical composition comprising a therapeutically effective amount of a PI3K inhibitor, or a pharmaceutically acceptable form thereof, and a XPO1 inhibitor, or a pharmaceutically acceptable form thereof, wherein the PI3K inhibitor is Compound 1:

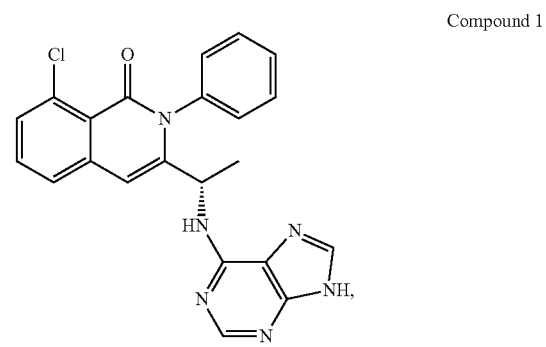 [SMILES: C[C@H](Nc1ncnc2[nH]cnc12)c1cc2cccc(Cl)c2c(=O)n1-c1ccccc1]

Compound 1 or a pharmaceutically acceptable form thereof.

In one embodiment of the compositions and methods provided herein, the PI3K inhibitor is Compound 1, and the XPO1 inhibitor is selinexor, KPT-251, KPT-276, or SL-801, or a combination thereof.

In one embodiment, the PI3K inhibitor is Compound 1, and the XPO1 inhibitor is selinexor.

In one embodiment of the methods described herein, Compound 1, or a pharmaceutically acceptable form thereof, is administered at a dosage of in the range of from about 0.01 mg to about 75 mg daily and the XPO1 inhibitor (e.g., selinexor), or a pharmaceutically acceptable form thereof, is administered at a dosage of in the range of from about 0.01 mg to about 1100 mg daily.

In one embodiment of the compositions and methods described herein, Compound 1, or a pharmaceutically acceptable form thereof, to the XPO1 inhibitor (e.g., selinexor), or a pharmaceutically acceptable form thereof, is in the range of from about 500:1 to about 1:500, from about 400:1 to about 1:400, from about 300:1 to about 1:300, from about 200:1 to about 1:200, from about 100:1 to about 1:100, from about 75:1 to about 1:75, from about 50:1 to about 1:50, from about 40:1 to about 1:40, from about 30:1 to about 1:30, from about 20:1 to about 1:20, from about 10:1 to about 1:10, from about 5:1 to about 1:5.

In one embodiment, Compound 1 is administered at an amount that is decreased by about 1.5 fold to about 50 fold, about 1.5 fold to about 25 fold, about 1.5 fold to about 20 fold, about 1.5 fold to about 15 fold, about 1.5 fold to about 10 fold, about 2 fold to about 10 fold, about 2 fold to about 8 fold, about 4 fold to about 6 fold, or about 5 fold of the amount when administered individually; and the XPO1 inhibitor (e.g., selinexor) is administered at an amount that is decreased by about 1.1 fold to about 50 fold, about 1.1 fold to about 40 fold, about 1.1 fold to about 30 fold, about 1.1 fold to about 25 fold, about 1.1 fold to about 20 fold, about 1.1 fold to about 15 fold, about 1.1 fold to about 10 fold of the amount when administered individually.

In one embodiment, the PI3K inhibitor is Compound 1, the XPO1 inhibitor is selinexor, and the cancer is a hematologic malignancy. In one embodiment, the hematologic malignancy is leukemia. In one embodiment, the hematologic malignancy is lymphoma. In one embodiment, the hematologic malignancy is myeloma.

In one embodiment, the PI3K inhibitor is Compound 1, the XPO1 inhibitor is selinexor, and the cancer is acute myeloid leukemia. In one embodiment, the AML is relapsed or refractory. In one embodiment, the AML is untreated. In one embodiment, the AML is adult acute myeloid leukemia with 11q23 (MLL) abnormalities, adult acute myeloid leukemia with Del(5q), adult acute myeloid leukemia with Inv(16)(p13;q22), adult acute myeloid leukemia with t(15;17)(q22;q12), adult acute myeloid leukemia with t(16;16)(p13;q22), adult acute myeloid leukemia with t(8;21)(q22;q22), recurrent adult acute myeloid leukemia, or secondary acute myeloid leukemia.

In one embodiment, the PI3K inhibitor is Compound 1, the XPO1 inhibitor is selinexor, and the cancer is multiple myeloma. In one embodiment, the multiple myeloma is relapsed or refractory.

In one embodiment, the PI3K inhibitor is Compound 1, the XPO1 inhibitor is selinexor, and the cancer is diffuse large B-cell lymphoma. In one embodiment, the DLBCL is relapsed or refractory.

In one embodiment, the PI3K inhibitor is Compound 1, the XPO1 inhibitor is selinexor, and the cancer is acute lymphoblastic leukemia (ALL). In on embodiment, the ALL is relapsed or refractory.

In one embodiment, the PI3K inhibitor is Compound 1, the XPO1 inhibitor is selinexor, and the cancer is mixed phenotype acute leukemia (MPAL).

In one embodiment, the PI3K inhibitor is Compound 1, the XPO1 inhibitor is selinexor, and the cancer is prolymphocytic leukemia.

In one embodiment, the PI3K inhibitor is Compound 1, the XPO1 inhibitor is selinexor, and the cancer is chronic lymphocytic leukemia (CLL). In one embodiment, the CLL is relapsed or refractory.

In one embodiment, the PI3K inhibitor is Compound 1, the XPO1 inhibitor is selinexor, and the cancer is chronic myeloid leukemia (CML). In one embodiment, the CML is relapsed or refractory.

In one embodiment, the PI3K inhibitor is Compound 1, the XPO1 inhibitor is selinexor, and the cancer is non-Hodgkin lymphoma (NHL). In one embodiment, the NHL is relapsed or refractory.

In one embodiment, the PI3K inhibitor is Compound 1, the XPO1 inhibitor is selinexor, and the cancer is Hodgkin lymphoma (HL). In one embodiment, the HL is relapsed or refractory.

In one embodiment, the PI3K inhibitor is Compound 1, the XPO1 inhibitor is selinexor, and the cancer is aggressive B-cell lymphoma.

In one embodiment, the PI3K inhibitor is Compound 1, the XPO1 inhibitor is selinexor, and the cancer is mantle cell lymphoma (MCL). In one embodiment, the MCL is relapsed or refractory.

In one embodiment, the PI3K inhibitor is Compound 1, the XPO1 inhibitor is selinexor, and the cancer is follicular lymphoma (FL). In one embodiment, the FL is relapsed or refractory.

In one embodiment, the PI3K inhibitor is Compound 1, the XPO1 inhibitor is selinexor, and the cancer is Waldenstrom macroglobulinemia. In one embodiment, the Waldenstrom macroglobulinemia is relapsed or refractory.

In one embodiment, the PI3K inhibitor is Compound 1, the XPO1 inhibitor is selinexor, and the cancer is myelodysplastic syndrome (MDS). In one embodiment, the MDS is de novo myelodysplastic syndrome or Secondary Myelodysplastic Syndrome.

In one embodiment, the PI3K inhibitor is Compound 1, the XPO1 inhibitor is selinexor, and the cancer is T-cell lymphoma. In one embodiment, the T-cell lymphoma is peripheral T cell lymphomas (PTCL). In another embodiment, the T-cell lymphoma is cutaneous T-cell lymphoma (CTCL).

In one embodiment, the PI3K inhibitor is Compound 1, the XPO1 inhibitor is selinexor, and the cancer is a solid tumor. In one embodiment, the solid tumor is a pediatric solid tumor.

In one embodiment, the PI3K inhibitor is Compound 1, the XPO1 inhibitor is selinexor, and the cancer is glioma. In one embodiment, the glioma is recurrent.

In one embodiment, the PI3K inhibitor is Compound 1, the XPO1 inhibitor is selinexor, and the cancer is ovarian carcinoma. In one embodiment, the PI3K inhibitor is Compound 1, the XPO1 inhibitor is selinexor, and the cancer is endometrial carcinoma. In one embodiment, the PI3K inhibitor is Compound 1, the XPO1 inhibitor is selinexor, and the cancer is cervical carcinoma.

In one embodiment, the PI3K inhibitor is Compound 1, the XPO1 inhibitor is selinexor, and the cancer is breast cancer. In one embodiment, the breast cancer is triple negative breast cancer (TNBC).

In one embodiment, the PI3K inhibitor is Compound 1, the XPO1 inhibitor is selinexor, and the cancer is pancreatic cancer. In one embodiment, the pancreatic cancer is acinar cell adenocarcinoma of the pancreas, duct cell adenocarcinoma of the pancreas, or stage IV pancreatic cancer.

In one embodiment, the PI3K inhibitor is Compound 1, the XPO1 inhibitor is selinexor, and the cancer is liposarcoma. In one embodiment, the cancer is dedifferentiated liposarcoma.

In one embodiment, the PI3K inhibitor is Compound 1, the XPO1 inhibitor is selinexor, and the cancer is melanoma. In one embodiment, the melanoma is recurrent.

In one embodiment, the PI3K inhibitor is Compound 1, the XPO1 inhibitor is selinexor, and the cancer is rectal cancer. In one embodiment, the rectal cancer is locally advanced.

In one embodiment, the PI3K inhibitor is Compound 1, the XPO1 inhibitor is selinexor, and the cancer is colorectal cancer.

In one embodiment, the PI3K inhibitor is Compound 1, the XPO1 inhibitor is selinexor, and the cancer is prostate cancer. In one embodiment, the prostate cancer is metastatic castration-resistant prostate cancer (mCRPC).

In one embodiment, the PI3K inhibitor is Compound 1, the XPO1 inhibitor is selinexor, and the cancer is esophageal cancer or gastric cancer.

In one embodiment, the PI3K inhibitor is Compound 1, the XPO1 inhibitor is selinexor, and the cancer is salivary gland cancer.

In one embodiment, the PI3K inhibitor is Compound 1, the XPO1 inhibitor is selinexor, and the cancer is liver cancer.

In one embodiment, the PI3K inhibitor is Compound 1, the XPO1 inhibitor is selinexor, and the cancer is lung cancer. In one embodiment, the lung cancer is small cell lung cancer. In one embodiment, the lung cancer is recurrent. In one embodiment, the lung cancer is recurrent squamous cell lung carcinoma or stage IV squamous cell lung carcinoma.

In one embodiment of the methods described herein, the XPO1 inhibitor (e.g., selinexor), or a pharmaceutically acceptable form thereof, is administered at a dosage of in the range of from about 30 mg to about 200 mg twice weekly, from about 45 mg to about 150 mg twice weekly, or from about 60 mg to about 100 mg twice weekly. In one embodiment, the XPO1 inhibitor (e.g., selinexor), or a pharmaceutically acceptable form thereof, is administered at a dosage of about 20 mg, about 30 mg, about 40 mg, about 50 mg, about 60 mg, about 70 mg, about 80 mg, about 90 mg, or about 100 mg twice weekly. In one embodiment, the dosage is about 60 mg twice weekly. In one embodiment, the dosage is about 80 mg twice weekly. In one embodiment, the dosage is about 100 mg twice weekly. In one embodiment, the administration is in a 28 day cycle.

In one embodiment of the methods described herein, the XPO1 inhibitor (e.g., selinexor), or a pharmaceutically acceptable form thereof, is administered at a dosage of in the range of from about 30 mg to about 200 mg once weekly, from about 45 mg to about 150 mg once weekly, or from about 60 mg to about 100 mg once weekly. In one embodiment, the XPO1 inhibitor (e.g., selinexor), or a pharmaceutically acceptable form thereof, is administered at a dosage of about 20 mg, about 30 mg, about 40 mg, about 50 mg, about 60 mg, about 70 mg, about 80 mg, about 90 mg, or about 100 mg once weekly. In one embodiment, the dosage is about 60 mg once weekly. In one embodiment, the dosage is about 80 mg once weekly. In one embodiment, the dosage is about 100 mg once weekly. In one embodiment, the administration is in a 28 day cycle.

In one embodiment, the XPO1 inhibitor (e.g., selinexor), or a pharmaceutically acceptable form thereof, is administered to the subject at least 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, 12 weeks, or 16 weeks before Compound 1, or a pharmaceutically acceptable form thereof, is administered. In another embodiment, the XPO1 inhibitor (e.g., selinexor), or a pharmaceutically acceptable form thereof, is administered concurrently with Compound 1, or a pharmaceutically acceptable form thereof, in a single dosage form or separate dosage forms. In yet another embodiment, the XPO1 inhibitor (e.g., selinexor), or a pharmaceutically acceptable form thereof, is administered to the subject at least 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, 12 weeks, or 16 weeks after Compound 1, or a pharmaceutically acceptable form thereof, is administered. In one embodiment, the XPO1 inhibitor is selinexor.

In certain embodiments, the PI3K inhibitor (e.g., Compound 1), or a pharmaceutically acceptable form thereof, and the XPO1 inhibitor (e.g., selinexor), or a pharmaceutically acceptable form thereof, are in a single dosage form. In other embodiments, the PI3K inhibitor (e.g., Compound 1), or a pharmaceutically acceptable form thereof, and the XPO1 inhibitor (e.g., selinexor), or a pharmaceutically acceptable form thereof, are in separate dosage forms.

In certain embodiments, the PI3K inhibitor (e.g., Compound 1), or a pharmaceutically acceptable form thereof, and the XPO1 inhibitor (e.g., selinexor), are administered via a same route, e.g., both are administered orally. In other embodiments, the PI3K inhibitor (e.g., Compound 1), or a pharmaceutically acceptable form thereof, and the XPO1 inhibitor (e.g., selinexor), are administered via different routes, e.g., one is administered orally and the other is administered intravenously.

In certain embodiments, the PI3K inhibitor (e.g., Compound 1), or a pharmaceutically acceptable form thereof, and the XPO1 inhibitor (e.g., selinexor), or a pharmaceutically acceptable form thereof, are the only therapeutically active ingredients of the compositions and methods provided herein. In other embodiments, the compositions provided herein comprise and the methods provided herein use at least one more therapeutically active ingredient. In one embodiment, the compositions provided herein comprise and the methods provided herein use a PI3K delta inhibitor (e.g., Idelalisib), a PI3K delta/gamma dual inhibitor, and an XPO1 inhibitor (e.g., selinexor).

2.4 Combinations of PI3K Inhibitors and Anti-CD19 Antibodies

In certain embodiments, provided herein are methods of treating, managing, or preventing a cancer in a subject comprising administering to the subject a therapeutically effective amount of a PI3K inhibitor, or a pharmaceutically acceptable form thereof, in combination with an anti-CD19 antibody, or a pharmaceutically acceptable form thereof.

In certain embodiments, provided herein are pharmaceutical compositions comprising a therapeutically effective amount of a PI3K inhibitor, or a pharmaceutically acceptable form thereof, and an anti-CD19 antibody, or a pharmaceutically acceptable form thereof.

B-lymphocyte antigen CD19, also known as CD19 (Cluster of Differentiation 19), is a protein that in humans is encoded by the CD19 gene. It is found on the surface of B-cells, a type of white blood cell.

In one embodiment, the anti-CD19 antibody is blinatumomab. Blinatumomab is a recombinant, single-chain monoclonal antibody that possesses antigen-recognition sites for CD3 and CD19.

In one embodiment, provided herein is a method of treating, managing, or preventing a cancer in a subject comprising administering to the subject a therapeutically effective amount of a PI3K inhibitor, or a pharmaceutically acceptable form thereof, in combination with a anti-CD19 antibody, or a pharmaceutically acceptable form thereof, wherein the PI3K inhibitor is a PI3K delta inhibitor.

In one embodiment, provided herein is a pharmaceutical composition comprising a therapeutically effective amount of a PI3K inhibitor, or a pharmaceutically acceptable form thereof, and a anti-CD19 antibody, or a pharmaceutically acceptable form thereof, wherein the PI3K inhibitor is a PI3K delta inhibitor.

In one embodiment of the compositions and methods provided herein, the PI3K inhibitor is a PI3K delta inhibitor, and the anti-CD19 antibody is blinatumomab.

In one embodiment of the methods described herein, the PI3K delta inhibitor (e.g., Idelalisib), or a pharmaceutically acceptable form thereof, is administered at a dosage of in the range of from about 0.01 mg to about 75 mg daily and the anti-CD19 antibody (e.g., blinatumomab), or a pharmaceutically acceptable form thereof, is administered at a dosage of in the range of from about 0.01 mg to about 1100 mg daily.

In one embodiment of the compositions and methods described herein, the molar ratio of the PI3K delta inhibitor (e.g., Idelalisib), or a pharmaceutically acceptable form thereof, to the anti-CD19 antibody (e.g., blinatumomab), or a pharmaceutically acceptable form thereof, is in the range of from about 500:1 to about 1:500, from about 400:1 to about 1:400, from about 300:1 to about 1:300, from about 200:1 to about 1:200, from about 100:1 to about 1:100, from about 75:1 to about 1:75, from about 50:1 to about 1:50, from about 40:1 to about 1:40, from about 30:1 to about 1:30, from about 20:1 to about 1:20, from about 10:1 to about 1:10, from about 5:1 to about 1:5.

In one embodiment, the PI3K delta inhibitor (e.g., Idelalisib) is administered at an amount that is decreased by about 1.5 fold to about 50 fold, about 1.5 fold to about 25 fold, about 1.5 fold to about 20 fold, about 1.5 fold to about 15 fold, about 1.5 fold to about 10 fold, about 2 fold to about 10 fold, about 2 fold to about 8 fold, about 4 fold to about 6 fold, or about 5 fold of the amount when administered individually; and the anti-CD19 antibody (e.g., blinatumomab) is administered at an amount that is decreased by about 1.1 fold to about 50 fold, about 1.1 fold to about 40 fold, about 1.1 fold to about 30 fold, about 1.1 fold to about 25 fold, about 1.1 fold to about 20 fold, about 1.1 fold to about 15 fold, about 1.1 fold to about 10 fold of the amount when administered individually.

In one embodiment, provided herein is a method of treating, managing, or preventing a cancer in a subject comprising administering to the subject a therapeutically effective amount of a PI3K inhibitor, or a pharmaceutically acceptable form thereof, in combination with a anti-CD19 antibody, or a pharmaceutically acceptable form thereof, wherein the PI3K inhibitor is Idelalisib.

In one embodiment, provided herein is a pharmaceutical composition comprising a therapeutically effective amount of a PI3K inhibitor, or a pharmaceutically acceptable form thereof, and a anti-CD19 antibody, or a pharmaceutically acceptable form thereof, wherein the PI3K inhibitor is Idelalisib.

In one embodiment of the compositions and methods provided herein, the PI3K inhibitor is Idelalisib, and the anti-CD19 antibody is blinatumomab.

In one embodiment of the methods described herein, Idelalisib, or a pharmaceutically acceptable form thereof, is administered at a dosage of in the range of from about 0.01 mg to about 75 mg daily and the anti-CD19 antibody (e.g., blinatumomab), or a pharmaceutically acceptable form thereof, is administered at a dosage of in the range of from about 0.01 mg to about 1100 mg daily.

In one embodiment of the compositions and methods described herein, Idelalisib, or a pharmaceutically acceptable form thereof, to the anti-CD19 antibody (e.g., blinatumomab), or a pharmaceutically acceptable form thereof, is in the range of from about 500:1 to about 1:500, from about 400:1 to about 1:400, from about 300:1 to about 1:300, from about 200:1 to about 1:200, from about 100:1 to about 1:100, from about 75:1 to about 1:75, from about 50:1 to about 1:50, from about 40:1 to about 1:40, from about 30:1 to about 1:30, from about 20:1 to about 1:20, from about 10:1 to about 1:10, from about 5:1 to about 1:5.

In one embodiment, Idelalisib is administered at an amount that is decreased by about 1.5 fold to about 50 fold, about 1.5 fold to about 25 fold, about 1.5 fold to about 20 fold, about 1.5 fold to about 15 fold, about 1.5 fold to about 10 fold, about 2 fold to about 10 fold, about 2 fold to about 8 fold, about 4 fold to about 6 fold, or about 5 fold of the amount when administered individually; and the anti-CD19 antibody (e.g., blinatumomab) is administered at an amount that is decreased by about 1.1 fold to about 50 fold, about 1.1 fold to about 40 fold, about 1.1 fold to about 30 fold, about 1.1 fold to about 25 fold, about 1.1 fold to about 20 fold, about 1.1 fold to about 15 fold, about 1.1 fold to about 10 fold of the amount when administered individually.

In one embodiment, provided herein is a method of treating, managing, or preventing a cancer in a subject comprising administering to the subject a therapeutically effective amount of a PI3K inhibitor, or a pharmaceutically acceptable form thereof, in combination with a anti-CD19 antibody, or a pharmaceutically acceptable form thereof, wherein the PI3K inhibitor is a PI3K delta/gamma dual inhibitor.

In one embodiment, provided herein is a pharmaceutical composition comprising a therapeutically effective amount of a PI3K inhibitor, or a pharmaceutically acceptable form thereof, and a anti-CD19 antibody, or a pharmaceutically acceptable form thereof, wherein the PI3K inhibitor is a PI3K delta/gamma dual inhibitor.

In one embodiment of the compositions and methods provided herein, the PI3K inhibitor is a PI3K delta/gamma dual inhibitor, and the anti-CD19 antibody is blinatumomab.

In one embodiment of the methods described herein, the PI3K delta/gamma dual inhibitor (e.g., Compound 1), or a pharmaceutically acceptable form thereof, is administered at a dosage of in the range of from about 0.01 mg to about 75 mg daily and the anti-CD19 antibody (e.g., blinatumomab), or a pharmaceutically acceptable form thereof, is administered at a dosage of in the range of from about 0.01 mg to about 1100 mg daily.

In one embodiment of the compositions and methods described herein, the molar ratio of the PI3K delta/gamma dual inhibitor (e.g., Compound 1), or a pharmaceutically acceptable form thereof, to the anti-CD19 antibody (e.g., blinatumomab), or a pharmaceutically acceptable form thereof, is in the range of from about 500:1 to about 1:500, from about 400:1 to about 1:400, from about 300:1 to about 1:300, from about 200:1 to about 1:200, from about 100:1 to about 1:100, from about 75:1 to about 1:75, from about 50:1 to about 1:50, from about 40:1 to about 1:40, from about 30:1 to about 1:30, from about 20:1 to about 1:20, from about 10:1 to about 1:10, from about 5:1 to about 1:5.

In one embodiment, the PI3K delta/gamma dual inhibitor (e.g., Compound 1) is administered at an amount that is decreased by about 1.5 fold to about 50 fold, about 1.5 fold to about 25 fold, about 1.5 fold to about 20 fold, about 1.5 fold to about 15 fold, about 1.5 fold to about 10 fold, about 2 fold to about 10 fold, about 2 fold to about 8 fold, about 4 fold to about 6 fold, or about 5 fold of the amount when administered individually; and the anti-CD19 antibody (e.g., blinatumomab) is administered at an amount that is decreased by about 1.1 fold to about 50 fold, about 1.1 fold to about 40 fold, about 1.1 fold to about 30 fold, about 1.1 fold to about 25 fold, about 1.1 fold to about 20 fold, about 1.1 fold to about 15 fold, about 1.1 fold to about 10 fold of the amount when administered individually.

In one embodiment, provided herein is a method of treating, managing, or preventing a cancer in a subject comprising administering to the subject a therapeutically effective amount of a PI3K inhibitor, or a pharmaceutically acceptable form thereof, in combination with a anti-CD19 antibody, or a pharmaceutically acceptable form thereof, wherein the PI3K inhibitor is Compound 1:

Compound 1

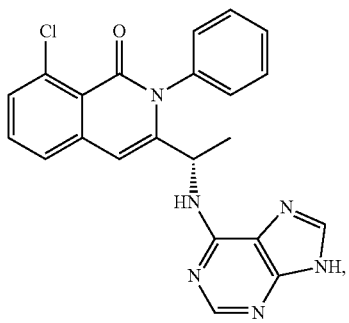

or a pharmaceutically acceptable form thereof.

In one embodiment, provided herein is a pharmaceutical composition comprising a therapeutically effective amount of a PI3K inhibitor, or a pharmaceutically acceptable form thereof, and a anti-CD19 antibody, or a pharmaceutically acceptable form thereof, wherein the PI3K inhibitor is Compound 1:

Compound 1

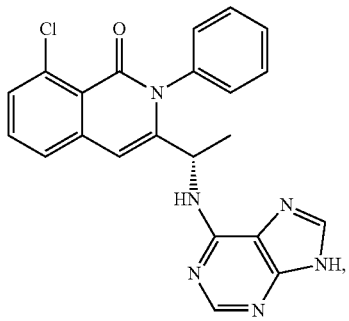

or a pharmaceutically acceptable form thereof.

In one embodiment of the compositions and methods provided herein, the PI3K inhibitor is Compound 1, and the anti-CD19 antibody is blinatumomab.

In one embodiment of the methods described herein, Compound 1, or a pharmaceutically acceptable form thereof, is administered at a dosage of in the range of from about 0.01 mg to about 75 mg daily and the anti-CD19 antibody (e.g., blinatumomab), or a pharmaceutically acceptable form thereof, is administered at a dosage of in the range of from about 0.01 mg to about 1100 mg daily.

In one embodiment of the compositions and methods described herein, Compound 1, or a pharmaceutically acceptable form thereof, to the anti-CD19 antibody (e.g., blinatumomab), or a pharmaceutically acceptable form thereof, is in the range of from about 500:1 to about 1:500, from about 400:1 to about 1:400, from about 300:1 to about 1:300, from about 200:1 to about 1:200, from about 100:1 to about 1:100, from about 75:1 to about 1:75, from about 50:1 to about 1:50, from about 40:1 to about 1:40, from about 30:1 to about 1:30, from about 20:1 to about 1:20, from about 10:1 to about 1:10, from about 5:1 to about 1:5.

In one embodiment, Compound 1 is administered at an amount that is decreased by about 1.5 fold to about 50 fold, about 1.5 fold to about 25 fold, about 1.5 fold to about 20 fold, about 1.5 fold to about 15 fold, about 1.5 fold to about 10 fold, about 2 fold to about 10 fold, about 2 fold to about 8 fold, about 4 fold to about 6 fold, or about 5 fold of the amount when administered individually; and the anti-CD19 antibody (e.g., blinatumomab) is administered at an amount that is decreased by about 1.1 fold to about 50 fold, about 1.1 fold to about 40 fold, about 1.1 fold to about 30 fold, about 1.1 fold to about 25 fold, about 1.1 fold to about 20 fold, about 1.1 fold to about 15 fold, about 1.1 fold to about 10 fold of the amount when administered individually.

In one embodiment of the methods provided herein, the anti-CD19 antibody is blinatumomab, and it is administered intravenously. In one embodiment, blinatumomab is administered at a dose of from about 1 mg/kg to about 60 $\mu g/m^2/day$, from about 1 mg/kg to about 50 $\mu g/m^2/day$, from about 1 mg/kg to about 40 $\mu g/m^2/day$, from about 1 mg/kg to about 30 $\mu g/m^2/day$, from about 1 mg/kg to about 20 $\mu g/m^2/day$, or from about 1 mg/kg to about 10 $\mu g/m^2/day$. In one embodiment, blinatumomab is administered at a dose of about 60 $\mu g/m^2/day$, about 50 $\mu g/m^2/day$, about 40 $\mu g/m^2/$ day, about 30 $g/m^2/day$, about 20 $\mu g/m^2/day$, or about 10 $\mu g/m^2/day$. In one embodiment, the frequency of the administration of blinatumomab is reduced to once every 2 days, once every 3 days, once every week, or once every 2 week.

In one embodiment, the anti-CD19 antibody (e.g., blinatumomab), or a pharmaceutically acceptable form thereof, is administered to the subject at least 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, 12 weeks, or 16 weeks before the PI3K inhibitor (e.g., Compound 1), or a pharmaceutically acceptable form thereof, is administered. In another embodiment, the anti-CD19 antibody (e.g., blinatumomab), or a pharmaceutically acceptable form thereof, is administered concurrently with the PI3K inhibitor (e.g., Compound 1), or a pharmaceutically acceptable form thereof, in a single dosage form or separate dosage forms. In yet another embodiment, the anti-CD19 antibody (e.g., blinatumomab), or a pharmaceutically acceptable form thereof, is administered to the subject at least 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, 12 weeks, or 16 weeks after the PI3K inhibitor (e.g., Compound 1), or a pharmaceutically acceptable form thereof, is administered.

In certain embodiments, the PI3K inhibitor (e.g., Compound 1), or a pharmaceutically acceptable form thereof, and the anti-CD19 antibody (e.g., blinatumomab) are administered via a same route. In other embodiments, the PI3K inhibitor (e.g., Compound 1), or a pharmaceutically acceptable form thereof, and the anti-CD19 antibody (e.g., blinatumomab) are administered via different routes, e.g., one is administered orally and the other is administered intravenously. In one embodiment, Compound 1 is administered orally and the anti-CD19 antibody (e.g., blinatumomab) is administered intravenously.

In certain embodiments, the PI3K inhibitor (e.g., Compound 1), or a pharmaceutically acceptable form thereof, and the anti-CD19 antibody (e.g., blinatumomab), or a pharmaceutically acceptable form thereof, are the only therapeutically active ingredients of the compositions and methods provided herein. In other embodiments, the compositions provided herein comprise and the methods provided herein use at least one more therapeutically active ingredient. In one embodiment, the compositions provided herein comprise and the methods provided herein use a PI3K delta inhibitor (e.g., Idelalisib), a PI3K delta/gamma dual inhibitor, and a anti-CD19 antibody (e.g., blinatumomab).

2.5 Combinations of PI3K Inhibitors and TLR Agonists

In certain embodiments, provided herein are methods of treating, managing, or preventing a cancer in a subject comprising administering to the subject a therapeutically effective amount of a PI3K inhibitor, or a pharmaceutically acceptable form thereof, in combination with a TLR agonist, or a pharmaceutically acceptable form thereof.

In certain embodiments, provided herein are pharmaceutical compositions comprising a therapeutically effective amount of a PI3K inhibitor, or a pharmaceutically acceptable form thereof, and a TLR agonist, or a pharmaceutically acceptable form thereof.

Toll-like receptors (TLRs) are a class of proteins that play a key role in the innate immune system. They are single, membrane-spanning, non-catalytic receptors usually expressed in sentinel cells such as macrophages and dendritic cells, that recognize structurally conserved molecules derived from microbes. Once these microbes have breached physical barriers such as the skin or intestinal tract mucosa, they are recognized by TLRs, which activate immune cell responses. The TLRs include TLR1, TLR2, TLR3, TLR4, TLR5, TLR6, TLR7, TLR8, TLR9, TLR10, TLR11, TLR12, and TLR13, though the latter two are not found in humans.

In one embodiment, provided herein is a method of treating, managing, or preventing a cancer in a subject comprising administering to the subject a therapeutically effective amount of a PI3K inhibitor, or a pharmaceutically acceptable form thereof, in combination with a TLR agonist, or a pharmaceutically acceptable form thereof, wherein the PI3K inhibitor is a PI3K delta inhibitor.

In one embodiment, provided herein is a pharmaceutical composition comprising a therapeutically effective amount of a PI3K inhibitor, or a pharmaceutically acceptable form thereof, and a TLR agonist, or a pharmaceutically acceptable form thereof, wherein the PI3K inhibitor is a PI3K delta inhibitor.

In one embodiment of the methods described herein, the PI3K delta inhibitor (e.g., Idelalisib), or a pharmaceutically acceptable form thereof, is administered at a dosage of in the range of from about 0.01 mg to about 75 mg daily and the TLR agonist, or a pharmaceutically acceptable form thereof, is administered at a dosage of in the range of from about 0.01 mg to about 1100 mg daily.

In one embodiment of the compositions and methods described herein, the molar ratio of the PI3K delta inhibitor (e.g., Idelalisib), or a pharmaceutically acceptable form thereof, to the TLR agonist, or a pharmaceutically acceptable form thereof, is in the range of from about 500:1 to about 1:500, from about 400:1 to about 1:400, from about 300:1 to about 1:300, from about 200:1 to about 1:200, from about 100:1 to about 1:100, from about 75:1 to about 1:75, from about 50:1 to about 1:50, from about 40:1 to about 1:40, from about 30:1 to about 1:30, from about 20:1 to about 1:20, from about 10:1 to about 1:10, from about 5:1 to about 1:5.

In one embodiment, the PI3K delta inhibitor (e.g., Idelalisib) is administered at an amount that is decreased by about 1.5 fold to about 50 fold, about 1.5 fold to about 25 fold, about 1.5 fold to about 20 fold, about 1.5 fold to about 15 fold, about 1.5 fold to about 10 fold, about 2 fold to about 10 fold, about 2 fold to about 8 fold, about 4 fold to about 6 fold, or about 5 fold of the amount when administered individually; and the TLR agonist is administered at an amount that is decreased by about 1.1 fold to about 50 fold, about 1.1 fold to about 40 fold, about 1.1 fold to about 30 fold, about 1.1 fold to about 25 fold, about 1.1 fold to about 20 fold, about 1.1 fold to about 15 fold, about 1.1 fold to about 10 fold of the amount when administered individually.

In one embodiment, provided herein is a method of treating, managing, or preventing a cancer in a subject comprising administering to the subject a therapeutically effective amount of a PI3K inhibitor, or a pharmaceutically acceptable form thereof, in combination with a TLR agonist, or a pharmaceutically acceptable form thereof, wherein the PI3K inhibitor is Idelalisib.

In one embodiment, provided herein is a pharmaceutical composition comprising a therapeutically effective amount of a PI3K inhibitor, or a pharmaceutically acceptable form thereof, and a TLR agonist, or a pharmaceutically acceptable form thereof, wherein the PI3K inhibitor is Idelalisib.

In one embodiment of the methods described herein, Idelalisib, or a pharmaceutically acceptable form thereof, is administered at a dosage of in the range of from about 0.01 mg to about 75 mg daily and the TLR agonist, or a pharmaceutically acceptable form thereof, is administered at a dosage of in the range of from about 0.01 mg to about 1100 mg daily.

In one embodiment of the compositions and methods described herein, Idelalisib, or a pharmaceutically acceptable form thereof, to the TLR agonist, or a pharmaceutically acceptable form thereof, is in the range of from about 500:1 to about 1:500, from about 400:1 to about 1:400, from about 300:1 to about 1:300, from about 200:1 to about 1:200, from about 100:1 to about 1:100, from about 75:1 to about 1:75, from about 50:1 to about 1:50, from about 40:1 to about 1:40, from about 30:1 to about 1:30, from about 20:1 to about 1:20, from about 10:1 to about 1:10, from about 5:1 to about 1:5.

In one embodiment, Idelalisib is administered at an amount that is decreased by about 1.5 fold to about 50 fold, about 1.5 fold to about 25 fold, about 1.5 fold to about 20 fold, about 1.5 fold to about 15 fold, about 1.5 fold to about 10 fold, about 2 fold to about 10 fold, about 2 fold to about 8 fold, about 4 fold to about 6 fold, or about 5 fold of the amount when administered individually; and the TLR agonist is administered at an amount that is decreased by about 1.1 fold to about 50 fold, about 1.1 fold to about 40 fold, about 1.1 fold to about 30 fold, about 1.1 fold to about 25 fold, about 1.1 fold to about 20 fold, about 1.1 fold to about 15 fold, about 1.1 fold to about 10 fold of the amount when administered individually.

In one embodiment, provided herein is a method of treating, managing, or preventing a cancer in a subject comprising administering to the subject a therapeutically effective amount of a PI3K inhibitor, or a pharmaceutically acceptable form thereof, in combination with a TLR agonist, or a pharmaceutically acceptable form thereof, wherein the PI3K inhibitor is a PI3K delta/gamma dual inhibitor.

In one embodiment, provided herein is a pharmaceutical composition comprising a therapeutically effective amount of a PI3K inhibitor, or a pharmaceutically acceptable form thereof, and a TLR agonist, or a pharmaceutically acceptable form thereof, wherein the PI3K inhibitor is a PI3K delta/gamma dual inhibitor.

In one embodiment of the methods described herein, the PI3K delta/gamma dual inhibitor (e.g., Compound 1), or a pharmaceutically acceptable form thereof, is administered at a dosage of in the range of from about 0.01 mg to about 75 mg daily and the TLR agonist, or a pharmaceutically acceptable form thereof, is administered at a dosage of in the range of from about 0.01 mg to about 1100 mg daily.

In one embodiment of the compositions and methods described herein, the molar ratio of the PI3K delta/gamma dual inhibitor (e.g., Compound 1), or a pharmaceutically acceptable form thereof, to the TLR agonist, or a pharmaceutically acceptable form thereof, is in the range of from about 500:1 to about 1:500, from about 400:1 to about 1:400, from about 300:1 to about 1:300, from about 200:1 to about 1:200, from about 100:1 to about 1:100, from about 75:1 to about 1:75, from about 50:1 to about 1:50, from about 40:1 to about 1:40, from about 30:1 to about 1:30, from about 20:1 to about 1:20, from about 10:1 to about 1:10, from about 5:1 to about 1:5.

In one embodiment, the PI3K delta/gamma dual inhibitor (e.g., Compound 1) is administered at an amount that is decreased by about 1.5 fold to about 50 fold, about 1.5 fold to about 25 fold, about 1.5 fold to about 20 fold, about 1.5 fold to about 15 fold, about 1.5 fold to about 10 fold, about 2 fold to about 10 fold, about 2 fold to about 8 fold, about 4 fold to about 6 fold, or about 5 fold of the amount when administered individually; and the TLR agonist is administered at an amount that is decreased by about 1.1 fold to about 50 fold, about 1.1 fold to about 40 fold, about 1.1 fold to about 30 fold, about 1.1 fold to about 25 fold, about 1.1 fold to about 20 fold, about 1.1 fold to about 15 fold, about 1.1 fold to about 10 fold of the amount when administered individually.

In one embodiment, provided herein is a method of treating, managing, or preventing a cancer in a subject comprising administering to the subject a therapeutically effective amount of a PI3K inhibitor, or a pharmaceutically acceptable form thereof, in combination with a TLR agonist, or a pharmaceutically acceptable form thereof, wherein the PI3K inhibitor is Compound 1:

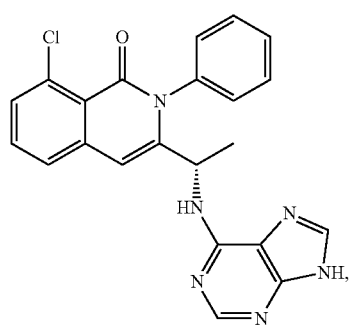

Compound 1 or a pharmaceutically acceptable form thereof.

In one embodiment, provided herein is a pharmaceutical composition comprising a therapeutically effective amount of a PI3K inhibitor, or a pharmaceutically acceptable form thereof, and a TLR agonist, or a pharmaceutically acceptable form thereof, wherein the PI3K inhibitor is Compound 1:

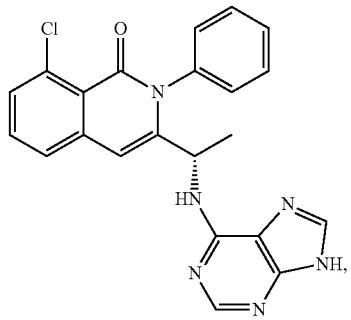

Compound 1 or a pharmaceutically acceptable form thereof.

In one embodiment of the methods described herein, Compound 1, or a pharmaceutically acceptable form thereof, is administered at a dosage of in the range of from about 0.01 mg to about 75 mg daily and the TLR agonist, or a pharmaceutically acceptable form thereof, is administered at a dosage of in the range of from about 0.01 mg to about 1100 mg daily.

In one embodiment of the compositions and methods described herein, Compound 1, or a pharmaceutically acceptable form thereof, to the TLR agonist, or a pharmaceutically acceptable form thereof, is in the range of from about 500:1 to about 1:500, from about 400:1 to about 1:400, from about 300:1 to about 1:300, from about 200:1 to about 1:200, from about 100:1 to about 1:100, from about 75:1 to about 1:75, from about 50:1 to about 1:50, from about 40:1 to about 1:40, from about 30:1 to about 1:30, from about 20:1 to about 1:20, from about 10:1 to about 1:10, from about 5:1 to about 1:5.

In one embodiment, Compound 1 is administered at an amount that is decreased by about 1.5 fold to about 50 fold, about 1.5 fold to about 25 fold, about 1.5 fold to about 20 fold, about 1.5 fold to about 15 fold, about 1.5 fold to about 10 fold, about 2 fold to about 10 fold, about 2 fold to about 8 fold, about 4 fold to about 6 fold, or about 5 fold of the amount when administered individually; and the TLR agonist is administered at an amount that is decreased by about 1.1 fold to about 50 fold, about 1.1 fold to about 40 fold, about 1.1 fold to about 30 fold, about 1.1 fold to about 25 fold, about 1.1 fold to about 20 fold, about 1.1 fold to about 15 fold, about 1.1 fold to about 10 fold of the amount when administered individually.

In one embodiment, the TLR agonist, or a pharmaceutically acceptable form thereof, is administered to the subject at least 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, 12 weeks, or 16 weeks before the PI3K inhibitor (e.g., Compound 1), or a pharmaceutically acceptable form thereof, is administered. In another embodiment, the TLR agonist, or a pharmaceutically acceptable form thereof, is administered concurrently with the PI3K inhibitor (e.g., Compound 1), or a pharmaceutically acceptable form thereof, in a single dosage form or separate dosage forms. In yet another embodiment, the TLR agonist, or a pharmaceutically acceptable form thereof, is administered to the subject at least 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, 12 weeks, or 16 weeks after the PI3K inhibitor (e.g., Compound 1), or a pharmaceutically acceptable form thereof, is administered.

In certain embodiments, the PI3K inhibitor (e.g., Compound 1), or a pharmaceutically acceptable form thereof, and the TLR agonist are administered via a same route, e.g., both are administered orally. In other embodiments, the PI3K inhibitor (e.g., Compound 1), or a pharmaceutically acceptable form thereof, and the TLR agonist are administered via different routes, e.g., one is administered orally and the other is administered intravenously. In one embodiment, Compound 1 is administered orally and the TLR agonist is administered intravenously.

In certain embodiments, the PI3K inhibitor (e.g., Compound 1), or a pharmaceutically acceptable form thereof, and the TLR agonist, or a pharmaceutically acceptable form thereof, are the only therapeutically active ingredients of the compositions and methods provided herein. In other embodiments, the compositions provided herein comprise and the methods provided herein use at least one more therapeutically active ingredient. In one embodiment, the compositions provided herein comprise and the methods provided herein use a PI3K delta inhibitor (e.g., Idelalisib), a PI3K delta/gamma dual inhibitor, and a TLR agonist.

2.6 Combinations of PI3K Inhibitors and STING Agonists

In certain embodiments, provided herein are methods of treating, managing, or preventing a cancer in a subject comprising administering to the subject a therapeutically effective amount of a PI3K inhibitor, or a pharmaceutically acceptable form thereof, in combination with a STING agonist, or a pharmaceutically acceptable form thereof.

In certain embodiments, provided herein are pharmaceutical compositions comprising a therapeutically effective amount of a PI3K inhibitor, or a pharmaceutically acceptable form thereof, and a STING agonist, or a pharmaceutically acceptable form thereof.

Stimulator of interferon genes (STING), also known as transmembrane protein 173 (TMEM173) and MPYS/MITA/ERIS, is a protein that in humans is encoded by the TMEM173 gene. STING plays an important role in innate immunity. STING induces type I interferon production when cells are infected with intracellular pathogens, such as viruses, mycobacteria and intracellular parasites. Type I interferon, mediated by STING, protects infected cells and nearby cells from local infection by binding to the same cell that secretes it (autocrine signaling) and nearby cells (paracrine signaling).

In one embodiment, provided herein is a method of treating, managing, or preventing a cancer in a subject comprising administering to the subject a therapeutically effective amount of a PI3K inhibitor, or a pharmaceutically acceptable form thereof, in combination with a STING agonist, or a pharmaceutically acceptable form thereof, wherein the PI3K inhibitor is a PI3K delta inhibitor.

In one embodiment, provided herein is a pharmaceutical composition comprising a therapeutically effective amount of a PI3K inhibitor, or a pharmaceutically acceptable form thereof, and a STING agonist, or a pharmaceutically acceptable form thereof, wherein the PI3K inhibitor is a PI3K delta inhibitor.

In one embodiment of the methods described herein, the PI3K delta inhibitor (e.g., Idelalisib), or a pharmaceutically acceptable form thereof, is administered at a dosage of in the range of from about 0.01 mg to about 75 mg daily and the STING agonist, or a pharmaceutically acceptable form thereof, is administered at a dosage of in the range of from about 0.01 mg to about 1100 mg daily.

In one embodiment of the compositions and methods described herein, the molar ratio of the PI3K delta inhibitor (e.g., Idelalisib), or a pharmaceutically acceptable form thereof, to the STING agonist, or a pharmaceutically acceptable form thereof, is in the range of from about 500:1 to about 1:500, from about 400:1 to about 1:400, from about 300:1 to about 1:300, from about 200:1 to about 1:200, from about 100:1 to about 1:100, from about 75:1 to about 1:75, from about 50:1 to about 1:50, from about 40:1 to about 1:40, from about 30:1 to about 1:30, from about 20:1 to about 1:20, from about 10:1 to about 1:10, from about 5:1 to about 1:5.

In one embodiment, the PI3K delta inhibitor (e.g., Idelalisib) is administered at an amount that is decreased by about 1.5 fold to about 50 fold, about 1.5 fold to about 25 fold, about 1.5 fold to about 20 fold, about 1.5 fold to about 15 fold, about 1.5 fold to about 10 fold, about 2 fold to about 10 fold, about 2 fold to about 8 fold, about 4 fold to about 6 fold, or about 5 fold of the amount when administered individually; and the STING agonist is administered at an amount that is decreased by about 1.1 fold to about 50 fold, about 1.1 fold to about 40 fold, about 1.1 fold to about 30 fold, about 1.1 fold to about 25 fold, about 1.1 fold to about 20 fold, about 1.1 fold to about 15 fold, about 1.1 fold to about 10 fold of the amount when administered individually.

In one embodiment, provided herein is a method of treating, managing, or preventing a cancer in a subject comprising administering to the subject a therapeutically effective amount of a PI3K inhibitor, or a pharmaceutically acceptable form thereof, in combination with a STING agonist, or a pharmaceutically acceptable form thereof, wherein the PI3K inhibitor is Idelalisib.

In one embodiment, provided herein is a pharmaceutical composition comprising a therapeutically effective amount of a PI3K inhibitor, or a pharmaceutically acceptable form thereof, and a STING agonist, or a pharmaceutically acceptable form thereof, wherein the PI3K inhibitor is Idelalisib.

In one embodiment of the methods described herein, Idelalisib, or a pharmaceutically acceptable form thereof, is administered at a dosage of in the range of from about 0.01 mg to about 75 mg daily and the STING agonist, or a pharmaceutically acceptable form thereof, is administered at a dosage of in the range of from about 0.01 mg to about 1100 mg daily.

In one embodiment of the compositions and methods described herein, Idelalisib, or a pharmaceutically acceptable form thereof, to the STING agonist, or a pharmaceutically acceptable form thereof, is in the range of from about 500:1 to about 1:500, from about 400:1 to about 1:400, from about 300:1 to about 1:300, from about 200:1 to about 1:200, from about 100:1 to about 1:100, from about 75:1 to about 1:75, from about 50:1 to about 1:50, from about 40:1 to about 1:40, from about 30:1 to about 1:30, from about 20:1 to about 1:20, from about 10:1 to about 1:10, from about 5:1 to about 1:5.

In one embodiment, Idelalisib is administered at an amount that is decreased by about 1.5 fold to about 50 fold, about 1.5 fold to about 25 fold, about 1.5 fold to about 20 fold, about 1.5 fold to about 15 fold, about 1.5 fold to about 10 fold, about 2 fold to about 10 fold, about 2 fold to about 8 fold, about 4 fold to about 6 fold, or about 5 fold of the amount when administered individually; and the STING agonist is administered at an amount that is decreased by about 1.1 fold to about 50 fold, about 1.1 fold to about 40 fold, about 1.1 fold to about 30 fold, about 1.1 fold to about 25 fold, about 1.1 fold to about 20 fold, about 1.1 fold to about 15 fold, about 1.1 fold to about 10 fold of the amount when administered individually.

In one embodiment, provided herein is a method of treating, managing, or preventing a cancer in a subject comprising administering to the subject a therapeutically effective amount of a PI3K inhibitor, or a pharmaceutically acceptable form thereof, in combination with a STING agonist, or a pharmaceutically acceptable form thereof, wherein the PI3K inhibitor is a PI3K delta/gamma dual inhibitor.

In one embodiment, provided herein is a pharmaceutical composition comprising a therapeutically effective amount of a PI3K inhibitor, or a pharmaceutically acceptable form thereof, and a STING agonist, or a pharmaceutically acceptable form thereof, wherein the PI3K inhibitor is a PI3K delta/gamma dual inhibitor.

In one embodiment of the methods described herein, the PI3K delta/gamma dual inhibitor (e.g., Compound 1), or a pharmaceutically acceptable form thereof, is administered at a dosage of in the range of from about 0.01 mg to about 75 mg daily and the STING agonist, or a pharmaceutically acceptable form thereof, is administered at a dosage of in the range of from about 0.01 mg to about 1100 mg daily.

In one embodiment of the compositions and methods described herein, the molar ratio of the PI3K delta/gamma dual inhibitor (e.g., Compound 1), or a pharmaceutically acceptable form thereof, to the STING agonist, or a pharmaceutically acceptable form thereof, is in the range of from about 500:1 to about 1:500, from about 400:1 to about 1:400, from about 300:1 to about 1:300, from about 200:1 to about 1:200, from about 100:1 to about 1:100, from about 75:1 to about 1:75, from about 50:1 to about 1:50, from about 40:1 to about 1:40, from about 30:1 to about 1:30, from about 20:1 to about 1:20, from about 10:1 to about 1:10, from about 5:1 to about 1:5.

In one embodiment, the PI3K delta/gamma dual inhibitor (e.g., Compound 1) is administered at an amount that is decreased by about 1.5 fold to about 50 fold, about 1.5 fold to about 25 fold, about 1.5 fold to about 20 fold, about 1.5 fold to about 15 fold, about 1.5 fold to about 10 fold, about 2 fold to about 10 fold, about 2 fold to about 8 fold, about 4 fold to about 6 fold, or about 5 fold of the amount when administered individually; and the STING agonist is administered at an amount that is decreased by about 1.1 fold to about 50 fold, about 1.1 fold to about 40 fold, about 1.1 fold to about 30 fold, about 1.1 fold to about 25 fold, about 1.1 fold to about 20 fold, about 1.1 fold to about 15 fold, about 1.1 fold to about 10 fold of the amount when administered individually.

In one embodiment, provided herein is a method of treating, managing, or preventing a cancer in a subject comprising administering to the subject a therapeutically effective amount of a PI3K inhibitor, or a pharmaceutically acceptable form thereof, in combination with a STING agonist, or a pharmaceutically acceptable form thereof, wherein the PI3K inhibitor is Compound 1:

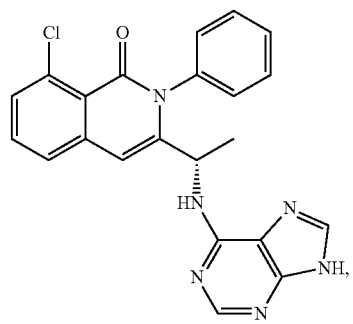

Compound 1 or a pharmaceutically acceptable form thereof.

In one embodiment, provided herein is a pharmaceutical composition comprising a therapeutically effective amount of a PI3K inhibitor, or a pharmaceutically acceptable form thereof, and a STING agonist, or a pharmaceutically acceptable form thereof, wherein the PI3K inhibitor is Compound 1:

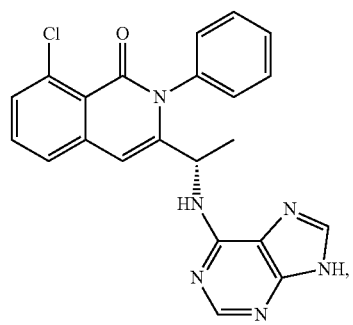

Compound 1 or a pharmaceutically acceptable form thereof.

In one embodiment of the methods described herein, Compound 1, or a pharmaceutically acceptable form thereof, is administered at a dosage of in the range of from about 0.01 mg to about 75 mg daily and the STING agonist, or a pharmaceutically acceptable form thereof, is administered at a dosage of in the range of from about 0.01 mg to about 1100 mg daily.

In one embodiment of the compositions and methods described herein, Compound 1, or a pharmaceutically acceptable form thereof, to the STING agonist, or a pharmaceutically acceptable form thereof, is in the range of from about 500:1 to about 1:500, from about 400:1 to about 1:400, from about 300:1 to about 1:300, from about 200:1 to about 1:200, from about 100:1 to about 1:100, from about 75:1 to about 1:75, from about 50:1 to about 1:50, from about 40:1 to about 1:40, from about 30:1 to about 1:30, from about 20:1 to about 1:20, from about 10:1 to about 1:10, from about 5:1 to about 1:5.

In one embodiment, Compound 1 is administered at an amount that is decreased by about 1.5 fold to about 50 fold, about 1.5 fold to about 25 fold, about 1.5 fold to about 20 fold, about 1.5 fold to about 15 fold, about 1.5 fold to about 10 fold, about 2 fold to about 10 fold, about 2 fold to about 8 fold, about 4 fold to about 6 fold, or about 5 fold of the amount when administered individually; and the STING agonist is administered at an amount that is decreased by about 1.1 fold to about 50 fold, about 1.1 fold to about 40 fold, about 1.1 fold to about 30 fold, about 1.1 fold to about 25 fold, about 1.1 fold to about 20 fold, about 1.1 fold to about 15 fold, about 1.1 fold to about 10 fold of the amount when administered individually.

In one embodiment, the STING agonist, or a pharmaceutically acceptable form thereof, is administered to the subject at least 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, 12 weeks, or 16 weeks before the PI3K inhibitor (e.g., Compound 1), or a pharmaceutically acceptable form thereof, is administered. In another embodiment, the STING agonist, or a pharmaceutically acceptable form thereof, is administered concurrently with the PI3K inhibitor (e.g., Compound 1), or a pharmaceutically acceptable form thereof, in a single dosage form or separate dosage forms. In yet another embodiment, the STING agonist, or a pharmaceutically acceptable form thereof, is administered to the subject at least 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, 12 weeks, or 16 weeks after the PI3K inhibitor (e.g., Compound 1), or a pharmaceutically acceptable form thereof, is administered.

In certain embodiments, the PI3K inhibitor (e.g., Compound 1), or a pharmaceutically acceptable form thereof, and the STING agonist are administered via a same route, e.g., both are administered orally. In other embodiments, the PI3K inhibitor (e.g., Compound 1), or a pharmaceutically acceptable form thereof, and the STING agonist are administered via different routes, e.g., one is administered orally and the other is administered intravenously. In one embodiment, Compound 1 is administered orally and the STING agonist is administered intravenously.

In certain embodiments, the PI3K inhibitor (e.g., Compound 1), or a pharmaceutically acceptable form thereof, and the STING agonist, or a pharmaceutically acceptable form thereof, are the only therapeutically active ingredients of the compositions and methods provided herein. In other embodiments, the compositions provided herein comprise and the methods provided herein use at least one more therapeutically active ingredient. In one embodiment, the compositions provided herein comprise and the methods provided herein use a PI3K delta inhibitor (e.g., Idelalisib), a PI3K delta/gamma dual inhibitor, and a STING agonist.

2.7 Combinations of PI3K Inhibitors and Flt3 Ligands

In certain embodiments, provided herein are methods of treating, managing, or preventing a cancer in a subject comprising administering to the subject a therapeutically effective amount of a PI3K inhibitor, or a pharmaceutically acceptable form thereof, in combination with a Flt3 ligand, or a pharmaceutically acceptable form thereof.

In certain embodiments, provided herein are pharmaceutical compositions comprising a therapeutically effective amount of a PI3K inhibitor, or a pharmaceutically acceptable form thereof, and a Flt3 ligand, or a pharmaceutically acceptable form thereof.

Fms-related tyrosine kinase 3 ligand (FLT3LG) is a protein which in humans is encoded by the FLT3LG gene. Flt3 ligand is a hematopoietic four helical bundle cytokine. It is structurally homologous to stem cell factor (SCF) and colony stimulating factor 1 (CSF-1). In synergy with other growth factors, Flt3 ligand stimulates the proliferation and differentiation of various blood cell progenitors.

In one embodiment, provided herein is a method of treating, managing, or preventing a cancer in a subject comprising administering to the subject a therapeutically effective amount of a PI3K inhibitor, or a pharmaceutically acceptable form thereof, in combination with a Flt3 ligand, or a pharmaceutically acceptable form thereof, wherein the PI3K inhibitor is a PI3K delta inhibitor.

In one embodiment, provided herein is a pharmaceutical composition comprising a therapeutically effective amount of a PI3K inhibitor, or a pharmaceutically acceptable form thereof, and a Flt3 ligand, or a pharmaceutically acceptable form thereof, wherein the PI3K inhibitor is a PI3K delta inhibitor.

In one embodiment of the methods described herein, the PI3K delta inhibitor (e.g., Idelalisib), or a pharmaceutically acceptable form thereof, is administered at a dosage of in the range of from about 0.01 mg to about 75 mg daily and the Flt3 ligand, or a pharmaceutically acceptable form thereof, is administered at a dosage of in the range of from about 0.01 mg to about 1100 mg daily.

In one embodiment of the compositions and methods described herein, the molar ratio of the PI3K delta inhibitor (e.g., Idelalisib), or a pharmaceutically acceptable form thereof, to the Flt3 ligand, or a pharmaceutically acceptable form thereof, is in the range of from about 500:1 to about 1:500, from about 400:1 to about 1:400, from about 300:1 to about 1:300, from about 200:1 to about 1:200, from about 100:1 to about 1:100, from about 75:1 to about 1:75, from about 50:1 to about 1:50, from about 40:1 to about 1:40, from about 30:1 to about 1:30, from about 20:1 to about 1:20, from about 10:1 to about 1:10, from about 5:1 to about 1:5.

In one embodiment, the PI3K delta inhibitor (e.g., Idelalisib) is administered at an amount that is decreased by about 1.5 fold to about 50 fold, about 1.5 fold to about 25 fold, about 1.5 fold to about 20 fold, about 1.5 fold to about 15 fold, about 1.5 fold to about 10 fold, about 2 fold to about 10 fold, about 2 fold to about 8 fold, about 4 fold to about 6 fold, or about 5 fold of the amount when administered individually; and the Flt3 ligand is administered at an amount that is decreased by about 1.1 fold to about 50 fold, about 1.1 fold to about 40 fold, about 1.1 fold to about 30 fold, about 1.1 fold to about 25 fold, about 1.1 fold to about 20 fold, about 1.1 fold to about 15 fold, about 1.1 fold to about 10 fold of the amount when administered individually.

In one embodiment, provided herein is a method of treating, managing, or preventing a cancer in a subject comprising administering to the subject a therapeutically effective amount of a PI3K inhibitor, or a pharmaceutically acceptable form thereof, in combination with a Flt3 ligand, or a pharmaceutically acceptable form thereof, wherein the PI3K inhibitor is Idelalisib.

In one embodiment, provided herein is a pharmaceutical composition comprising a therapeutically effective amount of a PI3K inhibitor, or a pharmaceutically acceptable form thereof, and a Flt3 ligand, or a pharmaceutically acceptable form thereof, wherein the PI3K inhibitor is Idelalisib.

In one embodiment of the methods described herein, Idelalisib, or a pharmaceutically acceptable form thereof, is administered at a dosage of in the range of from about 0.01 mg to about 75 mg daily and the Flt3 ligand, or a pharmaceutically acceptable form thereof, is administered at a dosage of in the range of from about 0.01 mg to about 1100 mg daily.

In one embodiment of the compositions and methods described herein, Idelalisib, or a pharmaceutically acceptable form thereof, to the Flt3 ligand, or a pharmaceutically acceptable form thereof, is in the range of from about 500:1 to about 1:500, from about 400:1 to about 1:400, from about 300:1 to about 1:300, from about 200:1 to about 1:200, from about 100:1 to about 1:100, from about 75:1 to about 1:75, from about 50:1 to about 1:50, from about 40:1 to about 1:40, from about 30:1 to about 1:30, from about 20:1 to about 1:20, from about 10:1 to about 1:10, from about 5:1 to about 1:5.

In one embodiment, Idelalisib is administered at an amount that is decreased by about 1.5 fold to about 50 fold, about 1.5 fold to about 25 fold, about 1.5 fold to about 20 fold, about 1.5 fold to about 15 fold, about 1.5 fold to about 10 fold, about 2 fold to about 10 fold, about 2 fold to about 8 fold, about 4 fold to about 6 fold, or about 5 fold of the amount when administered individually; and the Flt3 ligand is administered at an amount that is decreased by about 1.1 fold to about 50 fold, about 1.1 fold to about 40 fold, about 1.1 fold to about 30 fold, about 1.1 fold to about 25 fold, about 1.1 fold to about 20 fold, about 1.1 fold to about 15 fold, about 1.1 fold to about 10 fold of the amount when administered individually.

In one embodiment, provided herein is a method of treating, managing, or preventing a cancer in a subject comprising administering to the subject a therapeutically effective amount of a PI3K inhibitor, or a pharmaceutically acceptable form thereof, in combination with a Flt3 ligand, or a pharmaceutically acceptable form thereof, wherein the PI3K inhibitor is a PI3K delta/gamma dual inhibitor.

In one embodiment, provided herein is a pharmaceutical composition comprising a therapeutically effective amount of a PI3K inhibitor, or a pharmaceutically acceptable form thereof, and a Flt3 ligand, or a pharmaceutically acceptable form thereof, wherein the PI3K inhibitor is a PI3K delta/gamma dual inhibitor.

In one embodiment of the methods described herein, the PI3K delta/gamma dual inhibitor (e.g., Compound 1), or a pharmaceutically acceptable form thereof, is administered at a dosage of in the range of from about 0.01 mg to about 75 mg daily and the Flt3 ligand, or a pharmaceutically acceptable form thereof, is administered at a dosage of in the range of from about 0.01 mg to about 1100 mg daily.

In one embodiment of the compositions and methods described herein, the molar ratio of the PI3K delta/gamma dual inhibitor (e.g., Compound 1), or a pharmaceutically acceptable form thereof, to the Flt3 ligand, or a pharmaceutically acceptable form thereof, is in the range of from about 500:1 to about 1:500, from about 400:1 to about 1:400, from about 300:1 to about 1:300, from about 200:1 to about 1:200, from about 100:1 to about 1:100, from about 75:1 to about 1:75, from about 50:1 to about 1:50, from about 40:1 to about 1:40, from about 30:1 to about 1:30, from about 20:1 to about 1:20, from about 10:1 to about 1:10, from about 5:1 to about 1:5.

In one embodiment, the PI3K delta/gamma dual inhibitor (e.g., Compound 1) is administered at an amount that is decreased by about 1.5 fold to about 50 fold, about 1.5 fold to about 25 fold, about 1.5 fold to about 20 fold, about 1.5 fold to about 15 fold, about 1.5 fold to about 10 fold, about 2 fold to about 10 fold, about 2 fold to about 8 fold, about 4 fold to about 6 fold, or about 5 fold of the amount when administered individually; and the Flt3 ligand is administered at an amount that is decreased by about 1.1 fold to about 50 fold, about 1.1 fold to about 40 fold, about 1.1 fold to about 30 fold, about 1.1 fold to about 25 fold, about 1.1 fold to about 20 fold, about 1.1 fold to about 15 fold, about 1.1 fold to about 10 fold of the amount when administered individually.

In one embodiment, provided herein is a method of treating, managing, or preventing a cancer in a subject comprising administering to the subject a therapeutically effective amount of a PI3K inhibitor, or a pharmaceutically acceptable form thereof, in combination with a Flt3 ligand, or a pharmaceutically acceptable form thereof, wherein the PI3K inhibitor is Compound 1:

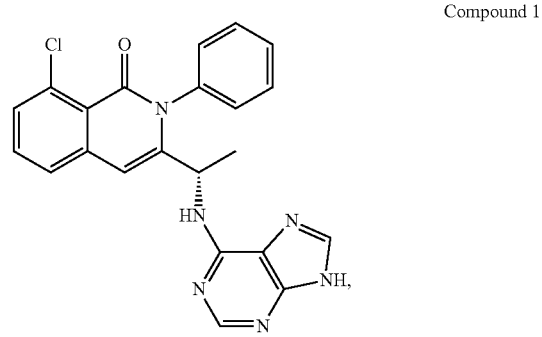 [SMILES: C[C@H](Nc1ncnc2[nH]cnc12)c1cc2cccc(Cl)c2c(=O)n1-c1ccccc1]

Compound 1 or a pharmaceutically acceptable form thereof.

In one embodiment, provided herein is a pharmaceutical composition comprising a therapeutically effective amount of a PI3K inhibitor, or a pharmaceutically acceptable form thereof, and a Flt3 ligand, or a pharmaceutically acceptable form thereof wherein the PI3K inhibitor is Compound 1:

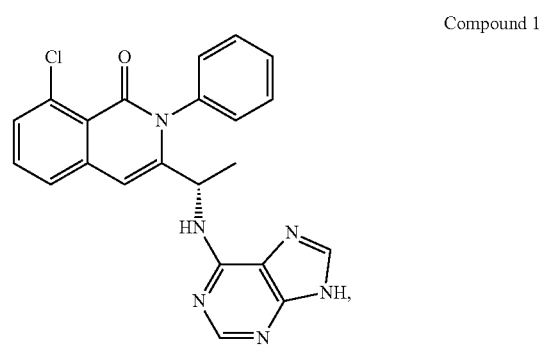 [SMILES: C[C@H](Nc1ncnc2[nH]cnc12)c1cc2cccc(Cl)c2c(=O)n1-c1ccccc1]

Compound 1 or a pharmaceutically acceptable form thereof.

In one embodiment of the methods described herein, Compound 1, or a pharmaceutically acceptable form thereof, is administered at a dosage of in the range of from about 0.01 mg to about 75 mg daily and the Flt3 ligand, or a pharmaceutically acceptable form thereof, is administered at a dosage of in the range of from about 0.01 mg to about 1100 mg daily.

In one embodiment of the compositions and methods described herein, Compound 1, or a pharmaceutically acceptable form thereof, to the Flt3 ligand, or a pharmaceutically acceptable form thereof, is in the range of from about 500:1 to about 1:500, from about 400:1 to about 1:400, from about 300:1 to about 1:300, from about 200:1 to about 1:200, from about 100:1 to about 1:100, from about 75:1 to about 1:75, from about 50:1 to about 1:50, from about 40:1 to about 1:40, from about 30:1 to about 1:30, from about 20:1 to about 1:20, from about 10:1 to about 1:10, from about 5:1 to about 1:5.

In one embodiment, Compound 1 is administered at an amount that is decreased by about 1.5 fold to about 50 fold, about 1.5 fold to about 25 fold, about 1.5 fold to about 20 fold, about 1.5 fold to about 15 fold, about 1.5 fold to about 10 fold, about 2 fold to about 10 fold, about 2 fold to about 8 fold, about 4 fold to about 6 fold, or about 5 fold of the amount when administered individually; and the Flt3 ligand is administered at an amount that is decreased by about 1.1 fold to about 50 fold, about 1.1 fold to about 40 fold, about 1.1 fold to about 30 fold, about 1.1 fold to about 25 fold, about 1.1 fold to about 20 fold, about 1.1 fold to about 15 fold, about 1.1 fold to about 10 fold of the amount when administered individually.

In one embodiment, the Flt3 ligand, or a pharmaceutically acceptable form thereof, is administered to the subject at least 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, 12 weeks, or 16 weeks before the PI3K inhibitor (e.g., Compound 1), or a pharmaceutically acceptable form thereof, is administered. In another embodiment, the Flt3 ligand, or a pharmaceutically acceptable form thereof, is administered concurrently with the PI3K inhibitor (e.g., Compound 1), or a pharmaceutically acceptable form thereof, in a single dosage form or separate dosage forms. In yet another embodiment, the Flt3 ligand, or a pharmaceutically acceptable form thereof, is administered to the subject at least 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, 12 weeks, or 16 weeks after the PI3K inhibitor (e.g., Compound 1), or a pharmaceutically acceptable form thereof, is administered.

In certain embodiments, the PI3K inhibitor (e.g., Compound 1), or a pharmaceutically acceptable form thereof, and the Flt3 ligand are administered via a same route, e.g., both are administered orally. In other embodiments, the PI3K inhibitor (e.g., Compound 1), or a pharmaceutically acceptable form thereof, and the Flt3 ligand are administered via different routes, e.g., one is administered orally and the other is administered intravenously. In one embodiment, Compound 1 is administered orally and the Flt3 ligand is administered intravenously.

In certain embodiments, the PI3K inhibitor (e.g., Compound 1), or a pharmaceutically acceptable form thereof, and the Flt3 ligand, or a pharmaceutically acceptable form thereof, are the only therapeutically active ingredients of the compositions and methods provided herein. In other embodiments, the compositions provided herein comprise and the methods provided herein use at least one more therapeutically active ingredient. In one embodiment, the compositions provided herein comprise and the methods provided herein use a PI3K delta inhibitor (e.g., Idelalisib), a PI3K delta/gamma dual inhibitor, and a Flt3 ligand.

Cancers

The diseases or disorders (e.g., cancer) that can be treated, managed, or prevented with a pharmaceutical composition as provided herein, or according to the methods as provided herein, include, but are not limited to, breast cancer such as a ductal carcinoma, lobular carcinoma, medullary carcinomas, colloid carcinomas, tubular carcinomas, and inflammatory breast cancer; ovarian cancer, including epithelial ovarian tumors such as adenocarcinoma in the ovary and an adenocarcinoma that has migrated from the ovary into the abdominal cavity; uterine cancer; cervical cancer such as adenocarcinoma in the cervix epithelial including squamous cell carcinoma and adenocarcinomas; prostate cancer, such as a prostate cancer selected from the following: an adenocarcinoma or an adenocarcinoma that has migrated to the bone; pancreatic cancer such as epitheliod carcinoma in the pancreatic duct tissue and an adenocarcinoma in a pancreatic duct; bladder cancer such as a transitional cell carcinoma in urinary bladder, urothelial carcinomas (transitional cell carcinomas), tumors in the urothelial cells that line the bladder, squamous cell carcinomas, adenocarcinomas, and small cell cancers; leukemia such as acute myeloid leukemia (AML), acute lymphocytic leukemia, chronic lymphocytic leukemia, chronic myeloid leukemia, hairy cell leukemia, myelodysplasia, myeloproliferative disorders, NK cell leukemia (e.g., blastic plasmacytoid dendritic cell neoplasm), acute myelogenous leukemia (AML), chronic myelogenous leukemia (CML), mastocytosis, chronic lymphocytic leukemia (CLL), multiple myeloma (MM), and myelodysplastic syndrome (MDS); bone cancer; lung cancer such as non-small cell lung cancer (NSCLC), which is divided into squamous cell carcinomas, adenocarcinomas, and large cell undifferentiated carcinomas, and small cell lung cancer; skin cancer such as basal cell carcinoma, melanoma, squamous cell carcinoma and actinic keratosis, which is a skin condition that sometimes develops into squamous cell carcinoma; eye retinoblastoma; cutaneous or intraocular (eye) melanoma; primary liver cancer; kidney cancer; thyroid cancer such as papillary, follicular, medullary and anaplastic; lymphoma such as diffuse large B-cell lymphoma, B-cell immunoblastic lymphoma, NK cell lymphoma (e.g., blastic plasmacytoid dendritic cell neoplasm), and Burkitt lymphoma; Kaposi's Sarcoma; viral-induced cancers including hepatitis B virus (HBV), hepatitis C virus (HCV), and hepatocellular carcinoma; human lymphotropic virus-type 1 (HTLV-1) and adult T-cell leukemia/lymphoma; and human papilloma virus (HPV) and cervical cancer; central nervous system cancers (CNS) such as primary brain tumor, which includes gliomas (astrocytoma, anaplastic astrocytoma, or glioblastoma multiforme), oligodendroglioma, ependymoma, meningioma, lymphoma, schwannoma, and medulloblastoma; peripheral nervous system (PNS) cancers such as acoustic neuromas and malignant peripheral nerve sheath tumor (MPNST) including neurofibromas and schwannomas, malignant fibrocytoma, malignant fibrous histiocytoma, malignant meningioma, malignant mesothelioma, and malignant mixed Müllerian tumor; oral cavity and oropharyngeal cancers such as, hypopharyngeal cancer, laryngeal cancer, nasopharyngeal cancer, and oropharyngeal cancer; stomach cancers such as lymphomas, gastric stromal tumors, and carcinoid tumors; testicular cancers such as germ cell tumors (GCTs), which include seminomas and nonseminomas, and gonadal stromal tumors, which include Leydig cell tumors and Sertoli cell tumors; thymus cancer such as to thymomas, thymic carcinomas, Hodgkin lymphoma, non-Hodgkin lymphomas carcinoids or carcinoid tumors; rectal cancer; and colon cancer.

In one embodiment, the cancer or disease is a blood disorder or a hematologic malignancy.

In some embodiments, the cancer or disease is selected from one or more of the following: acoustic neuroma, adenocarcinoma, adrenal gland cancer, anal cancer, angiosarcoma (e.g., lymphangiosarcoma, lymphangioendotheliosarcoma, hemangiosarcoma), benign monoclonal gammopathy, biliary cancer (e.g., cholangiocarcinoma), bladder cancer, breast cancer (e.g., adenocarcinoma of the breast, papillary carcinoma of the breast, mammary cancer, medullary carcinoma of the breast), brain cancer (e.g., meningioma; glioma, e.g., astrocytoma, oligodendroglioma; medulloblastoma), bronchus cancer, cervical cancer (e.g., cervical adenocarcinoma), choriocarcinoma, chordoma, craniopharyngioma, colorectal cancer (e.g., colon cancer, rectal cancer, colorectal adenocarcinoma), epithelial carcinoma, ependymoma, endotheliosarcoma (e.g., Kaposi's sarcoma, multiple idiopathic hemorrhagic sarcoma), endometrial cancer, esophageal cancer (e.g., adenocarcinoma of the esophagus, Barrett's adenocarinoma), Ewing sarcoma, familiar hypereosinophilia, gastric cancer (e.g., stomach adenocarcinoma), gastrointestinal stromal tumor (GIST), head and neck cancer (e.g., head and neck squamous cell carcinoma, oral cancer (e.g., oral squamous cell carcinoma (OSCC)), heavy chain disease (e.g., alpha chain disease, gamma chain disease, mu chain disease), hemangioblastoma, inflammatory myofibroblastic tumors, immunocytic amyloidosis, kidney cancer (e.g., nephroblastoma a.k.a. Wilms' tumor, renal cell carcinoma), liver cancer (e.g., hepatocellular cancer (HCC), malignant hepatoma), lung cancer (e.g., bronchogenic carcinoma, small cell lung cancer (SCLC), non-small cell lung cancer (NSCLC), adenocarcinoma of the lung), leukemia (e.g., acute lymphocytic leukemia (ALL), which includes B-lineage ALL and T-lineage ALL, chronic lymphocytic leukemia (CLL), prolymphocytic leukemia (PLL), hairy cell leukemia (HCL) and Waldenstrom's macroglobulinemia (WM); peripheral T cell lymphomas (PTCL), adult T cell leukemia/lymphoma (ATL), cutaneous T-cell lymphoma (CTCL), large granular lymphocytic leukemia (LGF), Hodgkin's disease and Reed-Sternberg disease; acute myelocytic leukemia (AML), chronic myelocytic leukemia (CML), chronic lymphocytic leukemia (CLL)), lymphoma (e.g., Hodgkin lymphoma (HL), non-Hodgkin lymphoma (NHL), follicular lymphoma, diffuse large B-cell lymphoma (DLBCL), mantle cell lymphoma (MCL)), leiomyosarcoma (LMS), mastocytosis (e.g., systemic mastocytosis), multiple myeloma (MM), myelodysplastic syndrome (MDS), mesothelioma, myeloproliferative disorder (MPD) (e.g., polycythemia Vera (PV), essential thrombocytosis (ET), agnogenic myeloid metaplasia (AMM) a.k.a. myelofibrosis (MF), chronic idiopathic myelofibrosis, chronic myelocytic leukemia (CML), chronic neutrophilic leukemia (CNL), hypereosinophilic syndrome (HES)), neuroblastoma, neurofibroma (e.g., neurofibromatosis (NF) type 1 or type 2, schwannomatosis), neuroendocrine cancer (e.g., gastroenteropancreatic neuroendoctrine tumor (GEP—N ET), carcinoid tumor), osteosarcoma, ovarian cancer (e.g., cystadenocarcinoma, ovarian embryonal carcinoma, ovarian adenocarcinoma), Paget's disease of the vulva, Paget's disease of the penis, papillary adenocarcinoma, pancreatic cancer (e.g., pancreatic andenocarcinoma, intraductal papillary mucinous neoplasm (IPMN)), pinealoma, primitive neuroectodermal tumor (PNT), prostate cancer (e.g., prostate adenocarcinoma), rhabdomyosarcoma, retinoblastoma, salivary gland cancer, skin cancer (e.g., squamous cell carcinoma (SCC), keratoacanthoma (KA), melanoma, basal cell carcinoma (BCC)), small bowel cancer (e.g., appendix cancer), soft tissue sarcoma (e.g., malignant fibrous histiocytoma (MFH), liposarcoma, malignant peripheral nerve sheath tumor (MPNST), chondrosarcoma, fibrosarcoma, myxosarcoma), sebaceous gland carcinoma, sweat gland carcinoma, synovioma, testicular cancer (e.g., seminoma, testicular embryonal carcinoma), thyroid cancer (e.g., papillary carcinoma of the thyroid, papillary thyroid carcinoma (PTC), medullary thyroid cancer), and Waldenstrom's macroglobulinemia.

In one embodiment, the cancer or disease provided herein, such as a blood disorder or hematologic malignancy, has a high expression level of one or more PI3K isoform(s) (e.g., PI3K-α, PI3K-β, PI3K-δ, or PI3K-γ, or a combination thereof).

In one embodiment, the cancer or disease is a blood disorder or a hematologic malignancy, including, but not limited to, myeloid disorder, lymphoid disorder, leukemia, lymphoma, myelodysplastic syndrome (MDS), myeloproliferative disease (MPD), mast cell disorder, and myeloma (e.g., multiple myeloma), among others.

In one embodiment, the blood disorder or the hematologic malignancy includes, but is not limited to, acute lymphoblastic leukemia (ALL), T-cell ALL (T-ALL), B-cell ALL (B-ALL), acute myeloid leukemia (AML), chronic lymphocytic leukemia (CLL), chronic myelogenous leukemia (CML), blast phase CML, small lymphocytic lymphoma (SLL), CLL/SLL, blast phase CLL, Hodgkin lymphoma (HL), non-Hodgkin lymphoma (NHL), B-cell NHL, T-cell NHL, indolent NHL (iNHL), diffuse large B-cell lymphoma (DLBCL), mantle cell lymphoma (MCL), aggressive B-cell NHL, B-cell lymphoma (BCL), Richter's syndrome (RS), T-cell lymphoma (TCL), peripheral T-cell lymphoma (PTCL), cutaneous T-cell lymphoma (CTCL), transformed mycosis fungoides, Sezary syndrome, anaplastic large-cell lymphoma (ALCL), follicular lymphoma (FL), Waldenstrom macroglobulinemia (WM), lymphoplasmacytic lymphoma, Burkitt lymphoma, multiple myeloma (MM), amyloidosis, MPD, essential thrombocytosis (ET), myelofibrosis (MF), polycythemia vera (PV), chronic myelomonocytic leukemia (CMML), myelodysplastic syndrome (MDS), angioimmunoblastic lymphoma, high-risk MDS, and low-risk MDS. In one embodiment, the hematologic malignancy is relapsed. In one embodiment, the hematologic malignancy is refractory. In one embodiment, the cancer or disease is in a pediatric patient (including an infantile patient). In one embodiment, the cancer or disease is in an adult patient. Additional embodiments of a cancer or disease being treated or prevented by methods, compositions, or kits provided herein are described herein elsewhere.

In exemplary embodiments, the cancer or hematologic malignancy is CLL. In exemplary embodiments, the cancer or hematologic malignancy is CLL/SLL. In exemplary embodiments, the cancer or hematologic malignancy is blast phase CLL. In exemplary embodiments, the cancer or hematologic malignancy is SLL.

In exemplary embodiments, the cancer or hematologic malignancy is iNHL. In exemplary embodiments, the cancer or hematologic malignancy is DLBCL. In exemplary embodiments, the cancer or hematologic malignancy is B-cell NHL (e.g., aggressive B-cell NHL). In exemplary embodiments, the cancer or hematologic malignancy is MCL. In exemplary embodiments, the cancer or hematologic malignancy is RS. In exemplary embodiments, the cancer or hematologic malignancy is AML. In exemplary embodiments, the cancer or hematologic malignancy is MM. In exemplary embodiments, the cancer or hematologic malignancy is ALL. In exemplary embodiments, the cancer or hematologic malignancy is T-ALL. In exemplary embodiments, the cancer or hematologic malignancy is B-ALL. In exemplary embodiments, the cancer or hematologic malignancy is TCL. In exemplary embodiments, the cancer or hematologic malignancy is ALCL. In exemplary embodiments, the cancer or hematologic malignancy is leukemia. In exemplary embodiments, the cancer or hematologic malignancy is lymphoma. In exemplary embodiments, the cancer or hematologic malignancy is T-cell lymphoma. In exemplary embodiments, the cancer or hematologic malignancy is MDS (e.g., low grade MDS). In exemplary embodiments, the cancer or hematologic malignancy is MPD. In exemplary embodiments, the cancer or hematologic malignancy is a mast cell disorder. In exemplary embodiments, the cancer or hematologic malignancy is Hodgkin lymphoma (HL). In exemplary embodiments, the cancer or hematologic malignancy is non-Hodgkin lymphoma. In exemplary embodiments, the cancer or hematologic malignancy is PTCL. In exemplary embodiments, the cancer or hematologic malignancy is CTCL (e.g., mycosis fungoides or Sezary syndrome). In exemplary embodiments, the cancer or hematologic malignancy is WM. In exemplary embodiments, the cancer or hematologic malignancy is CML. In exemplary embodiments, the cancer or hematologic malignancy is FL. In exemplary embodiments, the cancer or hematologic malignancy is transformed mycosis fungoides. In exemplary embodiments, the cancer or hematologic malignancy is Sezary syndrome. In exemplary embodiments, the cancer or hematologic malignancy is acute T-cell leukemia. In exemplary embodiments, the cancer or hematologic malignancy is acute B-cell leukemia. In exemplary embodiments, the cancer or hematologic malignancy is Burkitt lymphoma. In exemplary embodiments, the cancer or hematologic malignancy is myeloproliferative neoplasms. In exemplary embodiments, the cancer or hematologic malignancy is splenic marginal zone. In exemplary embodiments, the cancer or hematologic malignancy is nodal marginal zone. In exemplary embodiments, the cancer or hematologic malignancy is extranodal marginal zone.

In one embodiment, the cancer or hematologic malignancy is a B cell lymphoma. In a specific embodiment, provided herein is a method of treating or managing a B cell lymphoma comprising administering to a patient a therapeutically effective amount of a compound provided herein, or a pharmaceutically acceptable derivative (e.g., salt or solvate) thereof. Also provided herein is a method of treating or lessening one or more of the symptoms associated with a B cell lymphoma comprising administering to a patient a therapeutically effective amount of a compound provided herein, or a pharmaceutically acceptable derivative (e.g., salt or solvate) thereof. In one embodiment, the B cell lymphoma is iNHL. In another embodiment, the B cell lymphoma is follicular lymphoma. In another embodiment, the B cell lymphoma is Waldenstrom macroglobulinemia (lymphoplasmacytic lymphoma). In another embodiment, the B cell lymphoma is marginal zone lymphoma (MZL). In another embodiment, the B cell lymphoma is MCL. In another embodiment, the B cell lymphoma is HL. In another embodiment, the B cell lymphoma is aNHL. In another embodiment, the B cell lymphoma is DLBCL. In another embodiment, the B cell lymphoma is Richters lymphoma.

In one embodiment, the cancer or hematologic malignancy is a T cell lymphoma. In a specific embodiment, provided herein is a method of treating or managing a T cell lymphoma comprising administering to a patient a therapeutically effective amount of a compound provided herein, or a pharmaceutically acceptable derivative (e.g., salt or solvate) thereof. Also provided herein is a method of treating or lessening one or more of the symptoms associated with a T cell lymphoma comprising administering to a patient a therapeutically effective amount of a compound provided herein, or a pharmaceutically acceptable derivative (e.g., salt or solvate) thereof. In one embodiment, the T cell lymphoma is peripheral T cell lymphoma (PTCL). In another embodiment, the T cell lymphoma is cutaneous T cell lymphoma (CTCL).

In one embodiment, the cancer or hematologic malignancy is Sezary syndrome. In a specific embodiment, provided herein is a method of treating or managing Sezary syndrome comprising administering to a patient a therapeutically effective amount of a compound provided herein, or a pharmaceutically acceptable derivative (e.g., salt or solvate) thereof. Also provided herein is a method of treating or lessening one or more of the symptoms associated with Sezary syndrome comprising administering to a patient a therapeutically effective amount of a compound provided herein, or a pharmaceutically acceptable derivative (e.g., salt or solvate) thereof. The symptoms associated with Sezary syndrome include, but are not limited to, epidermotropism by neoplastic CD4+ lymphocytes, Pautrier's microabscesses, erythroderma, lymphadenopathy, atypical T cells in the peripheral blood, and hepatosplenomegaly.

The effectiveness of treatment in the preceding methods can for example be determined by measuring the decrease in size of tumors present in the patients with the neoplastic condition, or by assaying a molecular determinant of the degree of proliferation of the tumor cells.

Suitable test agents which can be tested in the preceding method include combinatorial libraries, defined chemical entities, peptide and peptide mimetics, oligonucleotides and natural product libraries, such as display (e.g. phage display libraries) and antibody products. Test agents may be used in an initial screen of, for example, 10 substances per reaction, and the substances of these batches which show inhibition or activation tested individually. Test agents may be used at a concentration of from lnM to 1000 µM, preferably from 1 µM to 100 µM, more preferably from 1 µM to 10M.

In certain embodiments, provided herein is a method of treating, managing, or preventing a cancer in a subject comprising administering to the subject a PI3K inhibitor (e.g., one or more PI3K inhibitors, e.g., Idelalisib and/or Compound 1), or a pharmaceutically acceptable form thereof, in combination with a second agent or a pharmaceutically acceptable form thereof, wherein the second agent is selected from one or more of 1) a checkpoint modulator, 2) an XPO1 inhibitor, 3) an anti-CD19 antibody, 4) a TLR agonist, 5) a STING agonist, or 6) a Flt3 ligand, wherein the cancer is diffuse large B-cell lymphoma (activated B-cell-like), diffuse large B-cell lymphoma (germinal center B-cell-like), follicular lymphoma, indolent non-Hodgkin lymphoma, T-cell lymphoma, mantle cell lymphoma, or multiple myeloma. In certain embodiments, the combination is therapeutically effective. In certain embodiments, the combination is synergistic.

In one embodiment of the methods provided herein, the subject shows decreased responsiveness to a PI3K inhibitor (e.g., is resistant or refractive to treatment with a PI3K inhibitor, e.g., Compound 1). In one embodiment, the subject is identified as having a decreased susceptibility (e.g., resistance or acquired resistance) to a monotherapy treatment of a PI3K inhibitor (e.g., Compound 1), or a pharmaceutically acceptable form thereof. In one embodiment, the subject is identified as having an increased susceptibility to a combination therapy treatment provided herein.

Also provided herein are methods of delaying resistance of a subject, or prolonging remission (e.g., complete remission or partial remission) of a subject, to a PI3K inhibitor, e.g., Compound 1 or CAL-101 or to a second agent such as a checkpoint modulator, an XPO1 inhibitor, an anti-CD19 antibody, a TLR agonist, a STING agonist, or a Flt3 ligand described herein. In some embodiments, the method of delaying resistance of the subject, or prolonging remission (e.g., complete remission or partial remission) of the subject, comprises administering a combination of a PI3K inhibitor (e.g., Compound 1 or CAL-101) and a second agent (e.g., a checkpoint modulator, an XPO1 inhibitor, an anti-CD19 antibody, a TLR agonist, a STING agonist, or a Flt3 ligand described herein to the subject before the subject develops resistance to the PI3K inhibitor (e.g., Compound 1 or CAL-101). In some embodiments, the method of delaying resistance of the subject, or prolonging remission (e.g., complete remission or partial remission) of the subject, comprises administering a combination of a PI3K inhibitor (e.g., Compound 1 or CAL-101) and a second agent (e.g., a checkpoint modulator, an XPO1 inhibitor, an anti-CD19 antibody, a TLR agonist, a STING agonist, or a Flt3 ligand described herein) to the subject before the subject develops resistance to the second agent.

In some embodiments, the subject is not resistant to a PI3K inhibitor (e.g., Compound 1 or CAL-101). In some embodiments, the subject is not resistant to a checkpoint modulator, an XPO1 inhibitor, an anti-CD19 antibody, a TLR agonist, a STING agonist, or a Flt3 ligand described herein. In some embodiments, the subject has previously been administered a PI3K inhibitor (e.g., Compound 1 or CAL-101) as a monotherapy or in combination with an agent other than a checkpoint modulator, an XPO1 inhibitor, an anti-CD19 antibody, a TLR agonist, a STING agonist, or a Flt3 ligand described herein. In some embodiments, the subject has previously been administered a checkpoint modulator, an XPO1 inhibitor, an anti-CD19 antibody, a TLR agonist, a STING agonist, or a Flt3 ligand described herein as a monotherapy or in combination with an agent other than a checkpoint modulator, an XPO1 inhibitor, an anti-CD19 antibody, a TLR agonist, a STING agonist, or a Flt3 ligand described herein. In some embodiments, the subject has a cancer, e.g., a cancer described herein. In some embodiments, in accordance with the method, resistance is delayed compared to the time in which resistance generally develops when the subject is treated with any of the agents or inhibitors alone as monotherapy. In some embodiments, the resistance is delayed by at least 2 weeks, e.g., at least 2 weeks, 4 weeks, 1 month, 2 months, 3 months, 4 months, 5 months, 6 months, 8 months, 10 months, 12 months, 1 year, 2 years, 4 years, 6 years, 8 years, or more. In some embodiments, in accordance with the method, remission (e.g., complete remission or partial remission) is prolonged compared to the time in which remission generally lasts when the subject is treated with any of the agents or inhibitors alone as monotherapy. In some embodiments, remission (e.g., complete remission or partial remission) is prolonged by at least 2 weeks, e.g., at least 2 weeks, 4 weeks, 1 month, 2 months, 3 months, 4 months, 5 months, 6 months, 8 months, 10 months, 12 months, 1 year, 2 years, 4 years, 6 years, 8 years, or more.

In some embodiments, once the subject becomes resistant to the PI3K inhibitor (e.g., Compound 1 or CAL-101) or the second agent (e.g., a checkpoint modulator, an XPO1 inhibitor, an anti-CD19 antibody, a TLR agonist, a STING agonist, or a Flt3 ligand described herein), the agent to which the subject is resistant is withdrawn. In other embodiments, once the subject becomes resistant to the PI3K inhibitor (e.g., Compound 1 or CAL-101) or the second agent (e.g., a checkpoint modulator, an XPO1 inhibitor, an anti-CD19 antibody, a TLR agonist, a STING agonist, or a Flt3 ligand described herein), the agent to which the subject is resistant continued. In some embodiments, addition of the PI3K inhibitor or the second agent to the therapeutic regimen increases or restores sensitivity to the agent to which the cancer is resistant. For instance, in some embodiments, addition of the second agent to the therapeutic regimen increases or restores sensitivity to the PI3K inhibitor to which the cancer is resistant.

Provided herein is also a method of reducing, e.g., overcoming, resistance of a subject to a PI3K inhibitor (e.g., Compound 1 or CAL-101), comprising administering the PI3K inhibitor as a monotherapy to the subject until development of resistance in the subject to the PI3K inhibitor, and subsequently administering a second agent (e.g., a checkpoint modulator, an XPO1 inhibitor, an anti-CD19 antibody, a TLR agonist, a STING agonist, or a Flt3 ligand described herein) to the subject. In some cases, the method comprises continuing administration of the PI3K inhibitor (e.g., at the same dosage, lower dosage, or higher dosage) to the subject in combination with the second agent. In other cases, the method comprises discontinuing administration of the PI3K inhibitor upon commencing administration of the second agent. For example the administration of the PI3K inhibitor is stopped before administration of the second agent commences. In other examples, the dosage of the PI3K inhibitor is decreased, e.g., gradually, upon commencing administration of the second agent. In some embodiments, provided herein is a method of reducing, e.g., overcoming, resistance of a subject to a PI3K inhibitor (e.g., Compound 1 or CAL-101), comprising administering the PI3K inhibitor and the second agent (e.g., a checkpoint modulator, an XPO1 inhibitor, an anti-CD19 antibody, a TLR agonist, a STING agonist, or a Flt3 ligand described herein) to the subject before the subject develops resistance to the PI3K inhibitor, in order to prevent resistance arising, reduce the likelihood of resistance developing, or increase the length of time before resistance develops.

In one embodiment, a method described herein further comprises administration of a third agent of a CD20 inhibitor, e.g., an anti-CD20 antibody, in addition to the PI3K inhibitor and the second agent provided herein. In one embodiment, a pharmaceutical composition described herein further comprises a third agent of a CD20 inhibitor, e.g., an anti-CD20 antibody, in addition to the PI3K inhibitor and the second agent provided herein. In some such embodiments, the CD20 inhibitor, e.g., the anti-CD20 antibody, is included in the same dosage form as the PI3K inhibitor and/or second agent. In some such embodiments, the CD20 inhibitor, e.g., the anti-CD20 antibody, is in a separate dosage form as the PI3K inhibitor and/or second agent. The CD20 inhibitor, e.g., the anti-CD20 antibody, can be administered before, after, or concurrent with the PI3K inhibitor and/or second agent. Exemplary CD20 inhibitors include, but are not limited to, anti-CD20 antibody and other inhibitors, such as rituximab, obinutuzumab (GA-101), tositumomab, $^{131}$I tositumomab, $^{90}$Y ibritumomab, $^{111}$I ibritumomab, ofatumumab, veltuzumab, and ocrelizumab), AME-133v, PRO131921 and TRU-015.

The combination of the PI3K inhibitor and the third agent, e.g., a CD20 inhibitor, e.g., an anti-CD20 antibody, can be administered together in a single dosage form or administered separately in two or more different dosage forms as described herein. In certain embodiments, the anti-CD20 antibody is selected from rituximab, ofatumumab and obinutuzumab.

In an embodiment, a composition described herein includes a combination of a PI3K inhibitor (e.g., a PI3K inhibitor described herein, e.g., Compound 1 or CAL-101), a second agent provided herein, and a third agent of an anti-CD20 antibody or fragment thereof, e.g., an anti-CD20 monoclonal antibody (mAb), such as obinutuzumab. In some embodiments, provided herein is a method of treating, managing, or preventing a cancer in a subject comprising administering to the subject a combination of a PI3K inhibitor (e.g., Compound 1 or CAL-101), a second agent provided herein, in combination with an anti-CD20 antibody or fragment thereof, e.g., an anti-CD20 monoclonal antibody (mAb), such as obinutuzumab. In some embodiments, the subject has a cancer, e.g., a cancer described herein, e.g., a hematological cancer, such as a lymphoma. In some embodiments, the effect of combining the Compound 1 or CAL-101, a second agent provided herein, with obinutuzumab includes an additive effect on cell killing, e.g., cancer cell killing. In some embodiments, the PI3K inhibitor (e.g., Compound 1 or CAL-101) is administered concurrently with, prior to, or subsequent to, the obinutuzumab. In some embodiments, combinations of the PI3K inhibitor (e.g., Compound 1 or CAL-101), the second agent, and obinutuzumab allows the PI3K inhibitor, the second agent, and/or the obinutuzumab to be administered at a lower dosage or a lower frequency than would be required to achieve the same therapeutic effect compared to a monotherapy dose. Such a combination provides advantageous effects, e.g., in reducing, preventing, delaying, and/or decreasing the occurrence of one or more of: a side effect, toxicity, or resistance that would otherwise be associated with administration of a higher dose of one or both of the agents.

As a monotherapy, obinutuzumab can be administered according to the following regimen of 28-day cycles: 100 mg on C1D1 (cycle 1, day one), 900 mg on C1D2, 1000 mg on C1D8, 1000 mg on C1D15, and 1000 mg on day 1 of each subsequent cycle, e.g., cycles 2-6. In some embodiments, when administered in combination with a PI3K inhibitor and a second agent provided herein, the dosage of obinutuzumab can be reduced compared to its monotherapy dose, e.g., 300-400, 400-500, 500-600, 600-700, 700-800, 800-900, or 900-1000 mg/cycle (e.g., for a 28-day cycle). In some embodiments, when administered in combination with a PI3K inhibitor, the frequency of administration of obinutuzumab can be reduced compared to its frequency as a monotherapy, e.g., to one administration every 28-30, 30-35, 35-40, 40-45, 45-50, 50-55, or 55-60 days.

Methods for monitoring minimal residual disease negativity (MRD) are known in the art. See, e.g., Zhou, J. et al., *Blood*, 2007, 110: 1607-1611. Such methods include DNA based tests or RNA based tests. In certain embodiments, MRD is monitored using flow cytometry, sequencing, or PCR.

In some embodiments, the compositions and methods described herein are effective to reduce MRD.

In some embodiments, the methods described herein include selecting a subject for treatment with the combination of a PI3K inhibitor and the second agent. In certain embodiments, the subject (e.g., a patient with a cancer, e.g., a cancer described herein) is selected for treatment with the combination based on the MRD in the subject. In certain embodiments, the selection is based on the presence of an MRD above a preselected level (e.g., 1 malignant cell in 100 normal cells, 1 malignant cell in 1000 normal cells, or 1 malignant cell in 10,000 normal cells).

In some embodiments, the methods described herein further comprise monitoring the MRD in a subject, e.g., evaluating MRD at at least one, two, three, four, five, six, nine months after initiating, continuing or ceasing treatment (e.g., PI3K inhibitor monotherapy or a second agent monotherapy, or a combination therapy disclosed herein).

In some embodiments, the combination of a PI3K inhibitor (e.g. a PI3K inhibitor described herein) and a second agent (e.g., a second agent described herein) is effective to reduce the MRD in the subject, e.g., below a level previously measured in the subject (e.g., the level measured before the combination treatment). In certain embodiments, the combination of a PI3K inhibitor and a second agent is effective to reduce the MRD in the subject below the level observed during or after treatment with a monotherapy, e.g., a monotherapy comprising either the PI3K inhibitor or the second agent inhibitor. In certain embodiments, the MRD is decreased below the level observed during treatment with a monotherapy comprising the PI3K inhibitor. In certain embodiments, the MRD is decreased below the level observed during treatment with a monotherapy comprising the PI3K inhibitor.

In certain embodiments, the combination is effective to reduce the MRD below a preselected cutoff value (e.g., 1 malignant cell in 100 normal cells, 1 malignant cell in 1000 normal cells, or 1 malignant cell in 10,000 normal cells). In certain embodiments, the preselected cutoff value is 1 malignant cell in 1000 normal cells. In those embodiments where the MRD is below a preselected cutoff value (e.g., preselected cutoff value as described herein), the treatment (e.g., PI3K inhibitor monotherapy or a second agent monotherapy, or a combination therapy disclosed herein) can be altered or discontinued. If upon monitoring the MRD (at at least one, two, three, four, five, six, nine months after altering or discontinuing the therapy), the MRD levels are increased above a preselected cutoff (e.g., a preselected cutoff as described herein), a second treatment can be initiated (e.g., PI3K inhibitor monotherapy or the second agent monotherapy, a combination therapy disclosed herein, or a combination with a third agent, e.g., an anti-CD20 inhibitor or a BTK inhibitor such as ibrutinib).

In some embodiments provided herein is a method of treating cancer in a subject, the method comprising (i) administering to the subject a monotherapy (e.g., a monotherapy comprising a PI3K inhibitor or a second therapeutic agent as described herein) and monitoring the MRD in the subject, and (ii) if the MRD increases above a preselected cutoff value (e.g., 1 malignant cell in 100 normal cells, 1 malignant cell in 1000 normal cells, or 1 malignant cell in 10,000 normal cells), administering to the subject a PI3K inhibitor in combination with a second agent. In certain embodiments, the combination is effective to reduce the MRD, e.g. to reduce the MRD below the cutoff value. In certain embodiments, the preselected cutoff value is 1 malignant cell in 1000 or 10,000 normal cells.

In certain embodiments, provided herein is a method of decreasing minimal residual disease (MRD) in a subject diagnosed with a cancer, the method comprising: (a) administering to the subject a PI3K inhibitor (e.g., Compound 1), or a pharmaceutically acceptable form thereof, in combination with a second agent (e.g., at least one second agent); (b) monitoring the MRD in the subject by one or more methods described herein or known in the art (e.g., flow cytometry, sequencing, or PCR), and administering a monotherapy comprising the PI3K inhibitor, or a pharmaceutically acceptable form thereof, to the subject if the MRD in the subject increases above a preselected cutoff value (e.g., 1 malignant cell in 100 normal cells, 1 malignant cell in 1000 normal cells, or 1 malignant cell in 10,000 normal cells); and (c) monitoring the amount of MRD negativity (by one or more methods described herein or known in the art (e.g., flow cytometry, sequencing, or PCR) in the subject receiving the monotherapy, and administering a further combination comprising the PI3K inhibitor, or a pharmaceutically acceptable form thereof, and a third agent (e.g., at least one third agent) to the subject if the MRD is greater than the preselected cutoff value. In one embodiment, the third agent is selected from one or more of an anti-CD20 antibody, a MEK inhibitor, dexamethasone, lenolidomide, an mTOR inhibitor, nitrogen mustard, and a nucleoside metabolic inhibitor.

In some embodiments, the third agent is a chemotherapeutic. In some embodiments, the chemotherapeutic is selected from mitotic inhibitors, alkylating agents, antimetabolites, intercalating antibiotics, growth factor inhibitors, cell cycle inhibitors, enzymes, topoisomerase inhibitors, biological response modifiers, anti-hormones, angiogenesis inhibitors, and anti-androgens. Non-limiting examples are chemotherapeutic agents, cytotoxic agents, and non-peptide small molecules such as Gleevec® (imatinib mesylate), Velcade® (bortezomib), Casodex™ (bicalutamide), Iressa® (gefitinib), Tarceva® (erlotinib), and Adriamycin® (doxorubicin) as well as a host of chemotherapeutic agents. Non-limiting examples of chemotherapeutic agents include alkylating agents such as thiotepa and cyclosphosphamide (CYTOXAN™); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; BTK inhibitors such as ibrutinib (PCI-32765), AVL-292, Dasatinib, LFM-AI3, ONO-WG-307, and GDC-0834; HDAC inhibitors such as vorinostat, romidepsin, panobinostat, valproic acid, belinostat, mocetinostat, abrexinostat, entinostat, SB939, resminostat, givinostat, CUDC-101, AR-42, CHR-2845, CHR-3996, 4SC-202, CG200745, ACY-1215 and kevetrin; EZH2 inhibitors such as, but not limited to, EPZ-6438 (N—((4,6-dimethyl-2-oxo-1,2-dihydropyridin-3-yl)methyl)-5-(ethyl(tetrahydro-2H-pyran-4-yl)amino)-4-methyl-4'-(morpholinomethyl)-[1,1'-biphenyl]-3-carboxamide), GSK-126 ((S)-1-(sec-butyl)—N—((4,6-dimethyl-2-oxo-,2-dihydropyridin-3-yl)methyl)-3-methyl-6-(6-(piperazin-1-yl)pyridin-3-yl)-1H-indole-4-carboxamide), GSK-343 (1-Isopropyl—N—((6-methyl-2-oxo-4-propyl-1,2-dihydropyridin-3-yl)methyl)-6-(2-(4-methylpiperazin-1-yl)pyridine-4-yl)-1H-indazole-4-carboxamide), Ell, 3-deazaneplanocin A (DNNep, 5R-(4-amino-1H-imidazo[4,5-c]pyridin-1-yl)-3-(hydroxymethyl)-3-cyclopentene-1S,2R-diol), small interfering RNA (siRNA) duplexes targeted against EZH2 (S. M. Elbashir et al., Nature 411:494-498 (2001)), isoliquiritigenin, and those provided in, for example, U.S. Publication Nos. 2009/0012031, 2009/0203010, 2010/0222420, 2011/0251216, 2011/0286990, 2012/0014962, 2012/0071418, 2013/0040906, and 2013/0195843, all of which are incorporated herein by reference; JAK/STAT inhibitors such as lestaurtinib, tofacitinib, ruxolitinib, pacritinib, CYT387, baricitinib, GLPG0636, TG101348, INCB16562, CP-690550, and AZD1480; PKC-β inhibitor such as Enzastaurin; SYK inhibitors such as, but not limited to, GS-9973, R788 (fostamatinib), PRT 062607, R406, (S)-2-(2-((3,5-dimethylphenyl)amino)pyrimidin-4-yl)—N—(1-hydroxypropan-2-yl)-4-methylthiazole-5-carboxamide, R112, GSK143, BAY61-3606, PP2, PRT 060318, R348, and those provided in, for example, U.S. Publication Nos. 2003/0113828, 2003/0158195, 2003/0229090, 2005/0075306, 2005/0232969, 2005/0267059, 2006/0205731, 2006/0247262, 2007/0219152, 2007/0219195, 2008/0114024, 2009/0171089, 2009/0306214, 2010/0048567, 2010/0152159, 2010/0152182, 2010/0316649, 2011/0053897, 2011/0112098, 2011/0245205, 2011/0275655, 2012/0027834, 2012/0093913, 2012/0101275, 2012/0130073, 2012/0142671, 2012/0184526, 2012/0220582, 2012/0277192, 2012/0309735, 2013/0040984, 2013/0090309, 2013/0116260, and 2013/0165431, all of which are incorporated herein by reference; SYK/JAK dual inhibitor such as PRT2070; nitrogen mustards such as bendamustine, chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomycins, actinomycin, authramycin, azaserine, bleomycins, cactinomycin, calicheamicin, carabicin, carminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pralatrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, androgens such as calusterone, dromostanolone propionate, epitiostanol, mepitiostane, testolactone; anti-adrenals such as aminoglutethimide, mitotane, trilostane; folic acid replenisher such as folinic acid; aceglatone; aldophosphamide glycoside; aminolevulinic acid; amsacrine; bestrabucil; bisantrene; edatrexate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK.R™ razoxane; sizofiran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside (Ara-C); cyclophosphamide; thiotepa; taxanes, e.g., paclitaxel (e.g., TAXOL™) and docetaxel (e.g., TAXOTERE™) and ABRAXANE® (paclitaxel protein-bound particles); retinoic acid; esperamicins; capecitabine; and pharmaceutically acceptable forms (e.g., pharmaceutically acceptable salts, hydrates, solvates, isomers, prodrugs, and isotopically labeled derivatives) of any of the above. Also included as suitable chemotherapeutic cell conditioners are anti-hormonal agents that act to regulate or inhibit hormone action on tumors such as anti-estrogens including for example tamoxifen (Nolvadex™), raloxifene, aromatase inhibiting 4(5)-imidazoles, 4-hydroxytamoxifen, trioxifene, keoxifene, LY 117018, onapristone, and toremifene (Fareston); and anti-androgens such as flutamide, nilutamide, bicalutamide, leuprolide, and goserelin; chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; camptothecin-11 (CPT-11); topoisomerase inhibitor RFS 2000; difluoromethylornithine (DMFO). Where desired, the compounds or pharmaceutical composition as provided herein can be used in combination with commonly prescribed anti-cancer drugs such as Herceptin®, Avastin®, Erbitux®, Rituxan®, Taxol®, Arimidex®, Taxotere®, ABVD, AVICINE, abagovomab, acridine carboxamide, adecatumumab, 17—N—allylamino-17-demethoxygeldanamycin, alpharadin, alvocidib, 3-aminopyridine-2-carboxaldehyde thiosemicarbazone, amonafide, anthracenedione, anti-CD22 immunotoxins, antineoplastic, antitumorigenic herbs, apaziquone, atiprimod, azathioprine, belotecan, bendamustine, BIBW 2992, biricodar, brostallicin, bryostatin, buthionine sulfoximine, CBV (chemotherapy), calyculin, crizotinib, cell-cycle nonspecific antineoplastic agents, dichloroacetic acid, discodermolide, elsamitrucin, enocitabine, epothilone, eribulin, everolimus, exatecan, exisulind, ferruginol, forodesine, fosfestrol, ICE chemotherapy regimen, IT-101, imexon, imiquimod, indolocarbazole, irofulven, laniquidar, larotaxel, lenalidomide, lucanthone, lurtotecan, mafosfamide, mitozolomide, nafoxidine, nedaplatin, olaparib, ortataxel, PAC-1, pawpaw, pixantrone, proteasome inhibitor, rebeccamycin, resiquimod, rubitecan, SN—38, salinosporamide A, sapacitabine, Stanford V, swainsonine, talaporfin, tariquidar, tegafur-uracil, temodar, tesetaxel, triplatin tetranitrate, tris(2-chloroethyl)amine, troxacitabine, uramustine, vadimezan, vinflunine, ZD6126, and zosuquidar.

In some embodiments, the chemotherapeutic is selected from hedgehog inhibitors including, but not limited to IPI-926 (See U.S. Pat. No. 7,812,164). Other suitable hedgehog inhibitors include, for example, those described and disclosed in U.S. Pat. No. 7,230,004, U.S. Patent Application Publication No. 2008/0293754, U.S. Patent Application Publication No. 2008/0287420, and U.S. Patent Application Publication No. 2008/0293755, the entire disclosures of which are incorporated by reference herein. Examples of other suitable hedgehog inhibitors include those described in U.S. Patent Application Publication Nos. US 2002/0006931, US 2007/0021493 and US 2007/0060546, and International Application Publication Nos. WO 2001/19800, WO 2001/26644, WO 2001/27135, WO 2001/49279, WO 2001/74344, WO 2003/011219, WO 2003/088970, WO 2004/020599, WO 2005/013800, WO 2005/033288, WO 2005/032343, WO 2005/042700, WO 2006/028958, WO 2006/050351, WO 2006/078283, WO 2007/054623, WO 2007/059157, WO 2007/120827, WO 2007/131201, WO 2008/070357, WO 2008/110611, WO 2008/112913, and WO 2008/131354, each incorporated herein by reference. Additional examples of hedgehog inhibitors include, but are not limited to, GDC-0449 (also known as RG3616 or vismodegib) described in, e.g., Von Hoff D. et al., *N. Engl. J. Med.* 2009; 361(12):1164-72; Robarge K. D. et al., *Bioorg Med Chem Lett.* 2009; 19(19):5576-81; Yauch, R. L. et al. (2009) *Science* 326: 572-574; Sciencexpress: 1-3 (10.1126/science.1179386); Rudin, C. et al. (2009) *New England J of Medicine* 361-366 (10.1056/nejma0902903); BMS-833923 (also known as XL139) described in, e.g., in Siu L. et al., *J. Clin. Oncol.* 2010; 28:15s (suppl; abstr 2501); and National Institute of Health Clinical Trial Identifier No. NCT006701891; LDE-225 described, e.g., in Pan S. et al., *ACS Med. Chem. Lett.,* 2010; 1(3): 130-134; LEQ-506 described, e.g., in National Institute of Health Clinical Trial Identifier No. NCT01106508; PF-04449913 described, e.g., in National Institute of Health Clinical Trial Identifier No. NCT00953758; Hedgehog pathway antagonists disclosed in U.S. Patent Application Publication No. 2010/0286114; SMOi2-17 described, e.g., U.S. Patent Application Publication No. 2010/0093625; SANT-1 and SANT-2 described, e.g., in Rominger C. M. et al., *J Pharmacol. Exp. Ther.* 2009; 329(3):995-1005; 1-piperazinyl-4-arylphthalazines or analogues thereof, described in Lucas B. S. et al., *Bioorg. Med. Chem. Lett.* 2010; 20(12):3618-22.

Other hormonal therapy and chemotherapeutic agents include, but are not limited to, anti-estrogens (e.g. tamoxifen, raloxifene, and megestrol acetate), LHRH agonists (e.g. goserelin and leuprolide), anti-androgens (e.g. flutamide and bicalutamide), photodynamic therapies (e.g. vertoporfin (BPD-MA), phthalocyanine, photosensitizer Pc4, and demethoxy-hypocrellin A (2BA-2-DMHA)), nitrogen mustards (e.g. cyclophosphamide, ifosfamide, trofosfamide, chlorambucil, estramustine, and melphalan), nitrosoureas (e.g. carmustine (BCNU) and lomustine (CCNU)), alkylsulphonates (e.g. busulfan and treosulfan), triazenes (e.g. dacarbazine, temozolomide), platinum containing compounds (e.g. cisplatin, carboplatin, oxaliplatin), vinca alkaloids (e.g. vincristine, vinblastine, vindesine, and vinorelbine), taxoids or taxanes (e.g. paclitaxel or a paclitaxel equivalent such as nanoparticle albumin-bound paclitaxel (Abraxane), docosahexaenoic acid bound-paclitaxel (DHA-paclitaxel, Taxoprexin), polyglutamate bound-paclitaxel (PG-paclitaxel, paclitaxel poliglumex, CT-2103, XYOTAX), the tumor-activated prodrug (TAP) ANG1005 (Angiopep-2 bound to three molecules of paclitaxel), paclitaxel-EC-1 (paclitaxel bound to the erbB2-recognizing peptide EC-1), and glucose-conjugated paclitaxel, e.g., 2'-paclitaxel methyl 2-glucopyranosyl succinate; docetaxel, taxol), epipodophyllins (e.g. etoposide, etoposide phosphate, teniposide, topotecan, 9-aminocamptothecin, camptoirinotecan, irinotecan, crisnatol, mytomycin C), anti-metabolites, DHFR inhibitors (e.g. methotrexate, dichloromethotrexate, trimetrexate, edatrexate), IMP dehydrogenase inhibitors (e.g. mycophenolic acid, tiazofurin, ribavirin, and EICAR), ribonucleotide reductase inhibitors (e.g. hydroxyurea and deferoxamine), uracil analogs (e.g. 5-fluorouracil (5-FU), floxuridine, doxifluridine, raltitrexed, tegafur-uracil, capecitabine), cytosine analogs (e.g. cytarabine (ara C, cytosine arabinoside), and fludarabine), purine analogs (e.g. mercaptopurine and thioguanine), Vitamin D3 analogs (e.g. EB 1089, CB 1093, and KH 1060), isoprenylation inhibitors (e.g. lovastatin), dopaminergic neurotoxins (e.g. 1-methyl-4-phenylpyridinium ion), cell cycle inhibitors (e.g. staurosporine), actinomycin (e.g. actinomycin D, dactinomycin), bleomycin (e.g. bleomycin A2, bleomycin B2, peplomycin), anthracyclines (e.g. daunorubicin, doxorubicin, pegylated liposomal doxorubicin, idarubicin, epirubicin, pirarubicin, zorubicin, mitoxantrone), MDR inhibitors (e.g. verapamil), Ca2+ ATPase inhibitors (e.g. thapsigargin), thalidomide, lenalidomide (REVLIMID®), tyrosine kinase inhibitors (e.g., axitinib (AG013736), bosutinib (SKI-606), cediranib (RECENTIN™, AZD2171), dasatinib (SPRYCEL®, BMS-354825), erlotinib (TARCEVA®), gefitinib (IRESSA®), imatinib (Gleevec®, CGP57148B, STI-571), lapatinib (TYKERB®, TYVERB®), lestaurtinib (CEP-701), neratinib (HKI-272), nilotinib (TASIGNA®), semaxanib (semaxinib, SU5416), sunitinib (SUTENT®, SU11248), toceranib (PALLADIA®), vandetanib (ZACTIMA®, ZD6474), vatalanib (PTK787, PTK/ZK), trastuzumab (HERCEPTIN®), bevacizumab (AVASTIN®), rituximab (RITUXAN®), cetuximab (ERBITUX®), panitumumab (VECTIBIX®), ranibizumab (Lucentis®), sorafenib (NEXAVAR®), everolimus (AFINITOR®), alemtuzumab (CAMPATH®), gemtuzumab ozogamicin (MYLOTARG®), temsirolimus (TORISEL®), ENMD-2076, PCI-32765, AC220, dovitinib lactate (TKI258, CHIR-258), BIBW 2992 (TOVOK™), SGX523, PF-04217903, PF-02341066, PF-299804, BMS-777607, ABT-869, MP470, BIBF 1120 (VARGATEF®), AP24534, JNJ-26483327, MGCD265, DCC-2036, BMS-690154, CEP-11981, tivozanib (AV-951), OSI-930, MM-121, XL-184, XL-647, and/or XL228), proteasome inhibitors (e.g., bortezomib (Velcade)), mTOR inhibitors (e.g., rapamycin, temsirolimus (CCI-779), everolimus (RAD-001), ridaforolimus, AP23573 (Ariad), AZD8055 (AstraZeneca), BEZ235 (Novartis), BGT226 (Norvartis), XL765 (Sanofi Aventis), PF-4691502 (Pfizer), GDC0980 (Genetech), SF1126 (Semafoe) and OSI-027 (OSI)), oblimersen, gemcitabine, carminomycin, leucovorin, pemetrexed, cyclophosphamide, dacarbazine, procarbazine, prednisolone, dexamethasone, camptothecin, plicamycin, asparaginase, aminopterin, methopterin, porfiromycin, melphalan, leurosidine, leurosine, chlorambucil, trabectedin, procarbazine, discodermolide, carminomycin, aminopterin, and hexamethyl melamine.

In some embodiments, a combination of a PI3K inhibitor provided herein (e.g., Compound 1 or CAL-101) and a second agent provided herein, is administered further in combination with an inhibitor of one or more members of TAM family, a receptor tyrosine kinase (RTK) subfamily comprising Tyro-3 (also called Sky), Axl and Mer. In one embodiment, the TAM inhibitor is BGB324 (R428), S49076, TP0903, CEP-40783, ONO-9330547, bosutinib (SKI606, PF5208763), cabozantinib (XL184), sunitinib (SU11248), foretinib (XL880, GSK1363089), MGCD265, BMS777607 (ASLAN002), LY2801653, SGI7079, amuvatinib (SGI-0470-02, MP470), SNS314, PF-02341066, diaminopyrimidine, spiroindoline, UNC569, UNC1062, UNC1666, UNC2025, or LDC1267. Additional TAM inhibitors include those described in Mollard et al., Med. Chem. Lett. 2011, 2, 907-912 and Feneyrolles et al., Mol. Cancer Ther. 13(9), Published Online First Aug. 19, 2014, the entireties of which are incorporated by reference herein.

4. Formulations

The formulations or compositions described herein can include a PI3K inhibitor (e.g., one or more PI3K inhibitors as described herein) and/or one or more additional agents (e.g., a second agent, e.g., one or more second agents) as described herein. In certain embodiments, the PI3K inhibitor (e.g., one or more PI3K inhibitors as described herein) and the second agent are included in the same dosage form. In certain embodiments, the PI3K inhibitor (e.g., one or more PI3K inhibitors as described herein) and the second agent are included in separate dosage forms.

Pharmaceutical compositions may be specially formulated for administration in solid or liquid form, including those adapted for the following: oral administration, for example, drenches (aqueous or non-aqueous solutions or suspensions), tablets (e.g., those targeted for buccal, sublingual, and systemic absorption), capsules, boluses, powders, granules, pastes for application to the tongue, and intraduodenal routes; parenteral administration, including intravenous, intraarterial, subcutaneous, intramuscular, intravascular, intraperitoneal or infusion as, for example, a sterile solution or suspension, or sustained-release formulation; topical application, for example, as a cream, ointment, or a controlled-release patch or spray applied to the skin; intravaginally or intrarectally, for example, as a pessary, cream, stent or foam; sublingually; ocularly; pulmonarily; local delivery by catheter or stent; intrathecally, or nasally.

The amount of PI3K inhibitor administered and the timing of PI3K inhibitor administration will depend on the type (species, gender, age, weight, etc.) and condition of the patient being treated, the severity of the disease or condition being treated, and on the route of administration. For example, small molecule PI3K inhibitors or second agent can be administered to a patient in doses ranging from 0.001 to 100 mg/kg of body weight per day or per week in single or divided doses, or by continuous infusion. In particular, compounds such as Compound 1, or similar compounds, can be administered to a patient in doses ranging from 5-200 mg per day, or 100-1600 mg per week, in single or divided doses, or by continuous infusion. In one embodiment, the dose is 150 mg/day. Antibody-based PI3K inhibitors or second agent, or antisense, RNAi or ribozyme constructs, can be administered to a patient in doses ranging from 0.1 to 100 mg/kg of body weight per day or per week in single or divided doses, or by continuous infusion. In some instances, dosage levels below the lower limit of the aforesaid range may be more than adequate, while in other cases still larger doses may be employed without causing any harmful side effect, provided that such larger doses are first divided into several small doses for administration throughout the day.

Examples of suitable aqueous and nonaqueous carriers which may be employed in pharmaceutical compositions include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity may be maintained, for example, by the use of coating materials, such as lecithin, by the maintenance of the required particle size in the case of dispersions, and by the use of surfactants.

These compositions can also contain adjuvants such as preservatives, wetting agents, emulsifying agents, dispersing agents, lubricants, and/or antioxidants. Prevention of the action of microorganisms upon the compounds described herein may be ensured by the inclusion of various antibacterial and antifungal agents, for example, paraben, chlorobutanol, phenol sorbic acid, and the like. It can also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

Methods of preparing these formulations or compositions include the step of bringing into association a compound described herein and/or the chemotherapeutic with the carrier and, optionally, one or more accessory ingredients. In general, the formulations are prepared by uniformly and intimately bringing into association a compound as disclosed herein with liquid carriers, or finely divided solid carriers, or both, and then, if necessary, shaping the product.

Preparations for such pharmaceutical compositions are well-known in the art. See, e.g., Anderson, Philip O.; Knoben, James E.; Troutman, William G, eds., *Handbook of Clinical Drug Data*, Tenth Edition, McGraw-Hill, 2002; Pratt and Taylor, eds., *Principles of Drug Action*, Third Edition, Churchill Livingston, N.Y., 1990; Katzung, ed., *Basic and Clinical Pharmacology*, Twelfth Edition, McGraw Hill, 2011; Goodman and Gilman, eds., *The Pharmacological Basis of Therapeutics*, Tenth Edition, McGraw Hill, 2001; *Remingtons Pharmaceutical Sciences*, 20th Ed., Lippincott Williams & Wilkins., 2000; Martindale, *The Extra Pharmacopoeia*, Thirty-Second Edition (The Pharmaceutical Press, London, 1999); all of which are incorporated by reference herein in their entirety. Except insofar as any conventional excipient medium is incompatible with the compounds provided herein, such as by producing any undesirable biological effect or otherwise interacting in a deleterious manner with any other component(s) of the pharmaceutically acceptable composition, the excipient's use is contemplated to be within the scope of this disclosure.

In some embodiments, the concentration of the PI3K inhibitor (e.g., Compound 1) or another agent (e.g., the second agent, e.g., one or more second agents as described herein) provided a pharmaceutical composition disclosed herein or administered in a method disclosed herein is less than about 100%, about 90%, about 80%, about 70%, about 60%, about 50%, about 40%, about 30%, about 20%, about 19%, about 18%, about 17%, about 16%, about 15%, about 14%, about 13%, about 12%, about 11%, about 10%, about 9%, about 8%, about 7%, about 6%, about 5%, about 4%, about 3%, about 2%, about 1%, about 0.5%, about 0.4%, about 0.3%, about 0.2%, about 0.1%, about 0.09%, about 0.08%, about 0.07%, about 0.06%, about 0.05%, about 0.04%, about 0.03%, about 0.02%, about 0.01%, about 0.009%, about 0.008%, about 0.007%, about 0.006%, about 0.005%, about 0.004%, about 0.003%, about 0.002%, about 0.001%, about 0.0009%, about 0.0008%, about 0.0007%, about 0.0006%, about 0.0005%, about 0.0004%, about 0.0003%, about 0.0002%, or about 0.0001%, w/w, w/v or v/v.

In some embodiments, the concentration of the PI3K inhibitor (e.g., Compound 1) or another agent, (e.g., the second agent, e.g., one or more second agents as described herein) provided a pharmaceutical composition disclosed herein or administered in a method disclosed herein is greater than about 90%, about 80%, about 70%, about 60%, about 50%, about 40%, about 30%, about 20%, about 19.75%, about 19.50%, about 19.25%, about 19%, about 18.75%, about 18.50%, about 18.25%, about 18%, about 17.75%, about 17.50%, about 17.25%, about 17%, about 16.75%, about 16.50%, about 16.25%, about 16%, about 15.75%, about 15.50%, about 15.25%, about 15%, about 14.75%, about 14.50%, about 14.25%, about 14%, about 13.75%, about 13.50%, about 13.25%, about 13%, about 12.75%, about 12.50%, about 12.25%, about 12%, about 11.75%, about 11.50%, about 11.25%, about 11%, about 10.75%, about 10.50%, about 10.25%, about 10%, about 9.75%, about 9.50%, about 9.25%, about 9%, about 8.75%, about 8.50%, about 8.25%, about 8%, about 7.75%, about 7.50%, about 7.25%, about 7%, about 6.75%, about 6.50%, about 6.25%, about 6%, about 5.75%, about 5.50%, about 5.25%, about 5%, about 4.75%, about 4.50%, about 4.25%, about 4%, about 3.75%, about 3.50%, about 3.25%, about 3%, about 2.75%, about 2.50%, about 2.25%, about 2%, about 1.75%, about 1.50%, about 1.25%, about 1%, about 0.5%, about 0.4%, about 0.3%, about 0.2%, about 0.1%, about 0.09%, about 0.08%, about 0.07%, about 0.06%, about 0.05%, about 0.04%, about 0.03%, about 0.02%, about 0.01%, about 0.009%, about 0.008%, about 0.007%, about 0.006%, about 0.005%, about 0.004%, about 0.003%, about 0.002%, about 0.001%, about 0.0009%, about 0.0008%, about 0.0007%, about 0.0006%, about 0.0005%, about 0.0004%, about 0.0003%, about 0.0002%, or about 0.0001%, w/w, w/v, or v/v.

In some embodiments, the concentration of the PI3K inhibitor (e.g., Compound 1) or another agent, (e.g., the second agent, e.g., one or more second agents as described herein) provided a pharmaceutical composition disclosed herein or administered in a method disclosed herein is in the range from approximately 0.0001% to approximately 50%, approximately 0.001% to approximately 40%, approximately 0.01% to approximately 30%, approximately 0.02% to approximately 29%, approximately 0.03% to approximately 28%, approximately 0.04% to approximately 27%, approximately 0.05% to approximately 26%, approximately 0.06% to approximately 25%, approximately 0.07% to approximately 24%, approximately 0.08% to approximately 23%, approximately 0.09% to approximately 22%, approximately 0.1% to approximately 21%, approximately 0.2% to approximately 20%, approximately 0.3% to approximately 19%, approximately 0.4% to approximately 18%, approximately 0.5% to approximately 17%, approximately 0.6% to approximately 16%, approximately 0.7% to approximately 15%, approximately 0.8% to approximately 14%, approximately 0.9% to approximately 12%, or approximately 1% to approximately 10%, w/w, w/v or v/v.

In some embodiments, the concentration of the PI3K inhibitor (e.g., Compound 1) or another agent (e.g., the second agent, e.g., one or more second agents as described herein) provided a pharmaceutical composition disclosed herein or administered in a method disclosed herein is in the range from approximately 0.001% to approximately 10%, approximately 0.01% to approximately 5%, approximately 0.02% to approximately 4.5%, approximately 0.03% to approximately 4%, approximately 0.04% to approximately 3.5%, approximately 0.05% to approximately 3%, approximately 0.06% to approximately 2.5%, approximately 0.07% to approximately 2%, approximately 0.08% to approximately 1.5%, approximately 0.09% to approximately 1%, or approximately 0.1% to approximately 0.9%, w/w, w/v or v/v.

In some embodiments, the concentration of the PI3K inhibitor (e.g., Compound 1) or another agent (e.g., the second agent, e.g., one or more second agents as described herein) provided a pharmaceutical composition disclosed herein or administered in a method disclosed herein is equal to or less than about 10 g, about 9.5 g, about 9.0 g, about 8.5 g, about 8.0 g, about 7.5 g, about 7.0 g, about 6.5 g, about 6.0 g, about 5.5 g, about 5.0 g, about 4.5 g, about 4.0 g, about 3.5 g, about 3.0 g, about 2.5 g, about 2.0 g, about 1.5 g, about 1.0 g, about 0.95 g, about 0.9 g, about 0.85 g, about 0.8 g, about 0.75 g, about 0.7 g, about 0.65 g, about 0.6 g, about 0.55 g, about 0.5 g, about 0.45 g, about 0.4 g, about 0.35 g, about 0.3 g, about 0.25 g, about 0.2 g, about 0.15 g, about 0.1 g, about 0.09 g, about 0.08 g, about 0.07 g, about 0.06 g, about 0.05 g, about 0.04 g, about 0.03 g, about 0.02 g, about 0.01 g, about 0.009 g, about 0.008 g, about 0.007 g, about 0.006 g, about 0.005 g, about 0.004 g, about 0.003 g, about 0.002 g, about 0.001 g, about 0.0009 g, about 0.0008 g, about 0.0007 g, about 0.0006 g, about 0.0005 g, about 0.0004 g, about 0.0003 g, about 0.0002 g, or about 0.0001 g.

In some embodiments, the concentration of the PI3K inhibitor (e.g., Compound 1) or another agent, (e.g., the second agent, e.g., one or more second agents as described herein) provided a pharmaceutical composition disclosed herein or administered in a method disclosed herein is more than about 0.0001 g, about 0.0002 g, about 0.0003 g, about 0.0004 g, about 0.0005 g, about 0.0006 g, about 0.0007 g, about 0.0008 g, about 0.0009 g, about 0.001 g, about 0.0015 g, about 0.002 g, about 0.0025 g, about 0.003 g, about 0.0035 g, about 0.004 g, about 0.0045 g, about 0.005 g, about 0.0055 g, about 0.006 g, about 0.0065 g, about 0.007 g, about 0.0075 g, about 0.008 g, about 0.0085 g, about 0.009 g, about 0.0095 g, about 0.01 g, about 0.015 g, about 0.02 g, about 0.025 g, about 0.03 g, about 0.035 g, about 0.04 g, about 0.045 g, about 0.05 g, about 0.055 g, about 0.06 g, about 0.065 g, about 0.07 g, about 0.075 g, about 0.08 g, about 0.085 g, about 0.09 g, about 0.095 g, about 0.1 g, about 0.15 g, about 0.2 g, about 0.25 g, about 0.3 g, about 0.35 g, about 0.4 g, about 0.45 g, about 0.5 g, about 0.55 g, about 0.6 g, about 0.65 g, about 0.7 g, about 0.75 g, about 0.8 g, about 0.85 g, about 0.9 g, about 0.95 g, about 1 g, about 1.5 g, about 2 g, about 2.5 g, about 3 g, about 3.5 g, about 4 g, about 4.5 g, about 5 g, about 5.5 g, about 6 g, about 6.5 g, about 7 g, about 7.5 g, about 8 g, about 8.5 g, about 9 g, about 9.5 g, or about 10 g.

In some embodiments, the amount of Compound 1 or one or more of the therapeutic agent disclosed herein is in the range of about 0.0001 to about 10 g, about 0.0005 to about 9 g, about 0.001 to about 8 g, about 0.005 to about 7 g, about 0.01 to about 6 g, about 0.05 to about 5 g, about 0.1 to about 4 g, about 0.5 to about 4 g, or about 1 to about 3 g.

4.1 Formulations for Oral Administration

In some embodiments of the methods described herein, PI3K inhibitor (e.g., one or more PI3K inhibitors) and/or another agent (e.g., the second agent, e.g., one or more second agents as described herein) is administered orally. In certain embodiments of the compositions described herein, PI3K inhibitor (e.g., Compound 1) and/or another agent (e.g., the second agent, e.g., one or more second agents as described herein) is formulated for oral administration. Some embodiments pertaining to such methods and compositions include the following.

In some embodiments, provided herein are pharmaceutical compositions for oral administration containing a compound as disclosed herein, and a pharmaceutical excipient suitable for oral administration. In some embodiments, provided herein are pharmaceutical compositions for oral administration containing: (i) an effective amount of a disclosed compound; optionally (ii) an effective amount of one or more second agents; and (iii) one or more pharmaceutical excipients suitable for oral administration. In some embodiments, the pharmaceutical composition further contains: (iv) an effective amount of a third agent.

In some embodiments, the pharmaceutical composition can be a liquid pharmaceutical composition suitable for oral consumption. Pharmaceutical compositions suitable for oral administration can be presented as discrete dosage forms, such as capsules, cachets, or tablets, or liquids or aerosol sprays each containing a predetermined amount of an active ingredient as a powder or in granules, a solution, or a suspension in an aqueous or non-aqueous liquid, an oil-in-water emulsion, or a water-in-oil liquid emulsion. Such dosage forms can be prepared by any of the methods of pharmacy, but all methods include the step of bringing the active ingredient into association with the carrier, which constitutes one or more ingredients. In general, the pharmaceutical compositions are prepared by uniformly and intimately admixing the active ingredient with liquid carriers or finely divided solid carriers or both, and then, if necessary, shaping the product into the desired presentation. For example, a tablet can be prepared by compression or molding, optionally with one or more accessory ingredients. Compressed tablets can be prepared by compressing in a suitable machine the active ingredient in a free-flowing form such as powder or granules, optionally mixed with an excipient such as, but not limited to, a binder, a lubricant, an inert diluent, and/or a surface active or dispersing agent. Molded tablets can be made by molding in a suitable machine a mixture of the powdered compound moistened with an inert liquid diluent.

The present disclosure further encompasses anhydrous pharmaceutical compositions and dosage forms comprising an active ingredient, since water can facilitate the degradation of some compounds. For example, water can be added (e.g., about 5%) in the pharmaceutical arts as a means of simulating long-term storage in order to determine characteristics such as shelf-life or the stability of formulations over time. Anhydrous pharmaceutical compositions and dosage forms can be prepared using anhydrous or low moisture containing ingredients and low moisture or low humidity conditions. For example, pharmaceutical compositions and dosage forms which contain lactose can be made anhydrous if substantial contact with moisture and/or humidity during manufacturing, packaging, and/or storage is expected. An anhydrous pharmaceutical composition can be prepared and stored such that its anhydrous nature is maintained. Accordingly, anhydrous pharmaceutical compositions can be packaged using materials known to prevent exposure to water such that they can be included in suitable formulary kits. Examples of suitable packaging include, but are not limited to, hermetically sealed foils, plastic or the like, unit dose containers, blister packs, and strip packs.

An active ingredient can be combined in an intimate admixture with a pharmaceutical carrier according to conventional pharmaceutical compounding techniques. The carrier can take a wide variety of forms depending on the form of preparation desired for administration. In preparing the pharmaceutical compositions for an oral dosage form, any of the usual pharmaceutical media can be employed as carriers, such as, for example, water, glycols, oils, alcohols, flavoring agents, preservatives, coloring agents, and the like in the case of oral liquid preparations (such as suspensions, solutions, and elixirs) or aerosols; or carriers such as starches, sugars, micro-crystalline cellulose, diluents, granulating agents, lubricants, binders, and disintegrating agents can be used in the case of oral solid preparations, in some embodiments without employing the use of lactose. For example, suitable carriers include powders, capsules, and tablets, with the solid oral preparations. In some embodiments, tablets can be coated by standard aqueous or nonaqueous techniques.

Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, microcrystalline cellulose, and mixtures thereof.

Examples of suitable fillers for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof.

Disintegrants can be used in the pharmaceutical compositions as provided herein to provide tablets that disintegrate when exposed to an aqueous environment. Too much of a disintegrant can produce tablets which can disintegrate in the bottle. Too little can be insufficient for disintegration to occur and can thus alter the rate and extent of release of the active ingredient(s) from the dosage form. Thus, a sufficient amount of disintegrant that is neither too little nor too much to detrimentally alter the release of the active ingredient(s) can be used to form the dosage forms of the compounds disclosed herein. The amount of disintegrant used can vary based upon the type of formulation and mode of administration, and can be readily discernible to those of ordinary skill in the art. About 0.5 to about 15 weight percent of disintegrant, or about 1 to about 5 weight percent of disintegrant, can be used in the pharmaceutical composition. Disintegrants that can be used to form pharmaceutical compositions and dosage forms include, but are not limited to, agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums or mixtures thereof.

Lubricants which can be used to form pharmaceutical compositions and dosage forms include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethylaureate, agar, or mixtures thereof. Additional lubricants include, for example, a syloid silica gel, a coagulated aerosol of synthetic silica, or mixtures thereof. A lubricant can optionally be added, in an amount of less than about 1 weight percent of the pharmaceutical composition.

When aqueous suspensions and/or elixirs are desired for oral administration, the active ingredient therein can be combined with various sweetening or flavoring agents, coloring matter or dyes and, for example, emulsifying and/or suspending agents, together with such diluents as water, ethanol, propylene glycol, glycerin and various combinations thereof.

The tablets can be uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Surfactant which can be used to form pharmaceutical compositions and dosage forms include, but are not limited to, hydrophilic surfactants, lipophilic surfactants, and mixtures thereof. That is, a mixture of hydrophilic surfactants can be employed, a mixture of lipophilic surfactants can be employed, or a mixture of at least one hydrophilic surfactant and at least one lipophilic surfactant can be employed.

A suitable hydrophilic surfactant can generally have an HLB value of at least about 10, while suitable lipophilic surfactants can generally have an HLB value of or less than about 10. An empirical parameter used to characterize the relative hydrophilicity and hydrophobicity of non-ionic amphiphilic compounds is the hydrophilic-lipophilic balance ("HLB" value). Surfactants with lower HLB values are more lipophilic or hydrophobic, and have greater solubility in oils, while surfactants with higher HLB values are more hydrophilic, and have greater solubility in aqueous solutions. Hydrophilic surfactants are generally considered to be those compounds having an HLB value greater than about 10, as well as anionic, cationic, or zwitterionic compounds for which the HLB scale is not generally applicable. Similarly, lipophilic (i.e., hydrophobic) surfactants are compounds having an HLB value equal to or less than about 10. However, HLB value of a surfactant is merely a rough guide generally used to enable formulation of industrial, pharmaceutical and cosmetic emulsions.

Hydrophilic surfactants can be either ionic or non-ionic. Suitable ionic surfactants include, but are not limited to, alkylammonium salts; fusidic acid salts; fatty acid derivatives of amino acids, oligopeptides, and polypeptides; glyceride derivatives of amino acids, oligopeptides, and polypeptides; lecithins and hydrogenated lecithins; lysolecithins and hydrogenated lysolecithins; phospholipids and derivatives thereof, lysophospholipids and derivatives thereof, carnitine fatty acid ester salts; salts of alkylsulfates; fatty acid salts; sodium docusate; acylactylates; mono- and di-acetylated tartaric acid esters of mono- and di-glycerides; succinylated mono- and di-glycerides; citric acid esters of mono- and di-glycerides; and mixtures thereof.

Within the aforementioned group, ionic surfactants include, by way of example: lecithins, lysolecithin, phospholipids, lysophospholipids and derivatives thereof, carnitine fatty acid ester salts; salts of alkylsulfates; fatty acid salts; sodium docusate; acylactylates; mono- and di-acetylated tartaric acid esters of mono- and di-glycerides; succinylated mono- and di-glycerides; citric acid esters of mono- and di-glycerides; and mixtures thereof.

Ionic surfactants can be the ionized forms of lecithin, lysolecithin, phosphatidylcholine, phosphatidylethanolamine, phosphatidylglycerol, phosphatidic acid, phosphatidylserine, lysophosphatidylcholine, lysophosphatidylethanolamine, lysophosphatidylglycerol, lysophosphatidic acid, lysophosphatidylserine, PEG-phosphatidylethanolamine, PVP-phosphatidylethanolamine, lactylic esters of fatty acids, stearoyl-2-lactylate, stearoyl lactylate, succinylated monoglycerides, mono/diacetylated tartaric acid esters of mono/diglycerides, citric acid esters of mono/diglycerides, cholylsarcosine, caproate, caprylate, caprate, laurate, myristate, palmitate, oleate, ricinoleate, linoleate, linolenate, stearate, lauryl sulfate, teracecyl sulfate, docusate, lauroyl carnitines, palmitoyl carnitines, myristoyl carnitines, and salts and mixtures thereof.

Hydrophilic non-ionic surfactants can include, but are not limited to, alkylglucosides; alkylmaltosides; alkylthioglucosides; lauryl macrogolglycerides; polyoxyalkylene alkyl ethers such as polyethylene glycol alkyl ethers; polyoxyalkylene alkylphenols such as polyethylene glycol alkyl phenols; polyoxyalkylene alkyl phenol fatty acid esters such as polyethylene glycol fatty acids monoesters and polyethylene glycol fatty acids diesters; polyethylene glycol glycerol fatty acid esters; polyglycerol fatty acid esters; polyoxyalkylene sorbitan fatty acid esters such as polyethylene glycol sorbitan fatty acid esters; hydrophilic transesterification products of a polyol with at least one member of glycerides, vegetable oils, hydrogenated vegetable oils, fatty acids, and sterols; polyoxyethylene sterols, derivatives, and analogues thereof, polyoxyethylated vitamins and derivatives thereof; polyoxyethylene-polyoxypropylene block copolymers; and mixtures thereof, polyethylene glycol sorbitan fatty acid esters and hydrophilic transesterification products of a polyol with at least one member of triglycerides, vegetable oils, and hydrogenated vegetable oils. The polyol can be glycerol, ethylene glycol, polyethylene glycol, sorbitol, propylene glycol, pentaerythritol, or a saccharide.

Other hydrophilic-non-ionic surfactants include, without limitation, PEG-10 laurate, PEG-12 laurate, PEG-20 laurate, PEG-32 laurate, PEG-32 dilaurate, PEG-12 oleate, PEG-15 oleate, PEG-20 oleate, PEG-20 dioleate, PEG-32 oleate, PEG-200 oleate, PEG-400 oleate, PEG-15 stearate, PEG-32 distearate, PEG-40 stearate, PEG-100 stearate, PEG-20 dilaurate, PEG-25 glyceryl trioleate, PEG-32 dioleate, PEG-20 glyceryl laurate, PEG-30 glyceryl laurate, PEG-20 glyceryl stearate, PEG-20 glyceryl oleate, PEG-30 glyceryl oleate, PEG-30 glyceryl laurate, PEG-40 glyceryl laurate, PEG-40 palm kernel oil, PEG-50 hydrogenated castor oil, PEG-40 castor oil, PEG-35 castor oil, PEG-60 castor oil, PEG-40 hydrogenated castor oil, PEG-60 hydrogenated castor oil, PEG-60 corn oil, PEG-6 caprate/caprylate glycerides, PEG-8 caprate/caprylate glycerides, polyglyceryl-10 laurate, PEG-30 cholesterol, PEG-25 phyto sterol, PEG-30 soya sterol, PEG-20 trioleate, PEG-40 sorbitan oleate, PEG-80 sorbitan laurate, polysorbate 20, polysorbate 80, POE-9 lauryl ether, POE-23 lauryl ether, POE-10 oleyl ether, POE-20 oleyl ether, POE-20 stearyl ether, tocopheryl PEG-100 succinate, PEG-24 cholesterol, polyglyceryl-10 oleate, Tween 40, Tween 60, sucrose monostearate, sucrose mono-laurate, sucrose monopalmitate, PEG 10-100 nonyl phenol series, PEG 15-100 octyl phenol series, and poloxamers.

Suitable lipophilic surfactants include, by way of example only: fatty alcohols; glycerol fatty acid esters; acetylated glycerol fatty acid esters; lower alcohol fatty acids esters; propylene glycol fatty acid esters; sorbitan fatty acid esters; polyethylene glycol sorbitan fatty acid esters; sterols and sterol derivatives; polyoxyethylated sterols and sterol derivatives; polyethylene glycol alkyl ethers; sugar esters; sugar ethers; lactic acid derivatives of mono- and di-glycerides; hydrophobic transesterification products of a polyol with at least one member of glycerides, vegetable oils, hydrogenated vegetable oils, fatty acids and sterols; oil-soluble vitamins/vitamin derivatives; and mixtures thereof. Within this group, non-limiting examples of lipophilic surfactants include glycerol fatty acid esters, propylene glycol fatty acid esters, and mixtures thereof, or are hydrophobic transesterification products of a polyol with at least one member of vegetable oils, hydrogenated vegetable oils, and triglycerides.

In one embodiment, the pharmaceutical composition can include a solubilizer to ensure good solubilization and/or dissolution of a compound as provided herein and to minimize precipitation of the compound. This can be especially important for pharmaceutical compositions for non-oral use, e.g., pharmaceutical compositions for injection. A solubilizer can also be added to increase the solubility of the hydrophilic drug and/or other components, such as surfactants, or to maintain the pharmaceutical composition as a stable or homogeneous solution or dispersion.

Examples of suitable solubilizers include, but are not limited to, the following: alcohols and polyols, such as ethanol, isopropanol, butanol, benzyl alcohol, ethylene glycol, propylene glycol, butanediols and isomers thereof, glycerol, pentaerythritol, sorbitol, mannitol, transcutol, dimethyl isosorbide, polyethylene glycol, polypropylene glycol, polyvinylalcohol, hydroxypropyl methylcellulose and other cellulose derivatives, cyclodextrins and cyclodextrin derivatives; ethers of polyethylene glycols having an average molecular weight of about 200 to about 6000, such as tetrahydrofurfuryl alcohol PEG ether (glycofurol) or methoxy PEG; amides and other nitrogen-containing compounds such as 2-pyrrolidone, 2-piperidone, e-caprolactam, N—alkylpyrrolidone, N—hydroxyalkylpyrrolidone, N—alkylpiperidone, N—alkylcaprolactam, dimethylacetamide and polyvinylpyrrolidone; esters such as ethyl propionate, tributylcitrate, acetyl triethylcitrate, acetyl tributyl citrate, triethylcitrate, ethyl oleate, ethyl caprylate, ethyl butyrate, triacetin, propylene glycol monoacetate, propylene glycol diacetate, c-caprolactone and isomers thereof, 6-valerolactone and isomers thereof, (3-butyrolactone and isomers thereof; and other solubilizers known in the art, such as dimethyl acetamide, dimethyl isosorbide, N—methyl pyrrolidones, monooctanoin, diethylene glycol monoethyl ether, and water.

Mixtures of solubilizers can also be used. Examples include, but not limited to, triacetin, triethylcitrate, ethyl oleate, ethyl caprylate, dimethylacetamide, N—methylpyrrolidone, N—hydroxyethylpyrrolidone, polyvinylpyrrolidone, hydroxypropyl methylcellulose, hydroxypropyl cyclodextrins, ethanol, polyethylene glycol 200-100, glycofurol, transcutol, propylene glycol, and dimethyl isosorbide. In some embodiments, solubilizers include sorbitol, glycerol, triacetin, ethyl alcohol, PEG-400, glycofurol and propylene glycol.

The amount of solubilizer that can be included is not particularly limited. The amount of a given solubilizer can be limited to a bioacceptable amount, which can be readily determined by one of skill in the art. In some circumstances, it can be advantageous to include amounts of solubilizers far in excess of bioacceptable amounts, for example to maximize the concentration of the drug, with excess solubilizer removed prior to providing the pharmaceutical composition to a subject using conventional techniques, such as distillation or evaporation. Thus, if present, the solubilizer can be in a weight ratio of about 10%, 25%, 50%, 100%, or up to about 200% by weight, based on the combined weight of the drug, and other excipients. If desired, very small amounts of solubilizer can also be used, such as about 5%, 2%, 1% or even less. Typically, the solubilizer can be present in an amount of about 1% to about 100%, more typically about 5% to about 25% by weight.

The pharmaceutical composition can further include one or more pharmaceutically acceptable additives and excipients. Such additives and excipients include, without limitation, detackifiers, anti-foaming agents, buffering agents, polymers, antioxidants, preservatives, chelating agents, viscomodulators, tonicifiers, flavorants, colorants, oils, odorants, opacifiers, suspending agents, binders, fillers, plasticizers, lubricants, and mixtures thereof.

Exemplary preservatives can include antioxidants, chelating agents, antimicrobial preservatives, antifungal preservatives, alcohol preservatives, acidic preservatives, and other preservatives. Exemplary antioxidants include, but are not limited to, alpha tocopherol, ascorbic acid, ascorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite. Exemplary chelating agents include ethylenediaminetetraacetic acid (EDTA), citric acid monohydrate, disodium edetate, dipotassium edetate, editic acid, fumaric acid, malic acid, phosphoric acid, sodium edetate, tartaric acid, and trisodium edetate. Exemplary antimicrobial preservatives include, but are not limited to, benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal. Exemplary antifungal preservatives include, but are not limited to, butyl paraben, methyl paraben, ethyl paraben, propyl paraben, benzoic acid, hydroxybenzoic acid, potassium benzoate, potassium sorbate, sodium benzoate, sodium propionate, and sorbic acid. Exemplary alcohol preservatives include, but are not limited to, ethanol, polyethylene glycol, phenol, phenolic compounds, bisphenol, chlorobutanol, hydroxybenzoate, and phenylethyl alcohol. Exemplary acidic preservatives include, but are not limited to, vitamin A, vitamin C, vitamin E, beta-carotene, citric acid, acetic acid, dehydroacetic acid, ascorbic acid, sorbic acid, and phytic acid. Other preservatives include, but are not limited to, tocopherol, tocopherol acetate, deteroxime mesylate, cetrimide, butylated hydroxyanisol (BHA), butylated hydroxytouened (BHT), ethylenediamine, sodium lauryl sulfate (SLS), sodium lauryl ether sulfate (SLES), sodium bisulfite, sodium metabisulfite, potassium sulfite, potassium metabisulfite, Glydant Plus, Phenonip, methylparaben, Germall 115, Germaben II, Neolone, Kathon, and Euxyl. In certain embodiments, the preservative is an anti-oxidant. In other embodiments, the preservative is a chelating agent.

Exemplary oils include, but are not limited to, almond, apricot kernel, avocado, babassu, bergamot, black current seed, borage, cade, chamomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, litsea cubeba, macadamia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and combinations thereof.

In addition, an acid or a base can be incorporated into the pharmaceutical composition to facilitate processing, to enhance stability, or for other reasons. Examples of pharmaceutically acceptable bases include amino acids, amino acid esters, ammonium hydroxide, potassium hydroxide, sodium hydroxide, sodium hydrogen carbonate, aluminum hydroxide, calcium carbonate, magnesium hydroxide, magnesium aluminum silicate, synthetic aluminum silicate, synthetic hydrocalcite, magnesium aluminum hydroxide, diisopropylethylamine, ethanolamine, ethylenediamine, triethanolamine, triethylamine, triisopropanolamine, trimethylamine, tris(hydroxymethyl)aminomethane (TRIS) and the like. Also suitable are bases that are salts of a pharmaceutically acceptable acid, such as acetic acid, acrylic acid, adipic acid, alginic acid, alkanesulfonic acid, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid, uric acid, and the like. Salts of polyprotic acids, such as sodium phosphate, disodium hydrogen phosphate, and sodium dihydrogen phosphate can also be used. When the base is a salt, the cation can be any convenient and pharmaceutically acceptable cation, such as ammonium, alkali metals, alkaline earth metals, and the like. Examples can include, but not limited to, sodium, potassium, lithium, magnesium, calcium and ammonium.

Suitable acids are pharmaceutically acceptable organic or inorganic acids. Examples of suitable inorganic acids include hydrochloric acid, hydrobromic acid, hydriodic acid, sulfuric acid, nitric acid, boric acid, phosphoric acid, and the like. Examples of suitable organic acids include acetic acid, acrylic acid, adipic acid, alginic acid, alkanesulfonic acids, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, methanesulfonic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid, uric acid and the like.

4.2 Formulations for Parenteral Administration

In some embodiments of the methods described herein, PI3K inhibitor (e.g., one or more PI3K inhibitors) and/or another agent (e.g., the second agent, e.g., one or more second agents as described herein) is administered parenterally. In certain embodiments of the compositions described herein, PI3K inhibitor (e.g., Compound 1) and/or another agent (e.g., the second agent, e.g., one or more second agents as described herein) is formulated for parenteral administration. Some embodiments pertaining to such methods and compositions include the following.

In some embodiments, provided herein are pharmaceutical compositions for parenteral administration containing a compound as disclosed herein, and a pharmaceutical excipient suitable for parenteral administration. In some embodiments, provided herein are pharmaceutical compositions for parenteral administration containing: (i) an effective amount of a disclosed compound; optionally (ii) an effective amount of one or more second agents; and (iii) one or more pharmaceutical excipients suitable for parenteral administration. In some embodiments, the pharmaceutical composition further contains: (iv) an effective amount of a third agent.

The forms in which the disclosed pharmaceutical compositions can be incorporated for administration by injection include aqueous or oil suspensions, or emulsions, with sesame oil, corn oil, cottonseed oil, or peanut oil, as well as elixirs, mannitol, dextrose, or a sterile aqueous solution, and similar pharmaceutical vehicles.

Aqueous solutions in saline are also conventionally used for injection. Ethanol, glycerol, propylene glycol, liquid polyethylene glycol, and the like (and suitable mixtures thereof), cyclodextrin derivatives, and vegetable oils can also be employed.

Aqueous solutions in saline are also conventionally used for injection. Ethanol, glycerol, propylene glycol, liquid polyethylene glycol, and the like (and suitable mixtures thereof), cyclodextrin derivatives, and vegetable oils can also be employed. The proper fluidity can be maintained, for example, by the use of a coating, such as lecithin, for the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like.

Sterile injectable solutions are prepared by incorporating a compound as disclosed herein in the required amount in the appropriate solvent with various other ingredients as enumerated above, as appropriate, followed by filtered sterilization. Generally, dispersions are prepared by incorporating the various sterilized active ingredients into a sterile vehicle which contains the basic dispersion medium and the appropriate other ingredients from those enumerated above. In the case of sterile powders for the preparation of sterile injectable solutions, certain methods of preparation are vacuum-drying and freeze-drying techniques which yield a powder of the active ingredient plus any additional ingredient from a previously sterile-filtered solution thereof.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use. Injectable compositions can contain from about 0.1 to about 5% w/w of a compound as disclosed herein.

5. Dosage

The PI3K inhibitor (e.g., Compound 1 or Idelalisib) or another agent disclosed herein (e.g., one or more of the second agents disclosed herein) may be delivered in the form of pharmaceutically acceptable compositions. In certain embodiments, the pharmaceutical compositions comprise the PI3K inhibitor (e.g., Compound 1) described herein and/or one or more additional therapeutic agents, formulated together with one or more pharmaceutically acceptable excipients. In some instances, the PI3K inhibitor (e.g., Compound 1) or one or more of the other therapeutic agents disclosed herein are administered in separate pharmaceutical compositions and may (e.g., because of different physical and/or chemical characteristics) be administered by different routes (e.g., one therapeutic is administered orally, while the other is administered intravenously). In other instances, the PI3K inhibitor (e.g., Compound 1) or one or more of the other therapeutic agents disclosed herein may be administered separately, but via the same route (e.g., both orally or both intravenously). In still other instances, the PI3K inhibitor (e.g., Compound 1) or one or more of the other therapeutic agents disclosed herein may be administered in the same pharmaceutical composition.

The selected dosage level will depend upon a variety of factors including, for example, the activity of the particular compound employed, the route of administration, the time of administration, the rate of excretion or metabolism of the particular compound being employed, the rate and extent of absorption, the duration of the treatment, other drugs, compounds and/or materials used in combination with the particular compound employed, the age, sex, weight, condition, general health and prior medical history of the patient being treated, and like factors well known in the medical arts.

In general, a suitable daily dose of Compound 1 described herein and/or a therapeutic agent will be that amount of the compound which, in some embodiments, may be the lowest dose effective to produce a therapeutic effect. Such an effective dose will generally depend upon the factors described herein. Generally, doses of Compound 1 or the therapeutic agent described herein for a patient, when used for the indicated effects, will range from about 0.0001 mg to about 100 mg per day, or about 0.001 mg to about 100 mg per day, or about 0.01 mg to about 100 mg per day, or about 0.1 mg to about 100 mg per day, or about 0.0001 mg to about 500 mg per day, or about 0.001 mg to about 500 mg per day, or about 0.01 mg to 1000 mg, or about 0.01 mg to about 500 mg per day, or about 0.1 mg to about 500 mg per day, or about 1 mg to 50 mg per day, or about 5 mg to 40 mg per day. An exemplary dosage is about 10 to 30 mg per day. In some embodiments, for a 70 kg human, a suitable dose would be about 0.05 to about 7 g/day, such as about 0.05 to about 2.5 g/day. Actual dosage levels of the active ingredients in the pharmaceutical compositions described herein may be varied so as to obtain an amount of the active ingredient which is effective to achieve the desired therapeutic response for a particular patient, composition, and mode of administration, without being toxic to the patient. In some instances, dosage levels below the lower limit of the aforesaid range may be more than adequate, while in other cases still larger doses may be employed without causing any harmful side effect, e.g., by dividing such larger doses into several small doses for administration throughout the day.

In some embodiments, the compounds may be administered daily, every other day, three times a week, twice a week, weekly, or bi-weekly. The dosing schedule can include a "drug holiday," e.g., the drug may be administered for two weeks on, one week off, or three weeks on, one week off, or four weeks on, one week off, etc., or continuously, without a drug holiday. The compounds may be administered orally, intravenously, intraperitoneally, topically, transdermally, intramuscularly, subcutaneously, intranasally, sublingually, or by any other route.

In some embodiments, Compound 1 or the therapeutic agent described herein may be administered in multiple doses. Dosing may be about once, twice, three times, four times, five times, six times, or more than six times per day. Dosing may be about once a month, about once every two weeks, about once a week, or about once every other day. In another embodiment, Compound 1 as disclosed herein and another therapeutic agent are administered together from about once per day to about 6 times per day. In another embodiment, the administration of Compound 1 as provided herein and a therapeutic agent continues for less than about 7 days. In yet another embodiment, the administration continues for more than about 6 days, about 10 days, about 14 days, about 28 days, about two months, about six months, or about one year. In some cases, continuous dosing is achieved and maintained as long as necessary.

Administration of the pharmaceutical compositions as disclosed herein may continue as long as necessary. In some embodiments, an agent as disclosed herein is administered for more than about 1, about 2, about 3, about 4, about 5, about 6, about 7, about 14, or about 28 days. In some embodiments, an agent as disclosed herein is administered for less than about 28, about 14, about 7, about 6, about 5, about 4, about 3, about 2, or about 1 day. In some embodiments, a therapeutic agent as disclosed herein is administered chronically on an ongoing basis, e.g., for the treatment of chronic effects.

Since Compound 1 described herein may be administered in combination with one or more therapeutic agent, the doses of each agent or therapy may be lower than the corresponding dose for single-agent therapy. The dose for single-agent therapy can range from, for example, about 0.0001 to about 200 mg, or about 0.001 to about 100 mg, or about 0.01 to about 100 mg, or about 0.1 to about 100 mg, or about 1 to about 50 mg per kilogram of body weight per day.

When Compound 1 is administered in a pharmaceutical composition that comprises one or more therapeutic agents, and the agent has a shorter half-life than Compound 1, unit dose forms of the agent and Compound 1 can be adjusted accordingly.

6. Kits

In some embodiments, provided herein are kits. The kits may include a pharmaceutical composition as described herein, in suitable packaging, and written material that can include instructions for use, discussion of clinical studies, listing of side effects, and the like. Such kits may also include information, such as scientific literature references, package insert materials, clinical trial results, and/or summaries of these and the like, which indicate or establish the activities and/or advantages of the pharmaceutical composition, and/or which describe dosing, administration, side effects, drug interactions, or other information useful to the health care provider. Such information may be based on the results of various studies, for example, studies using experimental animals involving in vivo models and studies based on human clinical trials.

In some embodiments, a memory aid is provided with the kit, e.g., in the form of numbers next to the tablets or capsules whereby the numbers correspond with the days of the regimen which the tablets or capsules so specified should be ingested. Another example of such a memory aid is a calendar printed on the card, e.g., as follows "First Week, Monday, Tuesday, . . . etc. . . . . Second Week, Monday, Tuesday, . . . " etc. Other variations of memory aids will be readily apparent. A "daily dose" may be a single tablet or capsule or several tablets or capsules to be taken on a given day.

The kit may contain Compound 1 and one or more therapeutic agents. In some embodiments, Compound 1 and the agent are provided as separate pharmaceutical compositions in separate containers within the kit. In some embodiments, Compound 1 as disclosed herein and the agent are provided as a single pharmaceutical composition within a container in the kit. Suitable packaging and additional articles for use (e.g., measuring cup for liquid preparations, foil wrapping to minimize exposure to air, and the like) are known in the art and may be included in the kit. In other embodiments, kits may further comprise devices that are used to administer the active agents. Examples of such devices include, but are not limited to, syringes, drip bags, patches, and inhalers. Kits described herein may be provided, marketed and/or promoted to health providers, including physicians, nurses, pharmacists, formulary officials, and the like. Kits can also, in some embodiments, be marketed directly to the consumer.

An example of such a kit is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process, recesses are formed in the plastic foil. The recesses have the size and shape of the tablets or capsules to be packed. Next, the tablets or capsules are placed in the recesses and the sheet of relatively stiff material is sealed against the plastic foil at the face of the foil which is opposite from the direction in which the recesses were formed. As a result, the tablets or capsules are sealed in the recesses between the plastic foil and the sheet. The strength of the sheet is such that the tablets or capsules may be removed from the blister pack by manually applying pressure on the recesses whereby an opening is formed in the sheet at the place of the recess. The tablet or capsule can then be removed via said opening.

Kits may further comprise pharmaceutically acceptable vehicles that may be used to administer one or more active agents. For example, if an active agent is provided in a solid form that must be reconstituted for parenteral administration, the kit can comprise a sealed container of a suitable vehicle in which the active agent may be dissolved to form a particulate-free sterile solution that is suitable for parenteral administration. Examples of pharmaceutically acceptable vehicles include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

The present disclosure further encompasses anhydrous pharmaceutical compositions and dosage forms comprising an active ingredient, since water can facilitate the degradation of some compounds. For example, water may be added (e.g., about 5%) in the pharmaceutical arts as a means of simulating long-term storage in order to determine characteristics such as shelf-life or the stability of formulations over time. Anhydrous pharmaceutical compositions and dosage forms may be prepared using anhydrous or low moisture containing ingredients and low moisture or low humidity conditions. For example, pharmaceutical compositions and dosage forms which contain lactose may be made anhydrous if substantial contact with moisture and/or humidity during manufacturing, packaging, and/or storage is expected. An anhydrous pharmaceutical composition may be prepared and stored such that its anhydrous nature is maintained. Accordingly, anhydrous pharmaceutical compositions may be packaged using materials known to prevent exposure to water such that they may be included in suitable formulary kits. Examples of suitable packaging include, but are not limited to, hermetically sealed foils, plastic or the like, unit dose containers, blister packs, and strip packs.

EXAMPLES

Example 1: Combination Study of Compound 1 with Selinexor

The synergistic effects of compounds provided herein and another therapeutic agent were carried out. The method is described as follows. Cells were thawed from a liquid nitrogen preserved state. Once cells were expanded and divided at their expected doubling times, screening began. Cells were seeded in growth media in either black 1536-well or 384-well tissue culture treated plates. Cells were then equilibrated in assay plates via centrifugation and placed in incubators attached to the Dosing Modules at 37° C. for 24 hours before treatment. At the time of treatment, a set of assay plates (which do not receive treatment) were collected and ATP levels were measured by adding ATPLite (Perkin Elmer). These Tzero (To) plates were read using ultrasensitive luminescence on Envision plate readers (Perkin Elmer). Treated assay plates were incubated with compound for 72 hours. After 72 hours, plates were developed for endpoint analysis using ATPLite. All data points were collected via automated processes, quality controlled and analyzed using Zalicus software. Assay plates were accepted if they passed the following quality control standards: relative luciferase values were consistent throughout the entire experiment, Z-factor scores were greater than 0.6, untreated/vehicle controls behaved consistently on the plate.

Inhibition (I) is defined as $$I=(1-T/V)*100\%$$

where T is treated cell count and V is untreated (vehicle) cell count (at 72 hours). I ranges from 0% (when T=V) to 100% (when T=0). The $IC_{50}$ value is defined as the drug concentration needed to inhibit 50% of the cell growth compared to growth of the vehicle treated cells (the drug concentration which gives I=50%). The measure of effect in the experiment can be the inhibition of cellular response relative to the untreated level (vehicle alone). For untreated vehicle and treated levels V and T, a fractional inhibition I=1-T/V is calculated. The inhibition ranges from 0% at the untreated level to 100% when T=0. Inhibition levels are negative for agents that actually increase levels. Other effect measures, such as an activity ratio r=T/V may be more appropriate for some assays. When activity ratios (e.g., fold increase over stimulated control) are being used, the effect can be measured using an induction I=ln(T/V). With this definition, all effect expressions are the same as for inhibition.

Growth Inhibition (GI) is used as a measure of cell viability. The cell viability of vehicle is measured at the time of dosing (TO) and after 72 hours (T72). A GI reading of 0% represents no growth inhibition—T72 compound-treated and T72 vehicle signals are matched. A GI reading of 100% represents complete growth inhibition—T72 compound-treated and T0 vehicle signals are matched. Cell numbers have not increased during the treatment period in wells with GI 100% and may suggest a cytostatic effect for compounds reaching a plateau at this effect level. A GI reading of 200% represents complete death of all cells in the culture well. Compounds reaching an activity plateau of GI 200% are considered cytotoxic. GI is calculated by applying the following test and equation:

$$\text{If } T < V_0: 100 * \left(1 - \frac{T - V_0}{V_0}\right)$$

$$\text{If } T \geq V_0: 100 * \left(1 - \frac{T - V_0}{V - V_0}\right)$$

where T is the signal measure for a test article, V is the vehicle-treated control measure, and Vo is the vehicle control measure at time zero. This formula is derived from the Growth Inhibition calculation used in the National Cancer Institute's NCI-60 high-throughput screen.

Combination analysis data were collected in a 9×9 dose matrix. Synergy was calculated by comparing a combination's response to those of its single compound, against the drug-with-itself dose-additive reference model. Deviations from dose additivity may be assessed visually on an isobologram or numerically with a Combination Index (CI). See the tables below for CI at 50% inhibition and CI at 50% growth inhibition. Additive effect is CI=1.0. Synergistic effect is CI<1. Antagonistic effect is CI>1.0.

Potency shifting was evaluated using an isobologram, which demonstrates how much less drug is required in combination to achieve a desired effect level, when compared to the single agent doses needed to reach that effect. The isobologram was drawn by identifying the locus of concentrations that correspond to crossing the indicated inhibition level. This was done by finding the crossing point for each single agent concentration in a dose matrix across the concentrations of the other single agent. Practically, each vertical concentration $C_Y$ was held fixed while a bisection algorithm was used to identify the horizontal concentration $C_X$ in combination with that vertical dose that gave the chosen effect level in the response surface $Z(C_X, C_Y)$. These concentrations were then connected by linear interpolation to generate the isobologram display. For synergistic interactions, the isobologram contour would fall below the additivity threshold and approach the origin, and an antagonistic interaction would lie above the additivity threshold. The error bars represented the uncertainty arising from the individual data points used to generate the isobologram. The uncertainty for each crossing point was estimated from the response errors using bisection to find the concentrations where $Z-\sigma_Z(C_X, C_Y)$ and $Z+\sigma_Z(C_X, C_Y)$ cross $I_{cut}$, where $\sigma_Z$ is the standard deviation of the residual error on the effect scale.

To measure combination effects in excess of Loewe additivity, a scalar measure to characterize the strength of synergistic interaction termed the Synergy Score was devised. The Synergy Score was calculated as:

Synergy Score=log $f_X$ log $f_Y$Σ max(0,$I_{data}$)($I_{data}$−$I_{Loewe}$)

The fractional inhibition for each component agent and combination point in the matrix was calculated relative to the median of all vehicle-treated control wells. The Synergy Score equation integrated the experimentally-observed activity volume at each point in the matrix in excess of a model surface numerically derived from the activity of the component agents using the Loewe model for additivity. Additional terms in the Synergy Score equation (above) were used to normalize for various dilution factors used for individual agents and to allow for comparison of synergy scores across an entire experiment. The inclusion of positive inhibition gating or an $I_{data}$ multiplier removed noise near the zero effect level, and biases results for synergistic interactions at that occur at high activity levels.

The Synergy Score measure was used for the self-cross analysis. Synergy Scores of self-crosses were expected to be additive by definition and, therefore, maintain a synergy score of zero. However, while some self-cross synergy scores were near zero, many were greater suggesting that experimental noise or non-optimal curve fitting of the single agent dose responses were contributing to the slight perturbations in the score. This strategy was cell line-centric, focusing on self-cross behavior in each cell line versus a global review of cell line panel activity. Combinations where the synergy score was greater than the mean self-cross plus two standard deviations or three standard deviations can be considered candidate synergies at 95% and 99% confidence levels, respectively. Additivity should maintain a synergy score of zero, and synergy score of two or three standard deviations indicate that the combination is synergistic at statistically significant levels of 95% and 99%.

Loewe Volume (Loewe Vol) was used to assess the overall magnitude of the combination interaction in excess of the Loewe additivity model. Loewe Volume was particularly useful when distinguishing synergistic increases in a phenotypic activity (positive Loewe Volume) versus synergistic antagonisms (negative Loewe Volume). When antagonisms is observed, the Loewe Volume should be assessed to examine if there is any correlation between antagonism and a particular drug target-activity or cellular genotype. This model defined additivity as a non-synergistic combination interaction where the combination dose matrix surface should be indistinguishable from either drug crossed with itself. The calculation for Loewe additivity is:

$I_{Loewe}$ that satisfies$(X/X_1)+(Y/Y_1)=1$ where $X_I$ and $Y_I$ are the single agent effective concentrations for the observed combination effect I. For example, if 50% inhibition is achieved separately by 1 μM of drug A or 1 μM of drug B, a combination of 0.5 μM of A and 0.5 μM of B should also inhibit by 50%.

Results

The $CI_{50}$ values for growth inhibition and inhibition in Table 1 are categorized as follows: S=0.01 to <0.5, T=0.5 to <0.7, U=0.7 to <1, and W=≥1. The synergy score values for growth inhibition and inhibition are categorized as follows: A1=0.0001 to <1, A2=1 to <3, and A3=>3.

The combination effects of Compound 1 and selinexor were tested in five types of T-cell lymphoma cell line: H9, HH, HuT 78, HuT 102, and MJ (G11). These cell lines may have different genomic profiles and thus, a combination of Compound 1 and selinexor can have different synergistic effects on these cell lines. The results are shown in Table 1 below. An isobologram depicting the effect of the combination of Compound 1 and selinexor in H9 cell line is provided in FIG. 1. The data show that the combination of Compound 1 and selinexor is synergistic in selected cell lines.

TABLE 1

Combination of Compound 1 and Selinexor

| Compound 1 in combination with | Cell Line | Synergy Score growth inhibition | | CI$_{50}$ growth inhibition | Synergy Score inhibition | | CI$_{50}$ inhibition |
|---|---|---|---|---|---|---|---|
| Selinexor | H9 | 10.4 | A3 | | 3.23 | A3 | |
| Selinexor | HH | 1.53 | A2 | | 1.25 | A2 | |
| Selinexor | HuT 102 | | | | 0.82 | A1 | |
| Selinexor | HuT 78 | 5.85 | A3 | | 1.94 | A2 | |
| Selinexor | MJ (G11) | 4.50 | A3 | | 1.50 | A2 | |

Example 2: Clinical Trial for Compound 1 and Anti-PD-1 Antibody Combination

A phase 1b clinical trial for treatment of patient with hematological malignancies with combination of Compound 1 and anti-PD-1 antibody is carried out. Some patients have advanced B and/or T cell maliganceis. The anti-PD-1 antibodies used in this study in combination with Compound 1 include Nivolumab and Pembrolizumab.

The starting dose for Compound 1 is 15 mg QD, and may be escalated to 15 mg BID, 25 mg BID, and 25 mg QD.

The combination of Compound 1 and the anti-PD-1 antibody are administered to three expansion cohorts: follicular lymphoma, DLBCL, and T-cell lymphoma.

EQUIVALENTS

While this invention has been disclosed with reference to specific aspects, it is apparent that other aspects and variations of this invention can be devised by others skilled in the art without departing from the true spirit and scope of the invention. The appended claims are intended to be construed to include all such aspects and equivalent variations.

What is claimed is:

1. A method of treating or managing a cancer in a subject, comprising administering to the subject a therapeutically effective amount of a PI3K inhibitor in combination with a second therapeutic agent, wherein the second therapeutic agent is a checkpoint modulator;
   wherein the PI3K-inhibitor is Compound 1 having the structure:

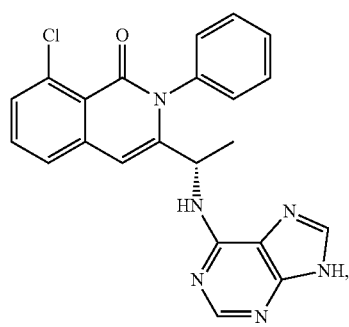

Compound 1 or a pharmaceutically acceptable form thereof;
wherein the checkpoint modulator is an anti-PD-1 antibody; and
wherein the cancer is lymphoma or leukemia.

2. The method of claim 1, wherein the anti-PD-1 antibody is Nivolumab, Pembrolizumab, Pidilizumab, AMP-514, or AMP-224, or a combination thereof.

3. The method of claim 2, wherein the anti-PD-1 antibody is Nivolumab.

4. The method of claim 2, wherein the anti-PD-1 antibody is Pembrolizumab.

5. The method of claim 1, wherein the PI3K inhibitor and the second therapeutic agent are the only therapeutically active ingredients.

6. The method of claim 1, wherein the PI3K inhibitor is administered concurrently with the second therapeutic agent.

7. The method of claim 1, wherein the PI3K inhibitor is administered subsequent to the second therapeutic agent.

8. The method of claim 1, wherein the PI3K inhibitor is administered prior to the second therapeutic agent.

9. A method of delaying or decreasing resistance of a subject having a cancer, comprising administering to the subject a therapeutically effective amount of a PI3K inhibitor in combination with a second therapeutic agent, wherein the second therapeutic agent is a checkpoint modulator, thereby delaying or decreasing resistance;
   wherein the PI3K-inhibitor is Compound 1 having the structure:

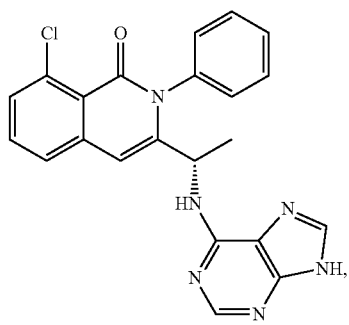

Compound 1 or a pharmaceutically acceptable form thereof;
wherein the checkpoint modulator is an anti-PD-1 antibody; and
wherein the cancer is lymphoma or leukemia.

10. A method of reducing the level of minimal residual disease (MRD) in a subject having a cancer, comprising administering to the subject a therapeutically effective amount of a PI3K inhibitor in combination with a second therapeutic agent, wherein the second therapeutic agent is a checkpoint modulator, wherein the PI3K-inhibitor is Compound 1 having the structure:

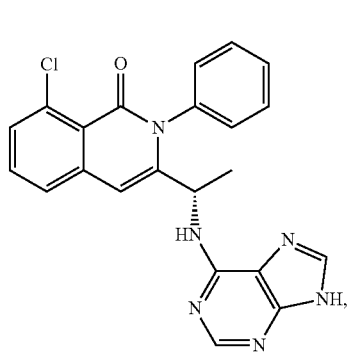

Compound 1 or a pharmaceutically acceptable form thereof;
wherein the checkpoint modulator is an anti-PD-1 antibody; and
wherein the cancer is lymphoma or leukemia.

11. The method of claim 1, wherein the cancer is B-cell lymphoma, mantle cell lymphoma, non-Hodgkin's B-cell lymphoma, non-Hodgkin's lymphoma T-cell lymphoma, cutaneous lymphoma, anaplastic large cell lymphoma, multiple myeloma, myeloma, plasmacytoma, follicular lymphoma, small lymphocytic lymphoma (SLL), Richter's syndrome, or chronic lymphocytic leukemia (CLL).

12. The method of claim 1, wherein the cancer is multiple myeloma.

13. The method of claim 1, wherein the cancer is non-Hodgkin's lymphoma.

14. The method of claim 13, wherein the non-Hodgkin's lymphoma is B cell non-Hodgkin's lymphoma.

15. The method of claim 14, wherein the B cell non-Hodgkin's lymphoma is diffuse large B-cell lymphoma.

16. The method of claim 15, wherein the diffuse large B-cell lymphoma is diffuse large B-cell lymphoma activated B-cell like or diffuse large B-cell lymphoma germinal center B-cell-like.

17. The method of claim 1, wherein the cancer is indolent non-Hodgkin's lymphoma.

18. The method of claim 1, wherein the cancer is follicular lymphoma.

19. The method of claim 1, wherein the cancer is mantle cell lymphoma.

20. The method of claim 1, wherein the cancer is T-cell lymphoma.

21. The method of claim 1, wherein the subject is a human.

22. A composition comprising a combination of a PI3K inhibitor and a second therapeutic agent, wherein the second therapeutic agent is a checkpoint modulator;

wherein the PI3K-inhibitor is Compound 1 having the structure:

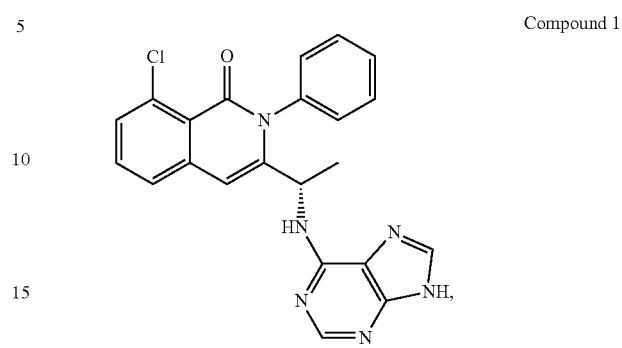

Compound 1 or a pharmaceutically acceptable form thereof; and
wherein the checkpoint modulator is an anti-PD-1 antibody.

23. The method of claim 1, wherein the cancer is small lymphocytic lymphoma (SLL).

24. The method of claim 1, wherein the cancer is Richter's syndrome.

25. The method of claim 1, wherein the cancer is chronic lymphocytic leukemia (CLL).

26. The method of claim 1, wherein the cancer is relapsed or refractory.

27. The method of claim 15, wherein the diffuse large B-cell lymphoma is relapsed or refractory.

28. The method of claim 1, wherein Compound 1 or a pharmaceutically acceptable form thereof is administered at daily dose of about 10 mg to about 75 mg.

29. The method of claim 1, wherein Compound 1 or a pharmaceutically acceptable form thereof is administered at a dose of about 10 mg BID to about 50 mg BID.

30. The method of claim 1, wherein Compound 1 or a pharmaceutically acceptable form thereof is administered at a dose of about 15 mg BID or about 25 mg BID.

31. The method of claim 1, wherein the pharmaceutically acceptable form of Compound 1 is a hydrate of Compound 1.

32. The method of claim 9, wherein the pharmaceutically acceptable form of Compound 1 is a hydrate of Compound 1.

33. The method of claim 10, wherein the pharmaceutically acceptable form of Compound 1 is a hydrate of Compound 1.

34. The composition of claim 22, wherein the composition comprises Compound 1 or a pharmaceutically acceptable form thereof in about 10 mg to about 75 mg.

35. The composition of claim 22, wherein the composition comprises Compound 1 or a pharmaceutically acceptable form thereof in about 15 mg or about 25 mg.

36. The composition of claim 22, wherein the pharmaceutically acceptable form of Compound 1 is a hydrate of Compound 1.

* * * * *

UNITED STATES PATENT AND TRADEMARK OFFICE
CERTIFICATE OF CORRECTION

PATENT NO. : 11,147,818 B2
APPLICATION NO. : 16/312896
DATED : October 19, 2021
INVENTOR(S) : Jeffery L. Kutok et al.

It is certified that error appears in the above-identified patent and that said Letters Patent is hereby corrected as shown below:

In the Claims

Claim 10, Column 112, Line 67: please replace "checkpoint modulator," with -- checkpoint modulator, thereby reducing the level of MRD in the subject; --.

Signed and Sealed this
Tenth Day of May, 2022

Katherine Kelly Vidal
*Director of the United States Patent and Trademark Office*